(12) United States Patent
Keegan et al.

(10) Patent No.: US 7,067,506 B2
(45) Date of Patent: Jun. 27, 2006

(54) COMPOUNDS USEFUL FOR INHIBITING CHK1

(75) Inventors: Kathleen S. Keegan, Mercer Island, WA (US); Edward A. Kesicki, Bothell, WA (US); John Joseph Gaudino, Longmont, CO (US); Adam Wade Cook, Longmont, CO (US); Scott Douglas Cowen, Longmont, CO (US); Laurence Edward Burgess, Boulder, CO (US)

(73) Assignee: ICOS Corporation, Bothwell, WA (US)

( * ) Notice: Subject to any disclaimer, the term of this patent is extended or adjusted under 35 U.S.C. 154(b) by 423 days.

(21) Appl. No.: 10/087,715

(22) Filed: Mar. 1, 2002

(65) Prior Publication Data

US 2003/0069284 A1 Apr. 10, 2003

Related U.S. Application Data

(60) Provisional application No. 60/273,124, filed on Mar. 2, 2001.

(51) Int. Cl.
*A61K 31/33* (2006.01)
*C07D 241/00* (2006.01)

(52) U.S. Cl. ............... 514/183; 514/252.1; 544/336
(58) Field of Classification Search ............ 514/183, 514/252.1; 544/336
See application file for complete search history.

(56) References Cited

U.S. PATENT DOCUMENTS

| 4,609,659 | A | * | 9/1986 | Hartman | ............ 514/255.06 |
| 5,041,653 | A | | 8/1991 | Lee et al. | |
| 5,215,738 | A | | 6/1993 | Lee et al. | |
| 6,218,109 | B1 | * | 4/2001 | Elledge et al. | ............ 435/6 |

FOREIGN PATENT DOCUMENTS

| CA | 2132771 | * | 4/1995 |
| EP | 1 054 004 | | 11/2000 |
| EP | 1 096 014 | | 5/2001 |
| EP | 1 143 920 | | 11/2001 |
| EP | 1 199 306 | | 4/2002 |
| RU | 1621447 | | 2/1996 |
| RU | 1624949 | | 2/1996 |
| WO | WO 93/07128 | | 4/1993 |
| WO | WO 94/26715 | | 11/1994 |
| WO | 9611930 | * | 4/1996 |
| WO | WO 99/00357 | | 1/1999 |
| WO | 9911621 | * | 3/1999 |
| WO | 9929674 | * | 6/1999 |
| WO | 9932433 | * | 7/1999 |
| WO | WO 99/32436 | | 7/1999 |
| WO | WO 99/32463 | | 7/1999 |
| WO | WO 00/03005 | | 1/2000 |
| WO | 2000018738 | * | 4/2000 |
| WO | WO 00/26203 | | 5/2000 |
| WO | WO 00/56725 | | 9/2000 |
| WO | WO 00/75120 | | 12/2000 |
| WO | WO 01/57034 | | 8/2001 |

OTHER PUBLICATIONS

Chemical Abstract DN 130:209605, also cited as WO 9911621.*
Chemical Abstract DN 131:44827, also cited as WO9929674).*
Chemical Abstract DN 128:13243, also cited as Arch. der Pharm.(Weinheim Germany) 330/7,207–10(1997).*
Chemical Abstract DN 127:277898, also cited as Magnetic Reson. in Chem. 35/9,653–55(1997).*
Chemical Abstract DN124:75535,also cited as J. Med. Chem. 39/1,304–13(1996).*
Chemical Abstract DN 123:143653, also cited as CA 2132771 dated 4/12995.*
Chemical Abstract DN 112:216860, also cited as Acta Poloniae Pharm. 46/2,101–13(1989).*
Chemical Abstract DN 91:117865,also cited as Acta Ploniae Pharm. 35/5,615–18(1978).*
Chaplin et al, Chemical Abstract DN 114:77895, also cited as British J. of Cancer, 62/4,561–6(1990).*
Chemical Abstract DN:4609659, also cited as U.S.P. 4609659.*
Carter et alChemotherapy of cancer, second edition, pp. 362–365(1981).*
PubMed ASbstract 12554671, also cited as EMBO J. 22/3, 713–23(2003).*
PubMed ASbstract 8384080, also cited as Cancer Res. 53/7,1599–601(1993).*
Cecil Textbook if medicine, 2oth edition, vol. 1, pp. 1004–1010(1996).*
Uckun et al,Current Cancer Drug Targets, 1,59–71(2001).*
PubMed Abstract 14593735, also cited as Prog. Cell Cycle Res.,5,413–21(2003).*
PubMed ASbstract 12576328, also cited as Blood, 101/11, 4589–97(2003).*
Sanchez et al, Science, vol. 277, 1497–1501(1997).*
S.P. Dutta et al., *J. Carbohydrates Nucleosides Nucleotides*, 7(4), 217–240 (1980).
US 1993/03539, Apr. 20, 1993.

* cited by examiner

*Primary Examiner*—Richard L. Raymond
*Assistant Examiner*—Sudhaker B. Patel
(74) *Attorney, Agent, or Firm*—Marshall, Gerstein & Borun LLP

(57) ABSTRACT

Aryl- and heteroaryl-substituted urea compounds useful in the treatment of diseases and conditions related to DNA damage or lesions in DNA replication are disclosed. Methods of making the compounds, and their use as therapeutic agents, for example, in treating cancer and other diseases characterized by defects in DNA replication, chromosome segregation, or cell division also are disclosed.

25 Claims, No Drawings

COMPOUNDS USEFUL FOR INHIBITING CHK1

CROSS REFERENCE TO RELATED APPLICATIONS

This application claims the benefit of U.S. provisional application Serial No. 60/273,124, filed Mar. 2, 2001.

TECHNICAL FIELD OF THE INVENTION

The present invention relates to compounds useful for inhibiting enzymes that maintain and repair the integrity of genetic material. More particularly, the present invention relates to a series of aryl- and heteroaryl-substituted urea compounds, methods of making the compounds, and their use as therapeutic agents, for example, in treating cancer and other diseases characterized by defects in deoxyribonucleic acid (DNA) replication, chromosome segregation, or cell division.

BACKGROUND OF THE INVENTION

An important and significant goal in healthcare is to discover and make available safer and more effective drugs for the treatment of cancer. Most chemotherapeutic agents act by disrupting DNA metabolism, DNA synthesis, DNA transcription, or microtubule spindle function, or by perturbing chromosomal structural integrity by introducing DNA lesions. These processes affect both normal and tumor cells. The maintenance of DNA integrity is essential to cell viability in normal cells, therefore, anticancer drugs have the lowest therapeutic index of any drug class.

An individual cell creates an exact copy of its chromosomes, and then segregates each copy into two cells by a process called mitosis. The mitotic cycle can be divided into three major events: DNA replication, chromosome segregation, and cell division. Cells have sensing mechanisms to maintain the order of these steps with respect to one another and to ensure that each step is executed with high fidelity. The sensing mechanisms for these processes are referred to as "checkpoints" in L. H. Hartwell et al., *Science,* Nov. 3, 1989, 246(4930) :629-34.

Cell cycle checkpoints have been reported to comprise at least three distinct classes of polypeptides. Each class of polypeptides acts sequentially in response to cell cycle signals or defects in chromosomal mechanisms (Carr, (1996) *Science,* 271:314-315). One family of proteins detects or senses DNA damage or abnormalities in the cell cycle. These sensors include Ataxia-Telangiectasia Mutated (Atm) and Ataxia-Telangiectasia Rad-related (Atr) (Keegan et al., (1996) *Genes Dev.,* 10:2423-2437). Another class of polypeptides amplify and transmit the signal detected by the detector and is exemplified by Rad53 (Allen et al. (1994) *Genes Dev.,* 8:2416-2488) and Chk1. In addition, cell cycle effectors, such as p53, mediate a cellular response, including, for example, arrest of mitosis and/or meiosis and apoptosis.

DNA damage can be induced by drugs, radiation, or can be spontaneously generated during the course of normal metabolism. DNA damage checkpoints ensure that cells with unrepaired DNA lesions do not progress into the DNA synthesis phase or mitosis until chromosomal lesions have been removed. Cell cycle arrest can enhance the opportunity for DNA repair and increase the fidelity of cell division. DNA damage can be recognized throughout the cell cycle. Checkpoints ensure that the growth of cells is arrested at multiple cell cycle phases. As a result, multiple cell cycle signaling pathways may result during sensitization of cells to DNA damaging agents.

Much of the current understanding of the function of cell cycle checkpoints has been derived from the study of tumor-derived cell lines. In many cases, tumor cells have lost key cell cycle checkpoints (Hartwell et al., *Science,* Dec. 16, 1994; 266(5192): 1821-8). It has been reported that a key step in the evolution of cells to a neoplastic state is the acquisition of mutations that inactivate cell cycle checkpoint pathways, such as p53. (Weinberg, R. A. (1995) *Cell* 81:323-330; Levine, A. J. (1997) *Cell* 88: 3234-331). Loss of these cell cycle checkpoints results in the inappropriate cycling of tumor cells in response to DNA damaging agents. When faced with cellular stresses, such as DNA damage, and cell cycle events with decreased fidelity, tumor cells have difficulty altering the kinetics of cell cycle progression. Therefore, inhibition and disruption of additional DNA damage checkpoint pathways may further sensitize tumor cells to anticancer treatments, such as radiation and chemotherapy.

Noncancerous tissue, which has intact cell cycle checkpoints, typically is insulated from temporary disruption of a single checkpoint pathway. Tumor cells, however, have defects in pathways controlling cell cycle progression such that the perturbation of additional checkpoints, for example, the DNA damage checkpoint, renders them particularly sensitive to DNA damaging agents. For example, tumor cells that contain mutant p53 are defective both in the G1 DNA damage checkpoint and in the ability to maintain the G2 DNA damage checkpoint. (Bunz et al., *Science,* Nov. 20, 1998; 282(5393): 1497-501; Levine). Checkpoint inhibitors that target initiation of the G2 checkpoint or the S phase checkpoint are expected to further cripple the ability of these tumor cells to repair DNA damage and, therefore, selectively kill them over normal cells. Therefore, checkpoint inhibitors are expected to enhance the therapeutic index, which is a measure of the probability of tumor control relative to the probability of toxicity to normal tissue, of both radiation and systemic chemotherapy.

The ability of checkpoint inhibitors to enhance the therapeutic index may be dependent upon tumor type. Tumors with cell cycle defects complementary to the DNA damage checkpoint pathways may be most sensitive to inhibitor drug treatment. In contrast, DNA-PK inhibitors, another distinct class of potential therapeutic agents, are expected to sensitize tumors independently of cell type. A systematic approach of applying checkpoint inhibitors and DNA-PK inhibitors also may be effective in the treatment of metastatic diseases that radiation therapy cannot target.

The checkpoint proteins Atm and Atr are hypothesized to initiate a signal transduction pathway leading to cell cycle arrest in the presence of DNA damage or any block to DNA replication. Atm has been shown to play a role in a DNA damage checkpoint in response to ionizing radiation (IR). Patients lacking functional Atm develop the disease Ataxia-Telangiectasia (A-T). Symptoms of A-T include extreme sensitivity to ionizing radiation (IR), cerebellar degeneration, oculotaneous telangiectasias, gonadal deficiencies, immunodeficiencies and increased risk of cancer (Shiloh, *Eur. J. Hum. Genet* 1995; 3(2):116-38). Fibroblasts derived from these patients are thought to have defects in G1, S, and G2 checkpoints and are defective in their response to IR (Kastan et al., *Cell,* Nov. 13, 1992; 71(4): 587-97; Scott et al., *Int. J. Radiat. Biol.,* Dec, 1994; 66(6 Suppl): S157-63; and Beamish et al., *J. Biol. Chem.* Aug. 26, 1993; 271(34):20486-93). Therefore, Atm may sense double-strand DNA damage caused by IR and radiomimetic drugs, and signal the cell cycle to arrest, such that damage can be repaired.

Atr is a checkpoint protein stimulated by agents that cause double strand DNA breaks, single strand DNA breaks, and agents that block DNA radiation. Overexpression of Atr in muscle cells on iso-chromosome 3q results in a block to differentiation, abnormal centrosome numbers, chromosome instability, and abolishes the G1 arrest in response to IR (Smith et al., *Nat. Genet.*, May 1998; 19(1): 39-46). Overexpression of a kinase inactive, dominant negative mutant of Atr sensitizes cells to IR, ultraviolet light (UV), MMS, and cisplatin (Cliby et al., *EMBO J.* Jan. 2, 1998, 17(1):159-69 and Wright et al., *Proc. Nat'l Acad. Sci. U.S.A.*, Jun. 23, 1998; 95(13):7445-50). Cells containing overexpressed, mutant strain Atr also fail to arrest in G2 in response to IR. In addition, Atr is associated with chromosomes in meiotic cells where DNA breaks and abnormal DNA structures persist as a result of the process of meiotic recombination (Keegan et al., *Genes Dev.* Oct. 1, 1996; 10(19): 433-37). Atr, like Atm, also senses DNA damage and agents that block DNA replication, as well as initiates a cell cycle arrest at G2 and S for DNA repair.

Chk1 is hypothesized to lie downstream from protein kinases Atm and/or Atr in the DNA damage checkpoint signal transduction pathway. (See, Sanchez et al., *Science*, 1997; 277:1497-1501; U.S. Pat. No. 6,218,109.) In mammalian cells, Chk1 is phosphorylated in response to agents that cause DNA damage including IR, UV, and hydroxyurea (Sanchez et al., 1997; Lui et al., *Genes Dev.* 2000; 14:1448-1459). The phosphorylation and activation of Chk1 in mammalian cells is dependent on Atm (Chen et al., 1999) and Atr (Lui et al., 2000). In the yeast *S. pombe*, Chk1 also appears to be involved in the response to IR and blocks to replication (Boddy et al., 1998; Walworth et al., 1993). Furthermore, Chk1 has been shown to phosphorylate both wee1 (O'Connell et al., *EMBO J.* 199,7; 16:545-554) and Pds1 (Sanchez et al., *Science* 1999; 286:1166-1171) gene products known to be important in cell cycle control. These studies demonstrate that mammalian Chk1 plays a role in both the Atm-dependent DNA damage checkpoint leading to arrest at S phase. However, a role for Chk1 in the S phase replication checkpoint in mammalian cells has yet to be elucidated. Interestingly, Chk1 knockout mice are embryonically lethal, thereby suggesting a role for Chk1 in a developing organism in addition to its role in DNA damage checkpoints.

Chk1 may invoke a G2 arrest by phosphorylating and inactivating Cdc25C, the dual specificity phosphatase that normally dephosphorylates cyclin B/cdc2 as cells progress into mitosis (Fernery et al., *Science, Sep.* 5, 1997; 277 (5331): 1495-7; Sanchez et al.; Matsuoka et al.; and Blasina et al., *Curr. Biol.*, Jan. 14, 1999; 9(1):1-10). This mechanism of regulation of Cdc2 activity stimulates cell cycle arrest to prevent cells from entering mitosis in the presence of DNA damage or unreplicated DNA.

SUMMARY OF THE INVENTION

The present invention is directed to potent and selective chemosensitizing agents useful in the treatment of diseases and conditions related to DNA damage or lesions in DNA replication. The present compounds are inhibitors of the checkpoint kinase Chk1. In particular, aryl- and heteroaryl-substituted urea compounds have demonstrated significant activity for inhibiting Chk1.

In one aspect, the present invention is directed to a method of inhibiting checkpoint kinase Chk1 comprising the step of administering a compound of formula (I), or a composition containing the same, to an individual. Compounds of formula (I) have a structural formula:

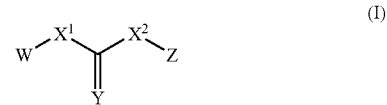

wherein:
$X^1$ is null, —O—, —S—, —CH$_2$—, or —N(R$^1$)—;
$X^2$ is —O—, —S—, or —N(R$^1$)—;
Y is O or S; or =Y represents two hydrogen atoms attached to a common carbon atom;
W is selected from the group consisting of heteroaryl, aryl, heterocycloalkyl, cycloalkyl, and $C_{1-3}$ alkyl substituted with a heteroaryl or aryl group; and
Z is selected from the group consisting of hydro, aryl, and heteroaryl;
wherein said aryl groups of W and Z are optionally substituted with one to four substituents represented by $R^2$, said heteroaryl groups of W and Z are optionally substituted with one to four substituents represented by $R^5$, and said heterocycloalkyl and cycloalkyl groups of W are optionally substituted with one to two substituents represented by $R^6$;
$R^1$ is selected from the group consisting of hydrogen, $C_{1-6}$alkyl, $C_{2-6}$alkenyl, $C_{2-6}$alkynyl, and aryl;
$R^2$ is selected from the group consisting of halogen, $C_{1-6}$alkyl, $C_{2-6}$alkenyl, OCF$_3$, NO$_2$, CN, NC, N(R$^3$)$_2$, OR$^3$, CO$_2$R$^3$, C(O)N(R$^3$)$_2$, C(O)R$^3$, N(R$^1$)COR$^3$, N(R$^1$)C(O) OR$^3$, N(R$^3$)C(O)OR$^3$, N(R$^3$)C(O)—$C_{1-3}$alkylene-C(O)R$^3$, N(R$^3$)C(O) —$C_{1-3}$alkylene-C(O)OR$^3$, N(R$^3$)C(O)—$C_{1-3}$alkylene-OR$^3$, N(R$^3$)C(O) —$C_{1-3}$alkylene-NHC(O)OR$^3$, N(R$^3$)C(O)—$C_{1-3}$alkylene-SO$_2$NR$^3$, $C_{1-3}$alkylene-OR$^3$, and SR$^3$;
$R^3$ is selected from the group consisting of hydro, $C_{1-6}$alkyl, $C_{2-6}$alkenyl, cycloalkyl, aryl, heteroaryl, SO$_2$R$^4$, $C_{1-6}$alkyl substituted with one or more of halo, hydroxy, aryl, heteroaryl, heterocycloalkyl, N(R$^4$)$_2$, and SO$_2$R$^4$, $C_{1-3}$alkylenearyl, $C_{1-3}$alkylene-heteroaryl, $C_{1-3}$alkyleneC$_{3-8}$heterocycloalkyl, $C_{1-3}$alkyleneSO$_2$aryl, optionally substituted $C_{1-3}$alkylene-N(R$^4$)$_2$, OCF$_3$, $C_{1-3}$alkyleneN(R$^4$)$_3^+$, $C_{3-8}$heterocycloalkyl, and CH($C_{1-3}$alkyleneN(R$^4$)$_2$)$_2$, or two $R^3$ groups are taken together to form an optionally substituted 3- to 6-membered aliphatic ring;
$R^4$ is selected from the group consisting of hydro, $C_{1-6}$alkyl, cycloalkyl, aryl, heteroaryl, $C_{1-3}$-alkylenearyl, and SO$_2$C$_{1-6}$alkyl, or two $R^4$ groups are taken together to form an optionally substituted 3- to 6-membered ring;
$R^5$ is selected from the group consisting of $C_{1-6}$alkyl, aryl, N(R$^3$)$_2$, OR$^3$, halo, N$_3$, CN, $C_{1-3}$alkylenearyl, $C_{1-3}$alkyleneN(R$^3$)$_2$, C(O)R$^3$, and

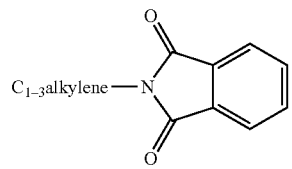

$R^6$ is selected from the group consisting of halo and $C_{1-6}$alkyl,
and pharmaceutically acceptable salts or solvates thereof.,
In another aspect, the present invention is directed to aryl- and heteroaryl-disubstituted urea compounds having a structural formula (II)

(II)

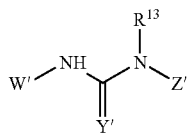

wherein Y' is O or S;
W' is selected from the group consisting of

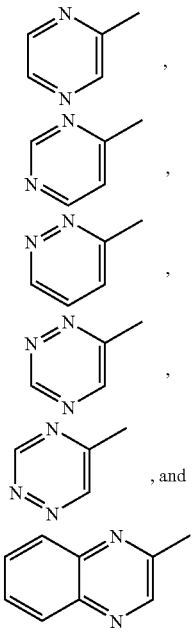, and

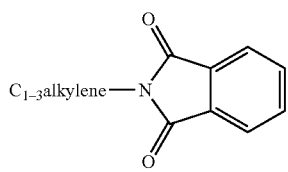

optionally substituted with from one to four substituents selected from the group consisting of $C_{1-6}$alkyl, aryl, $N(R^7)_2$, $OR^7$, $N_3$, CN, $C(O)R^7C_{1-3}$alkylenearyl, $C_{1-3}$alkyleneN$(R^{12})_2$,

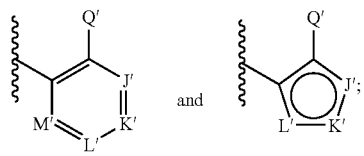

Z' is selected from the group consisting of:

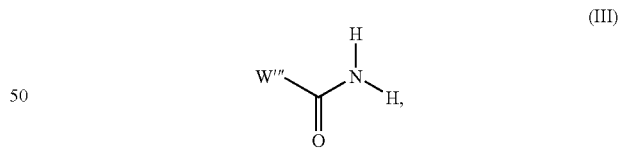

wherein:
Q' is selected from the group consisting of hydrogen, $OR^7$, $SR^7$, and $N(R^7)_2$;
J' is selected from the group consisting of C—$R^8$, N—$R^8$, O, and S;
K' is selected from the group consisting of C—$R^9$, N—$R^9$, O, and S;
L' is selected from the group consisting of C—$R^{10}$, N—$R^{10}$, O, and S;
M' is selected from the group consisting of C—$R^{11}$, N—$R^{11}$, O, and S;
wherein:
$R^7$, independently, is selected from the group consisting of hydro; $C_{1-6}$alkyl, $C_{2-6}$alkenyl, cycloalkyl, aryl, heteroaryl, $SO_2R^{12}$, $C_{1-6}$alkyl substituted with one or more of halo, hydroxy, aryl, heteroaryl, heterocycloalkyl, $N(R^{12})_2$, and $SO_2R^{12}$, $C_{1-3}$alkylenearyl, $C_{1-3}$alkyleneheteroaryl, $C_{1-3}$alkyleneC$_{3-8}$heterocycloalkyl, $C_{1-3}$alkyleneSO$_2$aryl, optionally substituted $C_{1-3}$alkyleneN$(R^{12})_2$, $OCF_3$, $C_{1-3}$alkyleneN$(R^{12})_3{}^+$, $C_{3-8}$heterocycloalkyl, and CH(C$_{1-3}$alkyleneN$(R^{12})_2)_2$, or two $R^7$ groups are taken together to form an optionally substituted 3- to 6-membered aliphatic ring;
$R^8$, $R^9$, and $R^{10}$ are each independently selected from the group consisting of null, hydro, halo, optionally substituted $C_{1-6}$alkyl, $C_{2-6}$alkenyl, $OCF_3$, $NO_2$, CN, NC, $N(R^7)_2$, $OR^7$, $CO_2R^7$, $C(O)N(R^7)_2$, $C(O)R^7$, $N(R^{13})COR^7$, $N(R^{13})C(O)OR^7$, $N(R^7)C(O)OR^7$, $N(R^7)C(O)C_{1-3}$alkyleneC(O)$R^7$, $N(R^7)C(O)C_{1-3}$alkyleneC(O)$OR^7$, $N(R^7)C(O)C_{1-3}$alkyleneOR$^7$, $N(R^7)C(O)C_{1-3}$alkyleneNHC(O)OR$^7$, $N(R^7)C(O)C_{1-3}$alkyleneSO$_2$NR$^7$, $CF_3$, $C_{1-3}$alkyleneN$(R^{12})$SO$_2$aryl, $C_{1-3}$alkyleneN$(R^{12})$SO$_2$heteroaryl, $C_{1-3}$alkyleneOC$_{1-3}$alkylenearyl, $C_{1-3}$alkyleneN$(R^{12})$C$_{1-3}$alkylenearyl, $C_{1-3}$alkyleneN$(R^{12})$C$_{1-3}$alkyleneheteroaryl, $C_{1-3}$alkyleneN$(R^{12})$C(O)R$^7$, $C_{1-3}$alkyleneN$(R^{12})$C(O)C$_{1-3}$alkyleneOR$^2$, $C_{1-3}$alkyleneN$(R^{12})$C(O)aryl, $C_{1-3}$alkyleneN$(R^{12})$C(O)C$_{1-3}$alkyleneN$(R^{12})_2$, $C_{1-3}$alkyleneN$(R^{12})$C(O)-heteroaryl, $C_{1-3}$alkyleneOR$^7$, and $SR^7$, wherein $R^7$ is as defined above;
$R^{11}$ is selected from the group consisting of null, hydro, $C_{1-6}$alkyl, and halo;
$R^{12}$ is selected from the group consisting of hydro, $C_{1-6}$alkyl, cycloalkyl, aryl, and $SO_2C_{1-6}$alkyl, or two $R^{12}$ groups are taken together to form a 3- to 6-membered ring; and
$R^{13}$ is selected from the group consisting of hydrogen, $C_{1-6}$alkyl, $C_{2-6}$alkenyl, $C_{2-6}$alkynyl, and aryl;
provided that when Q' is hydrogen or $OCH_3$, at least one of $R^8$, $R^9$, and $R^{10}$ is not selected from hydrogen, $CH_3$, $OCH_3$, or halo,
and pharmaceutically acceptable salts or solvates thereof.
Another aspect of the present invention relates to carbamido-substituted heteroaryl groups having the structural formula (III)

(III)

$$W'''\underset{O}{\overset{H}{\underset{\|}{C}}}N\underset{H}{\overset{}{}}$$

wherein W''' is selected from the group consisting of heteroaryl, aryl, heterocycloalkyl, cycloalkyl, and $C_{1-3}$alkyl substituted with a heteroaryl or aryl group;
wherein said aryl groups are optionally substituted with one to four substituents represented by $R^{14}$, said heteroaryl groups are optionally substituted with one to four substituents represented by $R^{18}$, and said heterocycloalkyl and cycloalkyl groups are optionally substituted with one to two substituents represented by $R^{19}$;
$R^{14}$ is selected from the group consisting of halo, $C_{1-6}$alkyl, $C_{2-6}$alkenyl, $OCF_3$, $NO_2$, CN, NC, $N(R^{16})_2$, $R^{16}$, $CO_2R^{16}$, $C(O)N(R^{16})_2$, $C(O)R^{16}$, $N(R^{15})COR^{16}N(R^{15})C(O)OR^{16}$, $N(R^{16})C(O)OR^{16}$, $N(R^{16})C(O)C_{1-3}$alkyleneC(O)$R^{16}$, $N(R^{16})C(O)C_{1-3}$alkyleneC(O)OR$^{16}$, $N(R^{1-6})C(O)C_{1-}$ ₃alkyleneOR¹⁶, N(R¹⁶)C(O)C₁₋₃alkyleneNHC(O)OR¹⁶, N(R¹⁶)C(O)C₁₋₃alkyleneSO₂NR¹⁶, C₁₋₃alkyleneOR¹⁶, and SR¹⁶;

R¹⁵ is selected from the group consisting of hydro, C₁₋₆alkyl, C₂₋₆alkenyl, C₂₋₆alkynyl, and aryl;

R¹⁶ is selected from the group consisting of hydro, C₁₋₆alkyl, C₂₋₆alkenyl, cycloalkyl, aryl, heteroaryl, SO₂R¹⁷, C₁₋₆alkyl substituted with one or more of halo, hydroxy, aryl, heteroaryl, heterocycloalkyl, N(R¹⁷)₂, and SO₂R¹⁷, C₁₋₃alkylenearyl, C₁₋₃alkyleneheteroaryl, C₁₋₃alkyleneC₃₋₆heterocycloalkyl, C₁₋₃alkyleneSO₂aryl, optionally substituted C₁₋₃alkyleneN(R¹⁷)₂, OCF₃, C₁₋₃alkyleneN(R¹⁷)₃⁺, C₃₋₈heterocycloalkyl, CH(C₁₋₃alkyleneN(R¹⁷)₂)₂;

or two R¹⁶ groups are taken together to form an optionally substituted 3- to 6-membered aliphatic ring.

R¹⁷ is selected from the group consisting of hydro, C₁₋₆alkyl, cycloalkyl, aryl, and SO₂C₁₋₆alkyl, or two R¹⁷ groups are taken together to form an optionally substituted 3- to 6-membered ring;

R¹⁸ is selected from the group consisting of C₁₋₆alkyl, aryl, N(R¹⁵)₂, OR¹⁵, and halo; and R¹⁹ is selected from the group consisting of halo and C₁₋₆alkyl.

The present invention also is directed to pharmaceutical compositions containing one or more compounds of structural formula (II), to use of the compounds and compositions containing the compounds in therapeutic treatment of a disease or disorder, and to methods of preparing the compounds and intermediates involved in the synthesis of the compounds of structural formula (II).

DETAILED DESCRIPTION OF THE PREFERRED EMBODIMENTS

Radiation and most chemotherapeutic agents are therapeutically beneficial because they take advantage of inappropriate tumor cell proliferation. Cellular processes, such as DNA damage repair and cell cycle checkpoints, protect tumor cells from the toxic effects of physical and chemical agents. Treatments that modulate the underlying molecular mechanisms of cell cycle progression and resistance to DNA damage can potentiate tumor cell killing and enhance the therapeutic index of existing therapies.

Most chemotherapeutic agents act by disrupting DNA metabolism. Because these processes are shared by both normal and tumor cells, and because the maintenance of DNA integrity is essential to cell viability, anticancer drugs have the lowest therapeutic index of any drug class. By identifying and inhibiting cellular processes that tumor cells rely upon, the effectiveness of radiation and chemotherapy treatment regimens can be enhanced.

The interruption of the DNA damage checkpoint protein function provides a novel means of killing tumor cells relative to normal cells. For example, Chk1 ensures that cells with unrepaired DNA lesions caused by certain drugs or radiation do not progress through DNA synthesis phase or mitosis until chromosomal lesions have been removed. Accordingly, a tumor cell treated with a Chk1 inhibitor in combination with a DNA damaging agent can kill using lower amounts of DNA damaging agent than tumor cells treated with the DNA damaging agent alone.

Failure of cell cycle checkpoints in normal cells predisposes an individual to, or directly causes, many disease states, such as cancer, ataxia telangiectasia, embryo abnormalities, and various immunological defects associated with aberrant B and T cell development. The latter are associated with the pathological states of lupus, arthritis, and autoimmune diseases. Intense research efforts, therefore, have focused on identifying cell cycle checkpoints and the proteins essential for the function of the checkpoints.

Noncancerous tissue having intact cell checkpoints typically is insulated from temporary disruption of a single checkpoint pathway, such as the Chk1 pathway. Tumor cells, however, have multiple defects in pathways controlling cell cycle progression such that perturbation of the DNA damage checkpoint can render cells particularly sensitive to DNA damaging agents. Therefore, checkpoint inhibitors are expected to enhance the therapeutic index, which is a measure of the probability of tumor control relative to the probability of toxicity to normal tissue to radiation and systemic chemotherapy. In contrast, other classes of inhibitors may not be amenable to combination chemotherapy because both normal and tumor tissue may be similarly sensitized.

One aspect of the present invention is directed to a method of inhibiting Chk1, comprising the step of administering a therapeutically effective amount of a compound of formula (I), or a composition containing the same, to an individual. Compounds of formula (I) have a structural formula

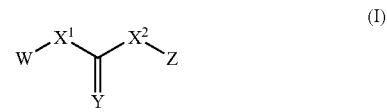

(I)

wherein X¹ is null, —O—, —S—, —CH₂—, or —N(R¹)—;

X² is —O—, —S—, or —N(R¹)—;

Y is O or S; or =Y represents two hydrogen atoms attached to a common carbon atom;

W is selected from the group consisting of heteroaryl, aryl, heterocycloalkyl, cycloalkyl, and C₁₋₃ alkyl substituted with a heteroaryl or aryl group; and Z is selected from the group consisting of hydrogen, aryl, and heteroaryl;

wherein said aryl groups of W and Z are optionally substituted with one to four substituents represented by R², said heteroaryl groups of W and Z are optionally substituted with one to four substituents represented by R⁵, and said heterocycloalkyl and cycloalkyl groups of W are optionally substituted with one to two substituents represented by R⁶;

R¹ is selected from the group consisting of hydrogen, C₁₋₆alkyl, C₂₋₆alkenyl, C₂₋₆alkynyl, and aryl;

R¹ is selected from the group consisting of halogen, C₁₋₆alkyl, C₂₋₆alkenyl, OCF₃, NO₂, CN, NC, N(R³)₂, OR³, CO₂R³, C(O)N(R³)₂, C(O)R³, N(R¹)COR³, N(R¹)C(O)OR³, N(R³)C(O)OR³, N(R³)C(O)C₁₋₃alkyleneC(O)R³, N(R³)C(O)C₁₋₃alkylene-C(O)OR³, N(R³)C(O)C₁₋₃alkyleneOR³, N(R³)C(O)C₁₋₃alkyleneNHC(O)OR³, N(R³)C(O)C₁₋₃alkyleneSO₂NR³, C₁₋₃alkyleneOR³, and SR³;

R³ is selected from the group consisting of hydro, C₁₋₆alkyl, C₂₋₆alkenyl, cycloalkyl, aryl, heteroaryl, SO₂R⁴, C₁₋₆alkyl substituted with one or more of halo, hydroxy, aryl, heteroaryl, heterocycloalkyl, N(R⁴)₂, and SO₂R⁴, C₁₋₃alkylenearyl, C₁₋₃alkyleneheteroaryl, C₁₋₃alkyleneC₃₋₈heterocycloalkyl, C₁₋₃alkyleneSO₂aryl, optionally substituted C₁₋₃alkyleneN(R⁴)₂, OCF₃, C₁₋₃alkyleneN(R⁴)₃⁺, C₃₋₈heterocycloalkyl, and CH(C₁₋₃alkyleneN(R⁴)₂)₂, or two R³ groups are taken together to form an optionally substituted 3- to 6-membered aliphatic ring;

R⁴ is selected from the group consisting of hydro, C₁₋₆alkyl, cycloalkyl, aryl, heteroaryl, C₁₋₃alkylenearyl, and $SO_2C_{1-6}$alkyl, or two $R^4$ groups are taken together to form an optionally substituted 3- to 6-membered ring;

$R^5$ is selected from the group consisting of $C_{1-6}$alkyl, aryl, $N(R^3)_2$, $OR^3$, halo, $N_3$, CN, $C_{1-3}$alkylenearyl, $C_{1-3}$alkyleneN$(R^3)_2$, $C(O)R^3$, and $C_{1-3}$alkylene—N(phthalimide)

$R^6$ is selected from the group consisting of halo and $C_{1-6}$alkyl, and pharmaceutically acceptable salts or solvates thereof.

Preferred compounds used in the method are those wherein $X^1$ and $X^2$ are —N(H)—;

Y is O or S;

W is heteroaryl containing at least two heteroatoms selected from the group consisting of N, O, and S, said ring is optionally substituted with from one to four substituents selected from the group consisting of $C_{1-6}$alkyl, aryl, $N(R^3)_2$, $OR^3$, and halo, wherein $R^3$ is as previously defined;

Z is selected from the group consisting of:

[two ring structures with substituents Q, J, K, L, M]

wherein:

Q is selected from the group consisting of hydrogen, $OR^3$, $SR^3$, and $N(R^3)_2$;

J is selected from the group consisting of $CR^{20}$, $NR^{20}$, O, and S;

K is selected from the group consisting of $CR^{21}$, $NR^{21}$, O, and S;

L is selected from the group consisting of $CR^{22}$, $NR^{22}$, O, and S;

M is selected from the group consisting of $CR^{23}$, $NR^{23}$, O, and S;

wherein:

$R^{20}$, $R^{21}$, and $R^{22}$ are each independently selected from the group consisting of null, hydro, halo, $C_{1-6}$alkyl, $C_{2-6}$alkenyl, $OCF_3$, $NO_2$, CN, NC, $N(R^{25})_2$, $OR^{25}$, $CO_2R^{25}$, $C(O)N(R^{25})_2$, $C(O)R^{25}$, $N(R^{24})COR^{25}$, $N(R^{24})$—C(O)$OR^{25}$, $N(R^{25})C(O)OR^{25}$, $N(R^{25})C(O)C_{1-3}$alkyleneC(O)$R^{25}$, $N(R^{25})C(O)C_{1-3}$alkyleneC(O)$OR^{25}$, $N(R^{25})C(O)C_{1-3}$alkyleneOR$^{25}$, $N(R^{25})C(O)C_{1-3}$alkyleneNHC(O)$OR^{25}$, $N(R^{25})C(O)C_{1-3}$alkyleneSO$_2$NR$^{25}$, $CF_3$, $C_{1-3}$alkyleneN$(R^{25})SO_2$aryl, $C_{1-3}$alkyleneN$(R^{25})SO_2$heteroaryl, $C_{1-3}$alkyleneOC$_{1-3}$alkylenearyl, $C_{1-3}$alkyleneN$(R^{25})C_{1-3}$alkylenearyl, $C_{1-3}$alkyleneN$(R^{25})C_{1-3}$alkyleneheteroaryl, $C_{1-3}$alkyleneN$(R^{25})C(O)R^7$, $C_{1-3}$alkyleneN$(R^{25})C(O)C_{1-3}$alkyleneOR$^2$, $C_{1-3}$alkyleneN$(R^{25})C(O)$aryl, $C_{1-3}$alkyleneN$(R^{25})C(O)C_{1-3}$alkyleneN$(R^{25})_2$, $C_{1-3}$alkyleneN$(R^{25})C(O)$heteroaryl, $C_{1-3}$alkyleneOR$^{25}$, and SR$^{25}$;

$R^{23}$ is selected from the group consisting of null, hydro, $C_{1-6}$alkyl, and halo;

$R^{24}$ is selected from the group consisting of hydro, $C_{1-6}$alkyl, $C_{2-6}$alkenyl, $C_{2-6}$alkynyl, and aryl;

$R^{25}$ is selected from the group consisting of hydro, $C_{1-6}$alkyl, $C_{2-6}$alkenyl, cycloalkyl, aryl, heteroaryl, $SO_2R^{26}$, and $C_{1-6}$alkyl substituted with halo, hydroxy, aryl, heteroaryl, heterocycloalkyl, $N(R^{26})_2$, or $SO_2R^{26}$; and $R^{26}$ is selected from the group consisting of hydro, $C_{1-6}$alkyl, cycloalkyl, aryl, and $SO_2C_{1-6}$alkyl, or two $R^{26}$ groups are taken together to form an optionally substituted 3- to 6-membered ring.

More preferred compounds of the method are those of structural formula (I) wherein W is selected from the group consisting of pyridazinyl, pyrimidinyl, pyrazinyl, and triazinyl, optionally substituted with from one to four substituents selected from the group consisting of $C_{1-6}$alkyl, aryl, $N(R^3)_2$, $OR^3$, $N_3$, CN, $C(O)R^7$, $C_{1-3}$alkylenearyl, $C_{1-3}$alkyleneN$(R^4)$, $C_{1-3}$alkylene—N(phthalimide)

and halo, wherein $R^3$, $X^1$, $X^2$, Y, and Z are as defined for formula (I).

Additional preferred compounds of formula (I) are those wherein W is selected from the group consisting of pyridazine, pyrimidine, pyrazine, and triazine, optionally substituted with from one to four substituents selected from the group consisting of optionally substituted $C_{1-6}$alkyl, aryl, $N(R^3)_2$, $OR^3$, $C_{1-3}$alkylenearyl, $C_{1-3}$alkyleneheteroaryl, $C_{1-3}$alkyleneC$_{3-8}$heterocycloalkyl, $C_{1-3}$alkyleneSO$_2$aryl, optionally substituted $C_{1-3}$alkyleneN$(R^4)_2$, $OCF_3$, $C_{1-3}$alkyleneN$(R^4)_3^+$, $C_{3-8}$heterocycloalkyl, $CH(C_{1-3}$alkyleneN$(R^4)_2)_2$, and halo; $X^1$ and $X^2$ are —N(H)—; Y is O or S; and Z is selected from the group consisting of:

[two ring structures with substituents Q, J, K, L, M]

wherein $R^3$, Q, J, K, L, and M are as previously defined.

Compounds preferred for use in the method also include those of formula (I) wherein J is selected from the group consisting of $CR^{20}$ and $NR^{20}$, wherein $R^{20}$ is null, hydro, $C_{1-6}$alkyl, and halo;

K is selected from the group consisting of $CR^{21}$ and $NR^{21}$;

L is selected from the group consisting of $CR^{22}$ and $NR^{22}$; and one of $R^{21}$ and $R^{22}$ is hydro and the other is a substituent selected from the group consisting of $CO_2R^{25}$ $C(O)N(R^{25})_2$, $C(O)R^{25}$, $N(R^{24})COR^{25}$, $N(R^{24})C(O)OR^{25}$, $N(R^{25})C(O)OR^{25}$, $N(R^{25})C(O)C_{1-3}$alkyleneC(O)$R^{25}$, $N(R^{25})$-C(O)$C_{1-3}$alkyleneC(O)$OR^{25}$, $N(R^{25})C(O)C_{1-3}$alkyleneOR$^{25}$, $N(R^{25})$C(O)CC$_{1-3}$alkyleneNHC(O)$OR^{25}$, $N(R^{25})C(O)C_{1-3}$alkyleneSO$_2$NR$^{25}$, $C_{1-3}$alkyleneOR$^{25}$, and SR$^{25}$, wherein $R^{24}$, $R^{25}$, W, $X^1$, $X^2$, Y and M are as previously defined.

Compounds useful in the method also include structures of formula (I) wherein $X^1$ is null, $X^2$ is —N(H)—, Y is O, Z is hydro, and W is as previously defined.

The method of inhibiting Chk1 also can be used to sensitize a tumor cell to a chemotherapeutic agent. As such, the present invention also is directed to a method of sensitizing a tumor cell to a chemotherapeutic agent comprising administering a compound of formula (I), or a salt, solvate, or derivative thereof, or a composition comprising the same, to an individual.

In another aspect, the present invention is directed to aryl- and heteroaryl-disubstituted urea compounds having a structural formula (II)

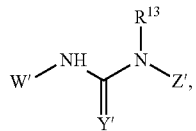
(II)

wherein Y' is O or S;
W' is selected from the group consisting of

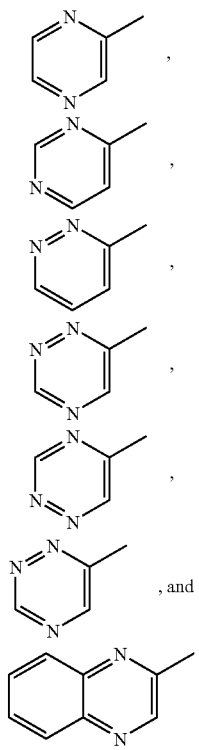
, and optionally substituted with from one to four substituents selected from the group consisting of $C_{1-6}$alkyl, aryl, $N(R^7)_2$, $OR^7$, $N_3$, CN, $C(O)R^7$, $C_{1-3}$alkylenearyl, $C_{1-3}$alkyleneN$(R^{12})_2$,

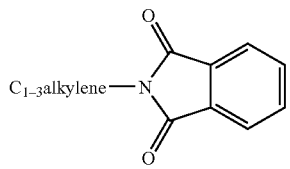

Z' is selected from the group consisting of:

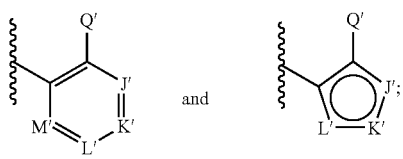

wherein:

Q' is selected from the group consisting of hydrogen, $OR^7$, $SR^7$, and $N(R^7)_2$;

J' is selected from the group consisting of C—$R^8$, N—$R^8$, O, and S;

K' is selected from the group consisting of C—$R^9$, N—$R^9$, O, and S;

L' is selected from the group consisting of C—$R_{10}$, N—$R^{10}$, O, and S;

M' is selected from the group consisting of C—$R^{11}$, N—$R^{11}$, O, and S; wherein:

$R^7$, independently, is selected from the group consisting of hydro, $C_{1-6}$alkyl, $C_{2-6}$alkenyl, cycloalkyl, aryl, heteroaryl, $SO_2R^{12}$, $C_{1-6}$alkyl substituted with one or more of halo, hydroxy, aryl, heteroaryl, heterocycloalkyl, $N(R^{12})_2$, and $SO_2R^{12}$, $C_{1-3}$alkylenearyl, $C_{1-3}$alkyleneheteroaryl, $C_{1-3}$alkyleneC$_{3-8}$heterocycloalkyl, $C_{1-3}$alkyleneSO$_2$aryl, optionally substituted $C_{1-3}$alkyleneN$(R^{12})_2$, $OCF_3$, $C_{1-3}$alkyleneN$(R^{12})_3^+$, $C_{3-8}$heterocycloalkyl, and CH$(C_{1-3}$alkyleneN$(R^{12})_2)_2$, or two $R^7$ groups are taken together to form an optionally substituted 3- to 6-membered aliphatic ring;

$R^8$, $R^9$, and $R^{10}$ are each independently selected from the group consisting of null, hydro, halo, optionally substituted $C_{1-6}$alkyl, $C_{2-6}$alkenyl, $OCF_3$, $NO_2$, CN, NC, $N(R^7)_2$, $OR^7$, $CO_2R^7$, $C(O)N(R^7)_2$, $C(O)R^7$, $N(R^{13})COR^7$, $N(R^{13})C(O)OR^7$, $N(R^7)C(O)OR^7$, $N(R^7)C(O)C_{1-3}$alkyleneC(O)$R^7$, $N(R^7)C(O)C_{1-3}$alkyleneC(O)O$R^7$, $N(R^7)C(O)C_{1-3}$alkyleneOR$^7$, $N(R^7)C(O)C_{1-3}$alkyleneNHC(O)O $R^7$, $N(R^7)C(O)C_{1-3}$alkyleneSO$_2$N$R^7$, $CF_3$, $C_{1-3}$alkyleneN$(R^{12})$SO$_2$aryl, $C_{1-3}$alkyleneN$(R^{12})$SO$_2$heteroaryl, $C_{1-3}$alkyleneOC$_{1-3}$alkylenearyl, $C_{1-3}$alkyleneN$(R^{12})C_{1-3}$alkylenearyl, $C_{1-3}$alkyleneN$(R^{12})C_{1-3}$alkyleneheteroaryl, $C_{1-3}$alkyleneN$(R^{12})C(O)R^7$, $C_{1-3}$alkyleneN$(R^{12})C(O)C_{1-3}$alkyleneOR$^2$, $C_{1-3}$alkyleneN$(R^{12})C(O)$aryl, $C_{1-3}$alkyleneN$(R^2)$-C(O)$C_{1-3}$alkyleneN$(R^{12})_2$, $C_{1-3}$alkyleneN$(R^{12})C(O)$heteroaryl, $C_{1-3}$alkyleneOR$^7$, and $SR^7$, wherein $R^7$, is as defined above;

$R^{11}$ is selected from the group consisting of null, hydro, optionally substituted $C_{1-6}$alkyl, and halo;

$R^{12}$ is selected from the group consisting of hydro, $C_{1-6}$alkyl, cycloalkyl, aryl, heteroaryl, $C_{1-3}$alkylenearyl, and $SO_2C_{1-6}$alkyl, or two $R^{12}$ groups are taken together to form an optionally substituted 3- to 6-membered ring; and $R^{13}$ is selected from the group consisting of hydro, $C_{1-6}$alkyl, $C_{2-6}$alkenyl, $C_{2-6}$alkynyl, and aryl;

provided that when Q' is hydro or $OCH_3$, at least one of $R^8$, $R^9$, and $R^{10}$ is different from hydro, $CH_3$, $OCH_3$, and halo, and pharmaceutically acceptable salts or solvates thereof.

Preferred compounds of structural formula (II) are those wherein W' is selected from the group consisting of

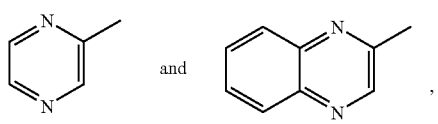
and optionally substituted with one to four substituents selected from the group consisting of $C_{1-6}$alkyl, optionally substituted aryl, $N(R^7)_2$, $CF_3$, $C(O)R^7$, $N_3$, CN, $C_{1-3}$alkylenearyl, $C_{1-3}$alkyleneN$(R^{12})_2$, $OR^7$, halo,

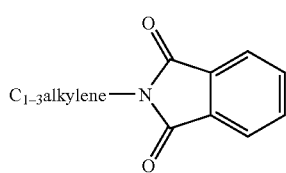

wherein $R^7$, Y and Z are as previously defined.

More preferred compounds of formula (II) are those wherein:

J' is selected from the group consisting of $CR^8$ and $NR^8$, wherein $R^8$ is null, hydro, $C_{1-6}$alkyl, and halo;

K' is selected from the group consisting of $CR^9$ and $NR^9$;

L' is selected from the group consisting of $CR^{10}$ and $NR^{10}$; and one of $R^9$ and $R^{10}$ is hydro and the other is a substituent selected from the group consisting of $CO_2R^7$, $C(O)N(R^7)_2$, $C(O)R^7$, $N(R^{13})COR^7$, $N(R^{13})C(o)OR^7$, $N(R^7)C(O)OR^7$, $N(R^7)C(O)C_{1-3}$alkyleneC(O)$R^7$, $N(R^7)C(O)C_{1-3}$alkyleneC(O)$OR^7$, $N(R^7)C(O)C_{1-3}$alkyleneOR$^7$, $N(R^7)C(O)C_{1-3}$alkyleneNHC(O)OR$^7$, $N(R^7)C(O)C_{1-3}$alkyleneSO$_2$NR$^7$, $C_{1-3}$alkyleneOR$^7$, $CF_3$, $C_{1-3}$alkyleneN(R$^{12}$)SO$_2$aryl, $C_{1-3}$alkyleneN(R$^{12}$)SO$_2$heteroaryl, $C_{1-3}$alkyleneOC$_{1-3}$alkylenearyl, $C_{1-3}$alkyleneN(R$^{12}$)C$_{1-3}$alkylenearyl, $C_{1-3}$alkyleneN(R$_{1-2}$)C$_{1-3}$alkyleneheteroaryl, $C_{1-3}$alkyleneN(R$^{12}$)C(O)R$^7$, $C_{1-3}$alkyleneN(R$^{12}$)C(O)C$_{1-3}$alkyleneOR$^{12}$, $C_{1-3}$alkyleneN(R$^{12}$)C(O)aryl, $C_{1-3}$alkyleneN(R$^{12}$)C(O)C$_{1-3}$alkyleneN(R$^{12}$)$_2$, $C_{1-3}$alkyleneN(R$^{12}$)C(O)heteroaryl, and $SR^7$, wherein $R^7$, $R^{13}$, W', Y', and M' are as previously defined.

Yet another aspect of the invention relates to compounds, and compositions containing compounds, of structural formula (III)

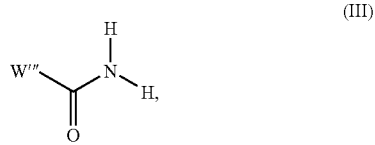

(III)

wherein W''' is selected from the group consisting of heteroaryl, aryl, heterocycloalkyl, cycloalkyl, and $C_{1-3}$ alkyl substituted with a heteroaryl or aryl group;

wherein said aryl groups are optionally substituted with one to four substituents represented by $R^{14}$, said heteroaryl groups are optionally substituted with one to four substituents represented by $R^{18}$, and said heterocycloalkyl and cycloalkyl groups are optionally substituted with one to two substituents represented by $R^{19}$;

$R^{14}$ is selected from the group consisting of halo, $C_{1-6}$alkyl, $C_{2-6}$alkenyl, OCF$_3$, NO$_2$, CN, NC, N(R$^{16}$)$_2$, OR$^{16}$, CO$_2$R$^{16}$, C(O)N(R$^{16}$)$_2$, C(O)R$^{16}$, N(R$^{15}$)COR$^{16}$, N(R$^{15}$)C(O)OR$^{16}$, N(R$^{16}$)C(O)OR$^{16}$; N(R$^{16}$)C(O)C$_{1-3}$alkyleneC(O) R$^{16}$, N(R$^{16}$)C(O)C$_{1-3}$alkyleneC(O)OR$^{16}$, N(R$^{16}$)C(O)C$_{1-3}$alkyleneOR$^{16}$, N(R$^{16}$)C(O)C$_{1-3}$alkyleneNHC(O)OR$^{16}$, N(R$^{16}$)C(O)C$_{1-3}$alkyleneSO$_2$NR$^{16}$, $C_{1-3}$alkyleneOR$^{16}$, and SR$^{16}$;

$R^{15}$ is selected from the group consisting of hydro, $C_{1-6}$alkyl, $C_{2-6}$alkenyl, $C_{2-6}$alkynyl, and aryl;

$R^{16}$ is selected from the group consisting of hydro, $C_{1-6}$alkyl, $C_{2-6}$alkenyl, cycloalkyl, aryl, heteroaryl, SO$_2$R$^{17}$, and $C_{16}$alkyl substituted with one or more of halo, hydroxy, aryl, heteroaryl, heterocycloalkyl, N(R$^{17}$)$_2$, and SO$_2$R$^7$, $C_{1-3}$alkylenearyl, $C_{1-3}$alkyleneheteroaryl, $C_{1-3}$alkyleneC$_{1-3}$heterocycloalkyl, $C_{1-3}$alkyleneSOaryl, optionally substituted $C_{1-3}$alkyleneN(R$^{17}$)$_2$, OCF$_3$, $C_{1-3}$alkylene N(R$^{17}$)$_3^+$, $C_{3-8}$heterocycloalkyl, CH(C$_{1-3}$alkyleneN(R$^{17}$)$_2$)$_2$, or two $R^{16}$ groups are taken together to form a 3- to 6-membered aliphatic ring.

$R^{17}$ is selected from the group consisting of hydro, $C_{1-6}$alkyl, cycloalkyl, aryl, and SO$_2$C$_{1-6}$alkyl, or two $R^{17}$ groups are taken together to form an optionally substituted 3- to 6-membered ring;

$R^{18}$ is selected from the group consisting of $C_{1-6}$alkyl, aryl, N(R$^{15}$)$_2$, OR$^{15}$, and halo; and $R^{19}$ is selected from the group consisting of halo and $C_{1-6}$alkyl.

As used herein, the term "alkyl" includes straight chained and branched hydrocarbon groups containing the indicated number of carbon atoms, typically methyl, ethyl, and straight-chain and branched propyl and butyl groups. Unless otherwise indicated, the hydrocarbon group can contain up to 20 carbon atoms. The term "alkyl" includes "bridged alkyl," i.e., a $C_6$-$C_{16}$ bicyclic or polycyclic hydrocarbon group, for example, norbornyl, adamantyl, bicyclo[2.2.2] octyl, bicyclo[2.2.1]heptyl, bicyclo-[3.2.1]octyl, or deca hydronaphthyl. Alkyl groups can be substituted, for example, with hydroxy (OH), halo, aryl, heteroaryl, cycloalkyl, heterocycloalkyl, amino (N(Ra)$_2$), and sulfonyl (SO$_2$Ra), wherein $R^a$ is selected from the group consisting of hydro, $C_{1-6}$alkyl, cycloalkyl, aryl, and SO$_2$C$_{1-6}$alkyl, or two $R^3$ groups are taken together to form an optionally substituted 3- to 6-membered ring.

The term "cycloalkyl" is defined as a cyclic $C_{3-8}$hydrocarbon group, e.g., cyclopropyl, cyclobutyl, cyclohexyl, and cyclopentyl. "Heterocycloalkyl", is defined similarly as cycloalkyl, and includes bicyclic and polycyclic groups, except the ring contains one to three heteroatoms selected from the group consisting of oxygen, nitrogen, and sulfur. Cycloalkyl and heterocycloalkyl groups can be saturated or partially unsaturated ring systems substituted with, for example, one to three groups, independently selected from $C_{1-4}$alkyl, $C_{1-3}$alkyleneOH, C(=O)NH$_2$, NH$_2$, oxo (=O), aryl, trifluoroethanoyl, and OH. Heterocycloalkyl groups optionally are further N-substituted with $C_{1-3}$alkylenearyl or $C_{1-3}$alkylene-heteroaryl.

The term "alkenyl" is defined identically as "alkyl," except the substituent contains a carbon-carbon double bond.

The term "alkynyl" is defined identically as "alkyl," except the substituent contains a carbon-carbon triple bond.

The term "alkylene" refers to an alkyl group having a substituent. For example, the term "$C_{1-3}$alkyleneC(O)OR" refers to an alkyl group containing one to three carbon atoms substituted with a —C(O)OR group. The alkylene group is optionally substituted with one or more of aryl, heteroaryl, and OR$^7$, wherein $R^7$ is defined hereafter.

The term "halo" or "halogen" is defined herein to include fluorine, bromine, chlorine, and iodine.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to four, halo, $C_{1-6}$alkyl, $C_{2-6}$alkenyl, OCF$_3$, NO$_2$, CN, NC, N(R$^a$)$_2$, OR$^b$, CO$_2$R$^b$, C(O)N(R$^b$)$_2$, C(O)R$^b$, N(R$^a$)COR$^b$, N(R$^a$)C(O)OR$^b$, N(R$^a$)C(O)OR$^b$, N(R$^a$)C(O)C$_{1-3}$alkyleneC(O)R$^b$, N(R$^b$)C(O)C$_{1-3}$alkyleneC(O)OR$^b$, N(R$^b$)C(O)C$_{1-3}$alkyleneOR$^b$, N(R$^b$)C(O)C$_{1-3}$alkyleneNHC(O)OR$^b$, N(R$^b$)C(O)C$_{1-3}$alkyleneSO$_2$NR$^b$, $C_{1-3}$alkyleneOR$^b$, and SR$^b$, wherein $R^b$ is selected from the group consisting of hydro, $C_{1-6}$alkyl, $C_{2-6}$alkenyl, cycloalkyl, heterocycloalkyl, aryl, heteroaryl, $SO_2R^a$, and $C_{1-6}$alkyl substituted with halo, hydroxy, aryl, heteroaryl, heterocycloalkyl, $N(R^a)_2$, or $SO_2R^a$, and $R^a$, as previously defined. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethyl phenyl, 4-nitrophenyl, 2-methoxyphenyl, 2,4-methoxychlorophenyl, and the like. The terms "aryl$C_{1-3}$alkyl" and "heteroaryl$C_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and that can be unsubstituted or substituted, for example, with one or more, and in particular one to four, substituents, for example, hydrogen, $C_{1-6}$alkyl, $C_{1-6}$alkoxy, aryl, $N(R^a)_2$, $OR^b$, and halo, wherein $R^a$ and $R^b$ are as previously defined. Examples of heteroaryl groups include, but are not limited to, thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "hydroxy" is defined as —OH.

The term "3- to 6-membered ring" as used herein refers to carbocyclic and heterocyclic aliphatic or aromatic groups, including, but not limited to, morpholinyl, piperidinyl, phenyl, thiophenyl, furyl, pyrrolyl, imidazolyl, pyrimidinyl, and pyridinyl, optionally substituted with one or more, and in particular one to three, groups exemplified above for "aryl" groups.

The carbon atom content of hydrocarbon-containing moieties is indicated by a subscript designating the minimum and maximum number of carbon atoms in the moiety, e.g., "$C_{1-6}$alkyl" refers to an alkyl group having one to six carbon atoms, inclusive.

In the structures herein, for a bond lacking a substituent, the substituent is methyl, for example,

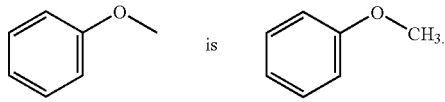

When no substituent is indicated as attached to a carbon atom on a ring, it is understood that the carbon atom contains the appropriate number of hydrogen atoms. In addition, when no substituent is indicated as attached to a carbonyl group or a nitrogen atom, for example, the substituent is understood to be hydrogen, e.g.,

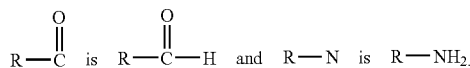

The abbreviation "Me" is methyl. The abbreviation CO and C(O) is carbonyl (C=(O)).

The notation $N(R^x)_2$, wherein x represents an alpha or numeric character, such as for example $R^a$, $R^b$, $R^4$, $R^{12}$, and the like, is used to denote two $R^x$ groups attached to a common nitrogen atom. When used in such notation, the $R^x$ group can be the same or different, and is selected from the group as defined by the $R^x$ group.

The present invention also is directed to pharmaceutical compositions containing one or more compounds of structural formula (II) and (III), to use of the compounds and compositions containing the compounds in therapeutic treatment of a disease or disorder, and to methods of preparing the compounds and intermediates involved in the synthesis of the compounds of structural formula (II) and (III).

Compounds useful for the method of the present invention have demonstrated activity in inhibiting Chk1 in vitro. Compounds of the present invention have demonstrated selectivity for Chk1 as against other protein kinases including Cdc2, Chk2, Atr, DNA-PK, PKA, and CaM KII.

Compounds of the present invention can be used to potentiate the therapeutic effects of radiation and/or chemotherapeutics used in the treatment of cancers and other cell proliferation disorders in humans or animals. For example, compounds of the invention can be used to enhance treatment of tumors that are customarily treated with an antimetabolite, e.g., methotrexate or 5-fluorouracil (5-FU). The method of the present invention comprises administration of a Chk1 inhibitor compound in combination with a chemotherapeutic agent that can effect single- or double-strand DNA breaks or that can block DNA replication or cell proliferation. Alternatively, the method of the present invention comprises administration of a Chk1 inhibitor compound in combination with therapies that include use of an antibody, e.g., herceptin, that has activity in inhibiting the proliferation of cancer cells. Accordingly, cancers such as colorectal cancers, head and neck cancers, pancreatic cancers, breast cancers, gastric cancers, bladder cancers, vulvar cancers, leukemias, lymphomas, melanomas, renal cell carcinomas, ovarian cancers, brain tumors, osteosarcomas, and lung carcinomas, are susceptible to enhanced treatment in combination with the Chk1 inhibitors of the invention.

Tumors or neoplasms include growths of tissue cells wherein multiplication of cells is uncontrolled and progressive. Some such growths are benign, but others are termed "malignant," and can lead to death of the organism. Malignant neoplasms, or "cancers," are distinguished from benign growths in that, in addition to exhibiting aggressive cellular proliferation, can invade surrounding tissues and metastasize. Moreover, malignant neoplasms are characterized by showing a greater loss of differentiation (greater "dedifferentiation") and organization relative to one another and surrounding tissues. This property is called "anaplasia."

Neoplasms treatable by the present invention also include solid tumors, i.e., carcinomas and sarcomas. Carcinomas include malignant neoplasms derived from epithelial cells which infiltrate (i.e., invade) surrounding tissues and give rise to metastases. Adenocarcinomas are carcinomas derived from glandular tissue, or from tissues that form recognizable glandular structures. Another broad category of cancers includes sarcomas, which are tumors whose cells are embedded in a fibrillar or homogeneous substance, like embryonic connective tissue. The invention also enables treatment of cancers of the myeloid or lymphoid systems, including leukemias, lymphomas, and other cancers that typically are not present as a tumor mass, but are distributed in the vascular or lymphoreticular systems.

Chk1 activity is associated with various forms of cancer in, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

Compounds of the present invention also can potentiate the efficacy of drugs in the treatment of inflammatory diseases. Examples of diseases that can benefit from combination therapy with compounds suitable for the method of the present invention are rheumatoid arthritis, psoriasis, vitiligo, Wegener's granulomatosis, and systemic lupus erythematosus (SLE). Treatment of arthritis, Wegener's granulomatosis, and SLE often involves the use of immunosuppressive therapies, such as ionizing radiation, methotrexate, and cyclophosphamide. Such treatments typically induce, either directly or indirectly, DNA damage. Inhibition of Chk1 activity within the offending immune cells render the cells more sensitive to control by these standard treatments. Psoriasis and vitiligo commonly are treated with ultraviolet radiation (UV) in combination with psoralen. The present DNA damaging agents induce the killing effect of UV and psoralen, and increase the therapeutic index of this treatment regimen. In general, compounds useful in methods of the present invention potentiate control of inflammatory disease cells when in combination with currently used immunosuppressive drugs.

The present invention includes all possible stereoisomers and geometric isomers of compounds of the present method and of structural formulae (I), (II), and (III). The present invention includes not only racemic compounds, but optically active isomers as well. When a compound of structural formulae (I), (II), or (III) is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883–888 (1997). Resolution of the final product, an intermediate, or a starting, material can be achieved by any suitable method known in the art. Additionally, in situations where tautomers of the compounds of structural formulae (I), (II), and (III) are possible, the present invention is intended to include all tautomeric forms of the compounds.

As demonstrated hereafter, specific stereoisomers can exhibit an exceptional ability to inhibit Chk1 in combination with chemo- or radiotherapy with diminshed adverse effects typically associated with chemotherapeutic or radiotherapeutic treatments.

Prodrugs of compositions of structural formulae (I), (II), and (III) also can be used as the compound and in the method of the present invention. It is well established that a prodrug approach, wherein a compound is derivatized into a form suitable for formulation and/or administration, and then is released as a drug in vivo, has been successfully employed to transiently (e.g., bioreversibly) alter the physicochemical properties of the compound (see, H. Bundgaard, Ed., *Design of Prodrugs*, Elsevier, Amsterdam, (1985); R. B. Silverman, *The Organic Chemistry of Drug Design and Drug Action*, Academic Press, San Diego, chapter 8, (1992); K. M. Hillgren et al., *Med. Res. Rev.*, 15, 83 (1995)).

Compounds of the present invention can contain several functional groups. The introduced functional groups, if desired or necessary, then can be modified to provide a prodrug for dose of formulation and/or administration. Suitable prodrugs include, for example, acid derivatives, like amides, esters, and the like. It also is appreciated by those skilled in the art that N-oxides can be used as a prodrug.

As used herein, the term pharmaceutically acceptable salts refers compounds of structural formula (I), (II), and (III) which contain acidic moieties and form salts with suitable cations. i Suitable pharmaceutically acceptable cations include alkali metal (e.g., sodium or potassium) and alkaline earth metal (e.g., calcium or magnesium) cations. The pharmaceutically acceptable salts of the compounds of structural formula (I), (II), and (III), which contain a basic center, are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzene sulphonate, and p-toluene-sulphonate salts. In light of the foregoing, any reference to compounds of the present invention appearing herein is intended to include compounds of structural formula (I), (II), and (III), as well as pharmaceutically acceptable salts and solvates thereof.

The compounds of the present invention can be therapeutically administered as the neat chemical, but it is preferable to administer compounds of structural formula (I), (II), and (III) as a pharmaceutical composition or formulation. Accordingly, the present invention further provides pharmaceutical formulations comprising a compound of structural formula (I), (II), and/or (III), or pharmaceutically acceptable salts thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

Inhibition of the checkpoint kinase typically is measured using a dose-response assay in which a sensitive assay system is contacted with a compound of interest over a range of concentrations, including concentrations at which no or minimal effect is observed, through higher concentrations at which partial effect is observed, to saturating concentrations at which a maximum effect is observed.

Theoretically, such assays of the dose-response effect of inhibitor compounds can be described as a sigmoidal curve expressing a degree of inhibition as a function of concentration. The curve also theoretically passes through a point at which the concentration is sufficient to reduce activity of the checkpoint enzyme to a level that is 50% that of the difference between minimal and maximal enzyme activity in the assay. This concentration is defined as structural formula (I), (II), and (III), as well as pharmaceutically acceptable salts and solvates thereof.

The compounds of the present invention can be therapeutically administered as the neat chemical, but it is preferable to administer compounds of structural formula (I), (II), and (III) as a pharmaceutical composition or formulation. Accordingly, the present invention further provides pharmaceutical formulations comprising a compound of structural formula (I), (II), and/or (III), or pharmaceutically acceptable salts thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

Inhibition of the checkpoint kinase typically is measured using a dose-response assay in which a sensitive assay system is contacted with a compound of interest over a range of concentrations, including concentrations at which no or minimal effect is observed, through higher concentrations at which partial effect is observed, to saturating concentrations at which a maximum effect is observed. Theoretically, such assays of the dose-response effect of inhibitor compounds can be described as a sigmoidal curve expressing a degree of inhibition as a function of concentration. The curve also theoretically passes through a point at which the concentration is sufficient to reduce activity of the checkpoint enzyme to a level that is 50% that of the difference between minimal and maximal enzyme activity in the assay. This concentration is defined as the Inhibitory Concentration (50%) or $IC_{50}$ value. Determination of $IC_{50}$ values preferably are made using conventional biochemical (acellular) assay techniques or cell-based assay techniques.

Comparisons of the efficacy of inhibitors often are provided with reference to comparative $IC_{50}$ values, wherein a higher $IC_{50}$ indicates that the test, compound is less potent, and a lower $IC_{50}$ indicates that the compound is more potent, than a reference compound. Compounds useful in the method of the present invention demonstrate an $IC_{50}$ value of at least 0.1 nM when measured using the dose-response assay. Preferred, compounds demonstrate an $IC_{50}$ value of less than 10 μM. More preferred compounds demonstrate an $IC_{50}$ value of less than 500 nM. Still more preferred compounds of the present invention demonstrate an $IC_{50}$ value of less than 250 nM, less than 100 nM, or less than 50 nM.

Compounds and pharmaceutical compositions suitable for use in the present invention include those wherein the active ingredient is administered in an effective amount to achieve its intended purpose. More specifically, a "therapeutically effective amount" means an amount effective to inhibit development of, or to alleviate the existing symptoms of, the subject being treated. Determination of the effective amount is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio of $LD_{50}$ to $ED_{50}$. Compounds that exhibit high therapeutic indices (i.e., a toxic dose that is substantially higher than the effective dose) are preferred. The data obtained can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage is chosen by the individual physician in view of the patient's condition. Dosage amount and interval can be adjusted individually to provide plasma levels of the active compound that are sufficient to maintain desired therapeutic effects.

Pharmaceutical compositions of the invention can be formulated to include one or more cytokines, lymphokines, growth factors, or other hematopoietic factors which can reduce negative side effects that may arise from, or be associated with, administration of the pharmaceutical composition alone. Cytokines, lymphokines, growth factors, or other hematopoietic factors particularly useful in pharmaceutical compositions of the invention include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF, G-CSF, Meg-CSF, GM-CSF, thrombopoietin, stem cell factor, erythropoietin, angiopoietins, including Ang-1, Ang-2, Ang-4, Ang-Y, and/or the human angiopoietin-like polypeptide, vascular endothelial growth factor (VEGF), angiogenin, bone morphogenic protein-1 (BMP-1), BMP-2, BMP-3, BMP-4, BMP-5, BMP-6, BMP-7, BMP-8, BMP-9, BMP-10, BMP-11, BMP-12, BMP-13, BMP-14, BMP-15, BMP receptor IA, BMP receptor IB, brain derived neurotrophic factor, ciliary neutrophic factor, ciliary neutrophic factor receptor cytokine-induced neutrophil chemotactic factor 1, cytokine-induced neutrophil chemotactic factor 2, cytokine-induced neutrophil chemotactic factor 2, endothelial cell growth factor, endothelin 1, epidermal growth factor, epithelial-derived neutrophil attractant, fibroblast growth factor (FGF) 4, FGF 5, FGF 6, FGF 7, FGF 8, FGF 8b, FGF 8c, FGF 9, FGF 10, FGF acidic, FGF basic, glial cell line-derived neutrophic factor receptor 1, glial cell line-derived neutrophic factor receptor 2, growth related protein, growth related protein, growth related protein, growth related protein, heparin binding epidermal growth factor, hepatocyte growth factor, hepatocyte growth * factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor, platelet derived growth factor receptor, pre-B cell growth stimulating factor, stem cell factor, stem cell factor receptor, transforming growth factor (TGF), TGF, TGF 1, TGF 1.2, TGF 2, TGF 3, TGF 5, latent TGF 1, TGF, binding protein I, TGF binding protein II, TGF binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

The compounds useful according to the invention may be conjugated or linked to auxiliary moieties that promote any property of the compounds that may be beneficial in methods of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, aligopeptides, or polypeptides, e.g., antibodies such as monoclonal antibodies and other engineered antibodies; and natural or synthetic ligands to receptors in target cells or tissues. Other suitable auxiliaries include fatty acid or lipid moieties, to promote biodistribution or uptake of the compound by target cells (see, e.g., Bradley et al., *Clin. Cancer Res.* (2001) 7:3229.

The therapeutic index of compositions comprising one or more compounds of the invention can be enhanced by conjugation of the compound(s) with antitumor antibodies as previously described (for example, Pietersz and McKinzie, *Immunol. Rev.* (1992) 129:57; Trail et al., *Science* (1993) 261:212; Rowlinson-Busza and Epenetos, *Curr. Opin. Oncol.* 1992; 4:1142). Tumor directed delivery of compounds of the invention would enhance the therapeutic benefit by minimizing potential nonspecific toxicities which can result from radiation treatment orchemotherapy. In another aspect, Chk1 inhibitors and radioisotopes or chemotherapeutic agents can be conjugated to the same antibody molecule. Alternatively, Chk1 inhibitor-conjugated tumor specific antibodies can be administered-before, during, or after administration of chemotherapeutic-conjugated antitumor antibody or radioimmunotherapy.

Compounds of the present invention can enhance the therapeutic benefit of radiation and chemotherapy treatment, including induction chemotherapy, primary (neoadjuvant) chemotherapy, and both adjuvant radiation therapy and adjuvant chemotherapy. In addition, radiation and chemotherapy are frequently indicated as adjuvants to surgery in the treatment of cancer. The goal of radiation and chemotherapy in the adjuvant setting is to reduce the risk of recurrence and enhance disease-free survival when the primary tumor has been controlled. Chemotherapy is utilized as a treatment adjuvant for colon, lung, and breast cancer, frequently when the disease is metastatic. Adjuvant radiation therapy is indicated in several diseases including colon, lung, and breast cancers as described above. For example, radiation frequently is used both pre- and post-surgery as components of the treatment strategy for rectal carcinoma. Compounds for the present invention are therefore particularly useful following surgery in the treatment of cancer in combination with radio- and/or chemotherapy.

A compound of the present invention also can radiosensitize a cell. The term "radiosensitize," as used herein, is defined as a molecule, preferably a low molecular weight molecule, administered to human or other animal in a therapeutically effective amount to increase the sensitivity of the cells to be radiosensitized to electromagnetic radiation and/or to promote the treatment of diseases that are treatable with electromagnetic radiation. Diseases that. are treatable with electromagnetic radiation include neoplastic diseases, benign and malignant tumors, and cancerous cells.

Electromagnetic radiation treatment of other diseases not listed herein also is contemplated by the present invention. The terms "electromagnetic radiation" and "radiation" as used herein include, but are not limited to, radiation having the wavelength of $10^{-20}$ to 100 meters. Preferred embodiments of the present invention employ the electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount. of one or more compounds in addition to the Chk1 inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil-(5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

Chemotherapeutic agents that can be used include, but are not limited to, alkylating agents, antimetabolites, hormones and antagonists thereof, radioisotopes, antibodies, as well as natural products, and combinations thereof. For example, an inhibitor compound of the present invention can be administered with antibiotics, such as doxorubicin and other anthracycline analogs, nitrogen mustards, such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Examples of chemotherapeutic agents useful for the method of the present invention are listed in the following table.

Alkylating agents
Nitrogen mustards mechlorethamine
cyclophosphamide
ifosfamide melphalan
chlorambucil
Nitrosoureas carmustine (BCNU)
lomustine (CCNU)
semustine (methyl-CCNU)
Ethylenimine/Methylmelamine thriethylenemelamine (TEM)
triethylene thiophosphoramide (thiotepa)
hexamethylmelamine (HMM, altretamine)
Alkyl sulfonates busulfan
Triazines dacarbazine (DTIC)
Antimetabolites Folic Acid analogs
methotrexate
trimetrexate
Pyrimidine analogs
5-fluorouracil
fluorodeoxyuridine
gemcitabine
cytosine arabinoside (AraC, cytarabine)
5-azacytidine
2,2'-difluorodeoxycytidine
Purine analogs
6-mercaptopurine
6-thioguanine
azathioprine
2'-deoxycoformycin (pentostatin)
erythrohydroxynonyladenine (EHNA)
fludarabine phosphate
2-chlorodeoxyadenosine (cladribine, 2-CdA)
Type I Topoisomerase Inhibitors camptothecin
topotecan
irinotecan
Natural products
Antimitotic drugs paclitaxel
Vinca alkaloids
vinblastine (VLB)
vincristine
vinorelbine
Taxotere ® (docetaxel)
estramustine
estramustine phosphate
Epipodophylotoxins etoposide
teniposide
Antibiotics actimomycin D
daunomycin (rubidomycin)
doxorubicin (adriamycin)
mitoxantroneidarubicin
bleomycinsplicamycin
(mithramycin)
mitomycinC
dactinomycin
Enzymes L-asparaginase
Biological response modifiers interferon-alpha
IL-2
G-CSF
GM-CSF
Differentiation Agents retinoic acid derivatives
Radiosensitizers metronidazole
misonidazole
desmethylmisonidazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinium coordination complexes cisplatin
carboplatin
Anthracenedione mitoxantrone
Substituted urea hydroxyurea
Methylhydrazine derivatives N-methylhydrazine (MIH)
procarbazine
Adrenocortical suppressant mitotane (o, p'-DDD)
ainoglutethimide
Cytokines interferon (α, β, γ)
interleukin-2
Hormones and antagonists
Adrenocorticosteroids/antagonists prednisone and equivalents
dexamethasone
ainoglutethimide
Progestins hydroxyprogesterone caproate
medroxyprogesterone acetate
megestrol acetate -continued Estrogens diethylstilbestrol
ethynyl estradiol/
equivalents
Antiestrogen tamoxifen
Androgens testosterone propionate
fluoxymesterone/equiv-
alents
Antiandrogens flutamide
gonadotropin-releasing
hormone analogs
leuprolide
Nonsteroidal
antiandrogens flutamide
Photosensitizers hematoporphyrin
derivatives
Photofrin ®
benzoporphyrin
derivatives
Npe6
tin etioporphyrin (SnET2)
pheoboride-a
bacteriochlorophyll-a
naphthalocyanines
phthalocyanines
zinc phthalocyanines Examples of chemotherapeutic agents that are particularly useful in conjunction with radiosensitizers include, for example, adriamycin, camptothecin, carboplatin, cisplatin, daunorubicin, doxorubicin, interferon (alpha, beta, gamma), interleukin 2, irinotecan, docetaxel, paclitaxel, topotecan, and therapeutically effective analogs and derivatives of the same.

As appreciated by persons skilled in the art, reference herein to treatment extends to prophylaxis; as well as to treatment of established diseases or symptoms. It is further appreciated that the amount of a compound of the invention required for use in treatment varies with the nature of the condition being treated, and with the age and the condition of the patient, and is ultimately determined by the attendant physician or veterinarian. In general, however, doses employed for adult human treatment typically are in the range of 0.001 mg/kg to about 100 mg/kg per day. The desired dose can be conveniently administered in a single dose, or as multiple doses administered at appropriate intervals, for example as two, three, four or more subdoses per day. In practice, the physician determines the actual dosing regimen most suitable for an individual patient, and the dosage varies with the age, weight, and response of the particular patient. The above dosages are exemplary of the average case, but there can be individual instances in which higher or lower dosages are merited, and such are within the scope of the present invention.

Formulations of the present invention can be administered in a standard manner for the treatment of the indicated diseases, such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™.

For oral administration, including buccal administration, the composition can be in the form of tablets or lozenges formulated in conventional manner. For example, tablets and capsules for oral administration can contain conventional excipients such as binding agents (for example, syrup, acacia, gelatin, sorbitol, tragacanth, mucilage of starch, or polyvinylpyrrolidone), fillers (for example, lactose, sugar, microcrystalline cellulose, maizestarch, calcium phosphate, or sorbitol), lubricants (for example, magnesium stearate, stearic acid, talc, polyethylene glycol or silica), disintegrants (for example, potato starch or sodium starch glycolate), or wetting agents (for example, sodium lauryl sulfate). The tablets can be coated according to methods well known in the art.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, for example suspending agents, such as sorbitol syrup, methyl cellulose, glucose/sugar syrup, gelatin, hydroxyethylcellulose, hydroxypropylmethylcellulose, carboxymethylcellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble derivatives (e.g., a sparingly soluble salt).

For veterinary use, a compound of formula (I), (II), or (III), or a nontoxic salt thereof, is administered as a suitably acceptable formulation in accordance with normal veterinary practice. The veterinarian can readily determine the dosing regimen and route of administration that is most appropriate for a particular animal.

Thus, the invention provides a pharmaceutical composition comprising a compound of the formula (I), (II), or (III), together with a pharmaceutically acceptable diluent or carrier therefor. Also provided is a process of preparing a pharmaceutical composition comprising a compound of formula (I), (II), or (III) comprising mixing a compound of formula (I), (II), or (III), together with a pharmaceutically acceptable diluent or carrier therefor.

Specific, nonlimiting examples of compounds of structural formula (I), (II), and (III) are provided below, the synthesis of which were performed in accordance with the procedures set forth below.

For ease of understanding, a compound having a particular structure is identified by the corresponding compound number provided in the following tables summarizing some of the compounds useful in the method. For example, the structure identified as Compound 1 is a compound of structural formula (IV), wherein $R^{27}$ is hydrogen and $R^{28}$ is —C(O)NH(CH$_2$)$_2$(2-N-methylpyrrolidyl).

Compounds suitable in the method include, but are not limited to:

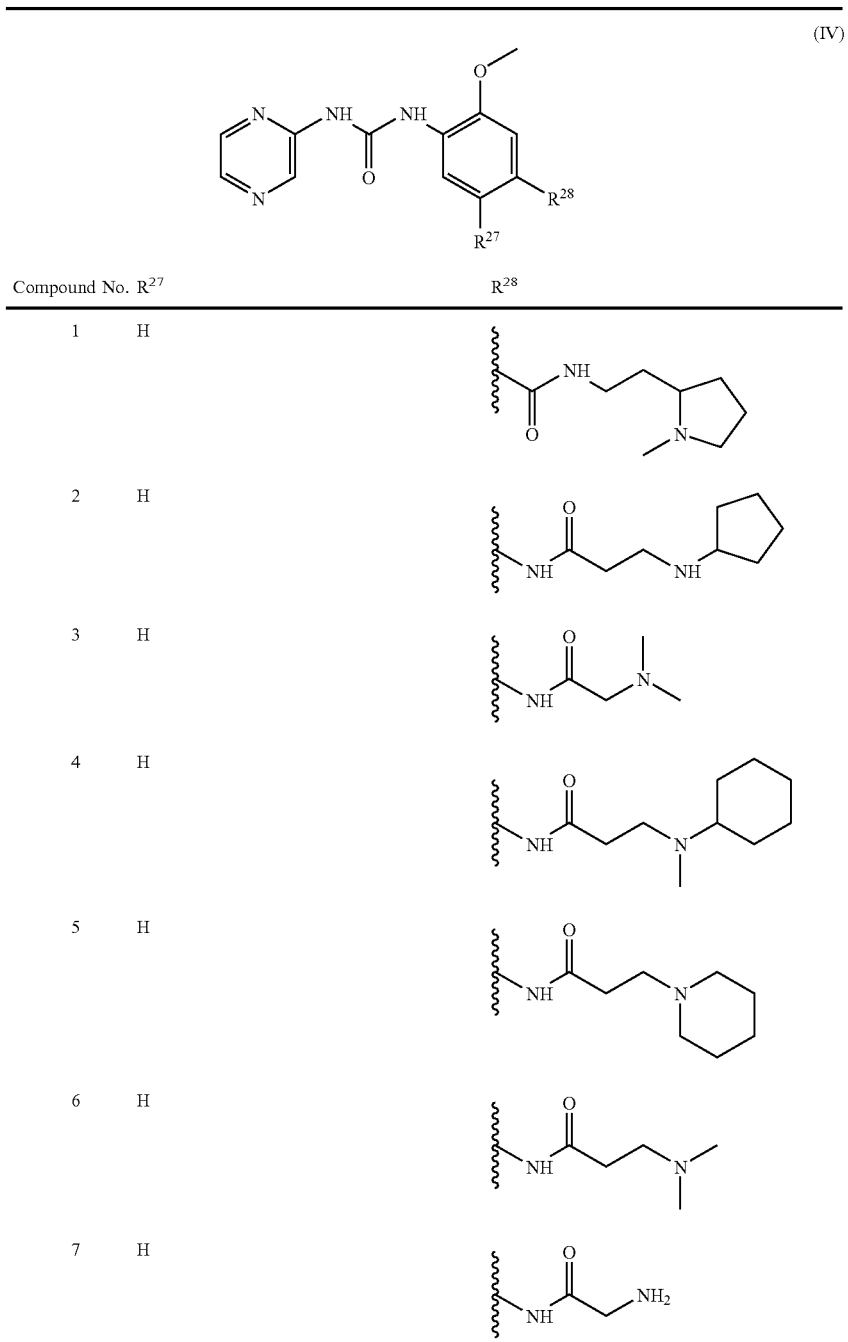

-continued
(IV)
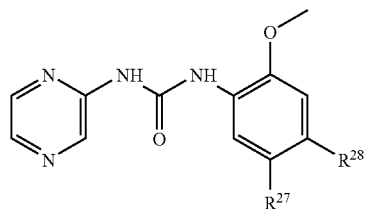
| Compound No. | $R^{27}$ | $R^{28}$ |
|---|---|---|
| 8 | H | 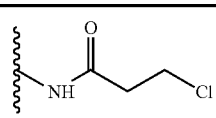 |
| 9 | H | 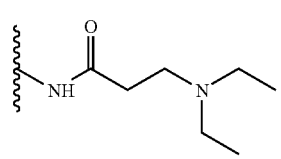 |
| 10 | 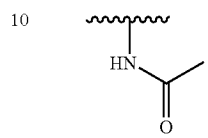 | H |
| 11 | 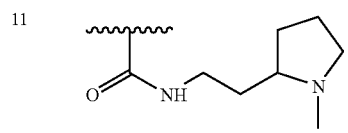 | H |
| 12 | $CH_3$ | H |
| 13 | 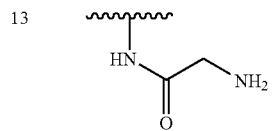 | H |
| 14 | $NH_2$ | H |
| 15 | 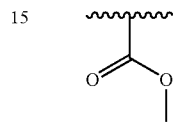 | H |
| 16 | 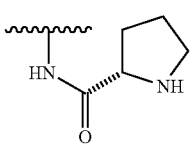 | H |
| 17 | 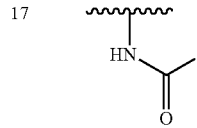 | H |
| 18 | 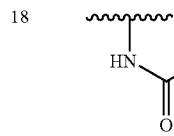 | H |

-continued
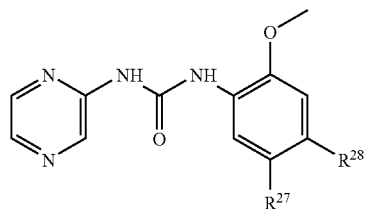
(IV)
| Compound No. | $R^{27}$ | $R^{28}$ |
|---|---|---|
| 19 | H | 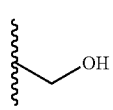 OH |
| 20 | 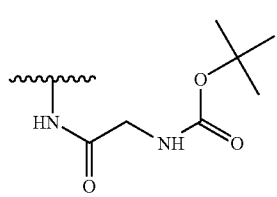 | H |
| 21 | Cl | 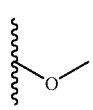 O— |
| 22 | 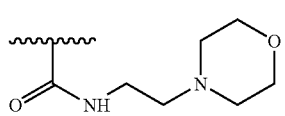 | H |
| 23 | Cl | H |
| 24 | H | 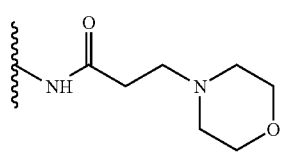 |
| 25 | H | 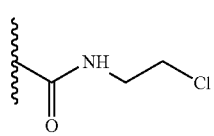 |
| 26 | 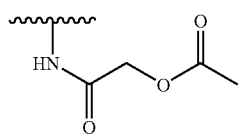 | H |
| 27 | H | 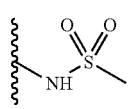 |
| 28 | H | 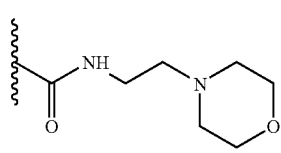 |
| 29 | H | Cl |

-continued
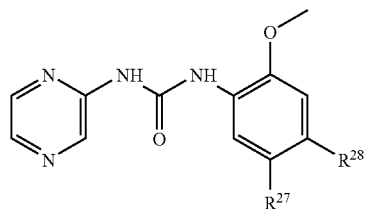
(IV)
| Compound No. | R²⁷ | R²⁸ |
|---|---|---|
| 30 | -NH-C(O)-CH₂-OH | H |
| 31 | -O-CH₃ | H |
| 32 | H | NH₂ |
| 33 | H | -NH-C(O)-CH₂-(4-pyridyl) |
| 34 | H | -C(O)-N(CH₃)-CH₂CH₂-N(CH₃)₂ |
| 35 | H | -C(O)-NH-CH₂CH₂-NH-S(O)₂-CH₃ |
| 36 | -NH-C(O)-[(2S)-1-(trifluoroacetyl)pyrrolidin-2-yl] | H |
| 37 | -NH-C(O)-CH(CH₃)-O-C(O)-CH₃ | H |
| 38 | H | H |
| 39 | H | -NH-C(O)-O-CH₃ |
| 40 | H | -C(O)-OH |

-continued
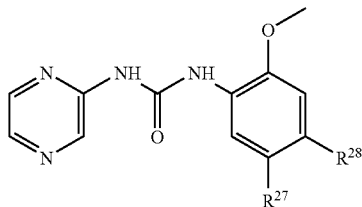
(IV)
| Compound No. | R²⁷ | R²⁸ |
|---|---|---|
| 41 | H | 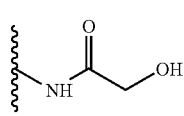 |
| 42 | 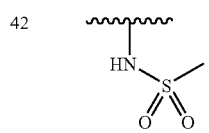 | H |
| 43 | H | 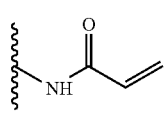 |
| 44 | H | 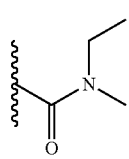 |
| 45 | 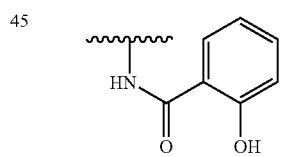 | H |
| 46 | H | 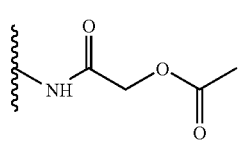 |
| 47 | H | 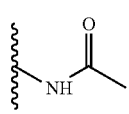 |
| 48 | 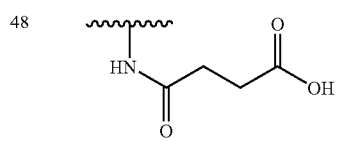 | H |
| 49 | 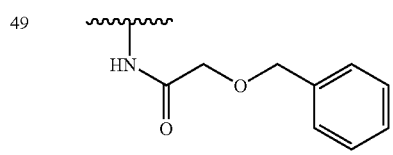 | H |

-continued
(IV)
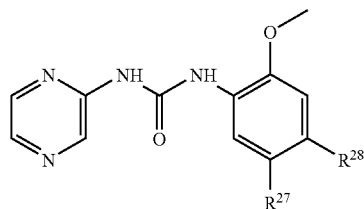
| Compound No. | R27 | R28 |
|---|---|---|
| 50 | 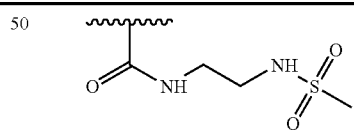 | H |
| 51 | 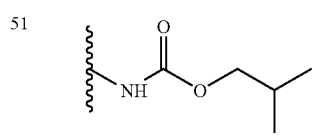 | H |
| 52 | H |  |
| 53 | H |  |
| 54 | 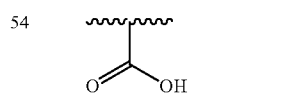 | H |
| 55 | 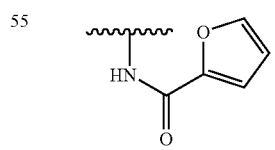 | H |
| 56 | 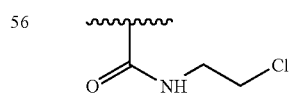 | H |
| 57 | H |  |
| 58 | H |  |
| 59 | 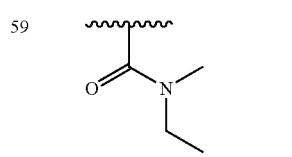 | H |

-continued
(IV)
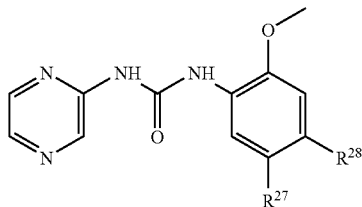
| Compound No. | $R^{27}$ | $R^{28}$ |
|---|---|---|
| 60 | H | 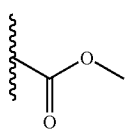 |
| 61 | H | 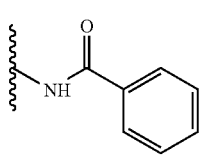 |
| 62 | 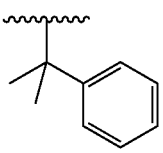 | H |
| 63 | 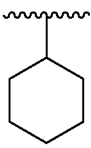 | H |
| 64 | 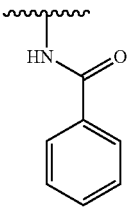 | H |
| 65 | H |  |
| 66 | H | 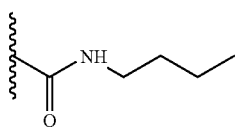 |
| 67 | H | 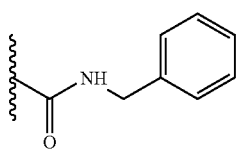 |

-continued
(IV)
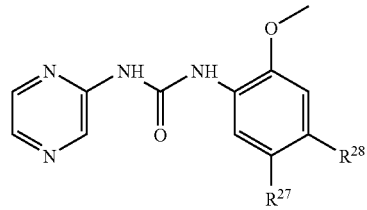
| Compound No. | R²⁷ | R²⁸ |
|---|---|---|
| 68 | H | 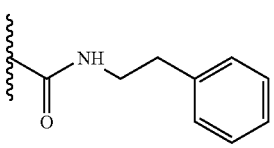 |
| 69 | H | 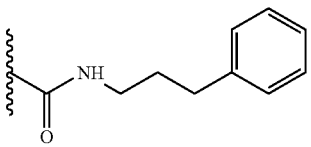 |
| 70 | H | 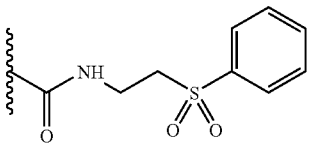 |
| 71 | H | 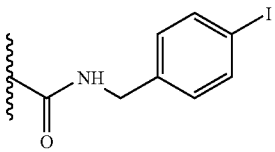 |
| 72 | H | 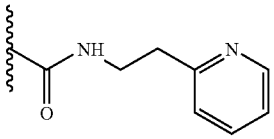 |
| 73 | H | 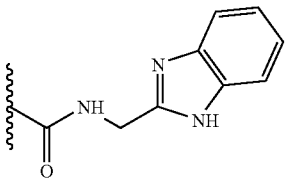 |
| 74 | H | 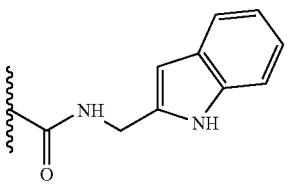 |
| 75 | H | 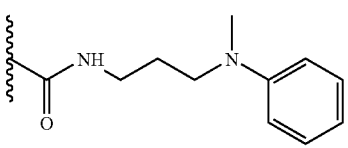 |

-continued
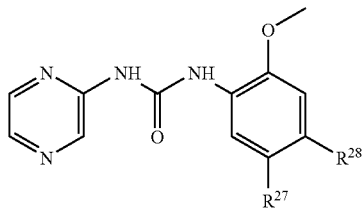
(IV)
| Compound No. | R²⁷ | R²⁸ |
|---|---|---|
| 76 | H | 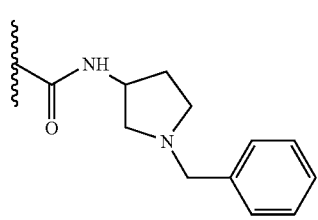 |
| 77 | 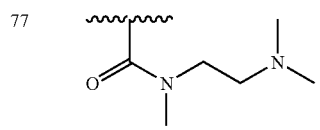 | H |
| 78 | 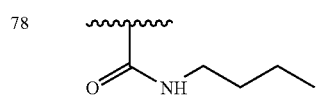 | H |
| 79 | 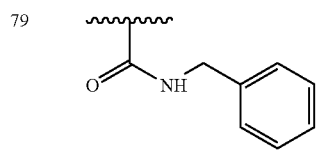 | H |
| 80 | 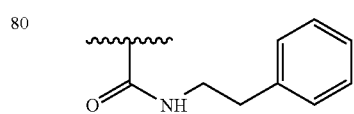 | H |
| 81 | 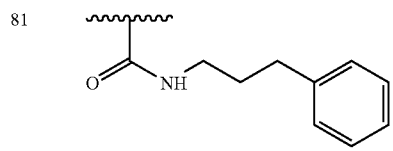 | H |
| 82 | 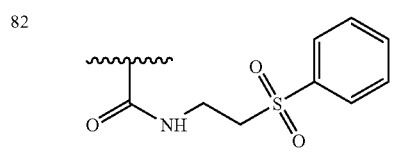 | H |
| 83 | 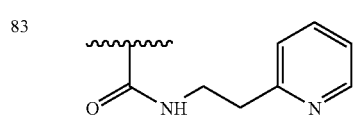 | H |
| 84 | 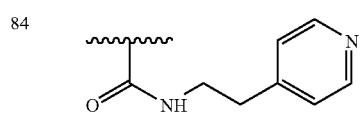 | H |

-continued
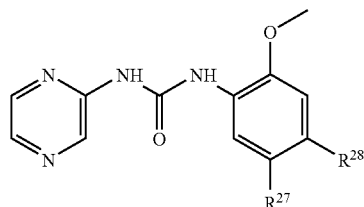
(IV)
| Compound No. | R²⁷ | R²⁸ |
|---|---|---|
| 85 | 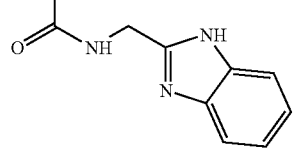 | H |
| 86 | 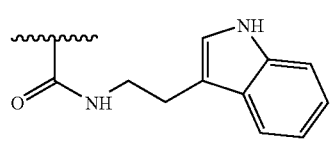 | H |
| 87 | 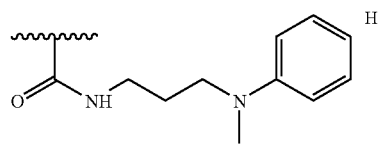 | H |
| 88 | 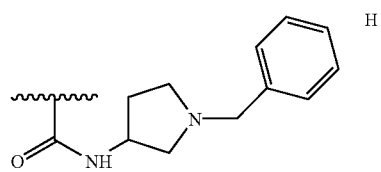 | H |
Hetero Ring Substitutions:
(V)
| Compound No. | R²⁹ |
|---|---|
| 89 | 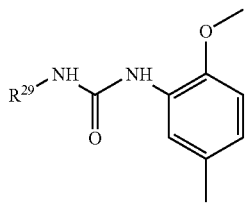 |
-continued
(V)
| Compound No. | R²⁹ |
|---|---|
| 90 | 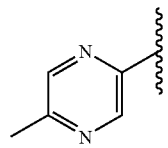 |

-continued (V)

Structure: R29-NH-C(=O)-NH-(2-methoxy-5-methylphenyl)

| Compound No. | R29 |
|---|---|
| 91 | 6-phenylpyrazin-2-yl |
| 92 | 6-chloropyrazin-2-yl |
| 93 | 1,3,5-triazin-2-yl |
| 94 | 1H-pyrazol-3-yl |
| 95 | 2-oxo-1,2-dihydropyrimidin-4-yl |
| 96 | 6-oxo-1,6-dihydropyrimidin-2-yl |
| 97 | 1,2,4-triazin-3-yl |
| 98 | pyrimidin-4-yl |
| 99 | 2H-tetrazol-5-yl |
| 100 | 3,5-dibromopyrazin-2-yl |
| 101 | 3-benzyl-5-(4-methoxyphenyl)pyrazin-2-yl |
| 102 | 3-bromo-6-phenylpyrazin-2-yl |
| 103 | 3,6-dimethylpyrazin-2-yl |

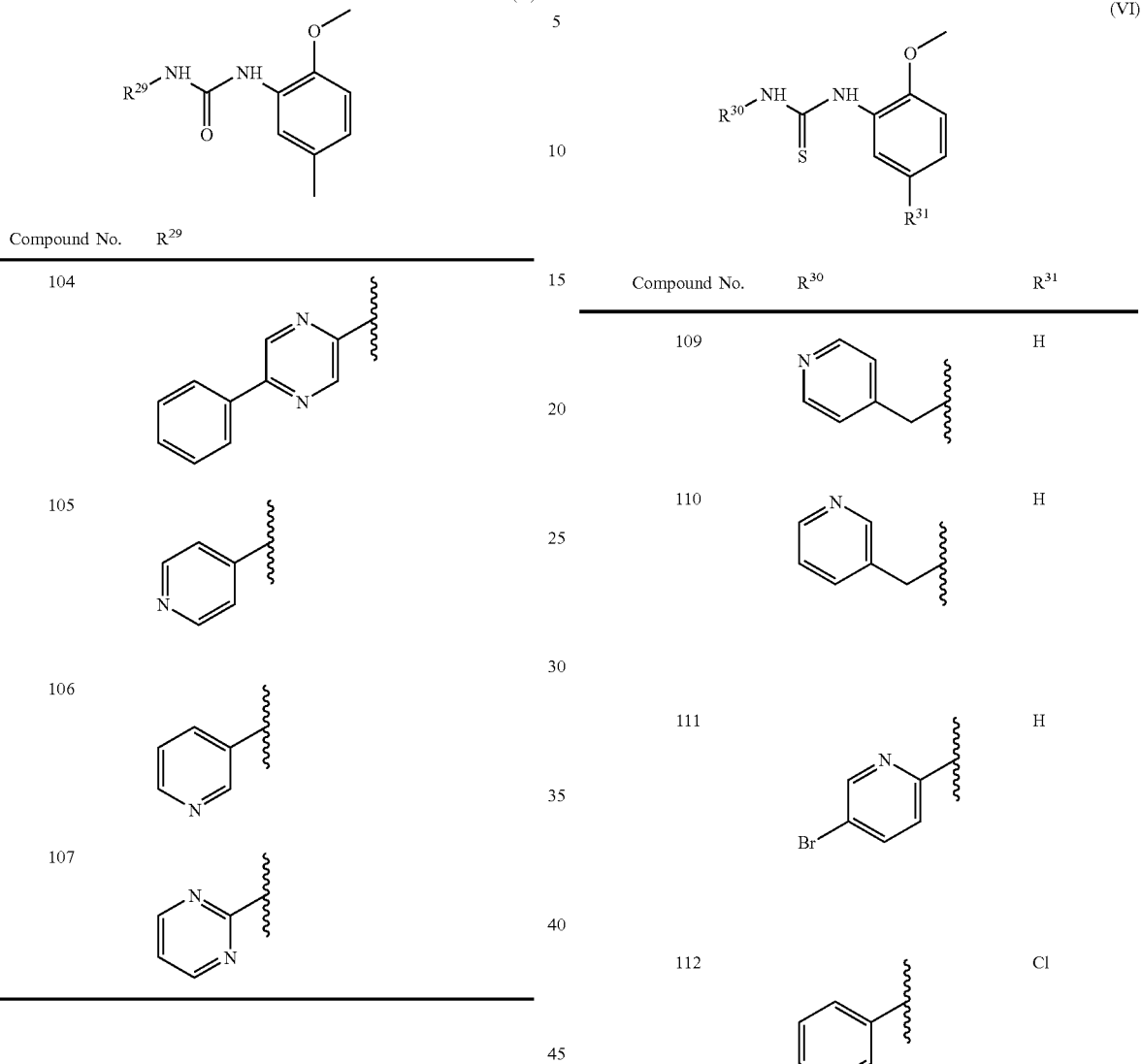
Thiourea Compounds:
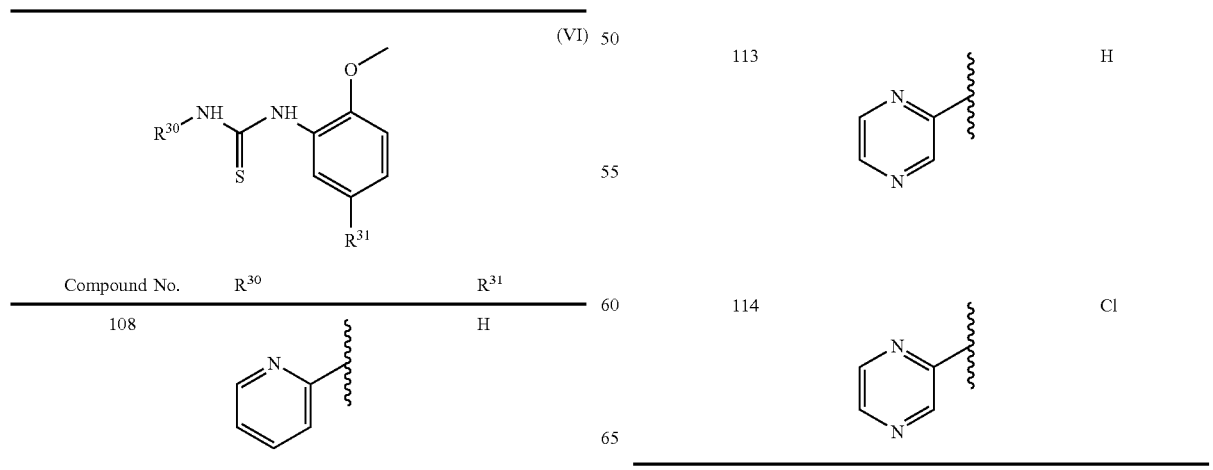

Miscellaneous Class:
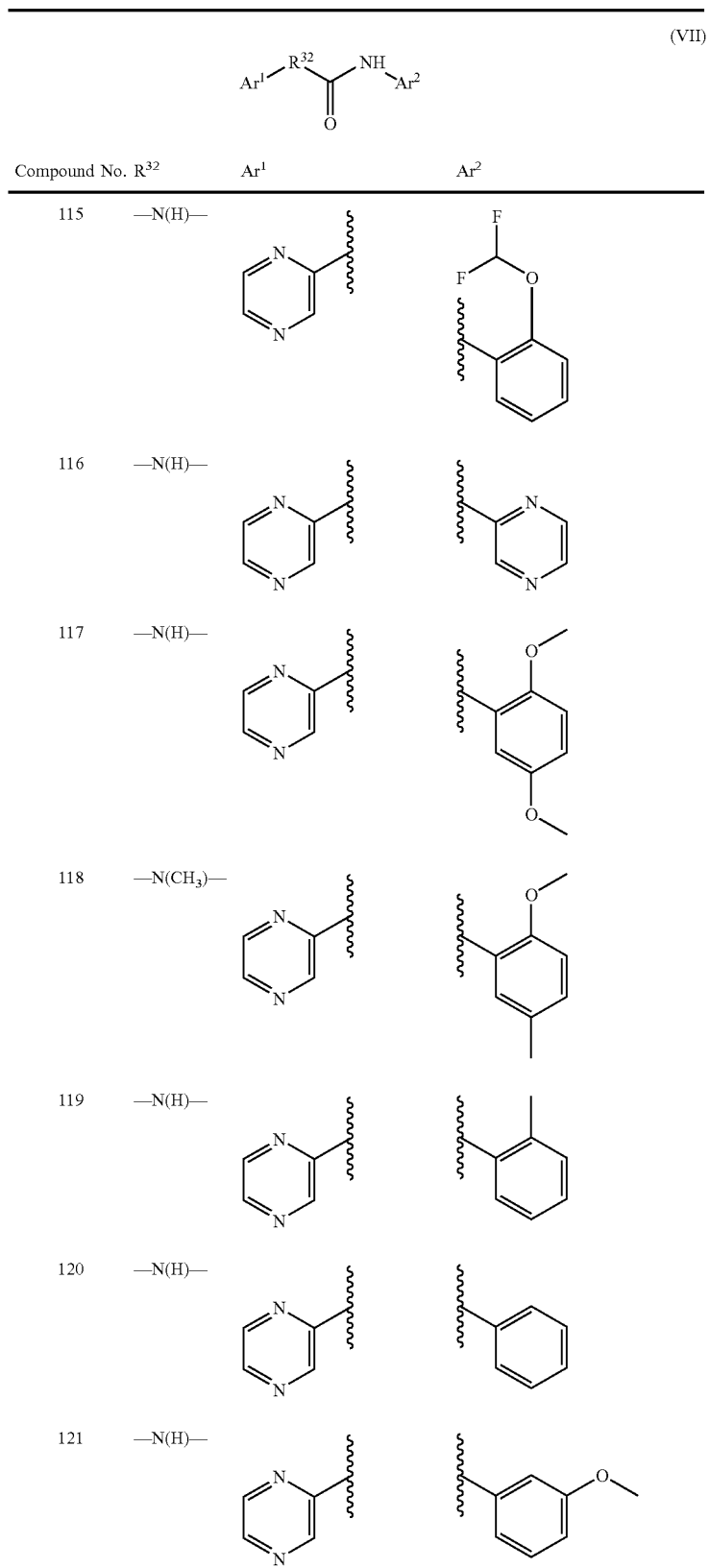

-continued
(VII)
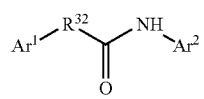
| Compound No. | R³² | Ar¹ | Ar² |
|---|---|---|---|
| 122 | —N(H)— | pyrazin-2-yl | 2-bromophenyl |
| 123 | —N(H)— | pyrazin-2-yl | 2-cyanophenyl |
| 124 | —N(H)— | 3,6-dimethylpyrazin-2-yl | phenyl |
| 125 | —N(H)— | pyrazin-2-yl | 4-(methoxycarbonyl)phenyl |
| 126 | —N(H)— | pyrazin-2-yl | 4-iodophenyl |
| 127 | —N(H)— | pyrazin-2-yl | 2,6-dimethyl-4-bromophenyl |
| 128 | —O— | pyridin-3-yl | 2,5-dimethoxyphenyl |

-continued
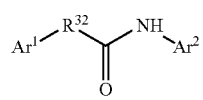
(VII)
| Compound No. | R³² | Ar¹ | Ar² |
|---|---|---|---|
| 129 | —N(H)— | 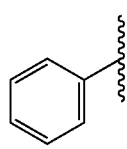 | 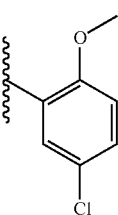 |
| 130 | —N(H)— | 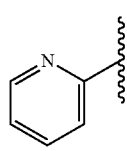 | 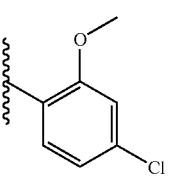 |
| 131 | —N(H)— | 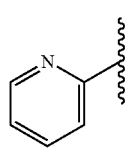 | 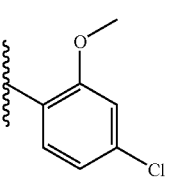 |
| 132 | null | 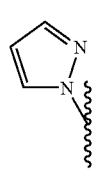 | 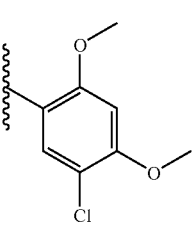 |
| 133 | —N(H)— | 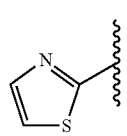 | 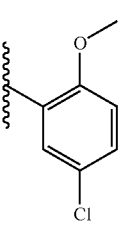 |
| 134 | —N(H)— | 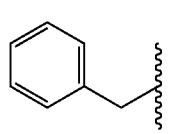 | 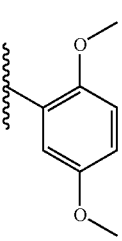 |

-continued
(VII)
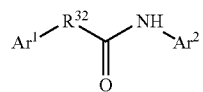
| Compound No. | R³² | Ar¹ | Ar² |
|---|---|---|---|
| 135 | —O— | | |
| 136 | —N(H)— | | |
| 137 | —N(H)— | | |
| 138 | —N(H)— | | |
| 139 | —N(H)— | | |
| 140 | —O— | | |
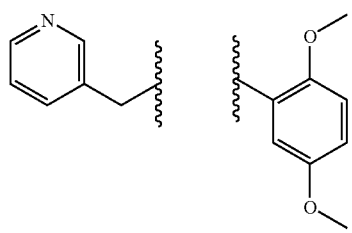
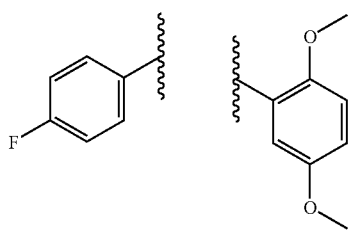
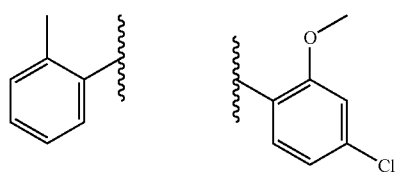
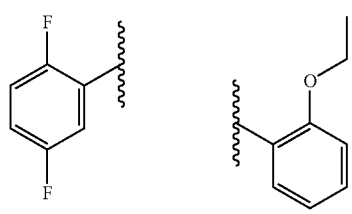
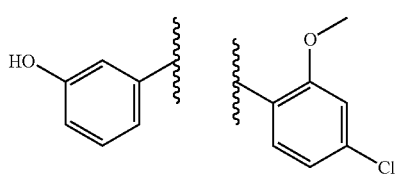
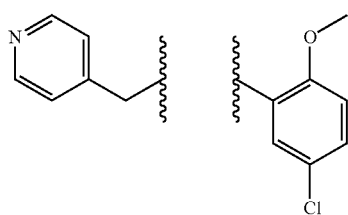

-continued
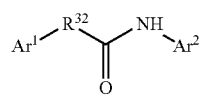
(VII)
| Compound No. | R³² | Ar¹ | Ar² |
|---|---|---|---|
| 141 | —O— | 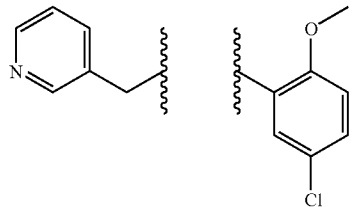 | |
| 142 | —N(H)— | 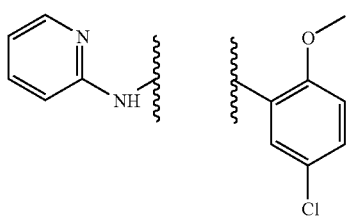 | |
| 143 | —O— | 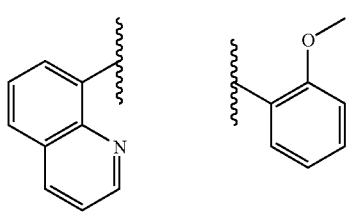 | |
| 144 | —N(H)— | 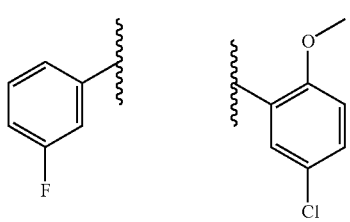 | |
| 145 | —N(H)— | 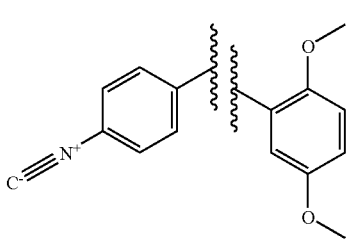 | |
| 146 | —N(H)— | 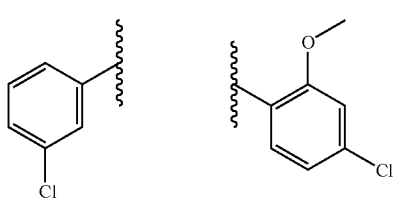 | |

-continued $$Ar^1\underset{\underset{O}{\|}}{\overset{R^{32}}{-}C-}NH-Ar^2 \quad (VII)$$

| Compound No. | R³² | Ar¹ | Ar² |
|---|---|---|---|
| 147 | —N(H)— | 2,5-difluorophenyl | 2-methoxy-5-chlorophenyl |
| 148 | —N(H)— | 4-acetylphenyl | 2,5-dimethoxyphenyl |
| 149 | —O— | 2-carbamoylphenyl | 2-methoxy-5-chlorophenyl |
| 150 | —N(H)— | 2,3-dimethoxyphenyl | 2,3-dimethoxyphenyl |
| 151 | —N(H)— | pyrazin-2-ylmethyl | 2-methoxy-6-methylphenyl |
| 152 | —N(H)— | pyrazin-2-yl | 2-(trifluoromethoxy)phenyl |
| 153 | —N(H)— | pyrazin-2-yl | 4-fluorophenyl |

-continued
(VII)
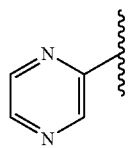
| Compound No. | R³² | Ar¹ | Ar² |
|---|---|---|---|
| 154 | —N(H)— | 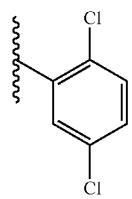 | 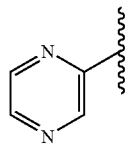 |
| 155 | —N(H)— | 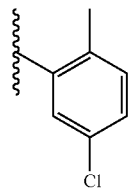 | 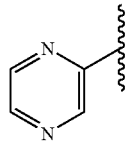 |
| 156 | —N(H)— | 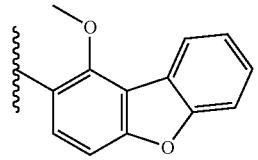 | 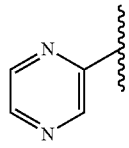 |
| 157 | —N(H)— | 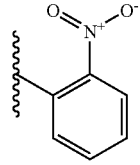 | 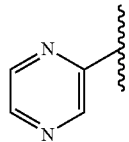 |
| 158 | —N(H)— | 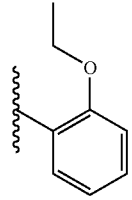 | 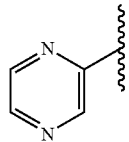 |
| 159 | —N(H)— | 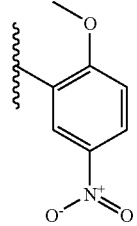 | 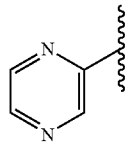 |
| 160 | —N(H)— | | 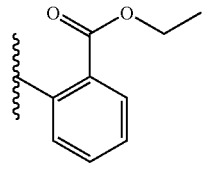 |

-continued

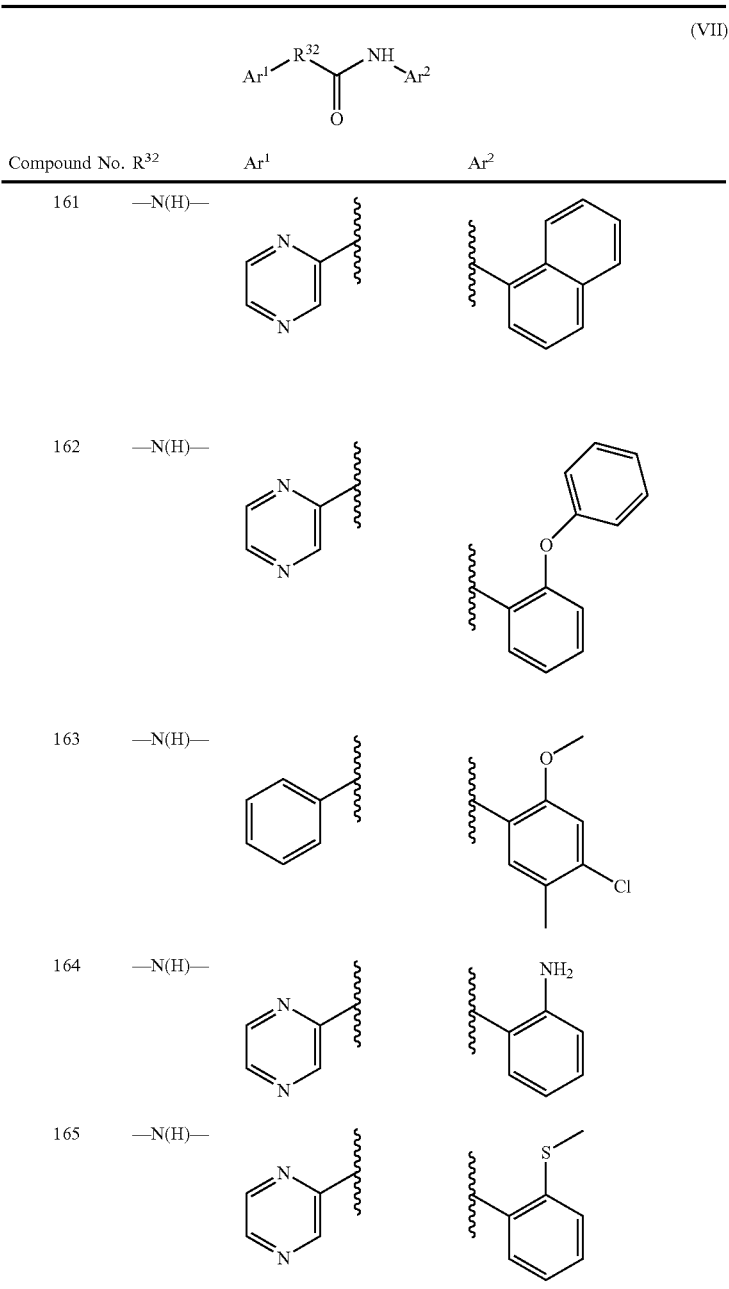

Some preferred compounds include Compound Nos. 2, 4, 6, 12, 72, 76, 83, 84, 88, 89, and 90.

Generally, compounds of structural formulae (I), (II), and (III), including those of formulae (IV), (V), (VI), and (VII), can be prepared according to the following synthetic scheme. In the scheme described below, it is understood in the art that protecting groups can be employed where necessary in accordance with general principles of synthetic chemistry. These protecting groups are removed in the final steps of the synthesis under basic, acidic, or hydrogenolytic conditions which are readily apparent to those skilled in the art. By employing appropriate manipulation and protection of any chemical functionalities, synthesis of compounds of structural formulae (I), (II), and (III) not specifically set forth herein can be accomplished by methods analogous to the schemes set forth below.

Unless otherwise noted, all starting materials were obtained from commercial suppliers and used without further purification. All reactions and chromatography fractions were analyzed by thin-layer chromatography on 250-mm silica gel plates, visualized with UV (ultraviolet) light and $I_2$ (iodine) stain. Flash column chromatography was carried out using Biotage 40M silica gel (230-400 mesh). Products and intermediates were purified by flash chromatography or reverse-phase HPLC.

As illustrated below, the compounds of general structural formulae (I) and (II) can be prepared by the following general synthetic schemes.

General Scheme 1

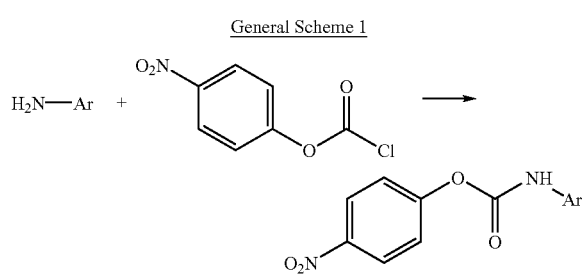

In general, an aryl amine represented by the formula Ar-NH$_2$ is reacted with about 0.75-1.25 molar equivalent of 4-nitrophenyl chloroformate. The reaction preferably is performed under an inert atmosphere, for example, nitrogen (N$_2$), and typically is maintained at low temperature (about 0° C.). The resulting product is treated with about 0.75-1.25 molar equivalent of a heteroaryl amine represented by the formula HetAr—NH$_2$, preferably under an inert atmosphere at room temperature (about 25° C.), to afford a crude aryl pyrazine-disubstituted urea compound.

A more particular illustration for the preparation compounds of standard formulae (I) and (II) can include, for example, the following General Scheme 2.

Step (1): TMS Diazomethane Esterification

To a cooled (about 0° C.), stirred solution of 4-amino-3-methoxybenzoic acid (5.0 g; 30 mmol) in dry methanol (150 mL) was added trimethylsilyl diazomethane (60 mL of 2.0 M solution in hexanes, 120 mmol) slowly over 1 hour. After stirring for 4 hours, the reaction was concentrated at reduced pressure, dissolved in ethyl acetate (200 mL), washed with 10% aqueous sodium carbonate and brine, then dried (MgSO$_4$), filtered, and concentrated in

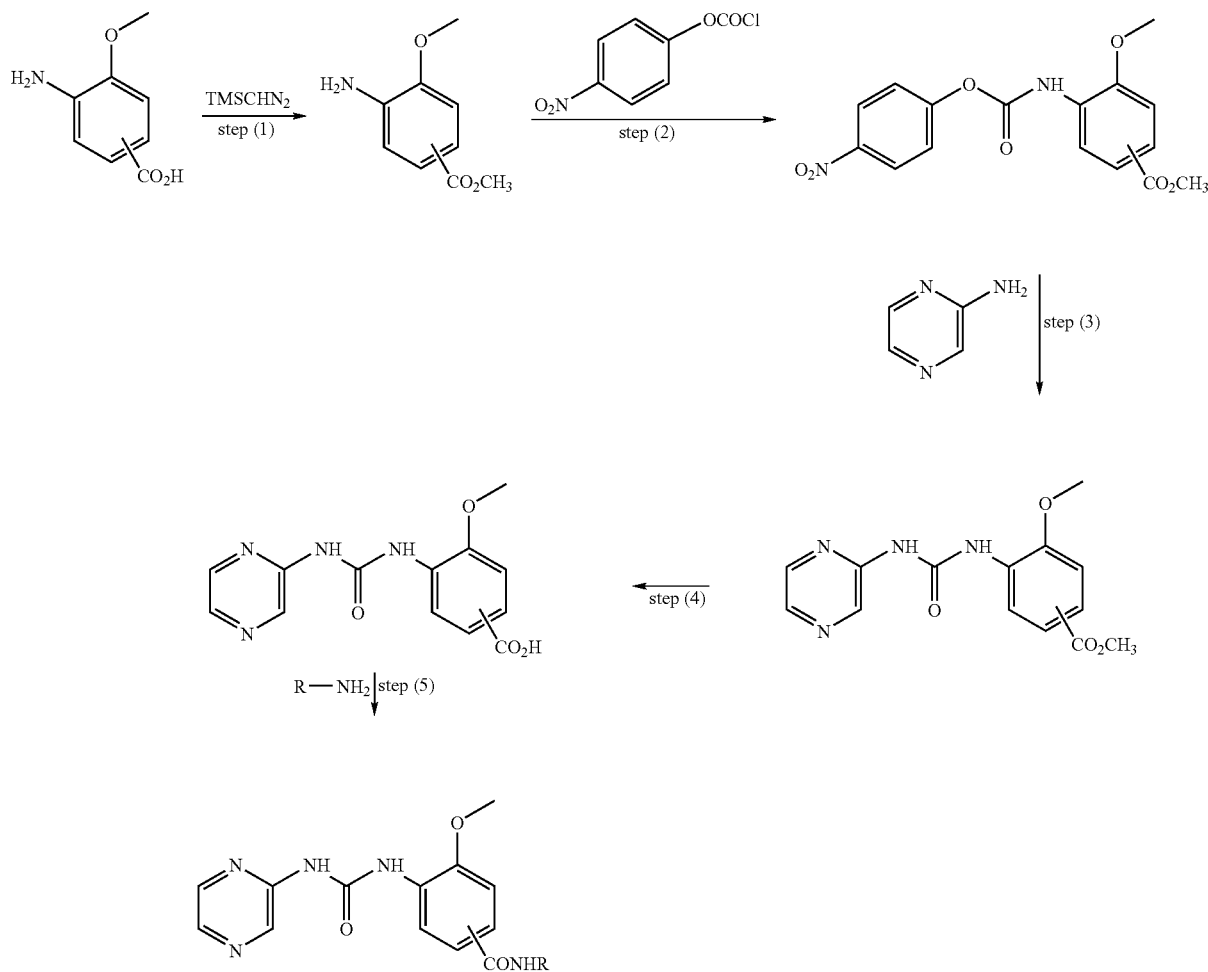

vacuo to provide the desired ester as an off-white solid (94% yield).

Step (2): p-Nitrophenyl Carbamate Procedure

To a stirred, cooled (about 0° C.) solution of methyl-3-amino-4-methoxy benzoate (5.0 g; 27.6 mmol) in dry dichloromethane (175 mL) was added pyridine (2.34 mL; 29 mmol) followed by 4-nitrophenyl chloroformate (5.8 9; 29 mmol) under a nitrogen ($N_2$) atmosphere. After stirring for 8 hours, the, reaction was washed with 2N aqueous hydrochloric acid (2×200 mL), saturated aqueous sodium bicarbonate (2×200 mL), and brine (200 mL), then dried ($MgSO_4$), and filtered. The filtered solution was diluted with ethyl acetate and hexanes (about 800 mL) until a precipitate formed. The solid was collected on a Buchner funnel with suction, and air dried to provide the desired carbamate as a white solid (70% yield).

Step (3): Carbamate Coupling Procedure

To a stirred solution of 4-methoxy-3-(4-nitro-phenoxycarbonylamino)-benzoic acid methyl ester (30 g; 8.7 mmol) in dry N-methyl pyrrolidine (50 mL) was added the amino pyrazine (0.84 g; 8.8 mmol) under a $N_2$ atmosphere at room temperature. The reaction mixture was heated to 80° C. for 6 hours, then allowed to cool to room temperature. Dilution with ethyl acetate (200 mL) and water (200 mL) provided the desired urea as a white solid (54% yield). Step (4): Lithium Hydroxide Hydrolysis Procedure To a stirred solution of 4-methoxy-4-(3-pyrazin-2-yl-ureido)-benzoic acid methyl ester (1.0 g; 3.3 mmol) in methanol (35 mL) was added aqueous lithium hydroxide (5 mL of a 2N solution; 10 mmol) at room temperature. The reaction was heated to 67° C. for 15 hours, then allowed to cool to room temperature. The reaction then was diluted with water (100 mL), and washed with ethyl acetate (2×100 mL). The pH of the, aqueous layer was adjusted to pH 5.2 with 2N aqueous hydrochloric acid, and the resulting precipitate was collected on a Buchner funnel with suction and air-dried to provide the desired acid as a white solid.

Step (5): HBTU Coupling Procedure

To a stirred solution of the acid (30 mg; 0.11 mmol) in dry N-methyl pyrrolidinone (2 mL) was added O-benzotrazol-1-yl-N,N, N',N'-tetramethyl-uronium hexafluorophosphate (HBTU; 45 mg; 0.12 mmol), 4-(2-aminioethyl)-morpholine (15.7 L; 0.12 mmol) and diisopropyl ethyl amine (34 L, 0.2 mmol) at room temperature under a nitrogen atmosphere. The resulting solution was stirred 5 hours, then diluted with ethyl acetate (30 mL) and 10% aqueous sodium carbonate (30 mL). After stirring vigorously at room temperature for 15 minutes, the precipitate was collected on a Buchner funnel with suction and air-dried to provide the desired amide as a white solid (59% yield).

The following compounds were prepared using the general procedure described accompanying General Scheme 2, but substituting the R group below for the R group shown in General Scheme 2:

| Compound No. | R group | Characterization |
|---|---|---|
| 22 | 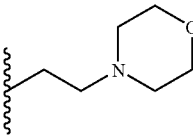 | $^1$H NMR(400 MHz, $D_6$ DMSO) d 10.15(br s, 1H), 8.90(s, 1H), 8.69(d, 1H), 8.53(t, 1H), 8.27(t, 1H), 8.18(d, 1H), 7.53(dd, 1H), 3.96(br s, 2H), 3.93(s, 3H), 3.67–3.53(m, 6H), 3.29(t, 2H), 3.10(t, 2H). LRMS(esi, positive) m/e 401.2(M+1). |
| 11 | 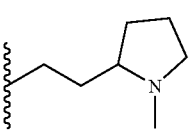 | $^1$H NMR(400 MHz, $D_6$ DMSO) d 10.14(br s, 1H), 8.91(s, 1H), 8.66(d, 1H), 8.27(dd, 1H), 8.18(d, 1H), 7.51(dd, 1H), 7.03(d, 1H), 3.91(s, 3H), 3.53(br s, 1H), 3.33 (d, 2H), 3.21(br s, 1H), 3.02(br s, 1H), 2.78(d, 2H), 2.48(s, 3H), 2.31(br s, 1H), 2.13(br s, 1H), 1.99–1.82(m, 2H). LRMS(esi, positive) m/e 399.2(M+1). |
| 25 | 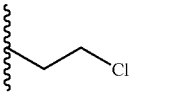 | $^1$H NMR(400 MHz, $D_6$ DMSO) d 10.20(br s, 1H), 8.87(s, 1H), 8.31–8.26(M, 2H), 8.21 (br s, 1H), 7.52–7.44(m, 2H), 3.95(s, 3H), 3.72(t, 2H), 3.56(t, 3H). |
| 28 | 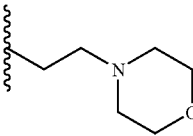 | $^1$H NMR(400 MHz, $D_6$ DMSO) d 10.22(br s, 1H), 8.90(br s, 1H), 8.64(t, 1H), 8.31–8.28 (m, 2H), 8.19(d, 1H), 7.51–7.47(m, 2H), 3.97(br s, 2H), 3.93(s, 3H), 3.69–3.52(m, 6H), 3.30(t, 2H), 3.11(t, 2H). LRMS(esi, positive) m/e 401.1(M+1). |
| 1 | 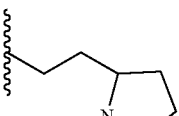 | $^1$H NMR(400 MHz, $D_6$ DMSO) d 10.20(br s, 1H), 8.88(br s, 1H), 8.40(t, 1H), 8.32(t, 1H), 8.23(dd, 2H), 7.47(d, 1H), 7.43(dd, 1H), 3.94(s, 3H), 2.91(c, 2H), 2.19(s, 3H), 2.05–1.98(m, 2H), 1.93–1.80(m, 2H), 1.60(c, 1H), 1.43(c, 1H). LRMS(esi, positive) m/e 399.0(M+1). |
| 35 | 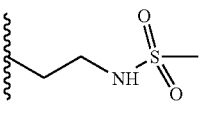 | $^1$H NMR(400 MHz, $D_6$ DMSO) d 10.21(br s, 1H), 8.88(br s, 1H), 8.48(br s, 1H), 8.32 (t, 1H), 8.26(s, 1H), 8.23 (d, 1H), 7.50(br s, 1H), 7.46(dd, 1H), 3.95(s, 3H), 3.36(c, 2H), 3.10(t, 2H), 2.83(s, 3H). LRMS(esi, positive) m/e 409.0(M+1). |
| 44 | 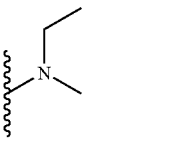 | $^1$H NMR(400 MHz, $D_6$ DMSO) d 11.47(br s, 1H), 8.48(br s, 1H), 8.41(s, 1H), 8.35(d, 1H), 8.25–8.23(M, 2H), 7.06–7.02(m, 2H), 3.98(s, 3H), 3.38(br s, 2H), 3.04(br s, 3H), 1.21(br s, 3H). LRMS(esi, positive) m/e 330.0(M+1). |

General Scheme 3

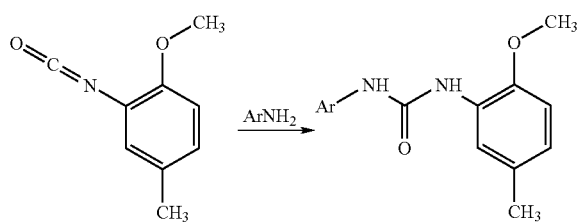

Isocyanate Procedure

To a stirred solution of 2-methoxy-5-methyl-phenylisocyanate (43 mL; 0.3 mmol) in dry dichloroethane (0.4 mL) was added 2-aminoquinoxaline (43.5 mg; 0.3 mmol) in a reaction vial under a nitrogen atmosphere. The vial was capped and heated to 80° C. overnight (14 hours). The reaction mixture then was filtered, and the residue washed with dichloromethane to provide the desired urea as a white solid (91% yield).

The following compounds were prepared using the procedure described accompanying General Scheme 3, but substituting the Ar group in the table below for the Ar group in General Scheme 3:

| Compound No. | Ar group | Characterization |
|---|---|---|
| 90 | quinoxalin-2-yl | $^1$H NMR(400 MHz, D$_6$ DMSO) d 11.65(br s, 1H), 10.58(br s, 1H), 10.58(br s, 1H), 8.80(s, 1H), 8.15(d, 1H), 7.98(d, 1H), 7.84–7.80(m, 2H), 7.65(c, 1H), 6.98(d, 1H), 6.98(d, 1H), 6.84(dd, 1H), 3.99(s, 3H), 2.25(s, 3H). LRMS(esi, positive) m/e 309.1(M+1). |
| 98 | pyrimidin-4-yl | $^1$H NMR(400 MHz, D$_6$ DMSO) d 9.61(s, 1H), 8.06(d, 1H), 7.35(d, 1H), 6.88(dd, 1H), 8.87(d, 1H), 5.42(d, 1H), 3.89(s, 3H), 2.33(s, 3H). LRMS(esi, positive) m/e 259.0(M+1). |
| 97 | 1,2,4-triazin-3-yl | $^1$H NMR(400 MHz, D$_6$ DMSO) d 11.29(s, 1H), 10.64(s, 1H), 9.05(d, 1H), 8.70(d, 1H), 8.05(d, 1H), 6.92(d, 1H), 6.81(c, 1H), 3.85(s, 3H), 2.24(s, 3H) LRMS(esi, positive) m/e 259.0(M+1). |
| 91 | 6-phenylpyrazin-2-yl | $^1$H NMR(400 MHz, D$_6$ CDCl$_3$) d 11.12(br s, 1H), 8.61(br s, 1H), 8.28(s, 1H), 8.24(s, 1H), 8.14(d, 1H), 8.04–8.01 (m, 2H), 7.55–7.50(m, 3H), 6.86(dd, 1H), 6.76(d, 1H), 3.52(s, 3H), 2.35(s, 3H). LRMS(esi, positive) m/e 335.2(M+1). |
| 12 | pyrazin-2-yl | $^1$H NMR(300 Mhz, d$_6$-DMSO) δ: 10.10(s, 1H), 10.00(br s, 1H), 8.90(s, 1H), 8.32(s, 1H), 8.23(s, 1H), 8.04(s, 1H), 7.93(d, 1H), 6.81(d, 1H), 3.87(s, 3H), 2.28(s, 3H). $^{13}$C NMR(75 Mhz, d$_6$-DMSO) δ: 151.5, 149.3, 146.0, 140.9, 137.2, 135.2, 129.2, 127.7, 122.7, 119.5, 110.8, 55.9, 20.5 |

EXAMPLES

Example 1

Preparation of Compound 115

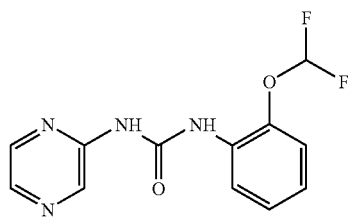

1-[2-(1,1-difluoromethoxy)-phenyl]-3-pyrazin-2-yl-urea 2-(Difluoromethoxy)phenylisocyanate (1.0 g, 5.4 mmol) and aminopyrazine (0.51 g, 5.4 mmol) were reacted for 6 hours in refluxing dimethoxy-ethane (20 mL). The reaction mixture was cooled to room temperature to precipitate the product, which was collected by filtration, washed with ethyl acetate, and dried in vacuo (765 mg, 50%). $^1$H NMR (300 Mhz, $d_6$-DMSO) δ: 10.49 (br s, 1H), 10.26 (s, 1H), 8.83 (s, 1 H), 8.35-8.24 (m, 3H), 7.53-7.00 (m,4H).

Example 2

Preparation of Compound 165

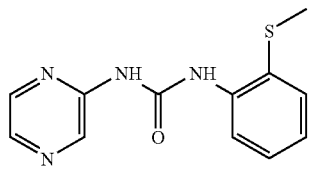

1-(2-methylsulfanylphenyl)-3-pyrazin-2-yl urea 2-(Methylthiophenyl)-isocyanate (1.0 g, 6.1 mmol) and aminopyrazine (0.58 g, 6.1 mmol) were reacted for 16 hours in refluxing dimethoxyethane (40 mL). The product precipitated from the cooled reaction mixture and was collected by filtration, washed with dimethoxyethane, and dried in vacuo (715 mg, 45%). $^1$H NMR (300 MHz, $d_6$-DMSO) δ: 10.35(br s, 1H), 10.29 (s, 1H), 8.84 (s, 1H), 8.33 (s, 1H), 8.27 (s, 1H), 8.09 (d, 1H), 7.45 (d, 1H), 7.29, (t, 1H), 7.10 (t, 1H) , 2.43 (s, 3H). $^{13}$C NMR (75 Mhz, $d_6$-DMSO) δ: 151.8, 149.2, 140.5, 137.5, 137.3, 135.2, 130.1, 127.1, 126.9, 123.7, 121.4, 16.5.

Example 3

Preparation of Compound 159

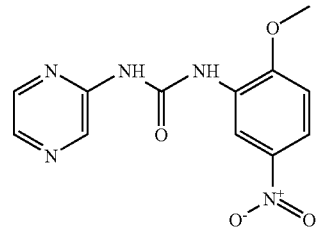

1-(2-methoxy-5-nitrophenyl)-3-pyrazin-2-yl-urea

A mixture of 2-methoxy-5-nitrophenyl iso-cyanate (5.0 g, 25 mmol) and aminopyrazine (2.5 g, 26 mmol) in tetrahydrofuran (THF, 250 mL) was stirred at reflux for 24 hours. The product was precipitated from the cooled reaction mixture and was collected by filtration, washed with ethyl acetate, and dried in vacuo (4.3 g, 57%). $^1$H NMR (300 MHz, $d_6$-DMSO) (mixture of rotamers) δ: 10.38 (br, s, 1H), 10.27 (s, 1H), 9.39, 8.88 (2 singlets, 1H), 9.10(d, 1H), 8.33 (s, 1H), 8.26 (d, 1H), 7.98-8.25 (m, 1H), 7.97-7.84 (m, 1H), 4.05, 4.03 (2 singlets, 77:28 ratio, 3H).

Example 4

Preparation of Compound 14

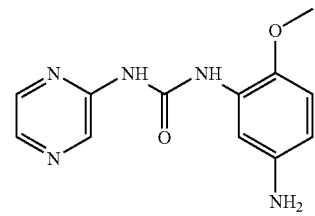

1-(5-amino-2-methoxyphenyl)-3-pyrazin-2-yl-urea

A solution of (2-methoxy-5-nitrophenyl)-3-pyrazin-2-yl-urea (Compound 159, Example 3) (16.9 g, 55 mmol) in dimethylformamide (DMF, 320 mL) was shaken under $H_2$ in the presence of palladium on carbon (Pd/C) catalyst (1.6 g, 10% Pd) at 80° C. for 12 h. A second portion of catalyst was added (1.6 g) and shaking was continued for an additional 8 h at the same temperature. The solution was filtered through a pad of celite using an additional 200 mL of DMF. The filtrate was concentrated in vacuo and the residue was triturated with methanol (100 mL). The solid was collected, stirred in boiling methanol, and solids present (1.8 g) were filtered off and discarded. The filtrate was cooled at 4° C. overnight. Solids (1.4 g) were removed by filtration and the filtrate was concentrated in vacuo to a tan solid (2.6 g). The crude solid product was triturated with THF (200 mL), collected by filtration, and dried in vacuo to afford the product as a tan solid (1.85 g, 13%). $^1$H NMR (300 Mhz, $d_6$ DMSO) δ: 10.10 (s, 1H), 9.94 (br s, 1H), 8.89 (s, 1H), 8.32 (s, 1H), 8.22 (s, 1H), 7.58 (d, 1H), 7.75 (d, 1H), 6.21 (d, 1 H), 4.70 (s, 2H), 3.76 (s, 3H). $^{13}$C NMR (75 Mhz, $d_6$-DMSO) δ: 151.4, 149.4, 142.6, 140.9, 139.8, 137.2, 135.2, 128.7, 112.8, 107.7, 106.0, 56.8.

Example 5

Preparation of Compound 48

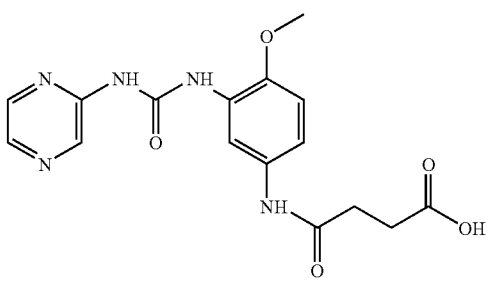

N-[4-methoxy-3-(3-pyrazin-2-yl-ureido) phenyl]-succinamic acid

A solution of 1-(5-amino-2-methoxyphenyl)-3-pyrazin-2-yl-urea (Compound 14, Example 4) (260 mg, 1 mmol), and succinic anhydride (131 mg, 1.3 mmol) in dry pyridine (10 mL) was stirred 16 h at room temperature. The resulting solid was collected by filtration and triturated with chloroform, and dried in vacuo to afford the off-white product (175 mg, 50%). $^1$H NMR (300 Mhz, $d_6$-DMSO) δ: 10.15 (s, 1H), 10.05 (s, 1H), 9.87 (s, 1H), 8.90 (s, 1H), 8.33 (s, 2H), 8.24 (s, 1H), 7.42 (dd, J=8.8, 2.2 Hz, 1H), 6.96 (d, J 8.8 Hz, 1H), 3.87 (s, 3H), 2.54 (br s, 4H).

Example 6

Preparation of Compound 36

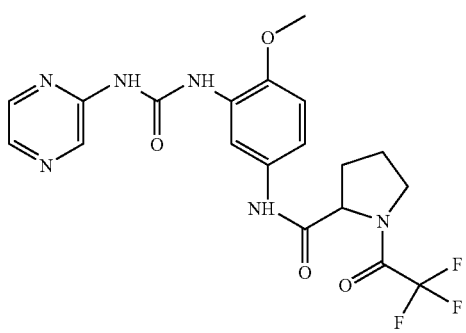

(S)-1-(2,2,2-trifluoroethanoyl)pyrrolidine-2-carboxylic acid [4-methoxy-3-(3-pyrazin-2-yl-ureido)phenyl]-amide A solution of 1-(5-amino-methoxyphenyl)-3-pyrazin-2-yl-urea (Compound 14, Example 4) (105 mg, 0.4 mmol) in dry pyridine (2 mL) at 0° C. was treated with a solution of N-trifluoroacetyl-(S)-prolyl chloride (0.1 M in dichloromethane, 4.5 mL, 0.45 mmol) and stirred 2 h at room temperature. The reaction was quenched with 1 N HCl (50 mL) and extracted with ethyl acetate (3×50 mL). The combined organic layers were washed with 1 N HCl (2×20 mL), water (20 mL), brine (20 mL), dried over sodium sulfate, and concentrated in vacuo to a beige solid (60 mg). Recrystallization from acetonitrile yielded the final solid product (30 mg, 17%). $^1$H NMR (300 Mhz, $d_6$-DMSO) δ: (10.16-10.06, m, 3H), 8.90 (s, 1H), 8.36-8.30 (m, 2H), 8.25 (d, J=2.6 Hz, 1H), 7.42 (dd, J=8.8, 2.6 Hz, 1H), 6.98 (d, J=8.8 Hz, 1H), 4.57 (dd, J=8.5, 4.4 Hz, 1 H), 3.88 (s, 3H), 3.73 (t, J=6.5 Hz, 1H), 2.27-2.21 (m, 1H), 2.06-1.90 (m, 3H). LRMS (ESI, positive) m/e 453.1 (M +1).

Example 7

Preparation of Compound 16

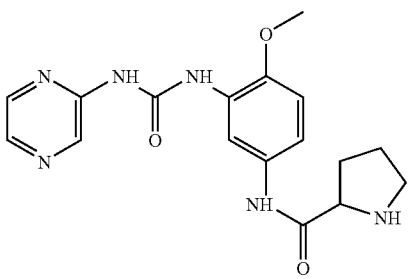

(S)-pyrrolidine-2-carboxylic acid [4-methoxy-3-(3-pyrazin-2-yl-ureido)-phenyl]-amide A suspension of (S)-1-(2,2,2-trifluoro-ethanoyl)-pyrrolidine-2-carboxylic acid [4-methoxy-3-(3-pyrazin-2-yl-ureido)-phenyl]-amide (Compound 36, Example 6) (22 mg, 0.05 mmol) in a mixture of methanol (MeOH, 5 mL) and water (about 0.25 mL) was treated with KOH (100 mg, large excess). Within 10 minutes, all ingredients were in solution. The reaction mixture was treated with water (20 mL) and extracted with ethyl acetate (2×20 mL). The organic layers were combined and washed with water (10 mL) and brine (10 mL), dried with sodium sulfate, and concentrated to a tan solid (13 mg, 75%). $^1$H NMR (300 MHz, $d_6$-DMSO) δ: 10.13 (s, 1H), 10.03 (s, 1H), 9.85 (s, 1H), 8.90 (s, 1H), 8.38-8.28 (m, 2H), 8.25 (d, J=2.6 Hz, 1H), 7.41 (dd, J=8.8, 2.6 Hz), 6.98 (d, J=8.8 Hz, 1H), 3.88 (s, 3H, 3.69 (dd, J=8.7, 5.6 Hz, 1H), 2.94-2.87 (m, 2H), 2.10-1.97 (m, 1H), 1.81-1.60 (m, 3H). LRMS (ESI, positive) m/e 357.1 (M +1).

Example 8

Preparation of Compound 42

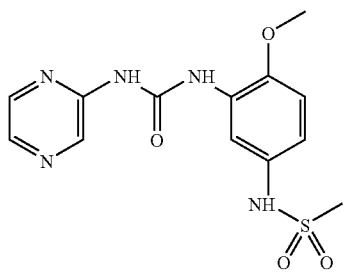

N-[4-methoxy-3-(3-pyrazin-2-yl-ureido)phenyl]-methanesulfonamide

A solution of 1-(5-amino-2-methoxyphenyl)-3-pyrazin-2-yl-urea (Compound 14, Example 4) (260 mg, 1 mmol) in dry pyridine (15 mL) was treated with methanesulfonyl chloride (0.08 mL, 1 mmol) and stirred 16 h at room temperature. The reaction mixture was concentrated in vacuo and the solid residue was triturated with ethanol, collected by filtration, and dried in vacuo to afford the product (205 mg, 61%). $^1$H NMR (300 Mhz, $d_6$-DMSO) δ: 10.16 (s, 1H), 10.07 (s, 1H), 9.40 (s, 1H), 8.92 (s, 1H), 8.35 (s, 1H), 8.27 (s, 1H), 8.19 (d, J=2.2 Hz, 1H), 7.04 (d, J=8.8 Hz, 1H), 6.91 (dd, J=8.7, 2.4 Hz, 1H), 3.91 (s, 3H), 2.91 (s, 3H).

Example 9

Preparation of Compound 65

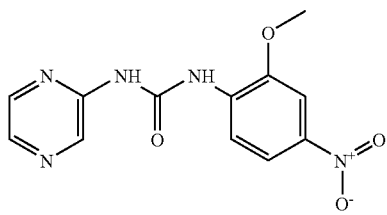

1-(2-methoxy-4-nitrophenyl)-3-pyrazin-2-yl-urea

A mixture of 2-methoxy-4-nitrophenyl iso-cyanate (15.0 g, 77 mmol) and aminopyrazine (7.35 g, 77 mmol) in THF (600 mL) was stirred at reflux for 24 hours. The product precipitated from the cooled reaction mixture and was collected by filtration, washed with ethyl acetate, triturated with hot ethanol, and dried in vacuo (16.3 g, 73%). $^1$H NMR (300 Mhz, d$_6$DMSO) δ: 10.50 (br s, 1H), 10.42 (s, 1H), 8.94 (s, 1H), 8.48 (d, 1H), 8.39 (s, 1H), 8.32 (d, 1H), 7.95 (dd, J=9.1, 2.4 Hz, 1H), 7.84(d, J=2.4 Hz, 1 H), 4.08 (s, 3H)

Example 10

Preparation of Compound 32

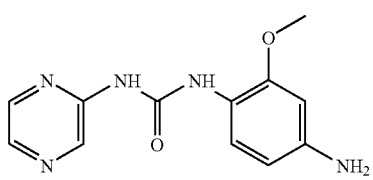

1-(4-amino-2-methoxyphenyl)-3-pyrazin-2-yl-urea

A solution of (2-methoxy-4-nitrophenyl)-3-pyrazin-2-yl-urea (Compound 65, Example 9) (7.9 g, 27 mmol) in DMF (300 mL) was shaken under H$_2$ in the presence of Pd/C catalyst (1.6 g, 10% Pd) at 110° C. for 4 h. The mixture was filtered through a pad of celite using an additional 200 mL of DMF. The filtrate was concentrated in vacuo and the residue was recrystallized from ethanol (with a hot filtration step) to yield the light gray product (2.9 g, 41%). $^1$H NMR (300 MHz, d$_6$-DMSO) δ: 9.83 (s, 1H), 9.50 (s, 1H), 8.86 (s, 1H), 8.28 (s, 1H), 8.19 (d, J=2.5 Hz, 1H), 7.64 (d, J=8.5 Hz, 1H), 6.31 (d, J=2.0 Hz, 1H), 6.13 (dd, J=8.5, 2.0 Hz, 1H), 4.92 (s, 2H), 3.79 (s, 3H). $^{13}$C NMR (75 Mhz, d$_6$-DMSO) δ: 151.6, 150.0, 149.6, 145.2, 140.9, 136.9, 135.1, 121.6, 116.8, 105.5, 98.0, 55.4.

Example 11

Preparation of Compound 3

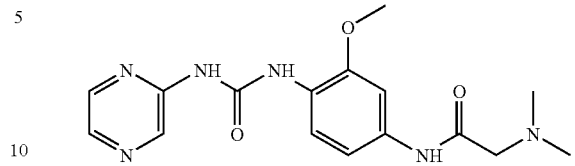

C-dimethylamino-N-[3-methoxy-4-(3-pyrazin-2-yl-ureido)phenyl]-acetamide

A solution of N,N-dimethylglycine (124 mg, 1.2 mmol) and triethylamine (0.33 mL, 2.4 mmol) in dry acetonitrile (5 mL) at 0° C. was treated dropwise with isobutyl chloroformate (0.16 mL, 1.2 mmol) and stirred 15 min. This mixture was treated dropwise with a solution of 1-(4-amino-2-methoxyphenyl)-3-pyrazin-2-yl-urea (Compound 32, Example 10) (100 mg, 0.4 mmol) in dimethyl sulfoxide (DMSO, 1 mL). The reaction mixture was stirred at room temperature for 3 h, quenched with water (20 mL), and extracted with ethyl acetate (2×15 mL). The combined organic layers were washed with water (10 mL) and brine (10 mL), dried over sodium sulfate, and concentrated in vacuc. The residue was dissolved in DMSO (1 mL) and purified by HPLC (YMC 20×50 mm C18 CombiPrep column, 20 mL/min, 2-50% CH$_3$CN/water in 6 min, all solvents contained 0.05% trifluoroacetic acid (TFA), 0.35 mL injections, detector at 254 nm, detector path length 0.2 mm). Fractions containing the product were concentrated in vacuo to afford the product as the trifluoroacetate (TFA) salt (24 mg, 17%).

Example 12

Preparation of Compound 8

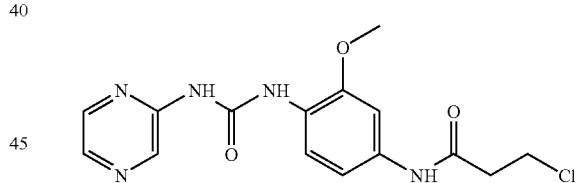

3-chloro-N-[3-methoxy-4-(3-pyrazin-2-yl-ureido) phenyl]-propionamide

A solution of 1-(4-amino-2-methoxyphenyl)-3-pyrazin-2-yl-urea (Compound 32, Example 10) (259 mg, 1 mmol) in pyridine (3 mL) at 0°C. was treated with chloroacetyl chloride (0.29 mL, 3 mmol). The suspension was warmed at 80° C. until most solids dissolved, the reaction mixture was cooled to room temperature and the product was precipitated with ether (10 mL). This crude product was used without purification for further reactions, but a portion (30 mg) was purified by HPLC (Luna 10×250 mm C18 column, 4.7 mL/min, 2-80% CH$_3$CN/water in 15 min, all solvents contained 0.05% TFA, 0.25 mL injections, detector at 254 nm, detector path length 0.3 mm). Fractions containing the product were concentrated in vacuo to afford the product. $^1$H NMR (300 Mhz, d$_6$-DMSO) δ: 10.00 (s, 2H), 9.94 (s, 1H), 8.87 (s, 1H), 8.32 (dd, J=2.5, 1.5 Hz, 1H), 8.23 (d, J=2.6 Hz, 1H), 8.05 (d, J=8.7 Hz, 1H), 7.49 (d, J=2.1 Hz, 1H), 7.07

(dd, J=8.7, 2.1 Hz, 1H), 3.90-3.80 (m, 5H), 2.80 (t, J=6.2 Hz, 2H). LRMS (ESI, positive)-m/e 350, 352 (M +1).

Example 13

Preparation of Compound 4

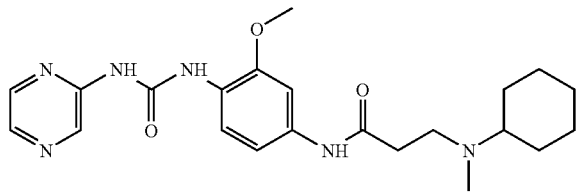

(cyclohexyl-methyl-amino)-N-[3-methoxy-4-(3-pyrazin-2-yl-ureido)phenyl]-propionamide A mixture of 3-chloro-N-[3-methoxy-4-(3-pyrazin-2-yl-ureido)phenyl]-propionamide (Compound 8, Example 12) and N-cyclohexyl-methylamine (0.5 mL, large excess) was warmed at 80° C. for 1 h and cooled to room temperature. Crude product was precipitated from ether (10 mL), collected by filtration, and dissolved in DMSO (0.5 mL). Aliquots (about 0.25 mL) were purified by HPLC (Luna 10×250 mm C18 column, 4.7 mL/min, 2-80% CH₃CN/water in 15 min, all solvents contained 0.05% trifluoroacetic acid, detector at 254 nm, detector path length 0.3 mm). Fractions containing the product were concentrated in vacuo to afford the product as the TFA salt (4.7 mg, 11%). $^1$H NMR (300 Mhz, d₆-DMSO) δ: 10.18 (s, 1H), 10.07 (s, 1H), 9.98 (s, 1H), 9.04 (br s, 1H), 8.88 (s, 1H), 8.33 (dd, J=2.6, 1.5 Hz, 1H), 8.24 (d, J=2.6 Hz, 1H), 8.08 (d, J=8.7 Hz, 1H), 7.43(d, J=2.1 Hz, 1H), 7.09(dd, J=8.7, 2.1 Hz, 1H), 3.90-3.83 (m, 1H), 3.30-3.16 (m, 2H), 2.81 (t, J=6.7 Hz, 1H), 2.74 (d, J=5.0 Hz, 2H), 2.03-1.89 (m, 2H), 1.89-1.75 (m, 2H), 1.70-1.53 (m, 1H), 1.46-1.10(m, 5H). LRMS (ESU, positive) m/e 427.2 (M+1).

Example 14

Preparation of Compound 2

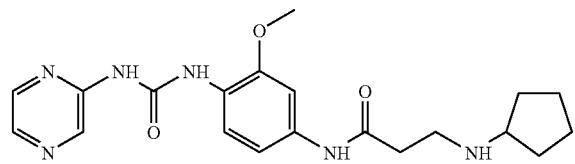

3-cyclopentylamino-N-[3-methoxy-4-(3-pyrazin -2-yl-ureido)phenyl]-propionamide

A mixture of 3-chloro-N-[3-methoxy-4-(3-pyrazin-2-yl-ureido)phenyl]-propionamide (Compound 8, Example 12) and cyclopentylamine (0.5 mL, large excess) was warmed at 80° C. for 1 h and cooled to room temperature. The product was precipitated from ether (10 mL), collected by filtration, washed with ether, and dried in vacuo (24 mg, 60%). $^1$H NMR (300 Mhz, d₆-DMSO) δ: 10.14 (s, 1H), 10.03 (s, 1H), 9.93 (s, 1H), 8.87 (d, J=1.1 Hz, 1H), 8.31 (dd, J=2.6, 1.5 Hz. 1H), 8.23 (d, J=2.7 Hz, 1H), 8.03(d, J=8.7 Hz, 1H), 7.47,(d, J=2.1 Hz, 1H), 7.04(dd, J=8.7, 2.1 Hz, 1H), 3.87 (s, 3H), 3.05 (quintet, J=6.3 Hz, 1H), 2.80 (t, J=6.6 Hz, 2H), 2.44 (t, J=6.6 Hz, 2H), 1.80-1.67 (m, 2H), 1.65-1.56 (m, 2H), 1.53-142 (m, 2H), 1.37-1.27 (m, 2H). LRMS (ESI, positive) m/e 399.1 (M+1).

Compound 166

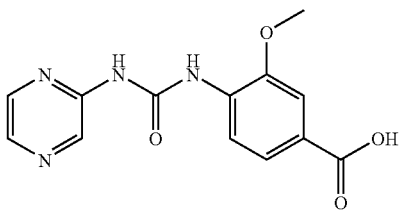

3-Methoxy-4-(3-pyrazin-2-yl-ureido)-benzoic acid

Step 1: Methyl-3-amino-4-methoxy benzoate. To a cooled (about 0° C.), stirred solution of 4-amino-3methoxybenzoic acid (5.0 g, 30 mmol) in dry methanol (150 mL) was added trimethylsilyldiazomethane (60 mL of 2M solution in hexanes, 120 mmol) slowly over 1 hour. After stirring for 4 hours, the reaction was concentrated at reduced pressure, dissolved in ethyl acetate (200 mL), washed with 10% aqueous sodium carbonate and brine, then dried (MgSO₄), filtered, and concentrated in vacuo to provide the desired ester as an off-white solid (94% yield).

Step 2: 4-Methoxy-3-(4-nitro-phenoxycarbonylamino)-benzoic acid methyl ester. To a stirred, cooled (about 0° C.) solution of methyl-3-amino-4-methoxy benzoate (5.0 g, 27.6 mmol) in dry dichloromethane (90 mL) was added pyridine (2.34 mL, 29 mmol) followed by 4-nitophenyl chloroformate (5.8 g, 29 mmol) under a nitrogen atmosphere. After stirring for I hour, the reaction was diluted to 200 mL with dichloromethane and washed with 2N aqueous hydrochloric acid (2×200 mL), saturated aqueous sodium bicarbonate (2×200 mL), and brine (200 mL), then dried (MgSO₄), and filtered. The filtered solution was concentrated to a white solid corresponding to the desired carbamate (98% yield).

Step 3: 3-Methoxy-4-(3-pyrazin-2-yl-ureido)-benzoic acid methyl ester. To a stirred solution of 4-methoxy-3-(4-nitro-phenoxycarbonylamino)-benzoic acid methyl ester (10.64 g, 30.7 mmol) in dry N-methyl pyrrolidinone (31 mL) at room temperature under nitrogen was added aminopyrazine (2.92 g, 30.7 mmol) and the reaction was warmed to 85° C. After 6 hours, the reaction was cooled to room temperature and triturated with ethyl acetate (200 mL). The precipitate formed was filtered off, rinsed with ethyl acetate and dried to give the urea as a tan solid (66 % yield).

Step 4: 3-Methoxy-4-(3-pyrazin-2-yl-ureido)-benzoic acid. To a stirred suspension of 3-methoxy-4-(3-pyrazin-2-yl-ureido)-benzoic acid methyl ester (6.07 g, 20 mmol) in 200 mL 3:1 MeOH:H₂O at room temperature under nitrogen was added lithium hydroxide monohydrate (8.4 g, 200 mmol) and the reaction heated to 65 ° C. overnight. The reaction was then cooled to room temperature and most of the methanol removed by rotary evaporation. The remaining suspension was neutralized to pH about 4 with concentrated HCl. The formed precipitate was isolated by filtration and rinsing with H₂O and then drying under high vacuum to give the desired acid as a white solid (5.34 g, 93%). $^1$H-NMR (400 MHz, d₆-DMSO) δ 8.89 (br s, 1H), 8.34 (s, 1H), 8.24 (s, 1H), 8.16 (d, 1H), 8.16 (d, 1H), 7.56 (s, 1H), 7.50 (d, 1H), 3.91 (s, 3H)

Compound 167

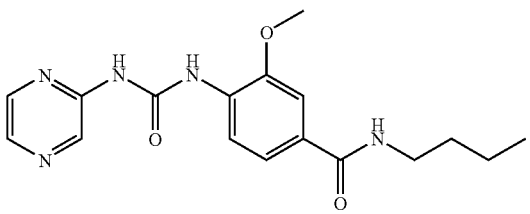

N-Butyl-3-methoxy-4-(3-pyrazin-2-yl-ureido)-benzamide

To a stirred suspension of Compound 1xx (32 mg, 0.11 mmol) in 1 mL of NMP at room temperature in a capped reaction vial was added HBTU (0.4 M in NMP, 300 μL, 0.12 mmol) and the suspension stirred for 15 minutes. N-Butyl amine (0.4 M in NMP, 300 mL, 0.12 mmol) was then added followed by DIEA(38 μL, 0.22 mmol). The reaction was stirred at room temperature overnight and was then diluted with EtOAc (20 mL) and 10% $Na_2CO_3$ (20 mL) and stirred rapidly for 5 minutes. A precipitate formed which was isolated by filtration and rinsing with H20 and EtOAc. After air drying, the amide was isolated as an off-white solid (12.2 mg, 32 %). $^1$H-NMR (400 MHz, $d_6$-DMSO) δ 8.92 (br s, 1H), 8.37 (br s, 2H), 8.23 (d, 1H), 8.21 (s, 1H), 7.53 (s, 1H), 7.47 (d, 1H), 3.97 (s. 3H), 3.23 (q, 2H), 1.52 (m, 2H), 1.35 (m, 2H), 0.92 (t, 3H) LRMS (apci, positive) m/e 344.1 (M+1)

Compound 168

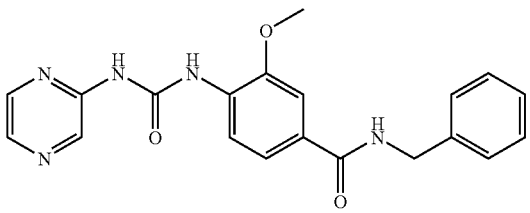

N-Benzyl-3-methoxy-4-(3-pyrazin-2-yl-ureido)-benzamide

Prepared according to the procedure of Compound 167 using benzyl amine (39% yield). $^1$H-NMR (400 MHz, $d_6$-DMSO) δ 8.96 (t, 1H), 8.91 (s, 1H), 8.56 (s, 1H), 8.50 (s, 1H), 8.44 (m, 1H), 7.58 (s, 1H), 7.56 (d, 1H), 7.35 (m, 4H), 7.23 (i, 1H), 4.46 (d, 2H), 3.97, (s, 3H) LRMS (apci, positive) m/e 378.1 (M+1)

Compound 169

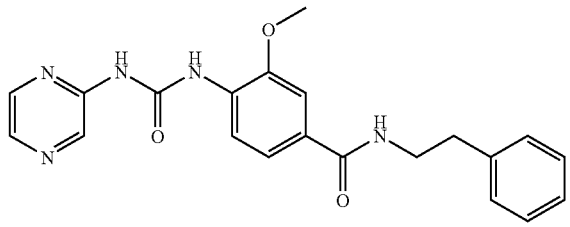

3-Methoxy-N-phenethyl-4-(3-pyrazin-2-yl-ureido)-benzamide

Prepared according to the procedure of Compound 167 using phenethyl amine (49% yield). $^1$H-NMR (400 MHz, $d_6$-DMSO) δ 8.92 (br s, 1H), 8.51 (t, 1H), 8.36 (br s, 1H), 8.25 (s, 1H), 8.22 (d 1H), 7.52 (s, 1H), 7.45 (d, 1H), 7.36-7.20 (m, 5H), 3.98 (s, 3H), 3.46 (m, 2H), 2.84 (dd, 2H) LRMS (apci, positive) m/e 392.1 (M+1)

Compound 170

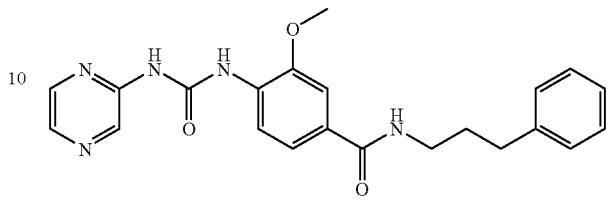

3-Methoxy-N-(3-phenyl-propyl)-4-(3-pyrazin-2-yl-ureido)-benzamide

Prepared according to the procedure of Compound 167 using phenpropyl amine (71% yield). $^1$H-NMR (400 MHz, $d_6$-DMSO) δ 8.92 (br s, 1H), 8.40 (t, 1H), 8.36 (br s, 1H), 8.25 (d, 1H), 8.23 (s, 1H), 7.52 (s, 1H), 7.46 (d, 1H), 7.32-7.18 (m, 5H), 3.97 (s, 3H), 3.25 (m, 2H) 2.61 (m, 2H), 1.82 (m, 2H) LRMS (apci, positive) m/e 406.1 (M+1)

Compound 171

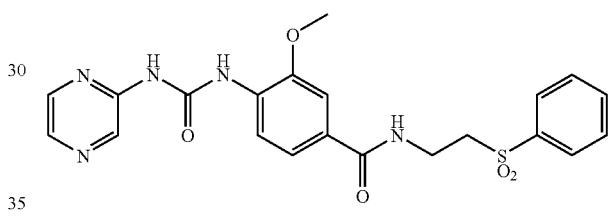

N-(2-Benzenesulfonyl-ethyl)-3-methoxy-4-(3-pyrazin-2-yl-ureido)-benzamide

Prepared according to the procedure of Compound 167 using 2-benzenesulfonyl-ethylamine (57% yield). $^1$H-NMR (400 MHz, $d_6$-DMSO) δ 8.90 (br s, 1H), 8.43 (br m, 1H), 8.35 (br s, 1H), 8.25 (s, 1H), 8.22 (d, 1H), 7.96 (s, 1H), 7.93 (s, 1H), 7.72 (m, 1H), 7.63 (m, 2H), 7.38 (s, 1H), 7.33 (d, 1H), 3.95 (s, 3H), 3.59 (m, 2H), 3.55 (m, 2H) LRMS (apci, positive) m/e 456.0 (M+1)

Compound 172

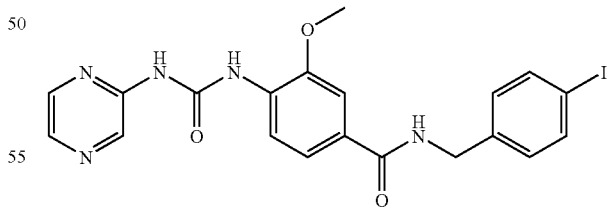

N-(4-Iodo-benzyl)-3-methoxy-4-(3-pyrazin-2-yl-ureido)-benzamide

Prepared according to the procedure of Compound 167 using 4-iodo benzyl amine (66% yield). $^1$H-NMR (400 MHz, $d_6$-DMSO) δ 8.97 (t, 1H), 8.90 (s, 1H), 8.36 (s, 1H), 8.26 (d, 1H), 8.24 (s, 1H), 7.69 (d, 2H), 7.56 (m, 2H), 7.16 (d, 2H), 4.41 (d, 2H), 3.97 (s, 3H) LRMS (apci, positive) m/e 504.0 (M+1)

Compound 173

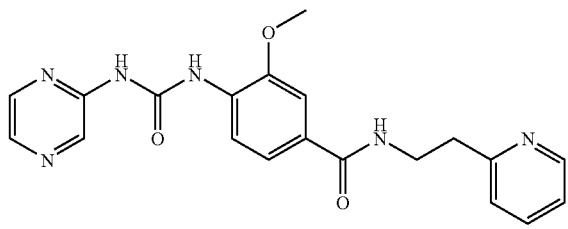

3-Methoxy-4-(3-pyrazin-2-yl-ureido)-N-(2-pyridin-2-yl-ethyl)-benzamide

Prepared according to the procedure of Compound 167 using,2-pyridin-2-yl-ethylamine (57% yield). $^1$H-NMR (400 MHz, d$_6$-DMSO) δ 8.90 (br s, 1H), 8.51 (br m, 2H), 8.36 (s, 1H), 8.22 (m, 2H), 7.71 (t, 1H), 7.48 (s, 1H), 7.43 (d, 1H), 7.26 (d, 1H), 7.21 (m, 1H), 3.97 (s, 3H), 3.60 (m, 2H), 3.00 (dd, 2H) LRMS (esi, positive) m/e 393.3 (M+1)

Compound 174

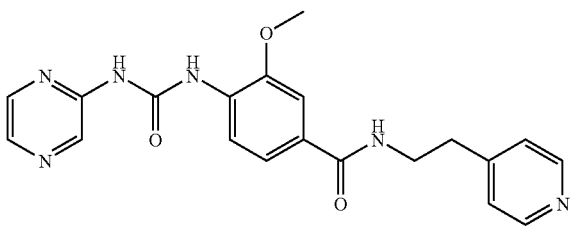

3-Methoxy-4-(3-pyrazin-2-yl-ureido)-N-(2-pyridin-4-yl-ethyl)-benzamide

Prepared according to the procedure of Compound 167 using 2-pyridin-4-yl-ethylamine (45% yield). $^1$H-NMR (400 MHz, d$_6$-DMSO) δ 8.93 (s, 1H), 8.63 (d, 2H), 8.51 (t, 1H), 8.37 (s, 1H), 8.27 (s,1H), 8.24 (d, 1H), 7.60 (d, 2H), 7.43 (m, 2H), 3.97 (s, 3H), 3.58 (m, 2H), 3.01 (m, 2H) LRMS (esi, positive) m/e 393.1 (M+1)

Compound 175

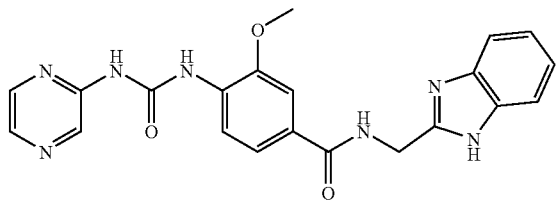

N-(H-Benzoimidazol-2-ylmethyl)-3-methoxy-4-(3-pyrazin-2-yl-ureido)-benzamide

Prepared according to the procedure of Compound 167 using C-(1H-benzoimidazol-2-yl)-methylamine (53% yield). $^1$H-NMR (400 MHz, d$_6$-DMSO) δ 8.90 (s, 1H), 8.35 (s, 1H), 8.32 (d, 1H), 8.22 (s, 1H), 7.61 (m, 3H), 7.47 (m, 2H), 7.12 (m, 2H), 4.66 (s, 2H), 3.98 (s, 3H) LRMS (esi, positive) m/e 418.2 (M+1)

Compound 176

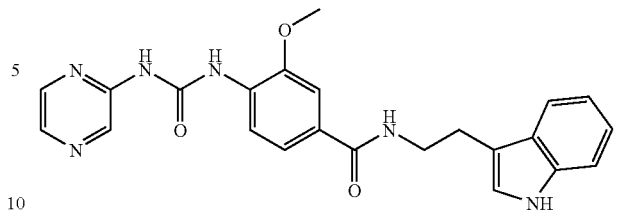

N-[2-(1 H-Indol-3-yl)-ethyl]-3-methoxy-4-(3-pyrazin-2-yl-ureido)-benzamide

Prepared according to the procedure of Compound 167 using tryptamine (74% yield). $^1$H-NMR (400 MHz, d$_6$-DMSO) δ 8.92 (s, 1H), 8.55 (br t, 1H), 8.26 (s, 1H), 8.24 (d, 1H), 8.23 (s, 1H), 7.60 (d, 1H), 7.53 (s, 1H), 7.50 (d, 1H), 7.26 (d, 1H), 7.19 (s, 1H), 7.05 (d 3H), 3.56 (m, 2H), 2.96 (in, 2H) LRMS (esi, positive) m/e 431.2 (M+1)

Compound 177

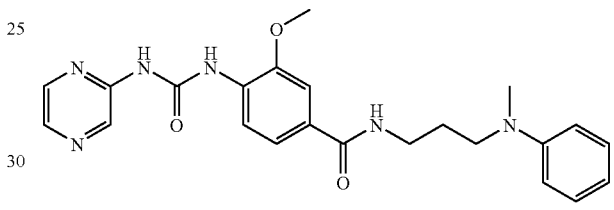

3-Methoxy-N-[3-(methyl-phenyl-amino)-propyl]-4-(3-pyrazin-2-yl-ureido)-benzamide Prepared according to the procedure of Compound 167 using N1-methyl-N1-phenyl-propane-1,3-diamine (68% yield).

$^1$H-NMR (400 MHz, d$_6$-DMSO) δ 8.89(s, 1H), 8.41 (br s, 1H), 8.36 (s, 1H), 8.23 (d, 1H), 8.22 (s, 1H), 7.52 (s, 1H), 7.49 (d, 1H), 7.16 (m, 2H), 6.70 (d, 2H), 6.59 (dd, 1H), 3.96 (s, 3H), 3.38 (m, 2H) 3.30 (m, 2H), 2.87 (s, 3H), 1.77 (m, 2H) LRMS (esi, positive) m/e 435.2 (M+1)

Compound 178

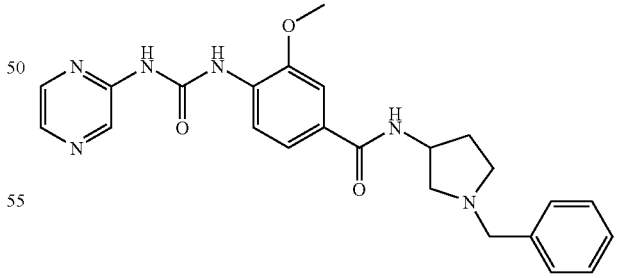

N-(1-Benzyl-pyrrolidin-3-yl)-3-methoxy-4-(3-pyrazin-2-yl-ureido)-benzamide

Prepared according to the procedure of Compound 167 using 3-amino-1-benzyl pyrrolidine (62% yield). $^1$H-NMR (400 MHz, d$_6$-DMSO) δ 8.88 (br s, 1H), 8.36 (br m, 2H), 8.24 (d, 1H), 8.21 (s, 1H), 7.51 s, 1H), 7.50 (d, 1H), 7.32 (m, 4H), 7.22 (m, 1H), 4.39 (br m, 1H), 3.96 (s, 3H), 3.59 (s, 2H), 2.79 (m, 1H), 2.62 (m, 1H), 2.40 (m, 1H), 2.16 (m, 1H), 1.81 (m, 2H) LRMS (esi, positive) m/e 447.2 (M+1)

Compound 179

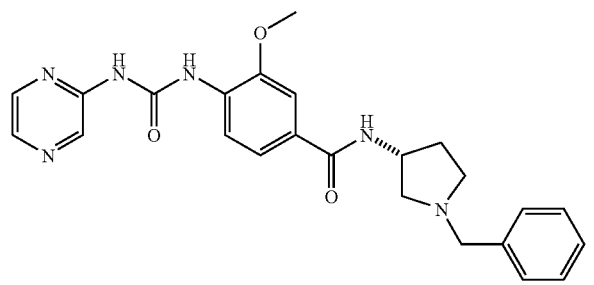

N-(3-(R)-1-Benzyl-pyrrolidin-3-yl)-3-methoxy-4-(3-pyrazin-2-yl-ureido)-benzamide Prepared according to the procedure of Compound 167 using 3-(R)-amino-1-benzyl pyrrolidine (57% yield).

$^1$H-NMR (400 MHz, d$_6$-DMSO) δ 8.83 (br s, 1H), 8.36-8.24 (m, 3H), 8.15 (m, 1H), 7.48 (m, 2H), 7.32 (m, 4H), 7.22 (m, 1H), 4.37 (m 1H), 3.96 (s, 3H), 3.59 (s, 2H), 2.78 (m 1H), 2.17 (m 1H), 1.80 (m, 2H) LRMS (esi, positive) m/e 447.1 (M+1)

Compound 180

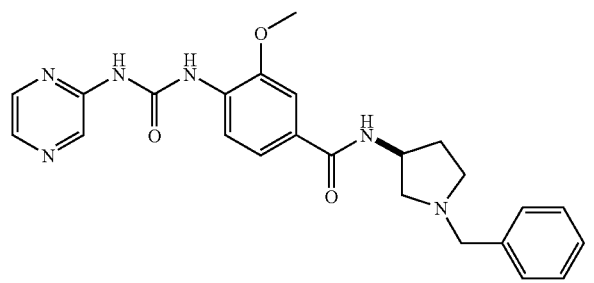

N-(3-(S)-1-Benzyl-pyrrolidin-3-yl)-3-methoxy-4-(3-pyrazin-2-yl-ureido)-benzamide Prepared according to the procedure of Compound 167 using 3-(S)-amino-1-benzyl pyrrolidine (57% yield).
$^1$H-NMR (400 MHz, d$_6$-DMSO) δ 8.85 (s, 1H), 8.34 (br s, 1H), 8.30 (s, 1H), 8.25 (d, 1H), 8.19 (s, 1H), 7.50 (m, 2H), 7.32 (m, 4H), 7.22 (m, 1H), 4.39 (m, 1H), 3.97 (s, 3H), 3.59 (s, 2H), 2.79 (m, 1H), 2.62 (m, 1H), 2.41 (m 1H), 2.16 (m, 1H), 1.81 (m 2H) LRMS (esi, positive) m/e 447.1 (M+1)

Compound 181

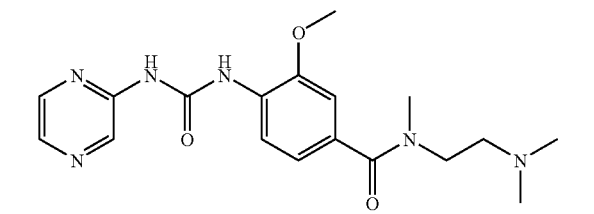

N-(2-Dimethylamino-ethyl)-3-methoxy-N-methyl-4-(3-pyrazin-2-yl-ureido)-benzamide Prepared according to the procedure of Compound 167 using N,N,N'-trimethyl-ethane-1,2-diamine (57% yield).

$^1$H-NMR (400 MHz, D$_2$O ) δ 8.17 (s, 1H), 8.05 (s, 1H), 7.94 (s, 1H), 7.76 (d, 1H), 6.92 (m, 2H), 3.79 (m, 2H), 3.75 (s, 3H), 3.36 (m, 2H), 2.97 (s, 3H), 2.88 (s, 6H) LRMS (esi, positive) m/e 373.2 (M+1)

Compound 182

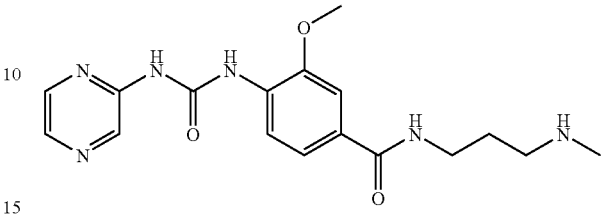

3-Methoxy-N-(3-methylamino-propyl)-4-(3-pyrazin-2-yl-ureido)-benzamide

Prepared according to the procedure of Compound 167 using N1-methyl-propane-1,3-diamine (25% yield).

$^1$H-NMR (400 MHz, d$_6$-DMSO) δ 8.93 (s, 1H), 8.38-8.25 (m, 4H), 7.59 (d, 1H), 7.52 (m, 1H), 3.98 (s, 3H), 3.92 (m, 2H), 2.92, (m, 2H), 2.50 (s, 3H), 1.82 (m, 2H) LRMS (esi, positive) m/e 359.1 (M+1)

Compound 183

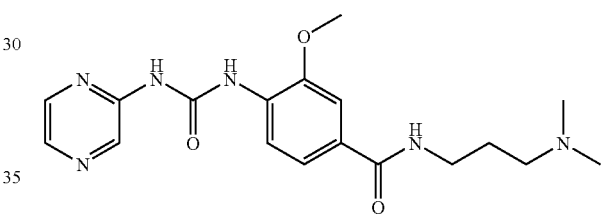

N-(3-Dimethylamino-propyl)-3-methoxy-4-(3-pyrazin-2-yl-ureido)-benzamide

Prepared according to the procedure of Compound 167 using N,N-dimethyl propyldiamine (81% yield).

$^1$H-NMR (400 MHz, d$_6$-DMSO) δ 8.93 (s, 1H), 8.56 (t, 1H), 8.37 (s, 1H), 8.25 (d, 1H), 8.23 (s, 1H), 7.52 (s, 1H), 7.50 (d, 1H), 4.10 (m, 2H), 3.97 (s, 3H), 3.35 (s, 6H), 3.05 (m. 2H), 1.84 (m, 2H) LRMS (esi, positive) m/e 373.1 (M+1)

Compound 184

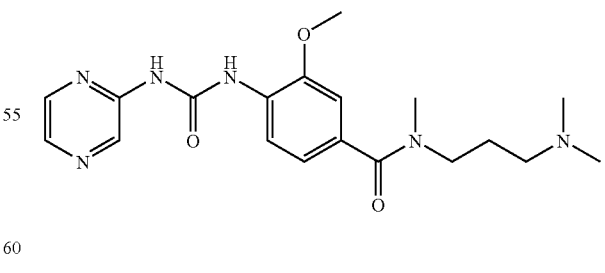

N-(3-Dimethylamino-propyl)-3-methoxy-N-methyl-4-(3-pyrazin-2-yl-ureido)-benzamide Prepared according to the procedure of Compound 167 using N,N,N'-trimethyl propyldiamine (88% yield).

$^1$H-NMR (400 MHz, CDCl$_3$/CD$_3$OD) δ 8.60 (s, 1H), 8.33 (d, 1H), 8.23 (s, 1H), 8.19 (s, 1H), 7.01 (m, 2H), 3.99 (s, 3H), 3.83 (s, 3H), 3.59 (m, 2H), 2.78 (m, 2H), 2.59 (s, 6H), 2.22 (m, 2H) LRMS (esi, positive) m/e 387.1 (M+1)

Compound 185

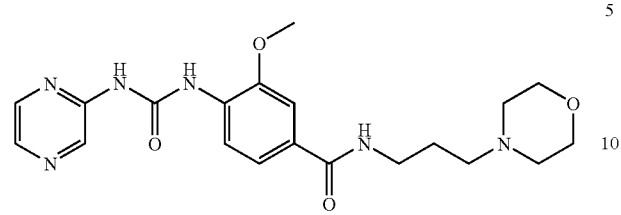

3-Methoxy-N-(3-morpholin-4-yl-propyl)-4-(3-pyrazin-2-yl-ureido)-benzamide

Prepared according to the procedure of Compound 167 using 3-morpholin-4-yl-propylamine (53% yield).

$^1$H-NMR (400 MHz, $d_6$-DMSO) δ 8.92 (s, 1H), 8.57 (t, 1H), 8.36 (s, 1H), 8.28 (d, 1H), 8.24 (s, 1H). 7.52 (s, 1H), 7.50 (d, 1H), 3.96 (s, 3H), 3.61 (m, 2H), 3.42 (m, 2H), 3.32 (m, 4H), 3.10 (m, 4H), 1.90 (m, 2H) LRMS (esi, positive) m/e 415.1 (M+1)

Compound 186

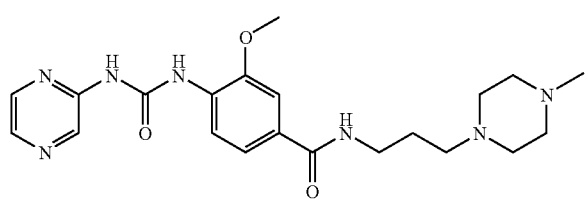

3-Methoxy-N-[3-(4-methyl-piperazin-1-yl)-propyl]-4-(3-pyrazin-2-yl-ureido)-benzamide Prepared according to the procedure of Compound 167 using 3-(4-methyl-piperazin-1-yl)-propylamine (63% yield).

$^1$H-NMR (400 MHz, $d_6$-DMSO) δ8.92 (s, 1H), 8.41 (m, 1H), 8.36 (s, 1H), 8.24 (m, 2H), 7.52 (s, 1H), 7.49 (d, 1H), 3.97 (s, 3H), 3.31 (m, 11H), 2.70 (m, 2H), 2.41 (m, 2H), 1.72 (m, 2H) LRMS (esi, positive) m/e 428.1 (M+1)

Compound 187

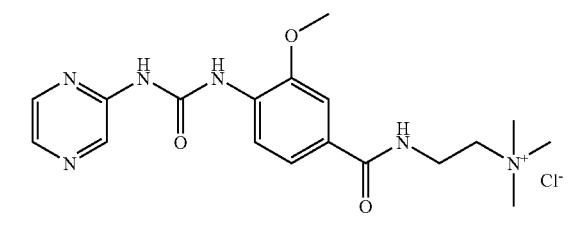

{2-[3-Methoxy-4-(3-pyrazin-2-yl-ureido)-benzoylamino]-ethyl}-trimethyl-ammonium chloride Prepared according to the procedure of Compound 167 using 2-N,N,N-trimethylammonium ethylamine(46% yield).

$^1$H-NMR (400 MHz, $d_6$-DMSO) δ8.92 (s, 1H), 8.77 (m, 1H), 8.36 (s, 1H), 8.30 (d, 1H), 8.24 (s, 1H), 7.53 (s, 1H), 7.51 (d, 1H), 3.97 (s, 3H), 3.70 (m, 2H), 3.50 (m, 2H), 3.15 (s, 9H) LRMS (esi, positive) m/e 373.1 (M+)

Compound 188

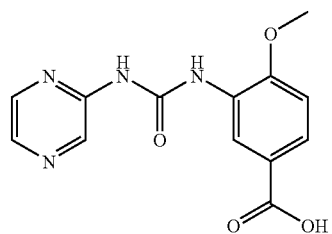

4-Methoxy-3-(3-pyrazin-2-yl-ureido)-benzoic acid

Step 1: 4-Methoxy-3-(4-nitro-phenoxycarbonylamino)-benzoic acid methyl ester. To a stirred, cooled (0° C.) solution of methyl-3-amino-4-methoxy benzoate (5.0 g; 27.6 mmol) in methylene chloride (100 mL) was added pyridine (2.34 mL; 29 mmol) followed by 4 nitrophenyl chloroformate (5.8 g; 29 mmol). After stirring for 8 hours, the reaction was diluted with methylene chloride (100 mL), washed with IN hydrochloric acid (2×125 mL), 10% aqueous sodium carbonate (2×125 mL), brine (1×125 mL), then dried (MgSO$_4$), and filtered. The filtered material was concentrated under reduced pressure. The residue was taken up in ethyl acetate (100 mL) followed by hexanes (700 mL). A precipitate formed which was filtered to yield an off white solid (80% yield).

Step 2: 4-Methoxy-3-(3-pyrazin-2-yl-ureido)-benzoic acid methyl ester. To a stirred solution of the carbamate piece (1.0 g; 2.9 mmol) in N-methyl pyrrolidinone (5 mL) was added amino pyrazine (285 mg; 3.0 mmol). The reaction was heated to 85 ° C. and stirred for 12 hours. The reaction was allowed to cool to room temperature, then diluted with ethyl acetate (50 mL) and water (50 mL). A precipitate formed which was filtered and dried under reduced pressure to yield an off white solid (55% yield).

Step 3: 4-Methoxy-3-(3-pyrazin-2-yl-ureido)-benzoic acid. To a stirred solution of 4-methoxy-3-(3-pyrazin-2-yl-ureido)-benzoic acid methyl ester (1.0 g; 3.3 mmol) in methanol (25 mL) was added lithium hydroxide (5 mL of a 2M aqueous solution). The reaction was heated to 60° C. and stirred for 12 hours. The reaction was allowed to cool to room temperature and the pH was adjusted to 5.5 with hydrochloric acid (IN). A precipitate formed which was filtered and dried under reduced pressure to yield an off white solid (58% yield).

Compound 189

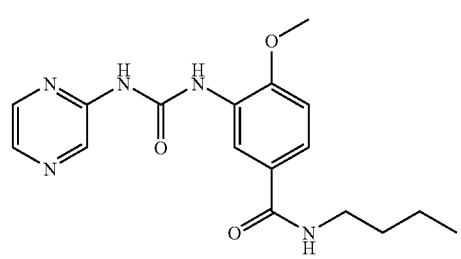

N-Butyl-4-methoxy-3-(3-pyrazin-2-yl-ureido)-benzamide

To a stirred solution of 4-Methoxy-3-(3-pyrazin-2-yl-ureido)-benzoic acid (32 mg; 0.11 mmol) in N-methyl pyrrolidinone (1 mL) was added O-benzotrazol-1-yl-N,N,N',N'-tetramethyl-uronium hexafluorophosphate (HBTU; 45 mg; 0.12 mmol), butyl amine (12 μL; 0.12 mmol), and diisopropylethylamine (35 μL; 0.20 mmol). The reaction was stirred at room temperature for 12 hours. The reaction was diluted with ethyl acetate (20 mL) and 10% aqueous sodium carbonate (20 mL) and stirred for 5 minutes. A precipitate formed which was filtered and dried under reduced pressure to yield an off white solid (49% yield).

$^1$H-NMR (400 MHz, d$_6$-DMSO) δ8.90 (s, 1H), 8.63 (s, 1H), 8.35 (s, 1H), 8.23 (m, 1H), 8.21 (s, 1H), 7.52 (d, 1H), 7.06 (d, 1H), 3.95 (s, 3H), 3.22 (m, 2H), 1.50 (m, 2H), 1.33 (m, 2H), 0.90 (t, 3H) LRMS (apci, positive) m/e 344.1 (M+1)

Compound 190

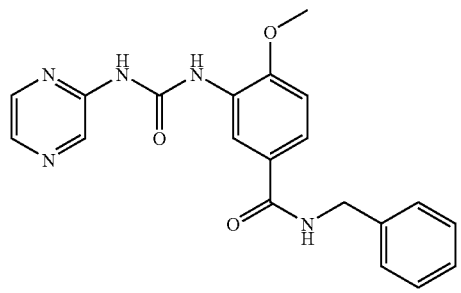

N-Benzyl-4-methoxy-3-(3-pyrazin-2-yl-ureido)-benzamide

Prepared according to the procedure of Compound 189 using benzyl amine (70% yield). $^1$H-NMR (400 MHz, d$_6$-DMSO) δ8.92 (s, 1H), 8.90 (br s, 1H), 8.73 (s, 1H), 8.33 (s, 1H), 8.23 (s, 1H), 7.60 (d, 1H), 7.33 (m, 4H), 7.23 (m, 1H), 7.12 (d, 1H), 4.44 (s, 2H), 3.96 (s, 3H) LRMS (apci positive) m/e 378.1 (M+1)

Compound 191

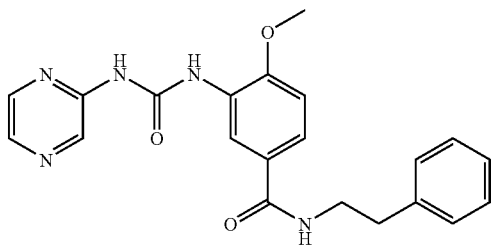

4-Methoxy-N-phenethyl-3-(3-pyrazin-2-yl-ureido)-benzamide

Prepared according to the procedure of Compound 189 using phenethyl amine (68% yield).

$^1$H-NMR (400 MHz, d$_6$-DMSO) δ8.92 (s, 1H), 8.64 (s, 1H), 8.40 (m, 1H), 8.35 (s, 1H), 8.23 (s, 1H) 7.52 (d, 1H), 7.33-7.18 (m, 5H), 7.08 (d, 1H), 3.96 (s, 3H), 3.44 (m, 2H), 2.82 (m, 2H) LRMS (apci positive) m/e 392.1 (M+1)

Compound 192

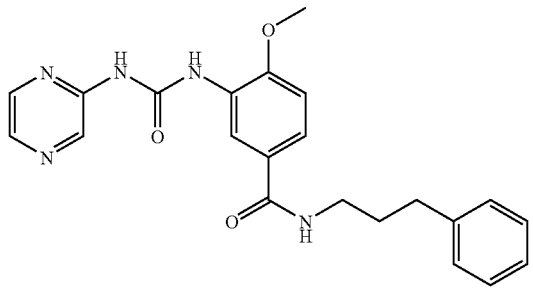

4-Methoxy-N-(3-phenyl-propyl)-3-(3-pyrazin-2-yl-ureido)-benzamide

Prepared according to the procedure of Compound 189 using phenpropyl amine (65% yield).

$^1$H-NMR (400 MHz, d$_6$-DMSO) δ8.92 (s, 1H), 8.64 (s, 1H), 8.36 (s, 1H), 8.23 (s, 1H), 7.56 (d, 1H), 7.32-7.22 (m, 5H), 7.18 (m, 1H), 7.10 (d, 1H), 3.97 (s, 3H), 3.24 (m, 2H), 2.62 (dd, 2H), 1.82 (m, 2H) LRMS (apci positive) m/e 406.1 (M+1)

Compound 193

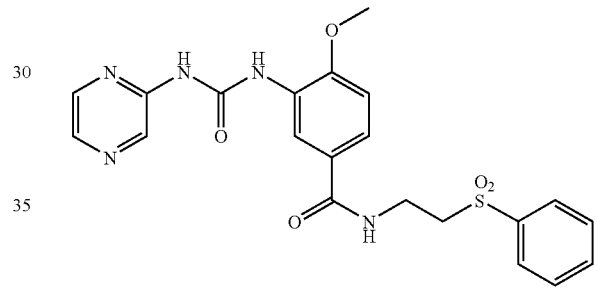

N-(2-Benzenesulfonyl-ethyl)-4-methoxy-3-(3-pyrazin-2-yl-ureido)-benzamide

Prepared according to the procedure of Compound 189 using 2-benzenesulfonyl-ethylamine (42% yield).

$^1$H-NMR (400 MHz, d$_6$-DMSO) δ8.90 (s, 1H), 8.58 (s, 1H), 8.38 (br s, 1H), 8.32 (s, 1H), 8.23 (s, 1H), 7.94 (d, 2H), 7.74 (m, 1H), 7.65 (d, 2H), 7.38 (d, 1H), 7.05 (d, 1H), 3.95 (s, 3H), 3.57 (m, 2H), 3.51 (m, 2H) LRMS (apci positive) m/e 456.0 (M+1)

Compound 194

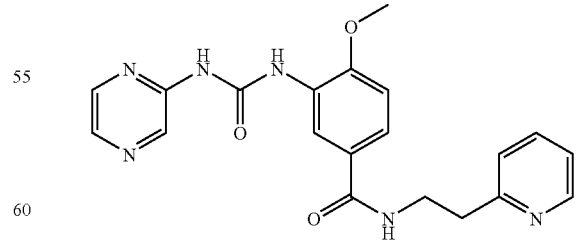

4-Methoxy-3-(3-pyrazin-2-yl-ureido)-N-(2-pyridin-2-yl-ethyl)-benzamide

Prepared according to the procedure of Compound 189 using 2-pyridin-2-yl-ethylamine (16% yield) $^1$H-NMR (400

MHz, d₆-DMSO) δ8.90 (s, 1H), 8.64 (s, 1H), 8.52 (d, 1H), 8.41 (m, 1H), 8.32 (s, 1H), 8.21 (s, 1H), 7.72 (m, 1H), 7.50 (d, 1H), 7.28 (d, 1H), 7.22 (m, 1H), 7.08 (d, 1H), 3.96 (s, 3H), 3.59 (m, 2H), 2.98 (m, 2H) LRMS (esi positive) m/e 415.2 (M+1)

Compound 195

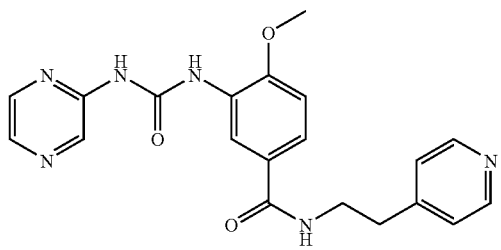

4-Methoxy-3-(3-pyrazin-2-yl-ureido)-N-(2-pyridin4-yl-ethyl)-benzamide

Prepared according to the procedure of Compound 189 using 2-pyridin-4-yl-ethylamine (41% yield)

¹H-NMR (400 MHz, d₆-DMSO) δ8.91 (s, 1H), 8.63 (s, 1H), 8.46 (d, 2H), 8.40 (m, 1H), 3.35 (s, 1H), 8.24 (s, 1H), 7.47 (d, 1H), 7.26 (d, 2H), 7.08 (d, 1H), 3.96 (s, 3H), 3.50 (m, 2H), 2.84(m, 2H) LRMS (esi positive) m/e 415.2 (M+1)

Compound 196

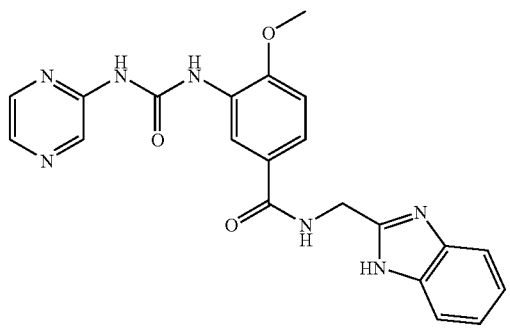

N-(1H-Benzoimidazol-2-ylmethyl)-4-methoxy-3-(3-pyrazin-2-yl-ureido)-benzamide

Prepared according to the procedure of Compound 189 using C-(1H-benzoimidazol-2-yl)-methylamine (26% yield).

¹H-NMR (400 MHz, d₆-DMSO) δ8.99 (t, 1H), 8.91 (s, 1H), 8.77 (s, 1H), 8.36 (s, 1H), 8.23 (s, 1H), 7.66 (d, ¹H), 7.56 (d, 1H), 7.44 (d, 1H), 7.15 (m, 3H), 4.65 (d, 2H), 3.97 (s, 3H) LRMS (esi positive) m/e 418.1 (M+1)

Compound 197

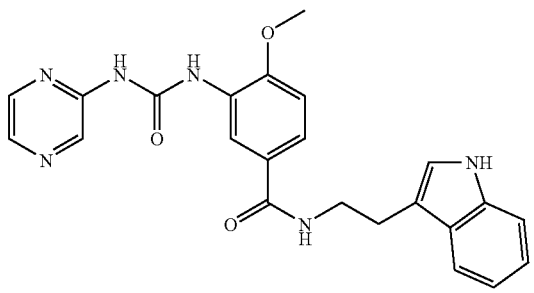

N-[2-( 1H-Indol-3-yl)-ethyl]-4-methoxy-3-(3-pyrazin-2-yl-ureido)-benzamide

Prepared according to the procedure of Compound 189 using tryptamine (51% yield).

¹H-NMR (400 MHz, d₆-DMSO) δ8.92 (s, 1H), 8.69 (s, 1H), 8.43 (t, 1H), 8.33 (s, 1H), 8.24 (s, 1H), 7.60 (d, 1H), 7.56 (d, 1H), 7.35 (d, 1H), 7.17 (s, 1H), 7.11 (d, 1H), 7.07 (m, 1H), 6.97 (m, 1H), 3,96 (s, 3H), 3.54 (m, 2H), 2.95 (m, 2H). LRMS (esi positive) m/e 431.1 (M+1)

Compound 198

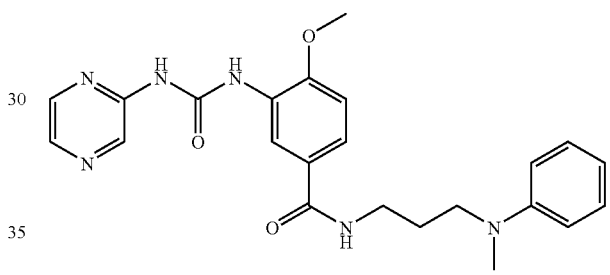

4-Methoxy-N-[3-(methyl-phenyl-amino)-propyl]-3-(3-pyrazin-2-yl-ureido)-benzamide Prepared according to the procedure of Compound 189 using N-methyl-N-phenyl propyldiamine (81% yield).

¹H-NMR (400 MHz, d₆-DMSO) δ8.92 (s, 1H), 8.64 (s, 1H), 8.37 (m, 1H), 8.35 (s, 1H), 8.23 (s, 1H), 7.55 (d, 1H), 7.14 (m, 3H), 6.70 (d, 2H), 6.58 (t, 1H), 3.96 (s, 3H), 3.37 (m, 2H), 3.25 (m, 2H), 2.86 (s, 3H), 1.77 (m, 2H). LRMS (esi positive) m/e 435.2 (M+1)

Compound 199

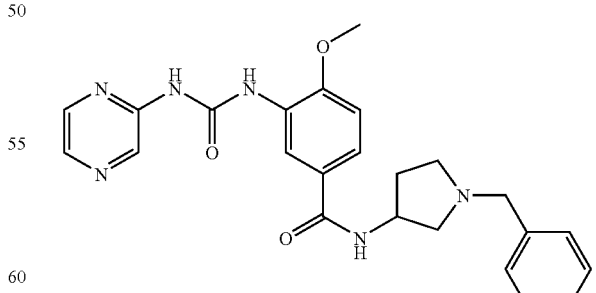

N-( 1-Benzyl-pyrrolidin-3-yl)-4-methoxy-3-(3-pyrazin-2-yl-ureido)-benzamide

Prepared according to the procedure of Compound 189 using 3-amino-1-benzyl pyrrolidine (48% yield).

¹H-NMR (400 MHz, d₆-DMSO) δ8.90 (s, 1H), 8.62 (s, 1H), 8.36 (s, 1H), 8.30 (d, 1H), 8.22 (s, 1H), 7.56 (d, 1H), 7.32 (m, 4H), 7.22 (m, 1H), 7.15 (d, 1H), 4.37 (m, 1H), 3.96 (s, 3H), 3.59 (s, 2H), 2.79 (m, 1H), 2.60 (m, 1H), 2.39 (m, 1H), 2.14 (m, 1H), 1.80 (m, 2H). LRMS (esi positive) m/e 447.2 (M+1)

Compound 200

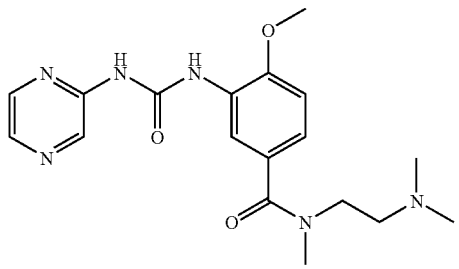

N-(2-Dimethylamino-ethyl)-4-methoxy-N-methyl-3-(3-pyrazin-2-yl-ureido)-benzamide Prepared according to the procedure of Compound 189 using N,N,N'-trimethyl ethyldiamine (93% yield).

¹H-NMR (400 MHz, d₆-DMSO) δ9.39 (br s, 1H), 8.91 (s, 1H), 8.35 (s, 1H), 8.33 (d, 1H), 8.23 (s, 1H) 7.16-7.09 (m, 2H), 3.96 (s, 3H), 3.76 (m, 2H), 3.37 (m, 2H), 2.99 (s, 3H), 2.85 (br s, 6H). LRMS (esi, positive) m/e 373.2 (M+1)

Compound 201

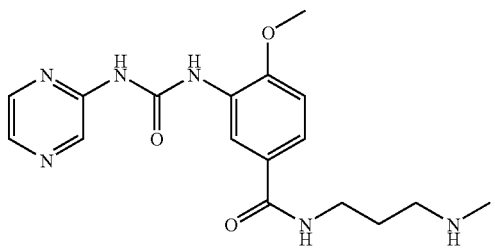

4-Methoxy-N-(3-methylamino-propyl)-3-(3-pyrazin-2-yl-ureido)-benzamide

Prepared according to the procedure of Compound 189 using N-methyl propyldiamine (15% yield).

¹H-NMR (400 MHz, D₂O) δ7.98 (m, 2H), 7.91 (s, 1H), 7.82 (s, 1H), 7.17 (d, 1H), 6.73 (d, 1H), 3.73 (s, 3H), 3.29 (m, 2H), 2.98 (m, 2H), 2.61 (s, 3H), 1.88 (m, 2H). LRMS (esi, positive) m/e 359.2 (M+1)

Compound 202

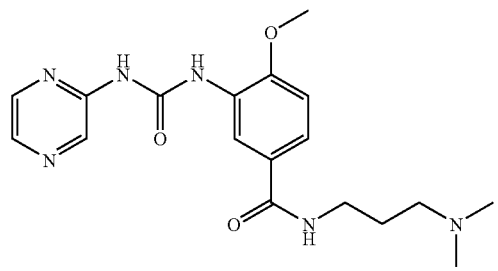

N-(3-Dimethylamino-propyl)-4-methoxy-3-(3-pyrazin-2-yl-ureido)-benzamide

Prepared according to the procedure of Compound 189 using N,N-dimethyl propyldiamine (51% yield).

¹H-NMR (400 MHz, D₂O) δ7.98 (s, 1H), 7.96 (s, 2H), 7.81 (s, 1H), 7.16 (d, 1H), 6.72 (d, 1H), 3.73 (s, 3H), 3.29 (m, 2H), 3.09 (m, 2H), 2.80 (s, 6H), 1.93 (m, 2H). LRMS (esi, positive) m/e 373.2 (M+1)

Compound 203

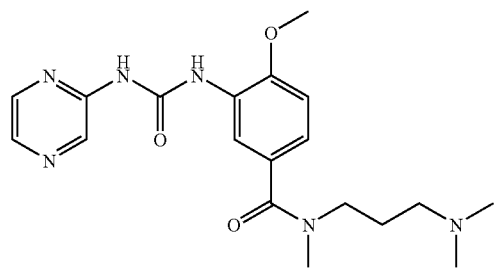

N-(3-Dimethylamino-propyl)-4-methoxy-N-methyl-3-(3-pyrazin-2-yl-ureido)-benzamide Prepared according to the procedure of Compound 189 using N,N,N'-trimethyl propyldiamine (60% yield).

¹H-NMR (400 MHz, D₂O) δ8.37 (s, 1H), 8.19 (s, 1H), 8.04 (s, 1H), 7.80 (d, 1H), 7.13 (m, 1H), 7.01 (m, 1H), 3.82 (s, 3H), 3.51 (m, 2H), 3.11 (m, 2H), 2.96 (s, 3H), 2.80 (s, 6H), 2.01 (m, 2H). LRMS (esi, positive) m/e 387.1 (M+1)

Compound 204

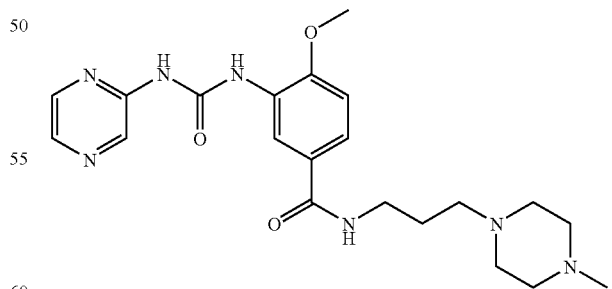

4-Methoxy-N-[3-(4-methyl-piperazin-1-yl)-propyl]-3-(3-pyrazin-2-yl-ureido)-benzamide Prepared according to the procedure of Compound 189 using 3-(4-methyl-piperazin-1-yl)-propylamine (57% yield).

¹H-NMR (400 MHz, D₂O) δ8.18 (s, 1H), 8.06 (s, 1H), 8.04 (s, 1H), 7.96 (s, 1H), 7.32 (d, 1H), 6.85 (d, 1H), 3.79 (s, 3H), 3.48 (br s, 8H), 3.36 (m, 2H), 3.17 (m, 2H), 2.83 (s, 3H), 1.96 (m, 2H). LRMS (esi, positive) m/e 428.2 (M+1)

Compound 205

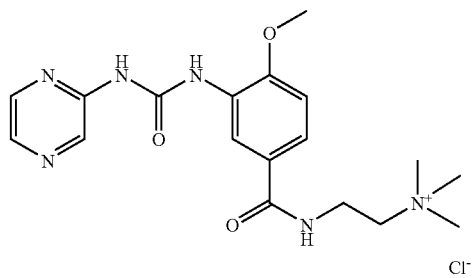

{2-[4-Methoxy-3-(3-pyrazin-2-yl-ureido)-benzoylamino]-ethyl}-trimethyl-ammonium chloride Prepared according to the procedure of Compound 189 using 2-trimethylammonium ethyl amine (63% yield).

¹H-NMR (400 MHz, D₂O) δ8.17 (s, 1H), 8.05 (s, 1H), 8.03 (s, 1H), 7.93 (s, 1H), 7.32 (d, 1H), 6.84 (d, 1H), 3.80 (s, 3H), 3.76 (m, 2H), 3.44 (m, 2H), 3.11 (s, 9H). LRMS (esi, positive) m/e 373.0 (M+)

Compound 206

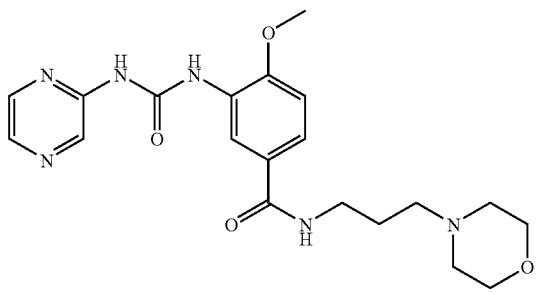

4-Methoxy-N-(3-morpholin-4-yl-propyl)-3-(3-pyrazin-2-yl-ureido)-benzamide

Prepared according to the procedure of Compound 189 using 3-morpholin-4-yl-propylamine (69% yield).

¹H-NMR (400 MHz, d₆-DMSO) δ8.91 (s, 1H), 8.63 (s, 1H), 8.36 (s, 1H), 8.35 (m, 1H), 8.23 (s, 1H), 7.54 (d, 1H), 7.10 (d, 1H), 3.96 (s, 3H), 3.57 (m, 4H), 3.26 (m, 2H), 2.34 (m, 4H), 2.32 (m, 2H), 1.66 (m, 2H). LRMS (esi, positive) m/e 415.2 (M+1)

Compound 207

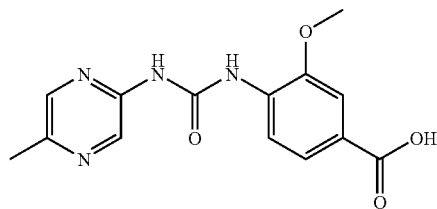

3-Methoxy-4-[3-(5-methyl-pyrazin-2-yl)-ureido]-benzoic acid

Step 1: (5-Methyl-pyrazin-2-yl)-carbamic acid tert-butyl ester. To a stirred solution of 5-methyl pyrazine carboxylic acid (13.8 g, 100 mmol) in 300 mL of toluene at room temperature under nitrogen was added triethyl amine (14 mL, 100 mmol) followed by diphenyl phosphoryl azide (21.6 mL, 100 mmol). After 30 min. at room temperature, 2-methyl-2-propanol (19 mL, 200 mmol) was added and the solution immersed in a 90 ° C. oil bath. After 2 hours, the reaction was cooled to RT, diluted to 600 mL with EtOAc, and washed 3×60 mL with 10% Na₂CO₃ and 1×600 mL with saturated NaCl. The organics were dried (MgSO₄), filtered and concentrated to a yellow solid (17.5 g, 83%). ¹H-NMR (400 MHz, CDCl₃) δ9.16 (s, 1H), 8.05 (s, 1H), 7.56 (br s, 1H), 2.50 (s, 3H), 1.55 (s, 9H)

Step 2: 5-Methyl-2-aminopyrazine. To a stirred solution of (5-methyl-pyrazin-2-yl)-carbamic acid tert-butyl ester (2.1 g, 10 mmol) in 30 mL CH₂Cl₂ at 0° C. under nitrogen was added trifluoroace (30 mL). The solution was allowed to warm to RT overnight. The solution was rotary evaporated to remove TFA and the residue was redissolved in 200 mL CH₂Cl₂ and stirred with 100 mL 10% Na₂CO₃. The organics were isolated and the aqueous solution extracted 3×100 mL with CH₂Cl₂. The organics were combined, dried (MgSO₄), filtered and concentrated to an orange solid (1 g, 92%). ¹H-NMR (400 MHz, CDCl₃) δ8.46 (s, 1H), 7.70 (s, 1H), 2.49 (s, 3H).

Step 3: 3-Methoxy-4-[3-(5-methyl-pyrazin-2-yl)-ureido]-benzoic acid methyl ester. To a stirred solution of 3-methoxy-4-(4-nitro-phenoxycarbonylamino)-benzoic acid methyl ester (11.7 g, 33.8 mmol) in 34 mL NMP at room temperature under nitrogen was added 5-methyl-2-aminopyrazine (3.69 g, 33.8 mmol) and the reaction was immersed in an 85° C. oil bath. After 6 hours the reaction was allowed to cool to room temperature and a precipitate formed. EtOAc (200 mL) was added and the precipitate was isolated by filtration (4.7 g, 44%). ¹H-NMR (400 MHz, d₆-DMSO) 6 8.79 (br s, 1H), 8.36 (d, 1H), 8.23 (s, 1H), 7.60 (d, 1H), 7.52 (s, 1H), 3.98 (s, 3H), 3.81 (s, 3H), 2.42 (s, 3H).

Step 4: 3-Methoxy-4-[3-(5-methyl-pyrazin-2-yl)-ureido]-benzoic acid. To a stirred suspension of 3-methoxy-4-[3-(5-methyl-pyrazin-2-yl)-ureido]-benzoic acid methyl ester (7.15 g, 22.6 mmol) in 3:1 MeOH:H₂O (226 mL) at RT under N₂ was added lithium hydroxide monohydrate (9.5 g, 226 mmol) as a solid and the mixture heated to 65 ° C. After reaching temperature, the suspension gradually became a bright yellow solution. After about 4 hours a precipitate formed but the reaction was continued overnight. After cooling to RT, MeOH was removed by rotovap and the aqueous suspension diluted with 100 mL H₂O and neutralized to pH=5 with concentrated HCl. As pH=5 was approached, the suspension turned from yellow to white. The suspension was then filtered through paper on a large ceramic funnel. The filtration went very slowly, taking several hours. The filter cake was washed twice with H₂O. When most of the H₂O was removed, the residue was dried under high vacuum in a dessicator overnight to give the free acid as a white solid (6 g, 88%). ¹H-NMR (400 MHz, d₆-DMSO) δ 8.79 (br s, 1H), 8.36 (d, 1H), 8.22 (s, 1H), 7.57 (d, 1H), 7.51 (s, 1H), 3.97 (s, 3H), 242 (s, 3H).

Compound 208

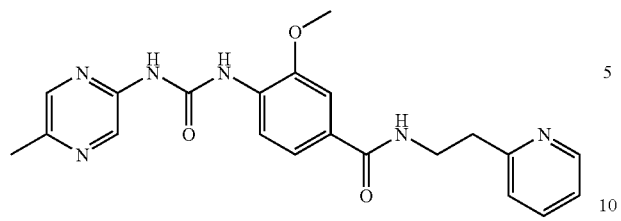

3-Methoxy-4-[3-(5-methyl-pyrazin-2-yl)-ureido]-N-(2-pyridin-2-yl-ethyl)-benzamide To a stirred solution of 3-methoxy-4-[3-(5-methyl-pyrazin-2-yl)-ureido]-benzoic acid (30 mg, 0.1 mmol) in 1 mL NMP at RT in a capped reaction vial was added HBTU (42 mg, 0.11 mmol). The suspension was stirred for 15 minutes and then treated with 2-ethylaminopyridine (13.2 µL, 0.11 mmol) followed by Hunigs Base (35 µL, 0.2 mmol). After stirring overnight, NMP was removed by bulb to bulb transfer at 70 ° C. under high vacuum and the residue stirred with a mixture of $CH_2Cl_2$ (10 mL) and 10% $Na_2CO_3$ (10 mL) until complete dissolution occurred. The organics were isolated, dried ($MgSO_4$), filtered and concentrated. The residue was triturated with EtOAc to produce a solid which was isolated by filtration (71 % yield).

$^1$H-NMR (400 MHz, $d_6$-DMSO) δ8.90 (s, 1H), 8.58 (d, 1H), 8.50 (t, 1H), 8.23 (d, 1H), 8.21 (s, 1H), 7.82 (t, 1H), 7.48-7.31 (m, 4H), 3.97 (s, 3H), 3.62 (m, 2H), 3.04 (m, 2H), 2.42 (s, 3H). LRMS (esi, positive) m/e 407.1 (M+1)

Compound 209

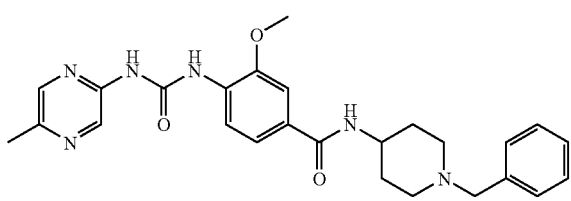

N-(1-Benzyl-piperidin-4-yl)-3-methoxy-4-[3-(5-methyl-pyrazin-2-yl)-ureido]-benzamide Prepared according to the method of Compound 208 using 4-amino-1-benzyl piperidine except the crude product was purified by chromatography on a Biotage 12S column eluting with 92.5/7.5 $CH_2Cl_2$/MeOH. (61% yield).

$^1$H-NMR (400 MHz, $CDCl_3/CD_3OD$) δ8.44 (br s, 1H), 8.32 (d, 1H), 8.09 (s, 1H), 7.47 (s, 1H), 7.38-7.28 (m, 6H), 7.09 (d, 1H), 4.00 (m, 1H), 3.99 (s, 3H), 3.60 (s, 2H), 2.98 (m, 2H), 2.52 (s, 3H), 2.25 (m, 2H), 2.00 (m, 2H), 1.64 (m, 2H) LRMS (esi, positive) m/e 475.2 (M+1)

Compound 210

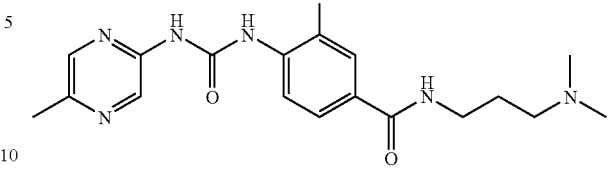

N-(3-Dimethylamino-propyl)-3-methoxy-4-[3-(5-methyl-pyrazin-2-yl)-ureido]-benzamide Prepared according to the method of Compound 208 using N,N-dimethyl propyldiamine (70% yield).

$^1$H-NMR (400 MHz, $d_6$-DMSO) δ8.90 (br s, 1H) 8.55 (t, 1H) 8.26 (d, 1H), 8.22 (s, 1H), 7.52 (s, 1H), 7.50 (d, 1H), 3.98 (s, 3H), 3.32 (m, 2H), 3.07 (m, 2H), 2.77 (s, 6H), 2.41 (s, 3H), 1.89 (m, 2H). LRMS (esi, positive) m/e 387.1 (M+1)

Compound 211

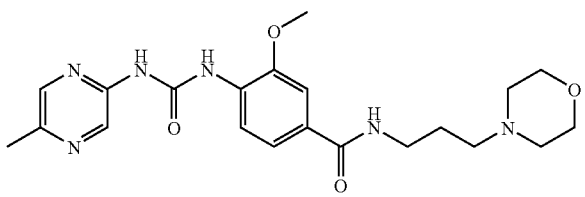

3-Methoxy-4-[3-(5-methyl-pyrazin-2-yl)-ureido]-N-(3-morpholin-4-yl-propyl)-benzamide Prepared according to the method of Compound 208 using 3-morpholin-4-yl-propylamine (79% yield).

$^1$H-NMR (400 MHz, $d_6$-DMSO) δ8.90 (br s, 1H), 8.57 (t, 1H), 8.25 (d, 1H), 8.21 (s, 1H), 7.51 (s, 1H), 7.50 (d, 1H), 3.97 (s, 3H), 3.62 (m, 2H), 3.31 (m, 8H), 3.12 (m, 2H), 2.41 (s, 3H), 1.92 (m, 2H) LRMS (esi, positive) m/e 429.1 (M+1)

Compound 212

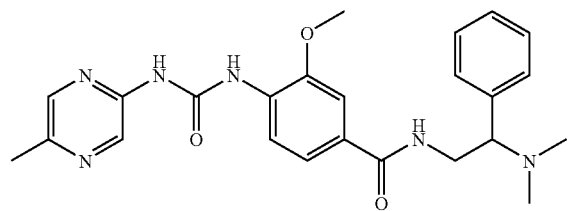

N-(2-Dimethylamino-2-phenyl-ethyl)-3-methoxy-4-[3-(5-methyl-pyrazin-2-yl)-ureido]-benzamide Prepared according to the method of Compound 208 using N-(2-dimethylamino)-2-phenyl ethyl amine except the crude product was purified by chromatography on a Biotage 12S column eluting with 92.5/7.5 $CH_2Cl_2$/MeOH. (12% yield).

$^1$H-NMR (400 MHz, $d_6$-DMSO) δ10.05 (s, 1H), 8.88 (s, 1H), 8.20 (m, 3H), 7.41-7.19 (m, 7H), 3.96 (s, 3H), 3.78 (m, 1H), 3.70 (m, 1H), 3.57 (m, 1H), 3.38 (m, 1H), 2.50 (s, 6H), 2.40 (s, 3H) LRMS (esi, positive) m/e 448.9 (M+1)

Compound 213

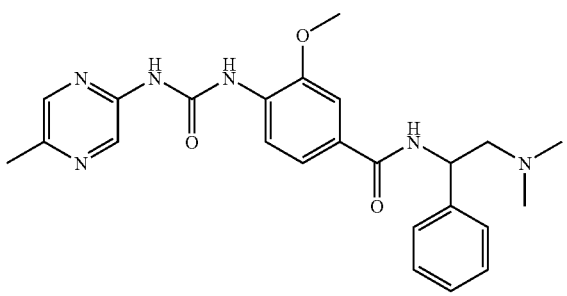

N-(2-Dimethylamino-1-phenyl-ethyl)-3-methoxy-4-[3-(5-methyl-pyrazin-2-yl)-ureido]-benzamide Prepared according to the method of Compound 208 using N-(2-dimethylamino)-1-phenyl ethyl amine except the crude product was purified by chromatography on a Biotage 12S column eluting with 92.5/7.5 $CH_2Cl_2$/MeOH. (27% yield).

$^1$H-NMR (400 MHz, $d_6$-DMSO) δ11.61 (br s, 1H), 9.71 (br s, 1H), 8.42 (d, 1H), 8.36 (s, 1H), 8.09 (s, 1H), 7.52-7.21 (m, 7H), 5.05 (br s, 1H), 3.93 (s, 3H), 2.80 (m, 1H), 2.52 (s, 3H), 2.37 (s, 6H), 1.79 (br s, 2H) LRMS (esi, positive) m/e 449.0 (M+1)

Compound 214

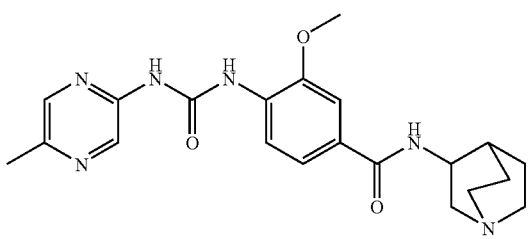

N-(1-Aza-bicyclo[2.2.2]oct-3-yl)-3-methoxy-4-[3-(5-methyl-pyrazin-2-yl)-ureido]-benzamide Prepared according to the method of Compound 208 using 1-aza-bicyclo[2.2.2]oct-3-ylamine (27% yield).

$^1$H-NMR (400 MHz, $d_6$-DMSO) δ10.17 (br s, 1H), 8.90 (br s, 1H), 8.24 (d, 1H), 8.23 (s, 1H), 8.17 (d, 1H), 7.53 (d, 1H), 7.50 (s, 1H), 3.98 (s, 3H), 3.95 (m, 1H), 3.10 (m, 1H), 2.90 (m,1H), 2.64 (m, 4H) 2.42 (s, 3H), 1.87 (m, 1H), 1.80 (m, 1H), 1.59 (m, 2H), 1.31 (m, 1H). LRMS (esi, positive) m/e 411.0 (M+1)

Compound 215

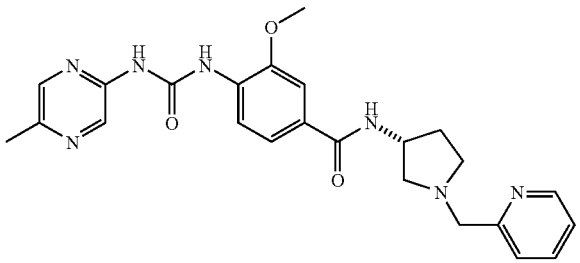

3-Methoxy-4-[3-(5-methyl-pyrazin-2-yl)-ureido]-N-(3-R-1-pyridin-2-ylmethyl-pyrrolidin-3-yl)-benzamide Step 1: (3-R-1-Pyridin-2-ylmethyl-pyrrolidin-3-yl)-carbamic acid tert-butyl ester. To a stirred solution of (R)-boc-3-aminopyrrolidine (372.5 mg, 2 mmol) in dichloroethane (6 mL) at room temperature under nitrogen was added pyridine-2-carboxaldehyde (190 μL, 2 mmol) followed by sodium triacetoxyborohydride (593 mg, 2.8 mmol). The reaction was stirred at room temperature overnight and was then quenched by addition of saturated $NaHCO_3$ (6 mL) with stirring for 15 minutes. The reaction was then partitioned between $CH_2Cl_2$ (25 mL) and 10% $Na_2CO_3$ (25 mL). The organics were isolated, dried ($MgSO_4$), filtered and concentrated to the pure product (526 mg, 95%).

Step 2: 3-R-1-Pyridin-2-ylmethyl-pyrrolidin-3-ylamine dihydrochloride. A stirred solution of (3-R-1-pyridin-2-ylmethyl-pyrrolidin-3-yl)-carbamic acid tert-butyl ester (277 mg, 1 mmol) in 10 mL 4N HCl in dioxane at room temperature in a capped flask was reacted overnight. The reaction was concentrated by rotary evaporation and high vacuum to give the di HCl salt (250 mg, quantitative).

Step 3: Prepared according to the procedure of Compound 208 except 3-R-1-pyridin-2-ylmethyl-pyrrolidin-3-ylamine dihydrochloride salt was mixed with excess DIEA (70 μL, 0.4 mmol) in 500 μL NMP to form a solution which was added to the acid/HBTU mixture. The crude product was purified by chromatography on a Biotage 12S column eluting with 9/1 $CH_2Cl_2$/MeOH (60% yield).

$^1$H-NMR (400 MHz, $CDCl_3$) δ8.57 (s, 1H), 8.51 (d, 1H), 8.39 (d, 1H), 8.17 (s, 1H), 8.09 (s, 1H), 7.92 (s, 1H), 7.64 (d, 1H), 7.50 (s, 1H), 7.30 (d, 1H), 6.70 (d, 1H), 4.69 (m, 1H), 4.00 (s, 3H), 3.66 (dd, 2H), 2.98 (m, 1H), 2.80 (m, 1H), 2.70 (m, 1H), 2.53 (s, 3H), 2.39 (m, 3H), 1.76 (m, 1H). LRMS (esi, positive) m/e 462.3 (M+1)

Compound 216

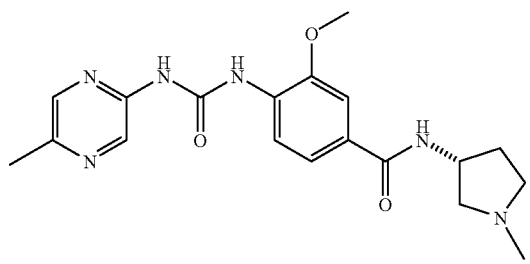

3-Methoxy-4-[3-(5-methyl-pyrazin-2-yl)-ureido]-N-(3-R-1-methyl-pyrrolidin-3-yl)-benzamide Prepared according to the procedure of Compound 215 using 3-(R)-amino-1-methyl pyrrolidine (29% yield).

¹H-NMR (400 MHz, d₆-DMSO) δ8.78 (br s, 1H), 8.36 (d, 1H), 8.22 (d, 1H), 8.20 (s, 1H), 7.52 (s, 1H), 7.50 (d, 1H), 4.39 (m, 1H), 3.96 (s, 3H), 2.64 (m, 1H), 2.61 (m, 1H), 2.43, (s, 3H), 2.39 (m, 2.24 (s, 3H), 2.17 (m, 1H), 1.76 (m, 1H). LRMS (esi, positive) mile 385.3 (M+1)

Compound 217

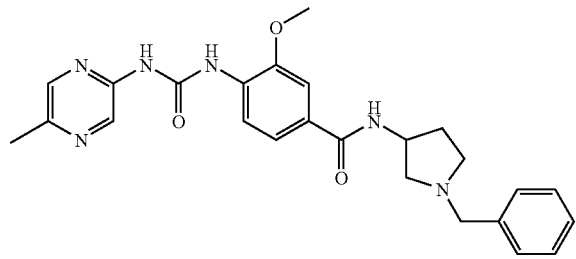

N-(3-R-1-Benzyl-pyrrolidin-3-yl)-3-methoxy-4-[3-(5-methyl-pyrazin-2-yl)-ureido]-benzamide Prepared according to the method of Compound 215 using 3-(R)-amino-1-benzyl pyrrolidine except the crude product was purified by chromatography on a Biotage 12S column eluting with 92.5/7.5 CH₂Cl₂/MeOH. (54% yield).

¹H-NMR (400 MHz, CDCl₃) δ9.09 (br s, 1H), 8.43 (d, 1H), 8.09 (s, 1H), 8.02 (s, 1H), 7.57 (m, 1H), 7.53 (s, 1H), 7.46 (d, 1H), 7.33-7.22 (m, 4H), 4.79 (m, 1H), 4.00 (s, 3H), 3.78 (dd, 2H), 3.13 (m, 2H), 2.76 (m, 1H), 2.55 (s, 3H), 2.44 (m, 1H), 1.79 (m, 1H). LRMS (esi, positive) m/e 461.1 (M+1)

Compound 218

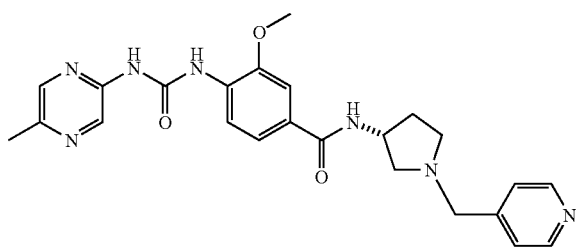

3-Methoxy-4-[3-(5-methyl-pyrazin-2-yl)-ureido]-N-(3-R-1-pyridin-4-ylmethyl-pyrrolidin-3-yl)-benzamide Prepared according to the procedure of Compound 215 using 1-(R)-Pyridin-4-ylmethyl-pyrrolidin-3-ylamine (60% yield).

¹H-NMR (400 MHz, CDCl₃) δ8.56 (d, 2H), 8.41 (d, 1H), 8.21 (d, 1H), 8.20 (s, 1H), 8.08 (s, 1H), 7.52 (s, 1H), 7.32 (d, 1H), 7.25 (d, 2H), 6.71 (d, 1H), 4.73 (m, 1H), 4.00 (s, 3H), 3.66 (dd, 2H), 2.97 (m, 1H), 2.82 (m, 1H), 2.71 (m, 1H), 2.54 (s, 3H), 2.39 (m, 2H), 1.78 (m, 1H). LRMS (esi, positive) m/e 462.3 (M+1)

Compound 219

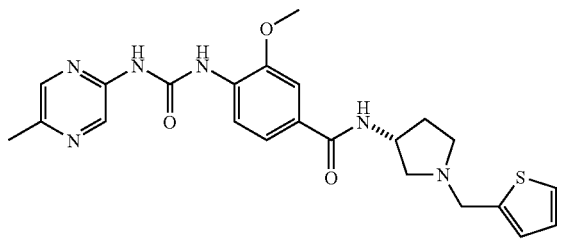

3-Methoxy-4-[3-(5-methyl-pyrazin-2-yl)-ureido]-N-(3-R-1-thiophen-2-ylmethyl-pyrrolidin-3yl)-benzamide Prepared according to the procedure of Compound 215 using (R)-1-thiophen-2-ylmethyl-pyrrolidin-3-ylamine (60% yield).

¹H-NMR (400 MHz, CDCl₃) δ8.96 (br s, 1H), 8.43 (d, 1H), 8.09 (d, 2H), 7.57 (s, 1H), 7.50 (d, 1H), 7.10 (d, 1H), 6.91 (m, 2H), 4.80 (m, 1H), 4.00 (s, 3H), 3.96 (dd, 2H), 3.17 (m, 1H), 3.08 (m, 1H), 2.71 (m, 1H), 2.54 (s, 3H), 2.42 (m, 2H), 1.80 (m, 1H). LRMS (esi, positive) m/e 467.2 (M+1)

Compound 220

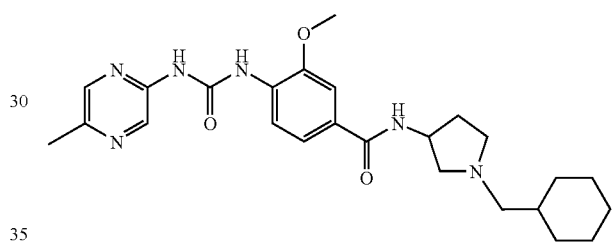

N-(3-R-1-Cyclohexylmethyl-pyrrolidin-3-yl)-3-methoxy-4-[3-(5-methyl-pyrazin-2-yl)-ureido]-benzamide Prepared according to the procedure of Compound 215 using 1-cyclohexylmethyl-pyrrolidin-3-R-ylamine (71% yield).

¹H-NMR (400 MHz, CDCl₃) δ8.89 (br s, 1H), 8.32 (d, 1H), 8.23 (d, 1H), 8.21 (s, 1H), 7.51 (s, 1H), 7.49 (d, 1H), 4.38 (m, 1H), 3.96 (s, 3H), 2.76 (m, 1H), 2.56 (m, 1H), 2.42 (s, 3H), 2.38 (m, 1H), 2.25 -2.06 (m, 3H), 1.77 (m, 3H), 1.61 (m, 3H), 1.40 (m 1H), 1.19 (m, 3H), 0.83 (m, 2H) LRMS (esi, positive) m/e 467.3 (M+1)

Compound 221

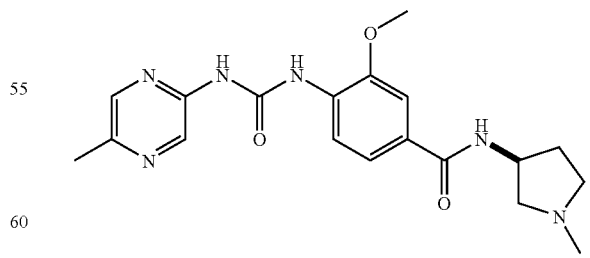

3-Methoxy-4-[3-(5-methyl-pyrazin-2-yl)-ureido]-N-(3-R-1-methyl-pyrrolidin-3-yl)-benzamide Prepared according to the procedure of Compound 215 using 1-methyl-pyrrolidin-3-R-ylamine (51% yield).

¹H-NMR (400 MHz, d₆-DMSO) δ 8.78 (br s, 1H), 8.35 (d, 1H), 8.22 (d, 1H), 8.21 (s, 1H), 7.52 (s, 1H), 7.49 (d, 1H). 4.39 (m, 1H), 3.96 (s, 3H), 2.66 (m, 1H), 2.61 (m, 1H), 2.43 (s, 3H), 2.39 (m, 2H), 2.24 (s, 3H), 2.17 (m, 1H), 1.75 (m, 1H) LRMS (esi, positive) m/e 385.4 (M+1)

Compound 222

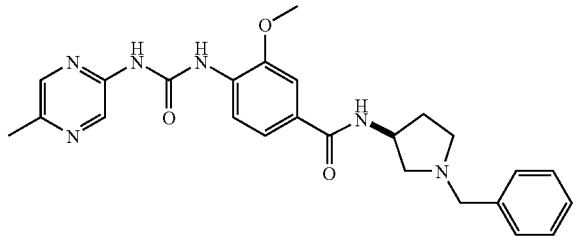

N-(3-S-1-Benzyl-pyrrolidin-3-yl)-3-methoxy-4-[3-(5-methyl-pyrazin-2-yl)-ureido]-benzamide Prepared according to the method of Compound 215 using 1-Benzyl-pyrrolidin-3-S-ylamine except the crude product was purified by chromatography on a Biotage 12S column eluting with 92.5/7.5 CH₂Cl₂/MeOH. (54% yield).

¹H-NMR (400 MHz, CDCl₃) δ 8.81 (br s, 1H), 8.43 (d, 1H), 8.06 (d, 2H), 7.53 (s, 1H), 7.42 (d, 1H), 7.35-7.20 (m, 5H), 4.78 (m, 1H), 3.99 (s, 3H), 3.78 (dd, 2H), 3.15 (m, 1H), 3.04 (m, 1H), 2.77 (m, 1H), 2.54 (s, 3H), 2.44 (m, 1H), 1.79 (m, 2H). LRMS (esi, positive) m/e 461.1 (M+1)

Compound 223

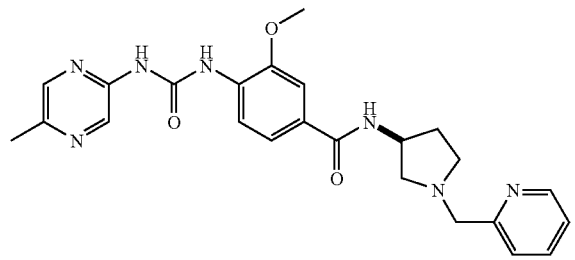

3-Methoxy-4-[3-(5-methyl-pyrazin-2-yl)-ureido]-N-(3-S-1-pyridin-2-ylmethyl-pyrrolidin-3-yl)-benzamide Prepared according to the procedure of Compound 215 using 1-pyridin-2-ylmethyl-pyrrolidin-3-S-ylamine (60% yield).

¹H-NMR (400 MHz, CDCl₃) δ 8.56 (d, 1H), 8.38 (s, 1H), 8.32 (d, 1H, 8.06 (s, 1 H), 7.68(t, 1H), 7.51 (s, 1H), 7.40 (d, 1H), 7.35 (d, 1H), 7.21 (m, 1H), 4.72 (m, 1H), 4.00 (s, 3H), 3.79 (dd, 2H), 3.40 (m 1H), 3.03 (m, 1H), 2.86 (m, 1H), 2.64 (m, 1H), 2.53 (s, 3H), 2.35 (m, 1H), 1.78 (m, 2H). LRMS (esi, positive) m/e 462.1 (M+1)

Compound 224

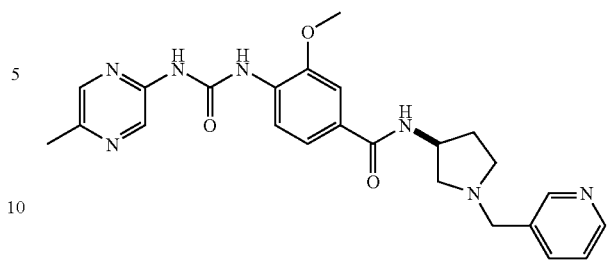

3-Methoxy-4-[3-(5-methyl-pyrazin-2-yl)-ureido]-N-(3-S-1-pyridin-3-ylmethyl-pyrrolidin-3yl)-benzamide Prepared according to the procedure of Compound 215 using 1-pyridin-3-ylmethyl-pyrrolidin-3-S-ylamine (60% yield).

¹H-NMR (400 MHz, CDCl₃) δ 8.56 (s, 1H), 8.51 (m, 1H), 8.39 (d, 1H), 8.18 (s, 1H), 8.08 (s, 2H), 7.64 (d, 1H), 7.50 (s, 1H), 7.33 (d, 1H), 6.77 (d, 1H), 4.72 (m, 1H), 4.00 (s, 3H), 3.66 (dd, 2H), 2.97 (m, 1H), 2.82 (m, 1H), 2.71 (m, 1H), 2.54 (s, 3H), 2.40 (m, 2H), 1.76 (m, 2H). LRMS (esi, positive) m/e 462.3 (M+1)

Compound 225

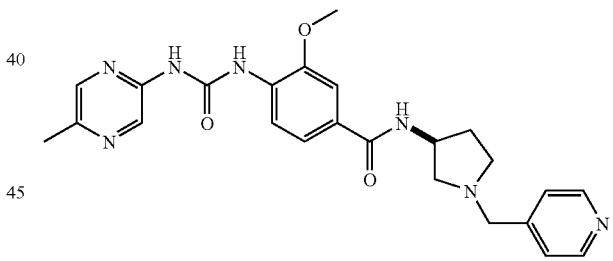

3-Methoxy-4-[3-(5-methyl-pyrazin-2-yl)-ureido]-N-(3-S-1-pyridin-4-ylmethyl-pyrrolidin-3-y benzamide Prepared according to the procedure of Compound 215 using 1-pyridin-4-ylmethyl-pyrrolidin-3-S-ylamine (60% yield).

¹H-NMR (400 MHz, CDCl₃) δ 8.56 (d, 2H), 8.41 (d, 1H), 8.24 (s, 1H), 8.20 (s, 1H), 8.08 (s, 1H), 7.53 (s, 1H), 7.32 (d, 1H), 7.24 (d, 2H), 6.75 (d, 1H), 4.72 (m, 1H), 4.00 (s, 3H), 3.67 (dd, 2H), 2.98 (m, 1H), 2.82 (m, 1H), 2.71 (m, 1H), 2.54 (s, 3H), 2.40 (m, 2H), 1.79 (m, 2H). LRMS (esi, positive) m/e 462.3 (M+1)

Compound 226

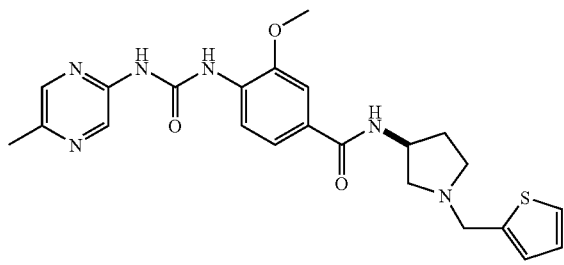

3-Methoxy-4-[3-(5-methyl-pyrazin-2-yl)-ureido]-N-(3-S-1-thiophen-2-ylmethyl-pyrrolidin-3-yl)-benzamide Prepared according to the procedure of Compound 215 using 1-thiophen-2-ylmethyl-pyrrolidin-3-S-ylamine (55% yield).

$^1$H-NMR (400 MHz, CDCl$_3$) δ8.71 (br s, 1H), 8.42 (d, 1H), 8.11 (d, 2H), 7.55 (s, 1H), 7.44 (d, 1H), 7.39 (d, 1H), 7.20 (d, 1H), 6.91 (m, 2H), 4.78 (m, 1H), 4.00 (s, 3H), 3.94 (dd, 2H), 3.17 (m, 1H), 3.05 (m, 1H), 2.69 (, 11H), 2.53 (s, 3H), 2,42 (m, 2H), 1.80 (m, 2H). LRMS (esi, positive) m/e 467.2 (M+1)

Compound 227

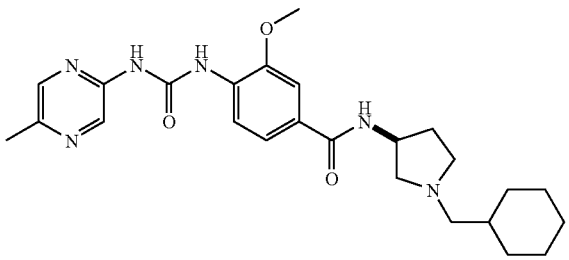

N-(3-S-1-Cyclohexylmethyl-pyrrolidin-3-yl)-3-methoxy-4-[3-(5-methyl-pyrazin-2-yl)-ureido]-benzamide Prepared according to the procedure of Compound 215 using 1-cyclohexylmethyl-pyrrolidin-3-S-ylamine (60% yield).

$^1$H-NMR (400 MHz, d$_6$-DMSO) δ8.78 (s, 1H), 8.31 (d, 1H), 8.23 (d, 1H), 8.20 (s, 1H), 7.51 (s, 1H), 7.48 (d, 1H), 4.37 (m, 1H), 3.96 (s, 3H), 2.76 (m, 1H), 2.56 (m, 1H), 2.42 (s, 3H), 2.38 (m, 1H), 2.25-2.06 (m, 3H), 1.77 (m, 3H), 1.61 (m, 3H), 1.40 (m, 1H), 1.19 (m, 3H), 0.83 (m, 2H). LRMS (esi, positive) m/e 467.3 (M+1)

Compound 228

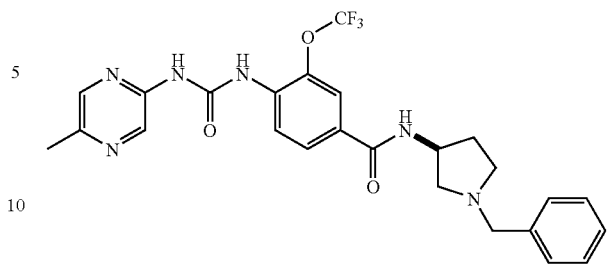

N-(3-S-1-Benzyl-pyrrolidin-3-yl)-4-[3-(5-methyl-pyrazin-2-yl)-ureido]-3-tifluoromethoxy-benzamide Step 1: 4-Amino-3-trifluoromethoxy-benzoic acid methyl ester. To a stirred solution of 4-amino-3-trifluoromethoxy-benzoic acid (1.2 g, 5.4 mmol) in 16 mL of 4:1 THF:MeOH at 0 °C. was added TMS-diazomethane (2M solution in hexane, 6 mL, 12 mmol) dropwise and conversion was monitored by TLC in ⅔ EtOAc/hexane. When complete, the reaction was concentrated to a white solid corresponding to the methyl ester (1.27 g, quantitative).

Step 2: 4-(4-Nitro-phenoxycarbonylamino)-3-trifluoromethoxy-benzoic acid methyl ester. To a stirred solution of 4-amino-3-trifluoromethoxy-benzoic acid methyl ester (1.38 gm, 5.9 mmol) in 18 mL CH$_2$Cl$_2$ at 0° C. under nitrogen was added pyridine (521 μL, 6.4 mmol) followed by p-nitrophenylchloroformate (1.18 gm, 5.9 mmol). After 4 hours at 0° C. the reaction was diluted to 60 mL with CH$_2$C$_{12}$ and washed 2×60 mL with 2N HCl, 1×60 mL with H$_2$O and 1×60 mL with saturated NaCl. The organics were dried (MgSO$_4$), filtered and concentrated to a white solid, corresponding to the carbamate (2.1 gm, 89 %).

Step 3: 4-[3-(5-Methyl-pyrazin-2-yl)-ureido]-3-trifluoromethoxy-benzoic acid methyl ester. To a stirred solution of 4-(4-nitro-phenoxycarbonylamino)-3-trifluoromethoxy-benzoic acid methyl ester (400 mg, 1 mmol) in 1 mL of NMP in a capped reaction vial at room temperature was added 2-amino-5-methyl-pyrazine (109 mg, 1 mmol) and the solution heated to 90° C. for 6 hours. After cooling to room temperature, the solution was diluted to 30 mL with EtOAc and washed 4×30 mL with 10% NaHCO$_3$ to remove the phenol by-product and 1×30 mL with saturated NaCl. The organics were dried (MgSO$_4$), filtered and concentrated. Trituration and filtration with EtOAc gave a beige solid corresponding to the urea ester (136 mg, 37%).

Step 4: 4-[3-(5-Methyl-pyrazin-2-yl)-ureido]-3-trifluoromethoxy-benzoic acid. To a stirred suspension of 4-[3-(5-methyl-pyrazin-2-yl)-ureido]-3-trifluoromethoxy-benzoic acid methyl ester (136 mg, 0.37 mmol) in 4 mL 3:1 MeOH:H$_2$O under nitrogen was added lithium hydroxide monohydrate (154 mg, 3.7 mmol), and the reaction heated to 65° C. The reaction turned yellow/green and eventually became a solution. After stirring overnight, the reaction was cooled to RT and partially concentrated by rotovap to remove most of the MeOH. The residual suspension was neutralized with 2N HCl until pH=6. The reaction formed a floculent precipitate which was filtered off with H$_2$O and dried overnight under high vacuum to give the acid as a white solid (102 mg, 78%).

Step 5: To a stirred suspension of 4-[3-(5-methyl-pyrazin-2-yl)-ureido]-3-trifluoromethoxy-benzoic acid (102 mg, 0.29 mmol) in 2.9 mL NMP in a capped reaction vial at room temperature was added HBTU (109 mg, 0.29 mmol). After 15 minutes 3-S-1-Benzyl-pyrrolidin-3-ylamine dihydrochloride (prepared analogously to 1-Pyridin-2-ylmethyl-pyrrolidin-3-ylamine used in the synthesis of Compound 215) (73 mg, 0.29 mmol) was added followed by DIEA (200 µL, 1.2 mmol). The reaction was stirred overnight and NMP was then removed under high vacuum at 70° C. The residue was partitioned between 30 mL $CH_2Cl_2$ and 30 mL 10% $Na_2CO_3$. The organics were isolated and washed 1×30 mL with saturated NaCl, dried ($MgSO_4$), filtered and concentrated to a yellow foam corresponding to the desired amide (103 mg, 70%).

$^1$H-NMR (400 MHz, $CDCl_3/CD_3OD$) δ8.56 (d, 1H, 8.37 (br s, 1H), 8.08 (s, 1H), 7.84 (s, 1H), 7.66 (d, 1H), 7.40-7.28 (m, 6H), 4.73 (m, 1H), 3.68 (dd, 2H), 2.77 (dd, 2H), 2.53 (s, 3H), 2.43 (m, 1H), 2.37 (dd, 2H), 1.78 (m, 1H) LRMS (esi, positive) m/e 514.9 (M+1)

Compound 229

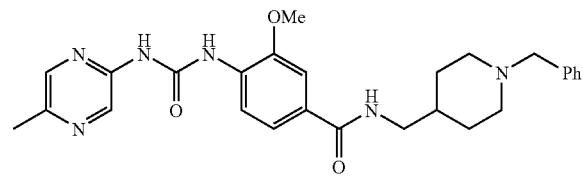

N-(1-Benzyl-piperidin-4-ylmethyl)-3methoxy-4-[3-(5-methyl-pyrazin-2-yl)-ureido]-benzamide Step 1: N-benzylisonipecotamide. To a suspension of isonipecotamide (12.3 g, 96 mmol) in 200 mL of dichloromethane, was added, benzaldehyde (10.6 g, 100 mmol) and sodium triacetoxyborohydride (29.7 gm, 140 mmol) and the mixture was stirred at room temperature for 5 days. The thick white mixture was diluted with 100 mL water and extracted with EtOAc (2×20 mL). The aqueous phase was basified with 1N NaOH to pH>12. The resulting white precipitate was collected by suction filtration. The white solid was subsequently taken up in 50 mL of EtOAc, and was washed with 20 mL of brine, then dried ($MgSO_4$), filtered and concentrated to give 10.84 g (50%) of the desired product. $^1$H-NMR (400 MHz, $CDCl_3$) δ7.85 (m, 5H), 5.45 (s, 1H), 5.34 (s, 1H), 3.5 (s, 2H), 2.93 (d, J=10.96 Hz, 2H), 2.16 (t, J=12.13 Hz, 1H), 2.01 (t, J=11.74 Hz, 2H), 1.87 (d, J=12.52 Hz, 2H), 1.76 (q, J=12.52 Hz, 2H).

Step 2: 4-Aminomethyl-1-benzyl piperdine. To a solution of N-benzylisonipecotamide (7.34g, 34 mmol) in 60 mL of anhydrous THF, was added, $LiAlH_4$ (1.9 g, 51 mmol) and the mixture was stirred at room temperature for 10 minutes followed by heating to reflux for 3 h. The reaction was quenched by addition of 100 mL sat'd. sodium potassium tartrate, and was extracted with EtOAc (3×50 mL). The combined extracts were washed with 20 mL water and 20 mL brine then dried over $MgSO_4$, filtered and concentrated to give the desired product. $^1$H-NMR (400 MHz, $CDCl_3$) δ7.13 (m, 5H), 3.42 (s, 2H), 2H), 2.91 (m, 2H), 2.59 (m, 2H), 1.97 (m, 2H), 1.62 (m, 2H), 2.21 (m, 5H).

Step 3: N-(1-Benzyl-piperidin-4-ylmethyl)-3-methoxy-4-[3-(5-methyl-pyrazin-2-yl)-ureido]-benzamide. Prepared from 4-aminomethyl-1-benzyl piperdine, according to the procedure of Compound 208:

$^1$H-NMR (400 MHz, d6-DMSO) δ10.1 (s, 2H), 8.81 (s, 1H), 8.48 (s, 1H), 8.26 (m, 2H), 7,52 (m, 7H), 3.97 (s, 5H), 3.33 (s, 3H), 3.18 (s, 3H), 2.43 (s, 3H), 1.75 (s, 3H), 1.44 (s, 2H), 7.52 (m, 7H), 489.1.

Compound 230

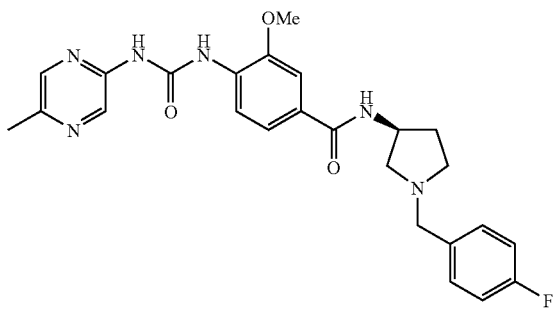

N-[3-S-1-(4-Fluoro-benzyl)-pyrrolidin-3-yl]-3-methoxy-4-[3-(5-methyl-pyrazin-2-yl)-ureido]-benzamide Step 1: (3S)-3-(tert-Butoxycarbonylamino)-1-(4-fluoro-benzyl)-pyrrolidine. To a solution of (3S)-(+) -3-(tert-butoxycarbonylamino)pyrrolidine (410 mg, 2.20 mmol), in 22 mL EtOH, was added, (288 µL, 2.31 mmol) of 4-fluorobenzyl bromide, and (788 mg, 2.42 mmol) of finely powdered cesium carbonate. The stirred reaction mixture was heated at 80° C., under nitrogen for 3 h, after which time, TLC indicated the reaction was complete. The reaction was then concentrated in vacuo to about 5 mL, and was then diluted with 30 mL of EtOAc, and washed with 20 mL of 5% $NH_4OH$. The aqueous fraction was extracted with diethyl ether (3×20 mL). The combined organics were washed with 20 mL of brine, dried ($MgSO_4$), filtered and concentrated. The crude white solid was triturated with 1:1 ether-hexane to give 501 mg (77%) of the desired product as a white solid. $^1$H-NMR (400 MHz, $CDCl_3$) δ7.2-7.3 (m, 2H), 6.9-7.1 (m, 2H), 4.85 (br. s, 1H, exchanges), 4.18 (br. s, 1H), 3.55 (s, 2H), 2.65 (br. m, 1H), 2.58 (n, 1H), 2.50 (m, 1H), 2.2-2.4 (m, 2H), 1.5-1.7, (m, 1H), 1.4 (s, 9H).

Step 2: (3S)-3-Amino-1-(4-fluoro-benzyl)-pyrrolidine. A solution of (3S)-3-(tert -butoxycarbonylamino)-1-(4-fluoro-benzyl)-pyrrolidine (400 mg, 1.36 mmol) was stirred in 15 mL of formic acid at room temperature. After 3 h, the clear colorless solution was concentrated to dryness and the residue was taken-up in 20 mL of EtOAc and washed with 10 mL of 5% $NH_4OH$, followed by 10 mL of brine. The solution was then dried over $MgSO_4$, filtered and concentrated to give 240 mg (91%) of product, as a yellow oil. $^1$H-NMR (400 MHz, $CDCl_3$) δ7.28 (m, 2H), 6.99 (m, 2H), 3.56 (d, J =6.2Hz, 2H), 3.47-3.53 (m, 1H), 2.67-2.71 (m, 2H), 2.42-2.48 (m, 1H), 2.28-2.31 (m, 1H), 2.21-2.28 (m, 1H), 1.59 (s, 2H, $NH_2$), 1.43-1.52 (m, 1H).

Step 3: N-[(3S)-1-(4-Fluoro-benzyl)-pyrrolidin-3-yl]-3-methoxy-4-[3-(5-methyl-pyrazin-2-yl)-ureido]-benzamide. Prepared from (3S)-3-amino-1-(4-fluoro-benzyl)-pyrrolidine, according to the procedure of Compound 208. $^1$H-NMR (400 MHz, $CDCl_3$) δ10.8 (s, 2H), 8.8 (s, 1H), 8.38 (s, 1H), 8.27 (s, 1H), 8.24 (s, 2H), 7.51 (s, 1H), 7.49 (s, 1H), 7.37 (s, 2H), 7.15 (m, 2H), 4.4 (br.s, 1H), 3.98 (s, 3H), 3.6 (br.s, 2H), 3.06 (br.s, 1H), 2.65 (br.s, 1H), 2.81 (br.s, 1H), 2.43 (s, 3H), 2.16 (s, 1H), 1.83 (s, 1H). MS apci-pos M+1=479.2.

Compound 231

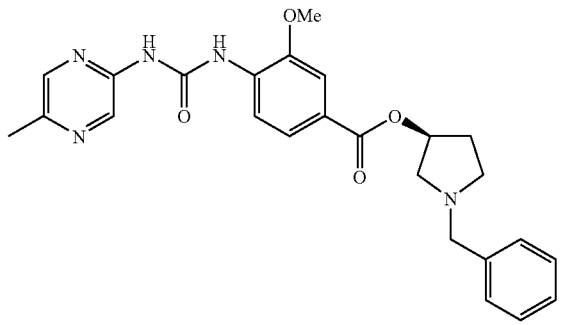

3-Methoxy-4-[3-(5-methyl-pyrazin-2-yl)-ureido]-benzoic acid 3-S-1-benzyl-pyrrolidin-3-yl ester Step 1: 3-Methoxy-4-nitro-benzoyl chloride. Thionyl chloride 3.7 mL, (50 mmol) was added drop wise, at room temperature, to a stirred solution of 3-methoxy-4-nitro-benzoic acid (1.0 g, 5.07 mmol) in 15 mL of dioxane under a nitrogen atmosphere. After the addition was complete, the reaction was allowed to stir at room temperature for 1 hr. The reaction flask was then fitted with a distillation head, and excess thionyl chloride and about ½ of the solvent was removed by distillation in a 120° C. oil bath. The remaining solvent was removed by rotary evaporation, and the residue was taken up in 20 mL toluene and again about 1 of the solvent was removed by distillation. The remaining solution was then cooled to 0° C., and the white solid which precipitated, was collected by suction filtration, and rinsed with 1-1 $Et_2O$-hexane. $^1$H-NMR (400 MHz, $CDCl_3$) δ7.87 (d, J=7.83 Hz, 1H), 7.82 (d, J=7.83 Hz, 1H), 7.77 (s, 1H), 4.04 (s, 3H).

Step 2: (3S)-1-Benzyl-pyrrolidin-3-ol. A solution of (3S)-3-hydroxypyrrolidine (2.0 g, 25 mmol) 50 mL $CH_2Cl_2$, under a nitrogen atmosphere, was cooled to 0° C. and benzaldehyde (2.92 g, 27.5 mmol was added, followed by 1 g of powdered 4A molecular sieves. Sodium triacetoxyborohydride (7.4 gm, 35 mmol)was added in several portions over 30 min, and the reaction was allowed to stir at room temperature for 18 h. The reaction was again cooled to 0° C. and quenched by addition of 10 mL methanol, followed by 5 mL of 1N HCl. The molecular sieve solids were removed by filtration through a glass fiber paper, and the filtrate was extracted with 20 mL diethyl ether. The organic phase was discarded, and the aqueous phase was first basified by addition of conc. ammonium hydroxide, and then extracted with EtOAc (3×20 mL). The combined extracts were washed with 20 mL brine, dried ($MgSO_4$), filtered, and concentrated in vacuo to furnish 3.2 g (73%) of clear yellow oil, which required no further purification. $^1$H-NMR (400 MHz, $CDCl_3$) δ7.2-7.4 (m, 5H), 4.33 (, 1H), 3.63, (s, 2H), 2.83-3.89 (m, 1H), 2.67 (d, J=9.9 Hz, 1H), 2.53-2.55 (m, 1H), 2.23-2.34 (m, 1H), 2.14-2.20 (m, 2H), 1.70-1.77 (n, 11H).

Step 3: 3-Methoxy-4-nitro-benzoic acid (3S)-1-benzyl-pyrrolidin-3-yl ester. A solution of 3-methoxy -4-nitro-benzoyl chloride (608 mg, 2.82 mmol) in 10 mL of $CH_2Cl_2$ was added to stirred solution of 500 mg (2.82 mmol) of (3S)-1-benzyl-pyrrolidin-3-ol and 1 mL of pyridine in 15 mL $CH_2Cl_2$ at room temperature. After stirring for 18 h, the reaction mixture was diluted with 20 mL of saturated aqueous $NaHCO_3$, and extracted with $CH_2Cl_2$ (2×10 mL). The combined extracts were washed with 20 mL of brine, dried over $MgSO_4$, filtered, and concentrated in vacuo to furnish 780 mg (71%) of the desired ester as a yellow oil, which solidified after drying under high vacuum. The resulting solid was further purified by trituration with 1:1 ether-hexane. $^1$H-NMR (400 MHz, $CDCl_3$) δ7.83 (d, J =7.83 Hz, 1H), 7.74 (s, 1H), 7.68 (d, J=7.83 Hz, 1H), 7.2-7.4 (m, 5H), 5.44 (br.m, 1H), 4.02 (s, 2H), 3.69 (dd, J=30 Hz, J=13 Hz, 1H), 2.8-3.0 (m, 2H), 2.5-2.6 (m, 1H), 2.3-2.45 (m, 1H), 2.0-2.1 (m, 1H)

Step 4: 4-Amino-3-methoxy-benzoic acid (3S)-1-benzyl-pyrrolidin-3-yl ester. The aniline was prepared by nickel boride reduction of 3-methoxy-4-nitro-benzoic acid (3S)-1-benzyl-pyrrolidin-3-yl ester analogously to the preparation of 4-[(Benzyl-methyl-amino)-methyl]-2-methoxy-phenylamine used in the synthesis of Compound 340. $^1$H-NMR (400 MHz, $CDCl_3$) δ7.54 (d, J =8.21 Hz, 1H), 7.44 (s, 1H), 7.2-7.4 (m, 5H) 6.65 (d, J=8.21 Hz, 1H), 5.38 (br.m, 1H), 4.22 (s, 1H), 3.90 (s, 3H), 3.69 (q, J=24.63 Hz, 1H), 3.0 (m, 1H), 2.7-2.9 (m, 2H), 2.5-2.6 (m, 1H), 2.3-2.4 (m, 1H), 1.9-2.1 (m, 1H). MS apci-pos M+1=327.2.

Step 5: 3-Methoxy-4-[3-(5-methyl-pyrazin-2-yl)-ureido]-benzoic acid (3S)-1-benzyl-pyrrolidin-3-yl ester. Prepared from 4-amino-3-methoxy-benzoic acid (3S)-1-benzyl-pyrrolidin-3-yl ester according to the procedure of Compound 208: $^1$H-NMR (400 MHz, $CDCl_3$) δ10.15 (s, 2H), 8.8 (s, 1H), 8.35 (d, J=8.61 Hz, 1H), 8.25 (s, 1H), 7.58 (d, J =8.61 Hz, 1H), 7.5 (s, 1H), 7.30-7.35 (m, 4H), 7.26-7.24 (m, 1H), 5.28 (s, 1H), 3.99 (s, 3H), 3.62 (s, 2H), 2.82 (m, 1H), 2.74 (m, 1H), 2.67 (m, 1H), 2.44 (s, 3H), 2.28 (m, 1H), 1.91 (m, 1H). MS apci-pos M+1=462.2.

Compound 232

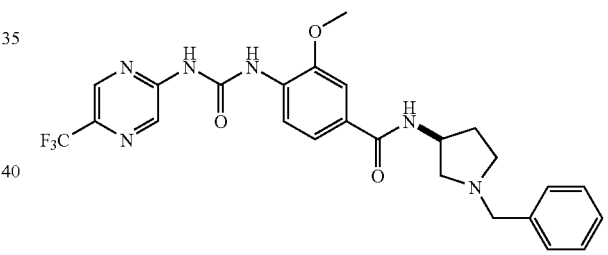

N-(3-S-1-Benzyl-pyrrolidin-3-yl)-3-methoxy-4-[3-(5-trifluoromethyl-pyrazin-2-yl)-ureido]-benzamide Step 1: 3-Methoxy-4-[3-(5-trifluoromethyl-pyrazin-2-yl)-ureido]-benzoic acid methyl ester. To a stirred solution of 5-trifluoromethylaminopyrazine (326 mg, 2 mmol) at room temperature in NMP (2 mL) in a capped reaction vial was added 4-methoxy-3-(4-nitrophenylcarbonylamino)-benzoic acid methyl ester (692 mg, 2 mmol) and the solution was heated to 85° C. for 6 hours. The reaction was cooled to RT and triturated with EtOAc (5 mL) and the tan solid that formed was isolated by filtration and rinsing with EtOAc (213 mg, 28%).
$^1$H-NMR (400 MHz, $d_6$-DMSO) δ10.78 (s, 1H), 10.16 (br s, 1H), 9.07 (s, 1H), 8.84 (s, 1H), 8.37 (d, 1H), 7.63 (d, 1H), 7.56 (s, 1H), 4.01 (s, 3H), 3.83 (s, 3H)

Step 2: 3-Methoxy-4-[3-(5-trifluoromethyl-pyrazin-2-yl)-ureido]-benzoic acid. To a stirred solution of 3-methoxy-4-[3-(5-trifluoromethyl-pyrazin-2-yl)-ureido]-benzoic acid methyl ester (213 mg, 0.575 mmol) in 5.75 mL 3:1 MeOH:H20 at room temperature under nitrogen was added lithium hydroxide monohydrate (240 mg, 5.8 mmol) and the reaction warmed to 65° C. After reaching temperature, the suspension gradually became a bright yellow solution. After about 4 hours a precipitate formed but the reaction was continued overnight. After cooling to RT, MeOH was removed by rotovap and the aqueous suspension neutralized to pH=5 with concentrated HCl. As pH=5 was approached, the suspension turned from yellow to white. The suspension was then filtered through paper on a ceramic funnel. When most of the H20 was removed the residue was dryed under high vacuum in a dessicator overnight (133 mg, 55%).

Step 3: To a stirred solution of 3-methoxy-4-[3-(5-trifluoromethyl-pyrazin-2-yl)-ureido]-benzoic acid (35 mg, 0.1 mmol) in 0.5 mL NMP in a capped reaction vial at RT was added HBTU (41 mg, 0.11 mmol) and the activation stirred for 15 min. 1-Benzyl-pyrrolidin-3-ylamine dihydrochloride (prepared analogously to 1-Pyridin-2-ylmethyl-pyrrolidin-3-ylamine used in the synthesis of Compound 215) (crude 0.1 mmol) was then added as a solution in 0.5 mL NMP with DIEA (69 µL, 0.4 mmol). After stirring overnight at RT, NMP was removed by distillation under high vacuum at 70° C. The residue was dissolved in 25 mL CH$_2$Cl$_2$ with a small amount of MeOH and washed 2×25 mL with 10% Na$_2$CO$_3$. The organics were dried (MgSO$_4$), filtered and concentrated to a residue that was chromatographed on a biotage 12S column with 5/95 MeOH/CH$_2$Cl$_2$. This material was concentrated to dryness and triturated/filtered with Et$_2$O to give pure product as a white solid (9.5 mg, 19%).

$^1$H-NMR (400 MHz, CDCl$_3$) δ11.53 (s, 1H), 9.86 (br s, 1H), 8.57 (s, 1H), 8.40 (d, 1H), 8.12 (s, 2H), 7.56 (s, 1H), 7.46 (m, 2H), 7.25 (m, 4H), 4.79 (m, 1H), 4.01 (s, 3H), 3.73 (dd, 2H), 3.22 (m, 2H), 2.76 (m, 1H), 2.47 (m, 2H), 1.76 (m, 1H) LRMS (esi, positive) m/e 515.1 (M+1)

Compound 233

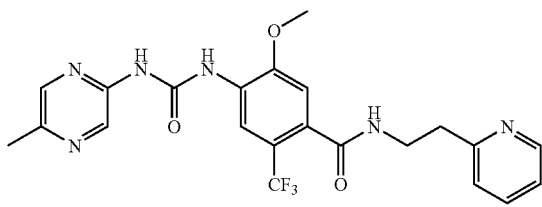

5-Methoxy-4-[3-(5-methyl-pyrazin-2-yl)-ureido]-N-(2-pyridin-2-yl-ethyl)-2-trifluoromethyl-benzamide Step 1: Mixture of 5-Fluoro-4-nitro-2-trifluoromethyl-benzoic acid and 5-Fluoro-3-nitro-2-trifluoromethyl-benzoic acid. To a stirred solution of 3-fluoro-6-trifluoromethylbenzoic acid (3.58 gm, 17.2 mmol) in 17 mL concentrated H$_2$SO$_4$ at 0° C. was carefully added 70% HNO$_3$ (17 mL) dropwise The reaction was heated to 100° C. overnight and was then cooled to room temperature and poured into 250 mL of H$_2$O/ice with stirring. EtOAc (250 mL) was added and the mixture stirred. The layers were separated and the organics washed 1×250 mL with H$_2$O and 1×250 mL with saturated NaCl. The organics were dried (MgSO$_4$), filtered and concentrated to an oil which solidified upon standing. The solid was a 1:1 mixture of regioisomers and was carried on crude.

Step 2: Mixture of 5-Fluoro-4-nitro-2-trifluoromethyl-benzoic acid methyl ester and 5-Fluoro-3-nitro-2-trifluoromethyl-benzoic acid methyl ester. To a stirred solution of the nitro acids (crude, 17.2 mmol) in 60 mL of 4:1 THF:MeOH at 0° C. was added 2M TMS-diazomethane in hexane dropwise until a yellow color persisted. After 30 minutes the reaction was concentrated to a crude oil and used directly in the next step.

Step 3: Mixture of 5-Methoxy-4-nitro-2-trifluoromethyl-benzoic acid methyl ester and 5-Methoxy-3-nitro-2-trifluoromethyl-benzoic acid methyl ester. To a stirred solution of the fluoro nitro esters (crude, 17.2 mmol) in 22 ml, MeOH at room temperature was added 150 mL of 0.5 M sodium methoxide in MeOH. The red solution was stirred for 30 minutes and then partitioned between CH$_2$Cl$_2$ (500 mL) and H$_2$O (500 mL). The organics were washed 2×500 mL with H$_2$O, dried (MgSO$_4$), filtered and concentrated to a white solid.

Step 4: 5-Methoxy-4-amino-2-trifluoromethyl-benzoic acid methyl ester. To a stirred solution of the methoxy nitro esters (crude, 17.2 mmol) in 172 mL MeOH at room temperature purged with nitrogen was carefully added 10% Pd on C (1 gm). The suspension was put through a vacuum/purge cycle three times with hydrogen gas and then held under 1 atmosphere of hydrogen. After stirring overnight the suspension was filtered through GF/F filter paper and concentrated to a clear oil. This material was loaded directly onto a Biotage 40M column with CH$_2$Cl$_2$ and eluted first with 9/1 hexane/EtOAc to elute the undesired hi Rf regioisomer and then with 85/15 hexane/EtOAc to elute the desired lower Rf regioisomer. After concentration, the lower Rf isomer solidified to a clear solid (1.75 gm, 41%). $^1$H-NMR (400 MHz, CDCl$_3$) δ7.33 (s, 1H), 6.98 (s, 1H), 3.92 (s, 3H), 3.85 (s, 3H)

Step 5: 5-Methoxy-4-(4-nitro-phenoxycarbonylamino)-2-trifluoromethyl-benzoic acid methyl ester. To a stirred solution of 5-methoxy-4-amino-2-trifluoromethyl-benzoic acid methyl ester (552 mg, 2.22 mmol) in 6.6 mL CH$_2$Cl$_2$ at 0° C. under nitrogen was added pyridine (180 µL, 2.22 mmol) followed by p-nitrophenyl chloroformate (448 mg, 2.22 mmol) as a solid. After stirring for 1 hour, the reaction was diluted to 30 mL with CH$_2$Cl$_2$ and washed 2×30 mL with 2N HCl and 1×30 mL with H$_2$O. The organics were dried (MgSO$_4$), filtered and concentrated to the p-nitrophenyl carbamate which was isolated as a white foam (878 mg, 96%). $^1$H-NMR (400 MHz, CDCl$_3$) S 8.57 (br s, 1H), 8.30 (d, 2H), 7.77 (br s, 1H), 7.40 (d, 2H), 7.37 (s, 1H), 4.03 (s, 3H), 3.94 (s, 3H)

Step 6: 5-Methoxy-4-[3-(5-methyl-pyrazin-2-yl)-ureido]-2-trifluoromethyl-benzoic acid methyl ester. To a stirred solution of 5-methoxy-4-(4-nitro-phenoxycarbonylamino)-2-trifluoromethyl-benzoic acid methyl ester (878 mg, 2.1 mmol) in 4.2 mL NMP at room temperature under nitrogen was added 2-amino-5-methylpyrazine (232 mg, 2.1 mmol) and the reaction heated to 85° C. After six hours the reaction was cooled to room temperature and a precipitate formed. The precipitate was triturated with EtOAc (25 mL) and the urea isolated by filtration as a tan solid (470 mg, 58%).

Step 7: 5-Methoxy-4-[3-(5-methyl-pyrazin-2-yl)-ureido]-2-trifluoromethyl-benzoic acid. To a stirred suspension of 5-methoxy-4-[3-(5-methyl-pyrazin-2-yl)-ureido]-2-trifluoromethyl-benzoic acid methyl ester (257 mg, 0.67 mmol) in 6.7 mL 3:1 MeOH:H$_2$O at room temperature under nitrogen was added lithium hydroxide monohydrate (281 mg, 6.7 mmol) and the mixture was heated to 85° C. After stirring overnight the reaction was cooled to room temperature, MeOH was removed by rotovap and the residual suspension was neutralized with concentrated HCl to pH of approximately 5. The suspension was filtered and rinsed with H$_2$O and the filter cake dried under high vacuum to give the acid as a white solid (161 mg, 61%). ¹H-NMR (400 MHz, d₆-DMSO) δ8.90 (br s, 1H), 8.63 (s, 1H), 8.22 (s, 1H), 7.38 (s, 1H), 4.00 (s, 3H), 2.42 (s, 3H). LRMS (esi, negative) m/e 369.0 (M−1).

Step 8: 5-Methoxy-4-[3-(5-methyl-pyrazin-2-yl)-ureido]-N-(2-pyridin-2-yl-ethyl)-2-trifluoromethyl -benzamide. To a stirred solution of 5-methoxy-4-[3-(5-methyl-pyrazin-2-yl)-ureido]-2-trifluoromethyl -benzoic acid (37 mg, 0.1 mmol) in 1 mL NMP at room temperature in a capped reaction vial was added HBTU (42 mg, 0.11 mmol) and the suspension stirred for 15 minutes. 2-aminoethylpyridine (13 μL, 0.11 mmol) was added followed by DIEA (35 μL, 0.2 mmol) and the reaction was stirred overnight. NMP was then removed by bulb to bulb transfer under high vacuum at 70° C. and the residue triturated and filtered with EtOAc to give the desired amide as a tan solid (32 mg, 68%). ¹H-NMR (400 MHz, d₆-DMSO) δ8.90 (br s, 1H), 8.66 (d, 1H, 8.61 (s, 1H), 8.52 (t, 1H), 8.23 (s, 1H), 8.10 (br m, 1H), 7.61 (br d, 1H), 7.57 (br m, 1H), 7.07 (s, 1H), 4.00 (s, 3H), 3.62 (m, 2H), 3.11 (m, 2H), 2.42 (s, 3H) LRMS (esi, positive) m/e 475.1 (M+1)

Compound 234

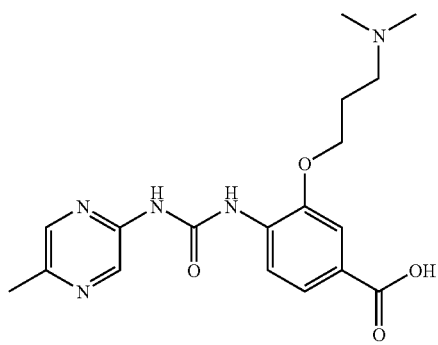

3-(3-Dimethylamino-propoxy)-4-[3-(5-methyl-pyrazin-2-yl)-ureido]-benzoic acid

Step 1: 3-(3-Dimethylamino-propoxy)-4-nitro-benzoic acid methyl ester. To a stirred, cooled (about 0° C.) solution of 3-hydroxy-4-nitro benzoic acid methyl ester. (394 mg, 2.0 mmol), triphenyl phosphine (525 mg, 2.0 mmol), arid 3-(dimethylamino)-propanol (237 μL, 2.0 mmol) in dry tetrahydrofuran (5 mL) was added diisopropyl azodicarboxylate (394 μL, 2.0 mmol in 1 mL of tetrahydrofuran). After stirring for 12 hours, the reaction was diluted with hydrochloric acid (30 mL of a 1M solution) and extracted with ethyl acetate (2×50 mL). The aqueous solution was basified with 10% aqueous sodium carbonate (50 mL) and the product was extracted with ethyl acetate (3×100 mL). The ethyl acetate was washed with brine (1×30 mL), then dried (MgSO₄), and filtered. The filtered solution was concentrated under reduced pressure to provide the desired crude product (86% yield). ¹H-NMR (400 MHz, CDCl₃) δ7.81 (d, 1H), 7.78 (s, 1H), 7.65 (d, 1H, 4.23 (t, 2H), 3.91 (s, 3H),2.44 (t, 2H), 2.22 (s, 6H), 2.05 (m, 2H).

Step 2: 4-Amino-3-(3-dimethylamino-propoxy)-benzoic acid methyl ester. To a stirred, cooled (about 0° C.) solution of 3-(3-dimethylamino-propoxy)-4-nitro-benzoic acid methyl ester (282 mg, 1.0 mmol) in methanol (2 mL) and saturated aqueous ammonium chloride (1 mL) was added zinc dust (2.0 mmol). After stirring for 12 hours, the reaction was diluted with 30 mL of ethyl acetate and washed with 30 mL of 10% aqueous sodium carbonate (2×30 mL), brine (1×30 mL), then dried (MgSO₄), and filtered. The filtered solution was concentrated under reduced pressure to yield the desired product as a tan solid (88% yield). ¹H-NMR (400 MHz, CDCl₃) δ7.52 (d, 1H), 7.48 (s, 1H), 7.25 (s, 1H), 6.65 (d, 1H), 4.29 (br s, 1H), 4.09 (t, 2H), 3.85 (s, 3H), 2.49 (t, 2H), 2.25 (s, 6H), 2.00 (m, 2H).

Step 3: 3-(3-Dimethylamino-propoxy)-4-[3-(5-methyl-pyrazin-2-yl)-ureido]-benzoic acid methyl ester. To a stirred, cooled (about 0° C.) solution of 4-amino-3-(3-dimethylamino-propoxy)-benzoic acid methyl ester (252 mg, 1.0 mmol) in toluene (3.0 mL) was added triethylamine (139 μL, 1.0 mmol) and triphosgene (98 mg, 0.33 mmol). After stirring for 30 minutes, 5-methyl-2-amino pyrazine (109 mg, 1.0 mmol) was added and the reaction was heated to 65 degrees C. The reaction was allowed to cool to room temperature, then diluted with ethyl acetate (50 mL) and water (50 mL). A precipitate formed which was filtered and dried under reduced pressure to yield the desired material as a white solid (40% yield). ¹H-NMR (400 MHz, d₆-DMSO) δ8.62 (br s, 1H), 8.41 (d, 1H), 8.19 (s, 1H), 7.59 (d, 1H), 7.49 (s, 1H), 4.15 (t, 2H), 3.81 (s, 3H), 2.42 (m, 5H), 2.18 (s, 6H), 2.01 (m, 2H).

Step 4: 3-(3-Dimethylamino-propoxy)-4-[3-(5-methyl-pyrazin-2-yl)-ureido]-benzoic acid. To a stirred solution of 3-(3-dimethylamino-propoxy)-4-[3-(5-methyl-pyrazin-2-yl)-ureido]-benzoic acid methyl ester (1.0 gm; 3.3 mmol) in methanol (25 mL) was added lithium hydroxide (5 mL of a 2M aqueous solution). The reaction was heated to 60 degrees and stirred for 12 hours. The reaction was allowed to cool to room temperature and the pH was adjusted to 5.5 with 1N hydrochloric acid. A precipitate formed which was filtered and dried under reduced pressure to yield the desired product as a tan solid (52% yield). ¹H-NMR (400 MHz, d₆-DMSO) δ8.62 (br s, 1H), 8.39 (d, 1H, 8.21 (s, 1H), 7.59 (d, 1H), 7.43 (s, 1H), 4.15 (t, 2H), 2.42 (m, 5H), 2.18 (s, 6H), 2.01 (m, 2H).

Compound 235

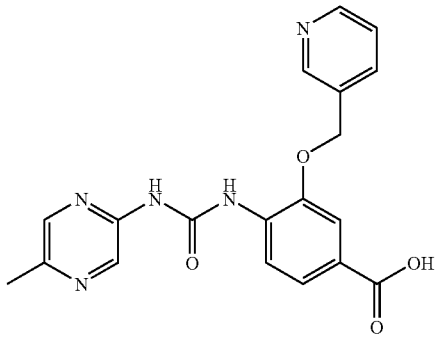

4-[3-(5-Methyl-pyrazin-2-yl)-ureido]-3-(pyridin-3-ylmethoxy)-benzoic acid

Step 1: 4-Nitro-3-(pyridin-3-ylmethoxy)-benzoic acid methyl ester. To a stirred, cooled (about 0° C.) solution of 3-hydroxy-4-nitro benzoic acid methyl ester (394 mg, 2.0 mmol.), triphenyl phosphine (525 mg, 2.0 mmol), and 3-pyridylcarbinol (194 μL, 2.0 mmol) in dry tetrahydrofuran (5 mL) was added diisopropyl azodicarboxylate (394 μL, 2.0 mmol in 1 mL of tetrahydrofuran). After stirring for 12 hours, the reaction was diluted with hydrochloric acid (30 mL of a 1M solution) and extracted with ethyl acetate (2×50mL). The aqueous solution was basified with 10% aqueous sodium carbonate (50 mL) and the product was extracted with ethyl acetate (3×100 mL). The ethyl acetate was washed with brine (1×30 mL), then dried (MgSO$_4$), and filtered. The filtered solution was concentrated under reduced pressure to provide the desired crude product as an off white solid (76% yield). $^1$H-NMR (400 MHz, CDCl$_3$) δ8.71 (s, 1H), 8.62 (d, 1H), 7.88 (m, 3H), 7.79 (d, 1H), 7.39 (M, 1H), 5.31 (s, 2H), 3.98 (s, 3H).

Step 2: 4-Amino-3-(pyridin-3-ylmethoxy)-benzoic acid methyl ester. To a stirred, cooled (about 0° C.) solution of 4-nitro-3-(pyridin-3-ylmethoxy)-benzoic acid methyl ester (288 mg, 1.0 mmol) in methanol (2 mL) and saturated aqueous ammonium chloride (1 mL) was added zinc dust (131 mg, 2.0 mmol). After stirring for 12 hours, the reaction was diluted with 30 mL of ethyl acetate and washed with 30 mL of 10% aqueous sodium carbonate (2×30 mL), brine (1×30 mL), then dried (MgSO$_4$), and filtered. The filtered solution was concentrated under reduced pressure to yield the desired product as a yellow solid (97% yield). $^1$H-NMR (400 MHz, CDCl$_3$) δ8.78 (s, 1H), 8.61 (d, 1H, 7.79 (d, 1H), 7.59 (m, 2H), 7.39 (m, 1H), 6.71 (d, 1H), 5.18 (s, 2H), 4.28 (br s, 2H), 3.85 (s, 3H).

Step 3: 4-[3-(5-Methyl-pyrazin-2-yl)-ureido]-3-(pyridin-3-ylmethoxy)-benzoic acid methyl ester. To a stirred, cooled (about 0° C.) solution of 4-amino-3-(pyridin-3-ylmethoxy)-benzoic acid methyl ester (258 mg, 1.0 mmol) in toluene (3.0 mL) was added triethylamine (139 μL, 1.0 mmol) and triphosgene (98 mg, 0.33 mmol). After stirring for 30 minutes, 5-methyl-2-amino pyrazine (109 mg, 1.0 mmol) was added and the reaction was heated to 65 degrees C. The reaction was allowed to cool to room temperature, then diluted with ethyl acetate (50 mL) and water (50 mL). A precipitate formed which was filtered and dried under reduced pressure to yield the desired material as a white solid (47% yield). $^1$H-NMR (400 MHz, d$_6$-DMSO) δ10.29 (s, 1H), 8.79 (s, 1H), 8.68 (d, 1H, 8.59 (br s, 1H), 8.48 (d, 1H), 7.70 (s, 1H), 7.62 (d, 1H), 7.51 (m, 1H), 5.32 (s, 2H), 3.88 (s, 3H), 2.32 (s, 3H).

Step 4: 4-[3-(5-Methyl-pyrazin-2-yl)-ureido]-3-(pyridin-3-ylmethoxy)-benzoic acid. To a stirred solution of 4-[3-(5-methyl-pyrazin-2-yl)-ureido]-3-(pyridin-3-ylmethoxy)-benzoic acid methyl ester (1.3 gm; 3.3 mmol) in methanol (25 mL) was added lithium hydroxide (5 mL of a 2M aqueous solution). The reaction was heated to 60 degrees and stirred for 12 hours. The reaction was allowed to cool to room temperature and the pH was adjusted to 5.5 with 1N hydrochloric acid. A precipitate formed which was filtered and dried under reduced pressure to yield the desired product as a tan solid (90% yield). $^1$H-NMR (400 MHz, d$_6$-DMSO) δ10.29 (s, 1H), 8.79 (s, 1H), 8.68 (d, 1H, 8.59 (br s, 1H), 8.48 (d, 1H, 7.70 (s, 1H), 7.62 (d, 1H), 7.51 (m, 1H), 5.32 (s, 2H), 2.32 (s, 3H).

Compound 236

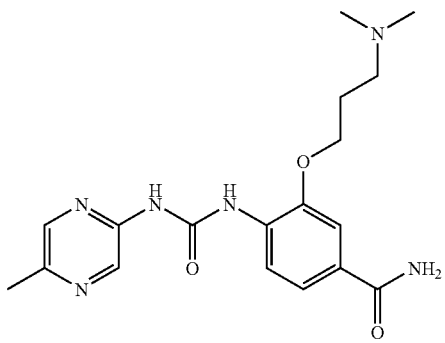

3-(3-Dimethylamino-propoxy)-4-[3-(5-methyl-pyrazin-2-yl)-ureido]-benzamide

Prepared according to the procedure of Compound 208 using ammonia (33% yield) $^1$H-NMR (400 MHz, d$_6$-DMSO) δ10.18 (s, 1H), 8.56 (br s, 1H), 8.20 (d, 1H), 8.11 (s, 1H), 7.43 (d, 1H), 7.40 (s, 1H), 4.03 (m, 2H), 2.40 (m, 2H), 2.33 (s, 3H), 2.05 (s, 6H), 1.91 (m, 2H) LRLCMS (esi, positive) m/e 374.2 (M+1)

Compound 237

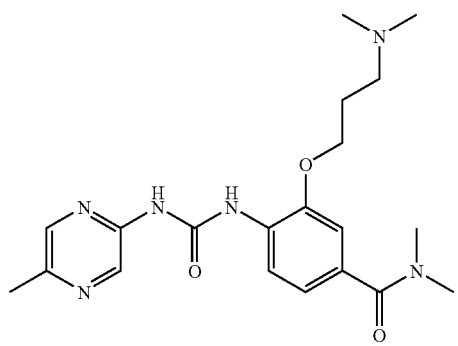

3-(3-Dimethylamino-propoxy)-N,N-dimethyl4-[3-(5-methyl-pyrazin-2-yl)-ureido]-benzamide Prepared according to the procedure of Compound 208 using dimethylamine (97% yield) $^1$H-NMR (400 MHz, CDCl$_3$) δ11.30 (br s, 1H), 8.39 (d, 1H), 8.29 (s, 1H), 8.20 (s, 1H), 7.78 (br s, 1H), 7.07 (s, 1H), 7.04 (d, 1H), 4.16 (t, 2H), 2.55 (s, 3H), 2.53 (m, 2H), 2.26 (s, 6H), 2.10 (m, 2H) LRMS (esi, positive) m/e 401.1 (M+1)

Compound 238

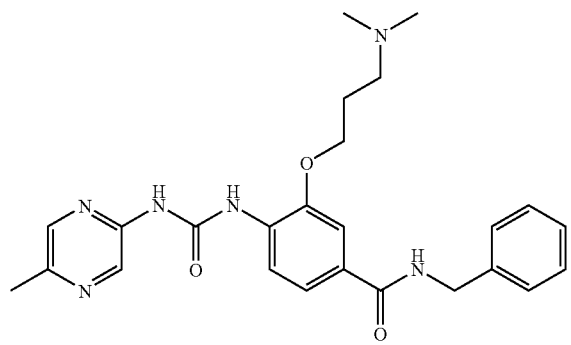

N-Benzyl-3-(3-dimethylamino-propoxy)-4-[3-(5-methyl-pyrazin-2-yl)-ureido]-benzamide Prepared according to the procedure of Compound 208 using benzylamine (65% yield)

$^{1}$H-NMR (400 MHz, CDCl$_3$) δ8.43 (d, 1H, 8.26 (s, 1H), 8.20 (s, 1H), 7.91 (br s, 1H), 7.56 (s, 1H), 7.38 (m, 4H), 7.31 (m, 1H), 6.41 (m, 1H), 4.64 (d, 2H), 4.20 (t, 2H), 2.53 (s, 3H), 2.52 (m, 2H), 2.24 (s, 6H), 2.14 (m, 2H) LRMS (esi, positive) m/e 463.2 (M+1)

Compound 240

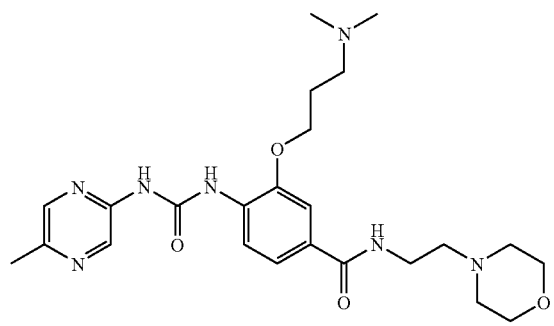

3-(3-Dimethylamino-propoxy-4-[3-(5-methyl-pyrazin-2-yl)-2-ureido]-N-(2-morpholin-4-yl-ethyl)-benzamide Prepared according to the procedure of Compound 208 using 2-morpholin-4-yl-ethylamine (69% yield).

$^{1}$H-NMR (400 MHz, CDCl$_3$) δ8.44 (d, 1H), 8.31 (s, 1H), 8.21 (s, 1H), 7.90 (br s, 1H), 7.55 (s, 1H), 7.24 (d, 1H), 6.76 (m, 1H1), 4.20 (t, 2H), 3.76 (m, 4H), 3.56 (m, 2lH), 2.61 (m, 2H), 2.53 (m, 7H), 2.24 (s, 1H), 2.13 (m, 1H) LRMS (esi, positive) m/e 486.2 (M+1)

Compound 239

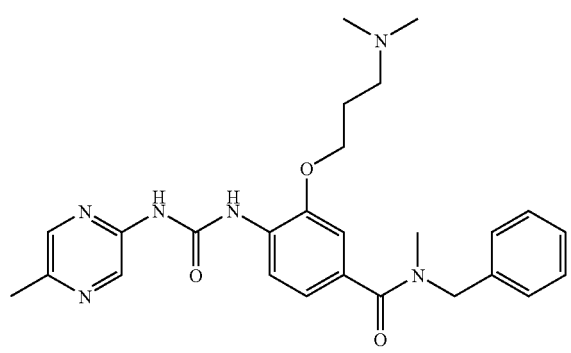

N-Benzyl-3-(3-dimethylamino-prop oxy)-N-methyl-4-[3-(5-methyl-pyrazin-2-yl)-ureido]-benzamide Prepared according to the procedure of Compound 208 using N-methyl benzylamine (68% yield).

$^{1}$H-NMR (400 MHz, CDCl$_3$) δ8.37 (br s, 1H), 8.25 (s, 1H), 8.18 (s, 1H), 7.37 (m, 4H), 7.31 (m, 1H), 7.18 (m, 2H), 4.67 (br m, 2H), 4.07 (br m, 2H), 2.99 (br s, 3H), 2.53 (s, 3H), 2.50 (br m, 2H), 2.24 (s, 6H), 2.06 (br m, 2H) LRMS (esi, positive) m/e 477.2 (M+1)

Compound 241

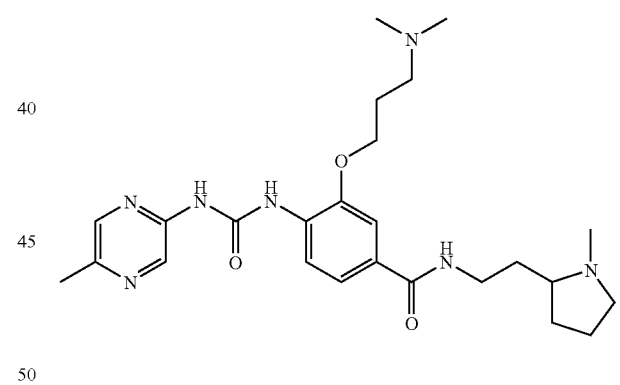

3-(3-Dimethylamino-propoxy)-4-[3-(5-methyl-pyrazin-2-yl)-ureido]-N-[2-(1-methyl-pyrrolidin-2-yl)-ethyl]-benzamide Prepared according to the procedure of Compound 208 using 2-(1-methyl-pyrrolidin-2-ylamine (68% yield).

$^{1}$H-NMR (400 MHz, CDCl$_3$) δ11.35 (br s, 1H), 8.42 (s, 1H), 8.40 (s, 1H), 8.24 (s, 1H), 8.20 (s, 1H), 7.57 (s, 1H), 7.46 (br s, 1H), 7.20 (m, 1H), 4.19 (m, 2H), 3.76 (m, 1H), 3.44 (m, 1H), 3.15 (m, 1H), 2.54 (s, 3H), 2.42 (m, 1H), 2.37 (s, 13H), 2.25 (s, 6H), 2.22 (m, 1H), 2.13 (m, 2H), 1.90 (m, 2H), 1.77 (m, 2H) LRMS (esi, positive) m/e 484.3 (M+1)

Compound 242

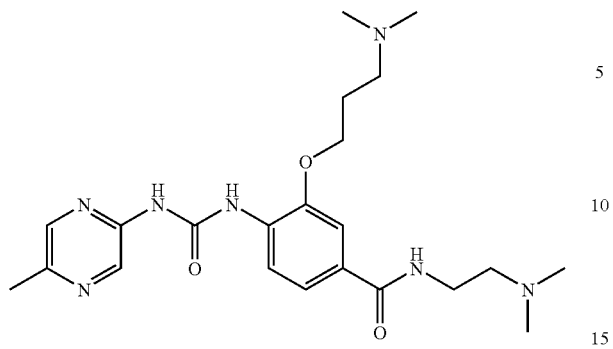

N-(2-Dimethylamino-ethyl)-3-(3-dimethylamino-propoxy)-4-[3-(5-methyl-pyrazin-2-yl)-ureido]-benzamide Prepared according to the procedure of Compound 208 using 2-dimethylamino-ethylamine (37% yield).

$^1$H-NMR (400 MHz, CDCl$_3$) δ11.38 (br s, 1H), 8.42 (d, 1H), 8.30 (s, 1H), 8.20 (s, 1H), 7.96 (br s, 1H), 7.53 (s, 1H), 7.27 (d, 1H), 6.79 (m, 1H), 4.20 (m, 2H), 3.53 (m, 2H), 2.52 (m, 2H) 2.52 (s, 3H), 2.26 (m, 2H), 2.24 (s, 6H), 2.22 (s, 6H), 2.12 (m, 2H) LRMS (esi, positive) m/e 444.2 (M+1)

Compound 244

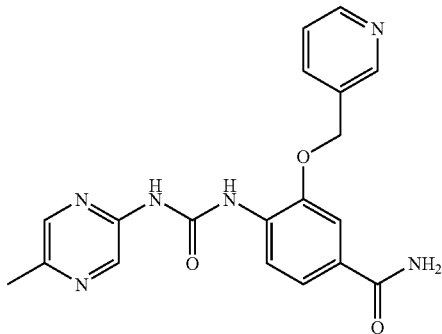

4-[3-(5-Methyl-pyrazin-2-yl)-ureido]-3-(pyridin-3-ylmethoxy)-benzamide

Prepared according to the procedure of Compound 208 using ammonia (99% yield).

$^1$H-NMR (400 MHz, d$_6$-DMSO) δ10.27 (s, 1H), 8.82 (s, 1H), 8.66 (d, 1H, 8.60 (br s, 1H), 8.29 (d, 1H), 8.03 (m, 1H), 8.00 (s, 1H), 7.76 (s, 1H), 7.56 (d, 1H), 7.50 (m, 1H), 7.37 (br m, 1H), 7.26 (br s, 1H), 5.32 (s, 2H), 2.32 (s, 3H) LRMS (apci, positive) m/e 379.1 (M+1)

Compound 243

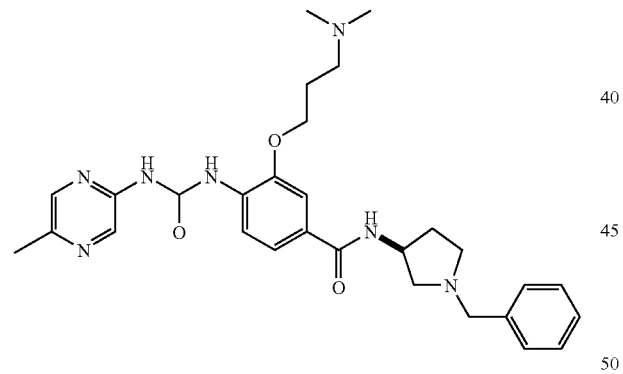

N-(3-S-1-Benzyl-pyrrolidin-3-yl)-3-(3-dimethylamino-propoxy)-4-[3-(5-methyl-pyrazin-2-yl)-ureido]-benzamide Prepared according to the procedure of Compound 215 using 1-benzyl-pyrrolidin-3-S-ylamine (20% yield)

$^1$H-NMR (400 MHz, CDCl$_3$) δ8.61 (br s, 1H), 8.45 (d, 1H), 8.20 (s, 1H), 8.16 (m, 1H), 7.51 (s, 1H), 7.39 (d, 1H, 7.31 (m, 4H), 7.16 (m, 1H), 4.72 (m, 1H), 4.18 (m, 2H), 3.72 (dd, 2H), 3.04 (m, 1H), 2.96 (m, 1H), 2.69 (m, 1H), 2.53 (m, 2H), 2.51 (s, 3H), 2.40 (m, 2H), 2.25 (s, 6H), 2.11 (m, 2H), 1.76 (m, 1H) LRMS (esi, positive) m/e 532.2 (M+1)

Compound 245

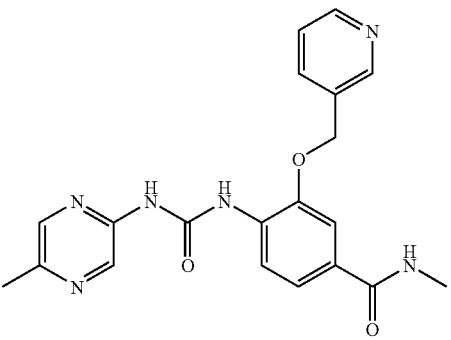

N-Methyl-4-[3-(5-methyl-pyrazin-2-yl)-ureido]-3-(pyridin-3-ylmethoxy)-benzamide

Prepared according to the procedure of Compound 208 using methylamine (99% yield).

$^1$H-NMR (400 MHz, d$_6$-DMSO) δ10.25 (s, 1H), 8.80 (s, 1H), 8.60 (m, 3H), 8.26 (d, 1H, 8.03 (d, 1H), 7.78 (s, 1H), 7.52 (m, 2H), 7.37 (m, 1H), 5.34 (s, 2H), 2.79 (d, 3H), 2.36 (s, 3H) LRMS (apci, positive) m/e 393.2 (M+1)

Compound 246

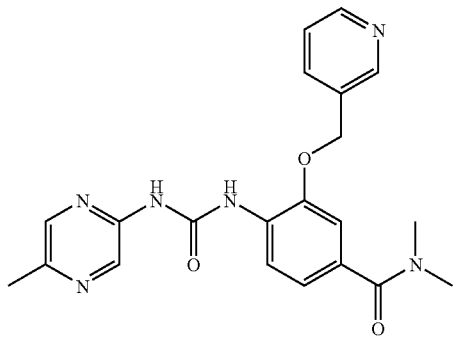

N,N-Dimethyl-4-[3-(5-methyl-pyrazin-2-yl)-ureido]-3-(pyridin-3-ylmethoxy)-benzamide Prepared according to the procedure of Compound 208 using dimethylamine (88% yield).

$^1$H-NMR (400 MHz, d$_6$-DMSO) δ10.16 (s, 1H), 8.80 (s, 1H), 8.66 (d, 1H, 8.58 (s, 1H), 8.28 (d, 1H), 7.96 (d, 1H), 7.50 (m, 1H), 7.37 (br s, 1H), 7.25 (s, 1H), 7.03 (d, 1H), 5.30 (s, 2H), 2.95 (s, 6H), 2.33 LRMS (apci, positive) m/e 407.4 (M+1)

Compound 248

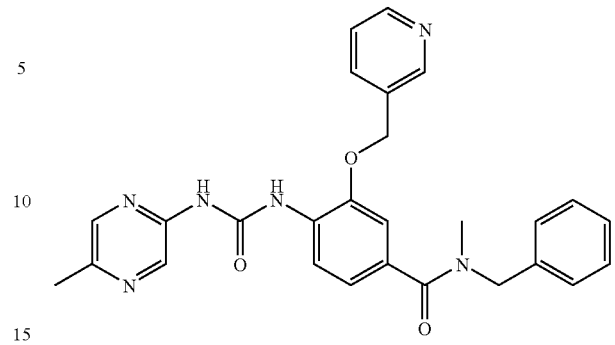

N-Benzyl-N-methyl-4-[3-(5-methyl-pyrazin-2-yl)-ureido]-3-(pyridin-3-ylmethoxy)-benzamide Prepared according to the procedure of Compound 208 using N-methyl benzylamine (71% yield).

$^1$H-NMR (400 MHz, d$_6$-DMSO) δ10.16 (s, 1H), 8.76 (br s, 1H), 8.64 (d, 1H), 8.57 (m, 1H), 8.28 (br m, 1H), 7.95 (br m, 1H), 7.48 (m, 1H), 7.40-7.23 (br m, 7H), 7.06 (m, 1H), 5.23 (br m, 2H), 4.62 (br m, 2H), 2.88 (s, 3H), 2.33 (s, 3H) LRMS (apci, positive) m/e 483.3 (M+1)

Compound 247

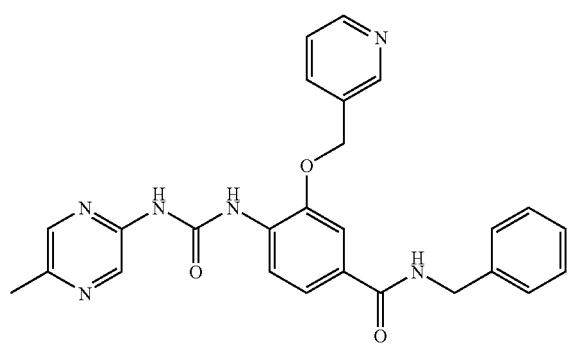

N-Benzyl-4-[3-(5-methyl-pyrazin-2-yl)-ureido]-3-(pyridin-3-ylmethoxy)-benzamide

Prepared according to the procedure of Compound 208 using benzylamine (41% yield).

$^1$H-NMR (400 MHz, d$_6$-DMSO) δ10.23 (s, 1H), 9.05 (t, 1H), 8.82 (s, 1H), 8.67 (d, 1H), 8.58 (br s, 1H), 8.33 (d, 1H, 8.00 (d, 1H, 7.78 (s, 1H), 7.59 (d, 1H), 7.50 (m, 1H), 7.33 (m, 4H), .25 (m, 1H), 5.32 (s, 2H), 4.50 (d, 2H), 2.32 (s, 3H) LRMS (apci, positive) m/e 469.1 (M+1)

Compound 249

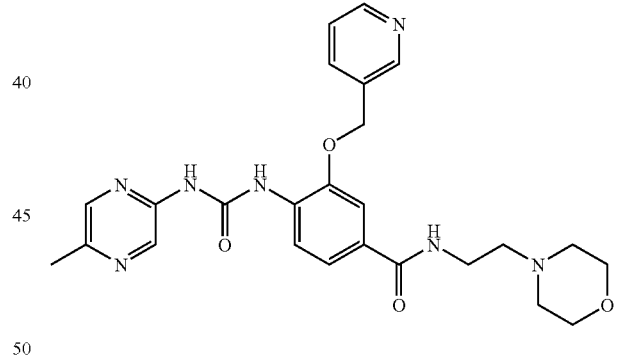

4-[3-(5-Methyl-pyrazin-2-yl)-ureido]-N-(2-morpholin-4-yl-ethyl)-3-(pyridin-3-ylmethoxy)-benzamide Prepared according to the procedure of Compound 208 using 2-morpholin-4-yl-ethylamine (99% yield).

$^1$H-NMR (400 MHz, tl$_6$-DMSO) δ10.27 (s, 1H), 8.81 (s, 1H), 8.66 (d, 1H), 8.61 (br s, 1H), 8.52 (t, 1H), 8.29 (d, 1H, 8.03 (d, 1H, 7.76 (s, 1H), 7.52 (m, 2H), 7.36 (m, 1H), 5.33 (s, 2H), 3.56 (m, 4H), 3.40 (m, 2H), 2.48 (m, 2H), 2.43 (m, 4H), 2.34 (s, 3H) LRMS (apci, positive) m/e 492.4 (M+1)

Compound 250

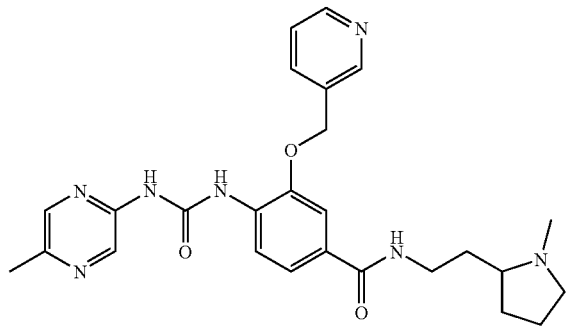

4-[3-(5-Methyl-pyrazin-2-yl)-ureido]-N-[2-(1-methyl-pyrrolidin-2-yl)-ethyl]-3-(pyridin-3-ylmethoxy)-benzamide Prepared according to the procedure of Compound 208 using 2-(1-methyl-pyrrolidin-2-yl)-ethylamine (99% yield).

$^1$H-NMR (400 MHz, $d_6$-DMSO) δ10.21 (s, 1H), 8.81 (s, 1H), 8.64 (d, 1H), 8.58 (br s, 1H), 8.49 (m, 1H), 8.33 (d, 1H, 8.00 (d, 1H), 7.70 (s, 1H), 7.52 (m, 2H), 7.34 (m, 1H), 5.33 (s, 2H), 3.28 (m, 2H), 2.95 (m, 1H), 2.36 (s, 3H), 2.21 (s, 3H), 2.04 (m, 2H), 1.90 (m, 2H), 1.62 (m, 2H), 1.44 (m, 2H) LRMS (apci, positive) m/e 490.3 (M+1)

Compound 251

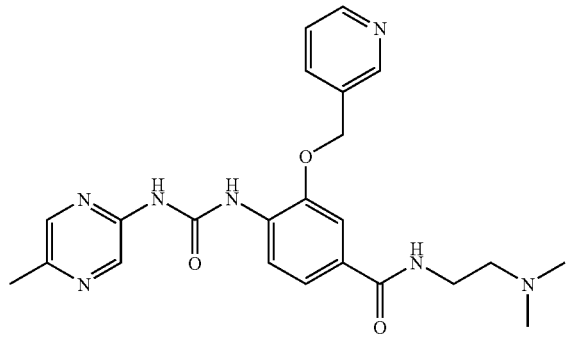

N-(2-Dimethylamino-ethyl)-4-[3-(5-methyl-pyrazin-2-yl)-ureido]-3-(pyridin-3-ylmethoxy)-benzamide Prepared according to the procedure of Compound 208 using 2-dimethylamino-ethylamine (99% yield).

$^1$H-NMR (400 MHz, $d_6$-DMSO) δ10.24 (s, 1H), 8.82 (s, 1H), 8.66 (d, 1H), 8.60 (br s, 1H), 8.43 (t, 1H), 8.30 (d, 1H), 8.02 (d, 1H), 7.74 (s, 1H), 7.52 (m, 2H), 7.35 (br m, 1H), 5.32 (s, 2H), 3.36 (m, 2H), 2.39 (m, 2H), 2.33 (s, 3H), 2.18 (s, 6H) LRMS (apci, positive) m/e 450.2 (M+1)

Compound 252

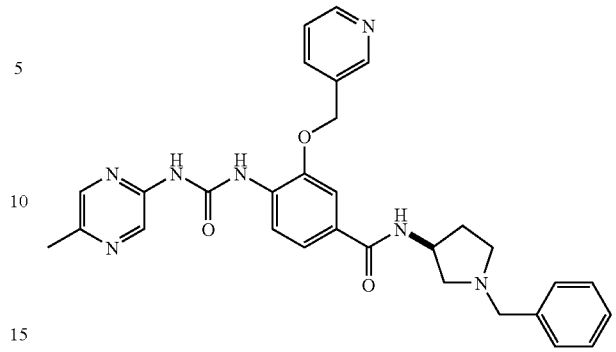

N-(3-S-1-Benzyl-pyrrolidin-3-yl)-4-[3-(5-methyl-pyrazin-2-yl)-ureido]-3-(pyridin-3-ylmethoxy)-benzamide Prepared according to the procedure of Compound 215 using 1-benzyl-pyrrolidin-3-S-ylamine (99% yield).

$^1$H-NMR (400 MHz, $d_6$-DMSO) δ10.26 (s, 1H), 8.82 (s, 1H), 8.66 (d, 1H, 8.60 (br s, 1H), 8.47 (d 1H), 8.28 (d, 1H, 8.02 (d, 1H), 7.74 (s, 1H), 7.55 (d, 1H, 7.51 (m, 1H), 7.32 (m, 4H), 7.24 (m, 1H), 5.31 (s, 2H), 4.40 (m, 1H), 3.60 (s, 2H), 2.80 (m, 1H), 2.64 (m, 1H), 2.45 (m, 2H), 2.34 (s, 3H), 2.15 (m, 1H), 1.85 (m, 1H) LRMS (apci, positive) m/e 538.2 (M+1)

Compound 253

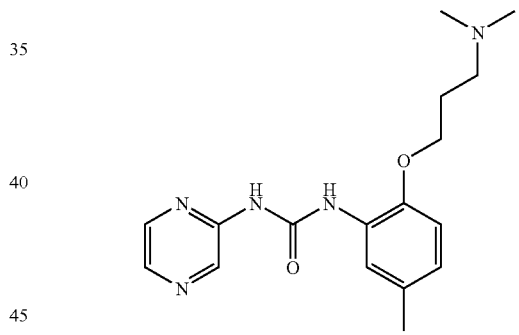

1-[2-(3-Dimethylamino-propoxy)-5-methyl-phenyl]-3-pyrazin-2-yl-urea

Step 1: (2-Hydroxy-5-methyl-phenyl)-carbamic acid tert-butyl ester. To a stirred solution of 2-amino-4-methyl-phenol (6.15 gm; 50 mmol) in dioxane (100 mL) was added carbonic acid di-tert-butyl ester (9.8 gm; 45 mmol) followed by sodium bicarbonate (12.6 gm; 150 mmol in 75 mL of H$_2$O). After stirring for 8 hours, the reaction was diluted with 100 mL of ethyl acetate and washed with 1N aqueous hydrochloric acid (2×100 mL), saturated aqueous sodium bicarbonate (1×100 mL), and brine (100 mL), then dried (MgSO$_4$), and filtered. The filtered solution was concentrated under reduced pressure to provide the desired (2-Hydroxy-5-methyl-phenyl)-carbamic acid tert-butyl ester as a brown solid (95% yield).

Step 2: [2-(3-Dimethylamino-propoxy)-5-methyl-phenyl]-carbamic acid tert-butyl ester. To a stirred, cooled (about 0° C.) solution of (2-hydroxy-5-methyl-phenyl)-carbamic acid tert-butyl ester (447 mg, 2.0 mmol), triphenyl phosphine (525 mg, 2.0 mmol), and 3-(dimethylamino)-1-propanol (237 µL, 2.0 mmol) in dry tetrahydrofuran (5 mL) was added diisopropyl azodicarboxylate (394 µL, 2.0 mmol) in 1 mL of tetrahydrofuran). After stirring for 12 hours, the reaction was diluted with 30 mL of ethyl acetate and washed with 30 mL of 10% aqueous sodium carbonate (2×30 mL), brine (1×30 mL), then dried (MgSO$_4$), and filtered. The filtered solution was concentrated under reduced pressure to provide the desired crude product.

Step 3: 2-(3-Dimethylamino-propoxy)-5-methyl-phenylamine. To a stirred solution of [2-(3-dimethylamino-propoxy)-5-methyl-phenyl]-carbamic acid tert-butyl ester (617 mg, 2.0 mmol) in 5 mL of dioxane was added hydrochloric acid (2 mL; 4N in dioxane). After stirring for 12 hours, the reaction was diluted with 20 ml of 1N hydrochloric acid and washed with ethyl acetate (2×30 mL). The aqueous layer was basified with 10% aqueous sodium carbonate (50 mL) and extracted with ethyl acetate (3×50 mL). The ethyl acetate was washed with brine (1×30 mL), then dried (MgSO$_4$), and filtered. The filtered solution was concentrated under reduced to yield the corresponding aniline.

Step 4: 1-[2-(3-Dimethylamino-propoxy)-5-methyl-phenyl]-3-pyrazin-2-yl-urea. To a stirred, cooled (about 0° C.) solution of 2-(3-dimethylamino-propoxy)-5-methyl-phenylamine (208 mg, 1.0 mmol) in toluene (3.0 mL) was added triethylamine (140 µL, 1.0 mmol) and triphosgene (98 mg, 0.33 mmol). After stirring for 30 minutes, amino pyrazine (95 mg, 1.0 mmol) was added and the reaction was heated to 65 degrees C. After stirring for 4 hours, the reaction was cooled to room temperature and stirred for 8 hours. The precipitate that formed was filtered, rinsed with toluene (2×1 mL), and dried under reduced pressure (35% yield).

$^1$H-NMR (400 MHz, CDCl$_3$) δ8.45 (s, 1H), 8.39 (br s, 1H), 8.22 (s, 1H), 8.21 (d, 1H), 8.19 (, 1H), 4.09 (t, 2H), 2.55 (t, 2H), 2.36 (s, 3H), 2.26 (s, 6H), 2.05 (m, 2H). LRMS (esi, positive) m/e 330.10 (M+1)

Compound 254

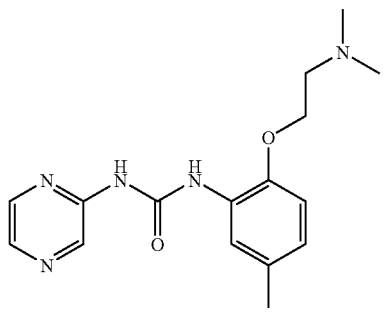

1-[2-(2-Dimethylamino-ethoxy)-5-methyl-phenyl]-3-pyrazin-2-yl-urea

Prepared according to the method of Compound 253 using N,N-dimethyl ethanolamine (36% yield).

$^1$H-NMR (400 MHz, d$_6$-DMSO) δ8.79 (br s, 1H), 8.25 (s, 1H), 8.22 (s, 1H), 8.05 (s, 1H), 6.95 (d, 1H), 6.80 (d, 1H), 4.15 (t, 2H), 2.55 (s, 3H), 2.31 (t, 2H), 2.26 (s, 6H). LRMS (esi, positive) m/e 316.21 (M+1)

Compound 255

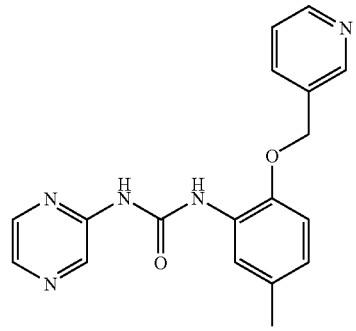

1-[5-Methyl-2-(pyridin-3-ylmethoxy)-phenyl]-3-pyrazin-2-yl-urea

Prepared according to the method of Compound 253 using 3-hydroxymethyl pyridine (10% yield).

$^1$H-NMR (400 MHz, CDCl$_3$) δ8.82 (s, 1H), 8.65 (d, 1H), 8.35 (s, 1H), 8.30 (s, 1H), 8.21 (s, 2H), 8.05 (s, 1H), 7.81 (m, 2H), 7.35 (m, 1H), 6.9 (dd, 2H), 5.15 (s, 2H), 2.39 (s, 3H). LRMS (esi, positive) m/e 336.21 (M+1)

Compound 256

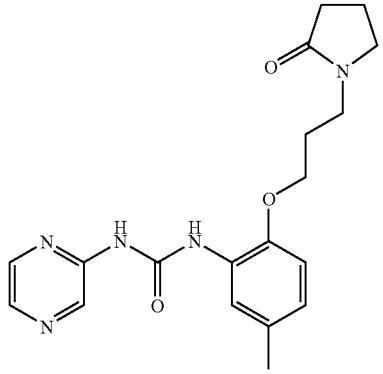

1-[5-Methyl-2-[3-(2-oxo-pyrrolidin-1-yl)-propoxy]-phenyl}-3-pyrazin-2-yl-urea

Prepared according to the method of Compound 253 using 3-(2-oxo-pyrrolidin-1-yl)-propanol (10% yield).

$^1$H-NMR (400 MHz, d$_6$-DMSO) δ8.79 (s, 1H), 8.29 (s, 1H), 8.25 (s, 1H), 8.05 (s, 1H), 6.92 (d, 1H), 6.79 (d, 1H), 3.99 (t, 2H), 3.38 (m, 4H), 2.22 (s, 3H), 2.20 (t, 2H), 2.00 (t, 2H). LRMS (esi, positive) m/e 392.2 (M+Na)

Compound 257

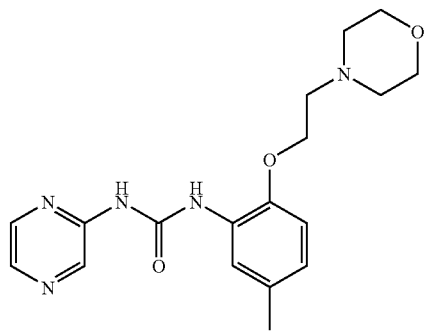

1-[5-Methyl-2-(2-morpholin-4-yl-ethoxy)-phenyl]-3-pyrazin-2-yl-urea

Prepared according to the method of Compound 253 using 2-morpholin-4-yl-ethanol (39% yield).

$^1$H-NMR (400 MHz, d$_6$-DMSO) δ8.79 (s, 1H), 8.29 (d, 1H), 8.25 (d, 1H), 8.05 (s, 1H) 6.95 (d, 1H), 6.79 (d, 1H), 4.19 (t, 2H), 3.59 (m, 4H), 2.80 (t, 2H), 2.49 (m, 4H), 2.22 (s, 3H). LRMS (esi, positive) m/e 358.2 (M+1)

Compound 258

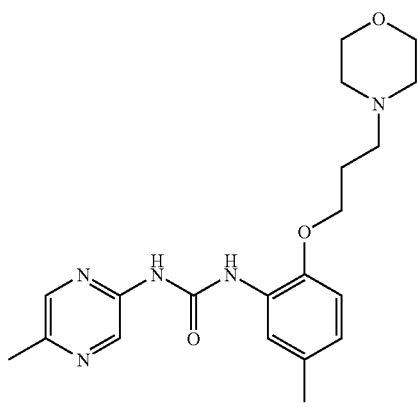

1-[5-Methyl-2-(3-morpholin-4-yl-propoxy)-phenyl]-3-(5-methyl-pyrazin-2-yl)-urea

Prepared according to the method of Compound 253 using 3-morpholin-4-yl-propanol (8% yield).

$^1$H-NMR (400 MHz, d$_6$-DMSO) δ9.01 (s, 1H), 8.62 (br s, 1H), 8.22 (s, 1H), 8.19 (s, 1H), 8.05 (s, 1H), 6.91 (d, 1H), 6.79 (d, 1H), 4.05 (t, 2H), 3.59 (m, 4H), 2.48 (s, 3H), 2.45 (t, 2H), 2.35 (m, 4H), 2.21 (s, 3H), 2.00 (t, 2H). LRMS (esi, positive) m/e 386.31 (M+1)

Compound 259

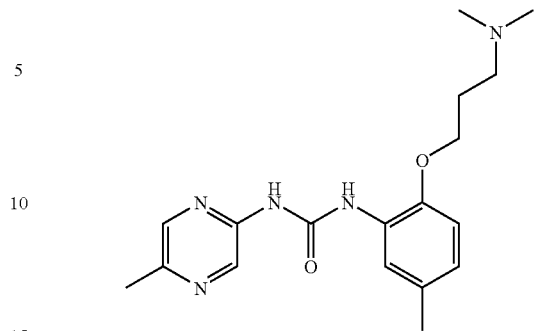

1-[2-(3-Dimethylamino-propoxy)-5-methyl-phenyl]-3-(5-methyl-pyrazin-2-yl)-urea

Prepared according to the method of Compound 253 3-dimethylamino-propanol (40% yield).

$^1$H-NMR (400 MHz, CDCl$_3$) δ8.37 (s, 1H), 8.19 (s, 1H), 8.18 (s, 1H), 8.09 (br s, 1H), 6.80 (dd, 2H), 4.05 (t, 2H), 2.55 (t, 2H), 2.54 (s, 3H), 2.36 (s, 3H), 2.26 (s, 6H), 2.05 (m, 2H). LRMS (esi, positive) m/e 344.20 (M+1)

Compound 260

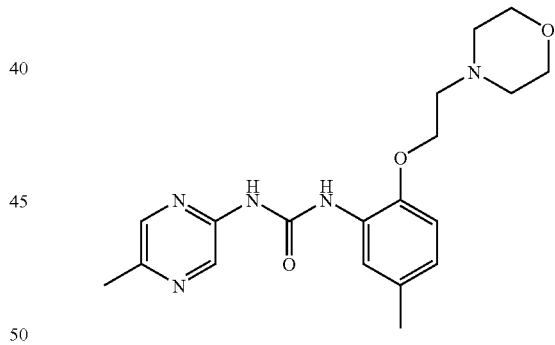

1-[5-Methyl-2-(2-morpholin-4-yl-ethoxy)-phenyl]-3-(5-methyl-pyrazin-2-yl)-urea

Prepared according to the method of Compound 253 using 2-morpholin-4-yl-ethanol (10% yield).

$^1$H-NMR (400 MHz, CDCl$_3$) δ10.79 (br s, 1H), 8.82 (s, 1H), 8.59 (s, 1H), 8.19 (s, 1H), 8.05 (s, 1H), 6.81 (dd, 2H), 4.20 (t, 2H), 3.75 (m, 4H), 2.91 (t, 2H), 2.61 (m, 4H), 2.55 (s, 3H), 2.35 (s, 3H). LRMS (esi, positive) m/e 372.1 (M+1)

Compound 261

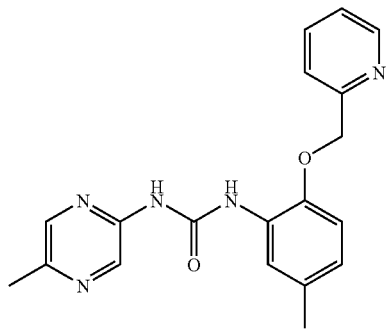

1-(5-Methyl-pyrazin-2-yl)-3-[5-methyl-2-(pyridin-2-ylmethoxy)-phenyl]-urea

Prepared according to the method of Compound 253 using 2-hydroxymethyl pyridine (21% yield).

$^1$H-NMR (400 MHz, CDCl$_3$) δ8.61 (d, 1H), 8.29 (s, 1H), 8.11 (s, 1H), 7.61 (t, 1H), 7.31 (d, 1H), 7.18 (t, 1H), 6.88 (d, 1H, 6.75 (d, 1H), 5.18 (s, 2H), 2.30 (s, 3H). LRMS (esi, positive) m/e 372.2 (M+Na)

Compound 263

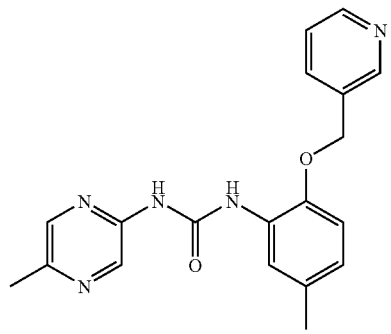

1-( 5-Methyl-pyrazin-2-yl)-3-[5-methyl-2-(pyridin-3-ylmethoxy)-phenyl]-urea

Prepared according to the method of Compound 253 using 3-hydroxymethyl pyridine (10% yield).

$^1$H-NMR (400 MHz, CDCl$_3$) δ8.82 (s, 1H), 8.68 (m, 2H), 8.25 (s, 1H), 8.20 (s, 1H), 7.84 (d, 1H), 7.38 (m, 1H), 6.99 (s, 1H), 6.88 (d, 1H), 6.80 (d, 1H), 5.10 (s, 2H), 2.38 (s, 3H) LRMS (esi, positive) m/e 350.21 (M+1)

Compound 262

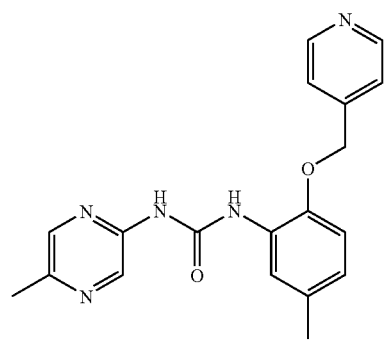

1-(5-Methyl-pyrazin-2-yl)-3-[5-methyl-2-(pyridin-4-ylmethoxy)-phenyl]-urea

Prepared according to the method of Compound 253 using 4-hydroxymethyl pyridine (18% yield).

$^1$H-NMR (400 MHz, d$_6$-DMSO) δ8.84 (s, 1H), 8.55 (d, 2H), 7.91 (s, 1H), 7.47 (d, 2H), 6.88 (d, 1H), 6.72 (d, 1H), 5.28 (s, 2H), 2.22 (s, 3H). LRMS (esi, positive) m/e 350.21 (M+1)

Compound 264

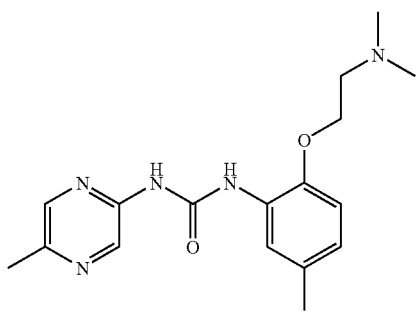

1-[2-(2-Dimethylamino-ethoxy)-5-methyl-phenyl]-3-(5-methyl-pyrazin-2-yl)-urea

Prepared according to the method of Compound 253 using N,N-dimethyl ethanolamine (11% yield).

$^1$H-NMR (400 MHz, d$_6$-DMSO) δ8.69 (s, 1H), 8.18 (s, 1H), 8.03 (s, 1H), 6.95 (d, 1H), 6.79 (s, 1H), 4.11 (t, 2H), 2.72 (t, 2H), 2.43 (s, 3H), 2.25 (s, 3H), 2.22 (s, 6H). LRMS (esi, positive) m/e 330.20 (M+1)

Compound 265

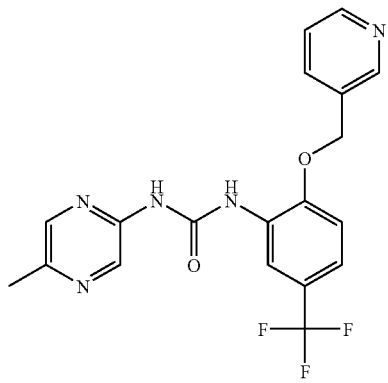

1-(5-Methyl-pyrazin-2-yl)-3-[2-(pyridin-3-ylmethoxy)-5-trifluoromethyl-phenyl]-urea Prepared according to the method of Compound 253 3-hydroxymethyl pyridine and 2-hydroxy-5-trifluoromethyl aniline (40% yield).

$^1$H-NMR (400 MHz, $d_6$-DMSO) δ8.81 (s, 1H), 8.69 (s, 1H), 8.65 (s, 1H), 8.59 (br s, 1H), 8.01 (d, 1H), 7.45 (t, 1H), 7.3 (br s, 1H), 5.39 (s, 2H), 2.35 (s, 3H). LRMS (esi, positive) m/e 404.10 (M+1)

Compound 266

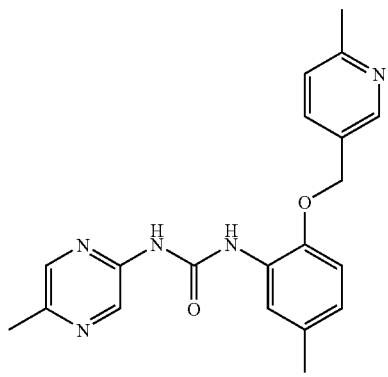

1-[5-Methyl-2-(6-methyl-pyridin-3-ylmethoxy)-phenyl]-3-(5-methyl-pyrazin-2-yl)-urea Step 1: (6-Methyl-pyridin-3-yl)-methanol. To a stirred, cooled (0° C.) solution of 6-methyl nicotinic acid (5.0 mmol) in tetrahydrofuran (10 mL) was added lithium aluminum hydride (20 mmol; 20 mL of a 1M solution in tetrahydrofuran.) dropwise. The reaction was stirred for 4 hours, treated sequentially with 1 mL of $H_2O$, 1 mL of 15% aqueous sodium hydroxide, and 3 mL of $H_2O$. The reaction was filtered and washed with tetrahydrofuran (3×50 mL). The filtrate was concentrated under reduced pressure to yield the alcohol as a clear viscous oil.

Steps 2-3: Mitsunobu reaction and aniline deprotection according to the method of Compound 253.

Step 4: To a stirred solution of 5-methyl-pyrazine-2-carboxylic acid (138 mg, 1.0 mmol) in toluene (3.0 mL) was added diphenylphosphoryl azide (216 μL, 1.0 mmol) and triethylamine (140 μL, 1.0 mmol). The reaction was placed under nitrogen and heated to 90 degrees C. for 15 minutes. The temperature was reduced to 65° C. and 5-methyl-2-(6-methyl-pyridin-3-ylmethoxy)-phenylamine (228 mg, 1.0 mmol) was added. The reaction was stirred at that temperature for 4 hours and then stirred at room temperature for 8 hours. The precipitate that formed during the reaction was filtered, rinsed with toluene (2×1 mL), and dried under reduced pressure (36% yield).

$^1$H-NMR (400 MHz, $CDCl_3$) δ11.45 (br s, 1H), 8.65 (s, 1H), 8.29 (s, 1H), 8.22 (s, 1H), 8.20 (s, 1H), 7.70 (d, 1H), 7.19 (d, 1H, 6.9 (m, 3H), 5.05 (s, 2H), 2.65 (s, 3H), 2.4 (s, 3H), 2.5 (s, 3H). LRMS (esi, positive) m/e 364.16 (M+1)

Compound 267

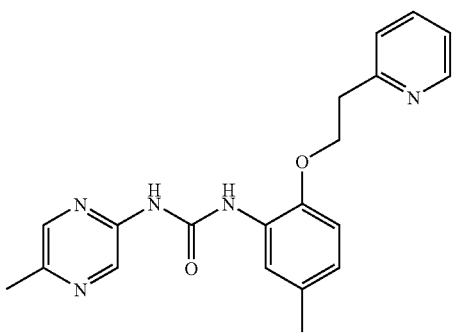

1-(5-Methyl-pyrazin-2-yl)-3-[5-methyl-2-(2-pyridin-2-yl-ethoxy)-phenyl]-urea

Steps 1-2: Mitsunobu reaction using 2-(2-pyridyl)-ethanol and aniline deprotection according to the method of Compound 253.

Step 3: Urea formation according to the method of Compound 266 using 5-methyl-2-(2-pyridin-2-yl-ethoxy)-phenylamine (37% yield).

$^1$H-NMR (400 MHz, $CDCl_3$) δ10.70 (br s, 1H), 8.65 (d, 1H), 8.45 (br s, 1H), 8.21 (s, 1H), 7.85 (s, 1H), 7.59 (t, 1H), 7.29 (t, 1H), 6.80 (dd, 2H), 4.49 (t, 2H), 3.39 (t, 2H), 2.49 (s, 3H), 2.39 (s, 3H). LRMS (esi, positive) m/e 364.14 (M+1)

Compound 268

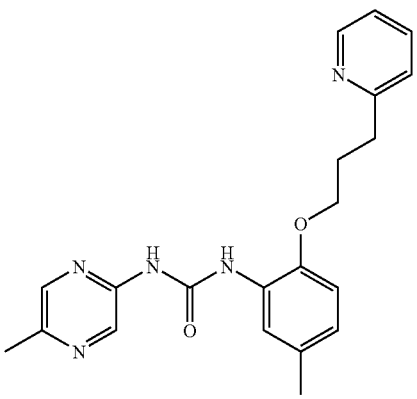

1-(5-Methyl-pyrazin-2-yl)-3-[5-methyl-2-(3-pyridin-2-yl-propoxy)-phenyl]-urea

Steps 1-2: Mitsunobu reaction using 3-(2-pyridyl)-propanol and aniline deprotection according to the method of Compound 253.

Step 3: Urea formation according to the method of Compound 266 using 5-methyl-2-(3-pyridin-2-yl-propoxy)-phenylamine (5% yield).

¹H-NMR (400 MHz, CDCl₃) δ10.89 (br s, 1H), 8.59 (d, 1H), 8.49 (s, 1H), 8.45 (br s, 1H), 8.22 (s, 1H), 8.15 (s, 1H), 7.59 (t, 1H), 7.15 (d, 2H), 6.88 (dd, 2H), 4.05 (t, 2H), 3.10 (t, 2H), 2.45 (s, 3H), 2.40 (t, 2H), 2.35 (s, 3H). LRMS (esi, positive) m/e 378.10 (M+1)

Compound 269

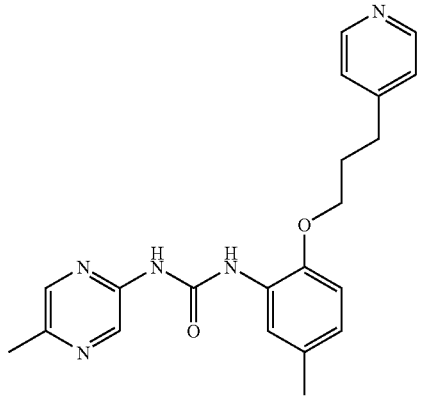

1-( 5-Methyl-pyrazin-2-yl)-3-[5-methyl-2-(3-pyridin-4-yl-propoxy)-phenyl]-urea

Steps 1-2: Mitsunobu reaction using 3-(4-pyridyl)-propanol and aniline deprotection according to the method of Compound 253.

Step 3: Urea formation according to the method of Compound 266 using 5-methyl-2-(4-pyridin-2-yl-propoxy)-phenylamine (28% yield).

¹H-NMR (400 MHz, CDCl₃) δ11.15 (br s, 1H), 8.51 (d, 2H), 8.25 (s, 1H), 8.20 (s, 1H), 7.79 (s, 1H), 7.75 (s, 1H), 7.15 (d, 2H), 6.82 (d, 1H), 6.75 (d, 1H, 4.05 (t, 2H), 2.91 (t, 2H), 2.40 (s, 3H), 2.36 (s, 3H), 2.25 (m, 2H). LRMS (esi, positive) m/e 378.16 (M+1)

Compound 270

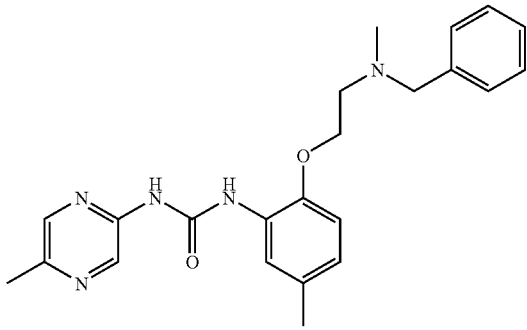

1-{2-[2-(Benzyl-methyl-amino)-ethoxy]-5-methyl-phenyl}-3-(5-methyl-pyrazin-2-yl)-urea Steps 1-2: Mitsunobu reaction using N-methyl-N-benzyl ethanolamine and aniline deprotection according to the method of Compound 253.

Step 3: Urea formation according to the method of Compound 266 using 2-[2-(benzyl-methyl-amino)-ethoxy]-5-methyl-phenylamine (17% yield).

¹H-NMR (400 MHz, CDCl₃) δ10.70 (br s, 1H), 8.49 (s, 1H), 8.20 (s, 1H), 7.95 (s, 1H), 7.85 (s, 1H), 7.32 (m, 5H), 6.85 (s, 2H), 4.15 (t, 2H), 3.62 (s, 2H), 2.92 (t, 2H), 2.49 (s, 3H), 2.33 (s, 3H), 2.29 (s, 3H). LRMS (esi, positive) m/e 406.01 (M+1)

Compound 271

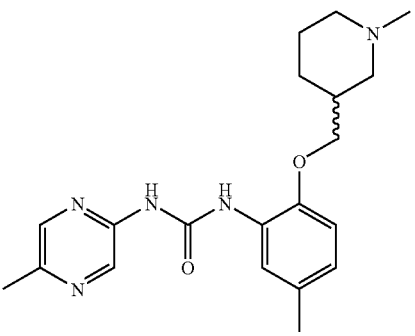

1-[5-Methyl-2-(1-methyl-piperidin-3-ylmethoxy)-phenyl]-3-(5-methyl-pyrazin-2-yl)-urea Steps 1-2: Mitsunobu reaction using 3-hydroxymethyl-1-methyl piperidine and aniline deprotection according to the method of Compound 253.

Step 3: Urea formation according to the method of Compound 266 using 5-methyl-2-(1-methyl-piperidin-3-ylmethoxy)-phenylamine (16% yield).

¹H-NMR (400 MHz, CDCl₃) δ11.25 (br s, 1H), 8.45 (br s, 1H), 8.35 (s, 1H), 8.22 (s, 2H), 6.80 (d, 1H), 6.74 (d, 1H), 3.80 (m, 2H), 3.15 (br d, 1H, 2.80 (br d, 1H), 2.51 (s, 3H), 2.35 (s, 3H), 2.30 (m, 1H), 2.22 (s, 3H), 1.50-2.00 (m, 6H), 1.00-1.25 (m, 2H). LRMS (esi, positive) m/e 370.01 (M+1)

Compound 272

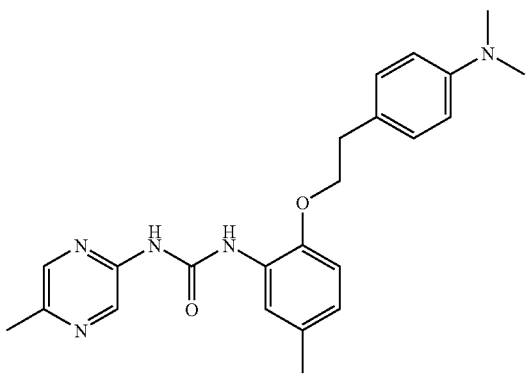

1-{2-[2-(4-Dimethylamino-phenyl)-ethoxy]-5-methyl-phenyl}-3-(5-methyl-pyrazin-2-yl)-urea Steps 1-2: Mitsunobu reaction using 2-(4-dimethylamino-phenyl)-ethanol and aniline deprotection according to the method of Compound 253.

Step 3: Urea formation according to the method of Compound 266 using 2-[2-(4-dimethylamino-phenyl)-ethoxy]-5-methyl-phenylamine (10% yield).

¹H-NMR (400 MHz, CDCl₃) δ11.15 (br s, 1H), 8.35 (s, 1H), 8.25 (s, 1H), 7.80 (m, 2H), 7.5 (m, 2H), 6.82 (s, 2H), 6.75 (d, 2H), 4.25 (t, 2H), 3.20 (t, 2H), 2.99 (s, 6H), 2.55 (s, 3H), 2.41 (s, 3H). LRMS (esi, positive) m/e 405.90 (M+1)

Compound 273

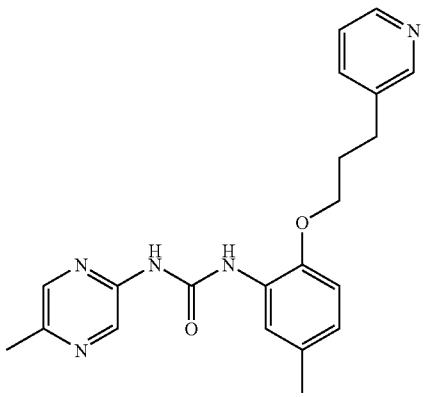

1-(5-Methyl-pyrazin-2-yl)-3-[5-methyl-2-(3-pyridin-3-yl-propoxy)-phenyl]-urea

Steps 1-2: Mitsunobu reaction using 3-(3-pyridyl)-propanol and aniline deprotection according to the method of Compound 253.

Step 3: Urea formation according to the method of Compound 266 using 5-methyl-2-(3-pyridin-3-yl-propoxy)-phenylamine (16% yield).

$^1$H-NMR (400 MHz, CDCl$_3$) δ10.95 (br s, 1H), 8.51 (m, 2H), 8.35 (s, 1H), 8.25 (s, 1H), 8.15 (s, 1H), 7.80 (s, 1H), 7.50 (d, 1H), 7.21 (t, 1H), 6.79 (d, 1H, 6.75 (d, 1H, 4.09 (t, 2H), 2.90 (t, 2H), 2.45 (s, 3H), 2.35 (s, 3H), 2.25 (m, 2H). LRMS (esi, positive) m/e 377.91 (M+1)

Compound 274

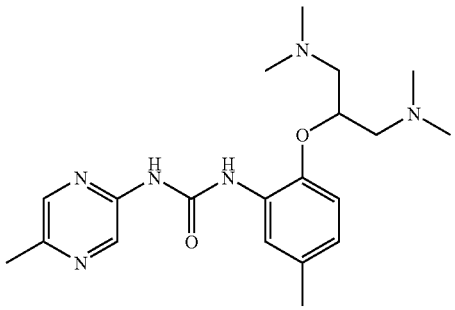

1-[2-(2-Dimethylamino-1-dimethylaminomethyl-ethoxy)-5-methyl-phenyl]-3-(5-methyl-pyrazin-2-yl)-urea Steps 1-2: Mitsunobu reaction using 1,3-bis-dimethylamino-propan-2-ol and aniline deprotection according to the method of Compound 253.

Step 3: Urea formation according to the method of Compound 266 using 2-(2-amino-4-methyl-phenoxy)-N,N,N',N'-tetramethyl-propane-1,3-diamine (4% yield).

$^1$H-NMR (400 MHz, CDCl$_3$) δ9.69 (br s, 1H), 8.95 (br s, 1H), 8.19 (s, 1H), 8.05 (s, 1H), 6.80 (dd, 2H), 4.19 (m, 1H), 4.09 (m, 1H), 3.05 (m, 1H), 2.65 (m, 2H), 2.50 (s, 3H), 2.45 (s, 6H), 2.38 (s, 6H), 2.35 (s, 3H). LRMS (esi, positive) m/e 386.92 (M+1)

Compound 275

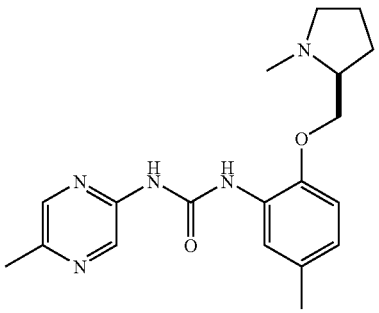

1-[5-Methyl-2-(2-S-1-methyl-pyrrolidin-2-ylmethoxy)-phenyl]-3-(5-methyl-pyrazin-2-yl)-urea Steps 1-2: Mitsunobu reaction using 1-methyl-pyrrolidin-2-S-ylmethanol and, aniline deprotection according to the method of Compound 253.

Step 3: Urea formation according to the method of Compound 266 using 5-methyl-2-(1-methyl-pyrrolidin-2-S-ylmethoxy)-phenylamine (12% yield).

$^1$H-NMR (400 MHz, d$_6$-DMSO) δ10.10 (s, 1H), 9.85 (br s, 1H), 9.65 (br s, 1H), 8.78 (s, 1H), 8.25 (s, 1H), 6.90 (s, 1H), 7.02 (d, 1H), 6.85 (d, 1H), 4.33 (br s, 2H), 3.88 (m, 1H), 3.59 (m, 1H), 3.19 (m, 1H), 2.99 (d, 2H) 2.70-2.85 (m, 2H), 2.45 (s, 3H), 2.29 (s, 3H), 1.80-2.10 (m, 3H). LRMS (esi, positive) m/e 355.91 (M+1)

Compound 276

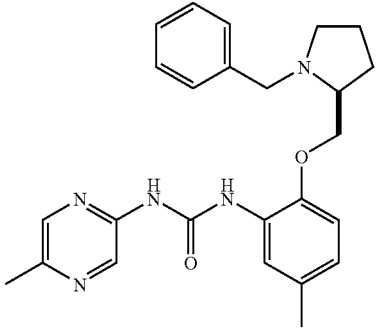

1-[2-(2-S-1-Benzyl-pyrrolidin-2-ylmethoxy)5-methyl-phenyl]-3-(5-methyl-pyrazin-2-yl)-urea Steps 1-2: Mitsunobu reaction using 1-benzyl-pyrrolidin-2-S-ylmethanol and aniline deprotection according to the method of Compound 253.

Step 3: Urea formation according to the method of Compound 266 using 5-methyl-2-(1-benzyl-pyrrolidin-2-S-ylmethoxy)-phenylamine (3% yield).

$^1$H-NMR (400 MHz, d$_6$-DMSO) δ9.95 (s, 1H), 9.90 (br s, 1H), 9.59 (br s, 1H), 8.69 (s, 1H), 8.10 (s, 1H), 7.89 (s, 1H), 7.25-7.50 (m, 6H), 6.96 (d, 1H), 6.90 (d, 1H), 4.75 (d, 2H), 4.33 (m, 4H), 4.10 (m, 2H), 2.40 (s, 3H), 2.25 (s, 3H), 1.80-2.10 (m, 3H), 1.10-1.30 (m, 2H). LRMS (esi, positive) m/e 432.31 (M+1)

Compound 277

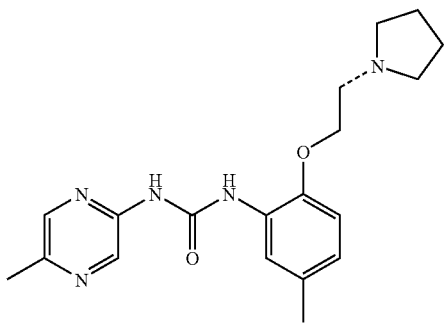

1-(5-Methyl-pyrazin-2-yl)-3-[5-methyl-2-(2-pyrrolidin-1-yl-ethoxy)-phenyl]-urea

Prepared according to the procedure for compound 266, using 2-pyrrolidin-1-yl-ethanol. (28% yield). $^1$H NMR (400 MHz, d6-DMSO) δ10.01 (s, 1H), 9.85 (br s, 1H), 9.72 (br s, 1H), 8.75 (s, 1H), 8.25 (s, 1H), 8.01 (s, 1H), 7.01 (d, 1H), 6.80 (d, 1H), 4.40 (t, 2H), 3.62 (m, 4H), 3.21 (m, 2H), 2.40 (s, 3H), 2.25 (s, 3H), 2.00 (m, 2H), 1.88 (m, 2H). LRMS (ESI, Positive) m/e 356.2 (M+1).

Compound 278

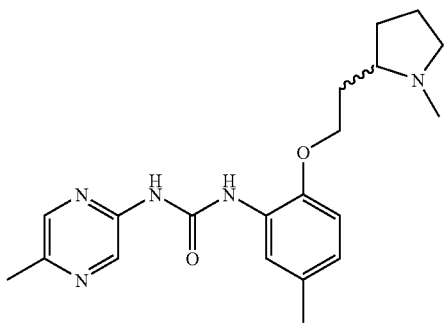

1 {5-Methyl-2-[2-(1-methyl-pyrrolidin-2-yl)-ethoxy]-phenyl}-3-(5-methyl-pyrazin-2-yl)-urea Prepared according to the procedure for compound 266, using 2-(1-methyl-pyrrolidin-2-yl)-ethanol. (32% yield). $^1$H NMR (400 MHz, d6-DMSO) δ10.01 (s, 1H), 9.85 (br s, 1H), 9.72 (br s, 1H), 8.75 (s, 1H), 8.25 (s, 1H), 8.01 (s, 1H), 7.01 (d, 1H), 6.80 (d, 1H), 4.20 (m, 3H), 3.00-4.00 (m, 11H), 2.80 (d, 2H), 2.40 (s, 3H), 2.25 (s, 3H). LRMS (ESI, Positive) m/e 370.2 (M+1).

Compound 279

1-[2-(3H-Imidazol-4-ylmethoxy)-5-methyl-phenyl]-3-(5-methyl-pyrazin-2-yl)-urea

Prepared according to the procedure for compound 266, using (3H-imidazol-4-yl)-methanol. (24% yield) 1H NMR (400 MHz, d6-DMSO) δ8.51 (br s, 1H), 8.01 (s, 1H), 7.69 (s, 1H), 7.20-7.50 (m, 2H), 7.10 (d, 1H), 6.75 (d, 1H), 4.99 (s, 2H), 2.40 (s, 3H), 2.25 (s, 3H). LRMS (ESI, Positive) m/e 339.1 (M+1).

Compound 280

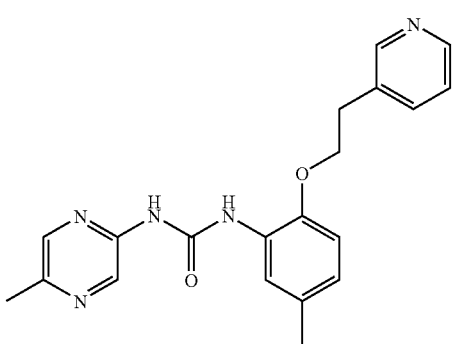

1-(5-Methyl-pyrazin-2-yl)-3-[5-methyl-2-(2-pyridin-3-yl-ethoxy)-phenyl]-urea

Prepared according to the procedure for compound 266, using 2-pyridin-3-yl-ethanol. (16% yield). $^1$H NMR (400 MHz, CDCl$_3$) δ10.98 (br s, 1H), 8.65 (s, 1H), 8.49 (d, 1H, 8.35 (s, 2H) 8.20 (s, 1H), 7.75 (s, 1H), 7.65 (d, 1H, 7.19 (m, 1H), 6.82 (dd, 2H), 4.31 (t, 2H), 3.21 (t, 2H), 2.48 (s, 3H), 2.35 (s, 3H). LRMS (ESI, Positive) m/e 364.2 (M4 1).

Compound 281

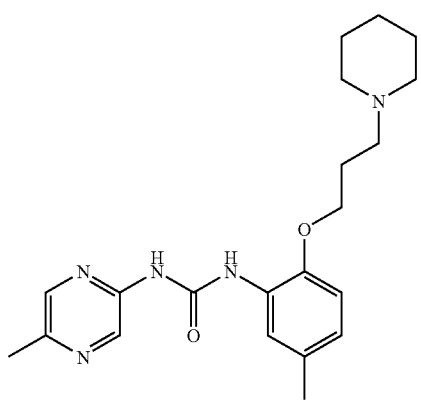

1-[5-Methyl-2-(3-piperidin-1-yl-propoxy)-phenyl]-3-(5-methyl-pyrazin-2-yl)-urea

Prepared according to the procedure for compound 266, using 3-piperidin-1-yl-propan-1-ol. (33% yield). $^1$H NMR (400 MHz, CDCl$_3$) δ11.21 (br s, 1H), 8.35 (s, 1H), 8.25 (s, 2H), 8.15 (s, 1H), 6.80 (dd, 2H), 4.15 (t, 2H), 2.53 (t, 2H), 2.52 (s, 3H), 2.45 (m, 4H), 2.39 (s, 3H), 2.10 (s, 2H), 1.61 (m, 4H), 1.45 (m, 2H). LRMS (ESI, Positive) m/e 384.2 (M+1).

Compound 282

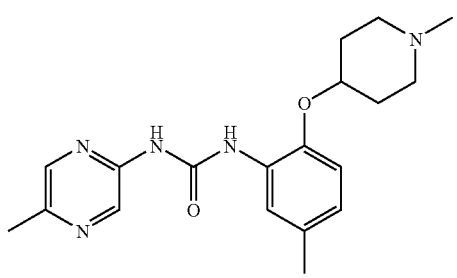

1-[5-Methyl-2-(1-methyl-piperidin-4-yloxy)-phenyl]-3-(5-methyl-pyrazin-2-yl)-urea Prepared according to the procedure for compound 266, using 1-methyl-piperidin-4-ol. (4% yield). $^1$H NMR (400 MHz, CDCl$_3$) δ11.22 (br s, 1H), 8.43 (s, 1H), 8.25 (s, 1H), 8.20 (s, 1(dd, 2H), 4.25 (m, 1H), 2.8 (m, 2H), 2.59 (s, 3H), 2.39 (s, 3H), 2.36 (s, 3H) 2H). LRMS (ESI, Positive) m/e 355.9 (M+1).

Compound 283

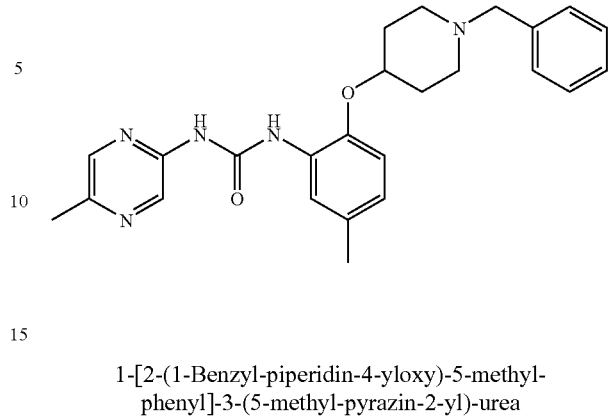

1-[2-(1-Benzyl-piperidin-4-yloxy)-5-methyl-phenyl]-3-(5-methyl-pyrazin-2-yl)-urea Prepared according to the procedure for compound 266, using 1-benzyl-piperidin-4-ol. (1% yield). LRMS (ESI, Positive) m/e 432.0 (M+1).

Compound 284

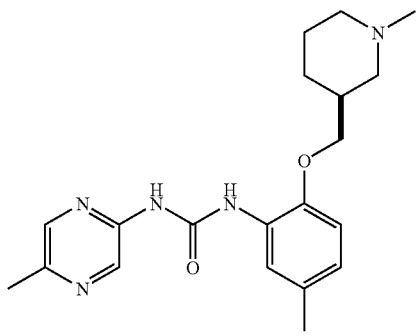

1-[5-Methyl-2-(3-(S)-1-methyl-piperidin-3-ylmethoxy)-phenyl]-3-(5-methyl-pyrazin-2-yl)-urea Step 1: (1-Methyl-piperidin-3-(S)-yl)-methanol To a stirred, cooled solution of (S)-(+)-N-boc nipecotic acid (5.0 mmol) in tetrahydrofuran (10 mL) lithium aluminum hydride (20 mL, 20 mmol, 1M in tetrahydrofuran.) was added dropwise. The reaction was refluxed for 12 hours and then cooled to 0° C. The reaction was quenched with 1 mL of H$_2$O, 1 mL of 15% aqueous sodium hydroxide, 3 mL of H$_2$O. The reaction was filtered and the filter cake was washed with tetrahydrofuran (3×50 mL). The filtrate was concentrated under reduced pressure to yield a clear viscous oil. Steps 2-3: 5-Methyl-2-(1-methyl-piperidin-3-(S)-ylmethoxy)-phenylamine Mitsunobu reaction and aniline deprotection according to procedure for compound 253.

Step 4: Prepared according to the procedure for compound 266 (33% yield). $^1$H NMR (400 MHz, CDCl$_3$) δ11.25 (br s, 1H), 8.45 (br s, 1H), 8.35 (s, 1H), 8.22 (s, 2H), 6.80 (d, 1H,) 6.74 (d, 1H), 3.80 (m, 2H), 3.15 (br d, 1H), 2.80 (br d, 1H), 2.51 (s, 3H), 2.35 (s, 3H), 2.30 (m, 1H) 2.00 (m, 6H), 1.00-1.25 (m, 2H). LRMS (ESI, Positive) m/e 370.0 (M+1).

Compound 285

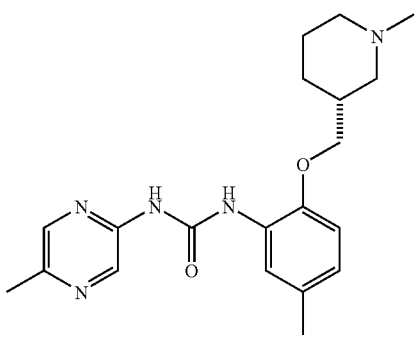

1-[5-Methyl-2-(3-(R)-1-methyl-piperidin-3-ylmethoxy)-phenyl]-3-(5-methyl-pyrazin-2-yl)-urea Steps 1-3: 5-Methyl-2-(1-methyl-piperidin-3-(R)-ylmethoxy)-phenylamine according to the method for compound 284, using (R)-(+)-N-boc nipecotic acid.

Step 4: 5-Methylpyrazine-2-carboxylic azide (1.2 eq.) dissolved in anhydrous toluene (0.1 M concentration) was heated to 90° C. After 20 minutes N$_2$ evolution had subsided, and the caramel colored reaction mixture was cooled to 60° C. before adding the aniline prepared above as a solution in toluene (1 eq.). After stirring for 4 hours at 60° C., the reaction mixture was cooled to room temperature overnight. A precipitate formed which was isolated by filtration (49% yield). $^1$H NMR (400 MHz, CDCl$_3$) δ11.25 (br s, 1H), 8.45 (br s, 1H), 8.35 (s, 1H), 8.22 (s, 2H), 6.80 (d, 1H), 6.74 (d, 1H), 3.80 (m, 2H), 3.15 (br d, 1H), 2.80 (br d, 1H), 2.51 (s, 3H), 2.35 (s, 3H), 2.30 (m, 1H), 2.22 (s, 3H), 1.50-2.00 (m, 6H), 1.00-1.25 (m, 2H). LRMS (ESI, Positive) m/e 370.0 (M+1).

Compound 286

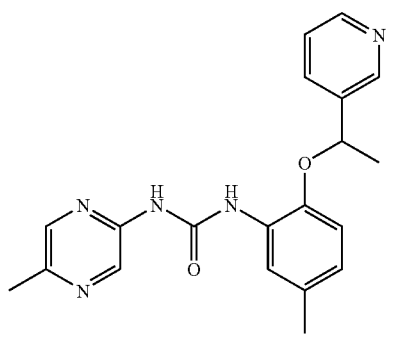

1-(5-Methyl-pyrazin-2-yl)-3-[5-methyl-2-(1-pyridin-3-yl-ethoxy)-phenyl]-urea

Step 1: 1-Pyridin-3-yl-ethanol To a stirred, cooled (-78° C.) solution of pyridine-3-carbaldehyde (15 mmol) in tetrahydrofuran (40 mL), methyl magnesium bromide (5 mL, 15 mmol, 3M in diethyl ether) was added. After stirring for 2 hours, the reaction was quenched with saturated aqueous ammonium chloride (5 mL). The pH was adjusted to ~5.0 with aqueous sodium carbonate and the product was extracted with ethyl acetate (3×100 mL). The ethyl acetate was washed with brine (1×100 mL), dried (MgSO$_4$), and filtered. The filtered material was concentrated under reduced pressure to yield a yellow oil.

Steps 2-3: 5-Methyl-2-(1-pyridin-3-yl-ethoxy)-phenylamine Mitsunobu reaction and aniline deprotection according to the method for compound 253.

Step 4: Urea formation was conducted according to the procedure for compound 285. (17% yield). $^1$H NMR (400 MHz, CDCl$_3$) δ11.49 (br s, 1H), 8.81 (s, 1H), 8.73 (s, 1H), 8.52 (d, 1H), 8.35 (s, 1H), 8.25 (s, 1H), 8.18 (s, 1H), 7.80 (s, 1H), 7.72 (d, 1H), 7.20 (t, 1H), 6.70 (d, 1H), 6,65 (d, 1H), 5.49 (q, 1H), 2.50 (s, 3H), 2.30 (s, 3H), 1.75 (d, 3H). LRMS (ESI, Positive) m/e 363.8 (M+1).

Compound 287

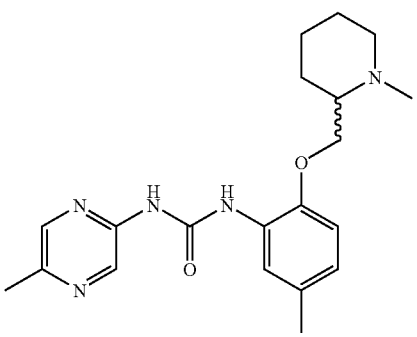

1-[5-Methyl-2-(1-methyl-piperidin-2-ylmethoxy)-phenyl]-3-(5-methyl-pyrazin-2-yl)-urea Steps 1-2: 5-Methyl-2-(1-methyl-piperidin-2-ylmethoxy)-phenylamine Mitsunobu reaction and aniline deprotection according to the method for compound 253.

Step 3: Urea formation was conducted according to the procedure for compound 285. (11% yield). $^1$H NMR (400 MHz, CDCl$_3$) δ10.90 (br s, 1H), 8.45 (s, 1H), 8.21 (s, 1H), 8.18 (s, 1H), 7.80 (s, 1H), 6.80 (s, 2H), 4.51 (m, 1H), 2.58-3.00 (m, 4H), 2.52 (s, 3H), 2.46 (s, 3H), 2.35 (s, 3H), 1.50-2.25 (m, 7H). LRMS (ESI, Positive) m/e 369.9 (M+1).

Compound 288

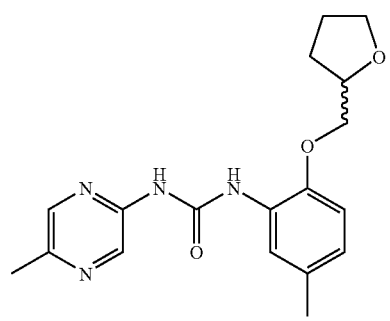

1-(5-Methyl-pyrazin-2-yl)-3-[5-methyl-2-(tetrahydro-furan-2-ylmethoxy)-phenyl]-urea Steps 1-2: 5-Methyl-2-(tetrahydro-furan-2-ylmethoxy)-phenylamine Mitsunobu reaction and aniline deprotection according to the method for compound 253.

Step 3: Urea formation was conducted according to the procedure for compound 285. (12% yield). $^1$H NMR (400 MHz, CDCl$_3$) δ11.25 (br s, 1H), 8.49 (s, 1H), 8.40 (s, 1H), 8.22 (s, 1H), 8.18 (s, 1H), 6.8 (s, 2H), 4.42 (m, 1H), 3.80-4.10 (m, 4H), 2.52 (s, 3H), 2.35 (s, 3H), 1.20-2.20 (m, 4H), LRMS (ESI, Positive) m/e 342.9 (M+1).

Compound 289

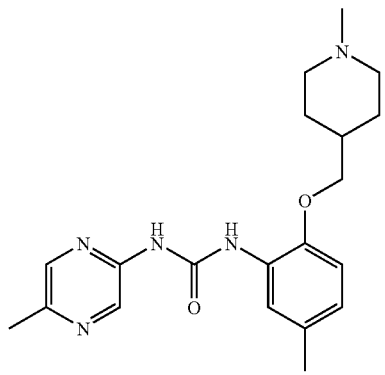

1-[5-Methyl-2-(1-methyl-piperidin-4-ylmethoxy)-phenyl-3-(5-methyl-pyrazin-2-yl)-urea Step 1: (1-Methyl-piperidin-4-yl)-methanol To a stirred, cooled solution of 1-methyl-piperdine-4-carboxylic acid (5.0 mmol) in tetrahydrofuran (10 mL) lithium aluminum hydride (20 mL, 20 mmol, 1M tetrahydrofuran.) was added dropwise. The reaction was stirred for 4 hours, quenched with 1 mL of $H_2O$, 1 mL of 15% aqueous sodium hydroxide, and 3 mL of $H_2O$. The reaction was filtered and washed with tetrahydrofuran (3×50 mL). The filtrate was concentrated under reduced pressure to yield a clear viscous oil.

Steps 2-3: 5-Methyl-2-(1-methyl-piperidin-4-ylmethoxy)-phenylamine Mitsunobu and aniline deprotection according to the procedure for compound 253.

Step 4: Urea formation according to the procedure for compound 285 (54% yield).

$^1$H NMR (400 MHz, $CDCl_3$) δ11.18 (br s, 1H), 8.62 (br s, 1H), 8.38 (br s, 1H), 8.25 (s, 1H), 8.18 (s, 1H), 6.82 (d, 1H), 6.78 (d, 1H), 3.85 (d, 2H), 2.90 (br d, 2H), 2.51 (s, 3H), 2.35 (m, 6H), 1.50-2.10 (m, 7H). LRMS (ESI, Positive) m/e 369.2 (M4 1).

Compound 290

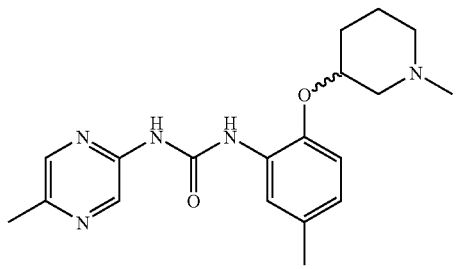

1-[5-Methyl-2-(1-methyl-piperidin-3-yloxy)-phenyl]-3-(5-methyl-pyrazin-2-yl)-urea Steps 1-2: 5-Methyl-2-(1-methyl-piperidin-3-yloxy)-phenylamine Mitsunobu reaction and aniline deprotection according to the method for compound 253.

Step 3: Urea formation according to the procedure for compound 285 (3% yield). $^1$H NMR (400 MHz, $CDCl_3$) δ10.75 (br s, 1H), 8.59 (br s, 1H), 8.18 (s, 1H), 8.05 (s, 1H), 7.62 (s, 1H), 6.90 (d, 1H), 6.80 (d, 1H), 4.40 (m, 1H), 2.58 (s, 3H), 2.39 (s, 6H), 1.60-2.80 (m, 8H). LRMS (ESI, Positive) m/e 356.1 (M+1).

Compound 291

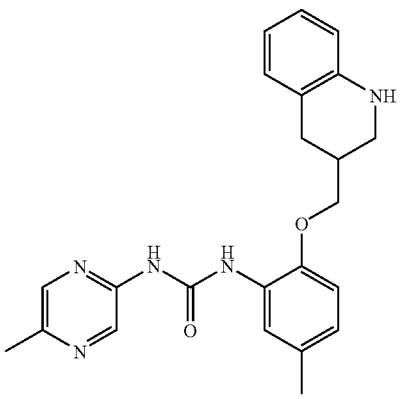

1-(5-Methyl-pyrazin-2-yl)-3-[5-methyl-2-(1,2,3,4-tetrahydro-quinolin-3-ylmethoxy)-phenyl]-urea Step 1: Quinoline-3-carboxylic acid methyl ester. To a stirred solution, of quinoline-3-carboxylic acid (346 mg, 2 mmol) dissolved in 4:1 THF:MeOH (6 mL ) at 0° C. was added TMS-diazomethane (2M in hexane) portionwise until a diazomethane yellow color persisted. The reaction was concentrated to the give the methyl ester as a tan solid (244 mg, 65%). $^1$H-NMR (400 MHz, $CDCl_3$) δ9.44 (s, 1H), 8.85 (s, 1 H), 8.17 (d, 1H), 7.96 (d, 11H), 7.84 (dd, 1H), 7.62 (dd, 11H), 4.02 (s, 3H)

Step 2: 1,2,3,4-Tetrahydro-quinoline-3-carboxylic acid methyl ester and 1-Ethyl-1,2,3,4-tetrahydro-quinoline-3-carboxylic acid methyl ester. To a stirred solution of the quinoline-3-carboxylic acid methyl ester (244 mg, 1.3 mmol) in glacial acetic acid (13 mL) at room temperature was added $NaBH_4$ (345 mg, 9.1 mmol) portionwise (vigorous reaction). After complete addition the reaction was dark yellow. After stirring for 3 hours the color had become pale yellow. The reaction mixture was poured into 50 mL of $H_2O$ and 50 mL of $CH_2Cl_2$ and stirred rapidly for 15 min. The layers were separated and the organics concentrated to a yellow oil. TLC in 15/85 EtOAc/hexane showed complete consumption of starting material. and two new lower rf spots. The compound was chromatographed using a Biotage 12M column (loaded with $CH_2Cl_2$) and eluted with 15/85 EtOAc/hexane. The higher rf spot corresponds the N-ethylated product (123 mg, 43%). The lower rf spot corresponds to the desired tetrahydroquinoline-3-carboxylic acid methyl ester (93 mg, 37%). N-ethyl derivative: $^1$H-NMR (400 MHz, $CDCl_3$) δ7.08 (dd, 1H), 6.99 (d, 1H), 6.60 (m, 2H), 3.73 (s, 3H), 3.42 (m, 3H), 3.27 (m, 1H), 2.98 (m, 3H), 1.14 (t, 3H) N-H derivative: $^1$H-NMR (400 MHz, $CDCl_3$) δ6.98 (m, 2H), 6.62 (dd, 1H), 6.47 (d, 1H), 3.71 (s, 3H), 3.52 (n, 11H), 3.34 (m, 1H), 3.00 (m, 2H), 2.90 (m, 1H)

Step 3: (1,2,3,4-Tetrahydro-quinolin-3-yl)-methanol. To a stirred solution of the 1,2,3,4-Tetrahydro-quinoline-3-carboxylic acid methyl ester (93 mg, 0.49 mmol) in 1.5 mL of $Et_2O$ at 0° C. under nitrogen was added $LiAlH_4$ (1M in $Et_2O$) dropwise with vigorous gas evolution and a white precipitate formation. After 30 min., the reaction was carefully quenched with 15% NaOH (3 mL) and 3 mL of $Et_2O$ was added and the mixture stirred rapidly at RT for 15 min. The layers were separated and the aqueous layer extracted (1×10 mL) with $Et_2O$. The organics were combined, dried ($MgSO_4$), filtered and concentrated to the alcohol (64 mg, 80%). $^1$H-NMR (400 MHz, $CDCl_3$) δ6.97 (m, 2H), 6.62 (dd, 1H), 6.47 (d, 1H), 3.66 (m, 1H), 3.58 (m, 1H), 3.40 (m, 1H), 3.08 (m, 1H), 2.82 (m, 1H), 2.53 (m, 1H), 2.18 (m, 1H).

Step 4: [5-Methyl-2-(1,2,3,4-tetrahydro-quinolin-3-ylmethoxy)-phenyl]-carbamic acid tert-butyl ester. To a stirred solution of 2-N-Boc-amino-4-methylphenol (88 mg, 0.39 mmol), (1,2,3,4-Tetrahydro-quinolin-3-yl)-methanol (64 mg, 0.39 mmol) and triphenylphosphine (103 mg, 0.39 mmol) in 850 μL of THF at 0° C. under nitrogen was added a solution of DIAD (77 μL, 0.39 mmol) in 850 μL THF. The reaction was allowed to warm to RT overnight, was concentrated and loaded directly onto a Biotage 12M column with CH$_2$Cl$_2$ and eluted with 96/4 hexane/EtOAc. The product was isolated as a yellow oil (129 mg, 89%). $^1$H-NMR (400 MHz, CDCl$_3$) δ7.92 (br s, 1H), 7.06 (br s, 1H), 6.99 (m, 2H), 6.81 (m, 1H), 6.73 (s, 2H), 6.65 (dd, 1H, 6.51 (d, 1H, 3.96 (mi, 2H), 3.37 (ddd, 2H), 2.79 (ddd, 2H), 2.56 (m, 1H), 2.28 (s, 3H), 1.54 (s, 9H)

Step 5: 3-(2-tert-Butoxycarbonylamino-4-methyl-phenoxymethyl)-3,4-dihydro -2H-quinoline-1-carboxylic acid benzyl ester. To a stirred solution of [5-Methyl-2-(1,2,3,4-tetrahydro-quinolin-3-ylmethoxy)-phenyl]-carbamic acid tert-butyl ester. To a stirred solution of 2-N-Boc-amino-4-methylphenol (129 mg, 0.35 mmol) in CH$_2$Cl$_2$ (1.5 mL) at 0° C. under nitrogen was added DIEA (61 μL, 0.35 mmol) followed by benzyl chloroformate (50 μL, 0.35 mmol) and DMAP (4 mg, 0.035 mmol). After 24 hours, the reaction was diluted to 30 mL with CH$_2$Cl$_2$ and washed (2×30 mL) with 2N HCl and (2×30 mL) with saturated NaHCO$_3$. The organics were dried (MgSO$_4$), filtered and concentrated to a brown oil, which appeared to be a mixture of product and starting material.

Step 6: 3-(2-Amino-4-methyl-phenoxymethyl)-3,4-dihydro-2H-quinoline-1-carboxylic acid benzyl ester. A solution of the crude 3-(2-tert-Butoxycarbonylamino-4-methyl-phenoxymethyl)-3,4-dihydro-2H-quinoline-1-carboxylic acid benzyl ester (crude, 0.35 mmol) in 4N HCl in dioxane (2 mL) at room temperature was stirred under a drying tube overnight. The suspension was concentrated by rotovap, diluted to 30 mL with CH$_2$Cl$_2$ and shaken with 10% Na$_2$CO$_3$ (30 mL). The organics were isolated, dried (MgSO$_4$), filtered and concentrated to a brown oil corresponding to the crude aniline, which was used without purification in the urea forming reaction.

Step 7: 3-{4-Methyl-2-[3-(5-methyl-pyrazin-2-yl)-ureido]-phenoxymethyl}-3,4-dihydro-2H-quinoline-1-carboxylic acid benzyl ester. A 0.5 M solution of the 5-methyl-pyrazine-2-carboxylic acid azide (204 μL) was diluted with toluene (408 μL) in a septum capped reaction vial under nitrogen and with stirring, immersed in a 90° C. oil bath. After about 20 minutes nitrogen gas evolution had stopped so the reaction was allowed to cool to RT and was treated with a solution of the crude 3-(2-Amino-4-methyl-phenoxymethyl)-3,4-dihydro-2H-quinoline-1-carboxylic acid benzyl ester (ca. 0.101 mmol) in toluene (620μL). The mixture was stirred at 65° C. for 2 hours. The reaction was cooled to rt overnight and a precipitate formed. The precipitate was filtered off with toluene and appeared to be a mixture of Cbz-protected and deprotected product.

Step 8: 1-(5-Methyl-pyrazin-2-yl)-3-[5-methyl-2-(1,2,3,4-tetrahydro-quinolin-3-ylmethoxy)-phenyl]-urea. A stirred suspension of the crude 3-{4-Methyl-2-[3-(5-methyl-pyrazin-2-yl)-ureido]-phenoxymethyl}-3,4-dihydro-2H-quinoline-1-carboxylic acid benzyl ester (6.6 mg, 12 μmol) was heated in 5 mL EtOAc on a heat gun until in solution. The clear solution was cooled to rt and treated with triethylamine (3.4 μL, 24 μmol) followed by Pearlman's catalyst (20% palladium hydroxide on carbon, 9 mg). The mixture was put through a vacuum/purge cycle three times with hydrogen gas and then held under 1 atmosphere hydrogen pressure for 1 hour. The reaction was filtered through GF/F filter paper with EtOAc and concentrated to a white solid which corresponds to the desired product (4.7 mg, 100%). $^1$H-NMR (400 MHz, CDCl$_3$/CD$_3$OD) δ8.23 (s, 1H), 8.18 (s, 1H), 7.96 (s, 1H), 7.04(t, 1H), 6.97 (d, 1H, 6.81 (m, 2H), 6.67 (t, 1H), 6.58 (d, 1H, 4.04 (m, 2H), 3.57 (d, 1H, 3.26 (t, 1H), 2.92 (ddd, 2H), 2.64 (m, 1H), 2.34 (s, 3H), 2.31 (s, 3H) LRMS (APCI, Positive) m/e 404.2 (M+1).

Compound 292

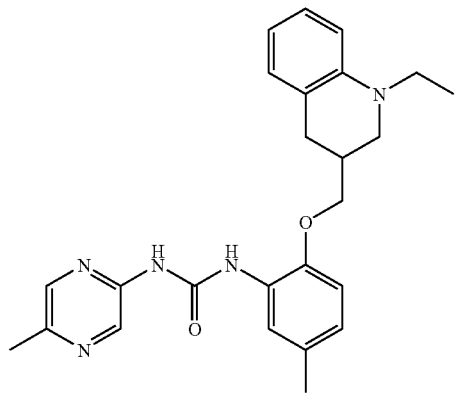

1-[2-(1-Ethyl-1,2,3,4-tetrahydro-quinolin-3-ylmethoxy)-5-methyl-phenyl]-3-(5-methyl-pyrazin-2-yl)-urea Step 1: (1-Ethyl-1,2,3,4-tetrahydro-quinolin-3-yl)-methanol. To a stirred solution of 1-Ethyl-1,2,3,4-tetrahydro-quinoline-3-carboxylic acid methyl ester (123 mg, 0.56 mmol) in 1.5 mL of Et$_2$O at 0° C. under nitrogen. LAH (1M in Et$_2$O) was added dropwise with vigorous gas evolution and a white precipitate formation. After 30 min., TLC in 3/7 EtOAc/hexane showed complete loss of s.m. and appearance of a clean lower rf spot. The reaction was carefully quenched with 15% NaOH (3 mL) and 3 mL of Et$_2$O was added and the mixture stirred rapidly at RT for 15 min. The layers were separated and the aqueous layer extracted 1×10 mL with Et$_2$O. The organics were combined, dried (MgSO$_4$), filtered and concentrated to a clear oil corresponding to the desired alcohol (105 mg, 95%).

Step 2: [2-(1-Ethyl-1,2,3,4-tetrahydro-quinolin-3-ylmethoxy)-5-methyl-phenyl]-carbamic acid tert-butyl ester. To a stirred solution of (1-Ethyl-1,2,3,4-tetrahydro-quinolin-3-yl)-methanol (105 mg, 0.55 mmol, prepared in step 2, compound 126xx), 2-N-Boc-amino-4-methylphenol (123 mg, 0.55 mmol), and triphenylphosphine (144 mg, 0.55 mmol) in 850 μL of THF at 0° C. under nitrogen was added a solution of DIAD (108 μL, 0.55 mmol) in 850 μL THF. The reaction was allowed to warm to RT overnight, was concentrated and loaded directly onto a Biotage 12M column with CH$_2$Cl$_2$ and eluted with 96/4 hexane/EtOAc to give the desired alkylated phenol as a white foam (40 mg, 18%). $^1$H-NMR (400 MHz, CDCl$_3$) δ 7.92 (br s, 1H), 7.08 (dd, 1H, 7.02 (m, 1H), 6.99 (d, 1H), 6.75 (s, 2H), 6.62 (d, 1H), 6.59 (dd, 1H, 3.98 (m, 2H), 3.39 (m, 4H), 3.20 (m, 1H), 2.79 (ddd, 2H), 2.58 (m, 1H), 2.28 (s, 3H), 1.56 (s, 9H), 1.16 (t, 3H).

Step 3: 2-(1-Ethyl-1,2,3,4-tetrahydro-quinolin-3-ylmethoxy)-5-methyl-phenylamine. A solution of [2-(1-

Ethyl-1,2,3,4-tetrahydro-quinolin-3-ylmethoxy)-5-methyl-phenyl]-carbamic acid tert-butyl ester (40 mg, 0.1 mmol) was stirred in 4N HCl in dioxane (2 mL) at room temperature under a drying tube overnight. The suspension was concentrated by rotovap, diluted to 30 mL with CH$_2$Cl$_2$ and shaken with 10% Na$_2$CO$_3$ (30 mL). The organics were isolated, dried (MgSO$_4$), filtered and concentrated to a brown oil, which was used without purification in the following reaction.

Step 4: 1-[2-(1-Ethyl-1,2,3,4-tetrahydro-quinolin-3-ylmethoxy)-5-methyl-phenyl]-3-(5-methyl-pyrazin-2-yl)-urea. A 0.5 M solution of the acyl azide (182 μL) was diluted with 364 μL toluene in a septum capped reaction vial under nitrogen and with stirring, immersed in a 90° C. oil bath. After about 20 minutes N$_2$ gas evolution had stopped so the reaction was allowed to cool to rt and was treated with a solution of 2-(1-ethyl-1,2,3,4-tetrahydro-quinolin-3-ylmethoxy)-5-methyl-phenylamine (27 mg, 0.91 mmol) in 550 μL of toluene. The mixture was stirred at 65 ° C. for 2 hours. The reaction was cooled to rt overnight and a precipitate formed. The precipitate was filtered off with toluene and the desired urea isolated as a tan solid (7 mg, 18%). $^1$H-NMR (400 MHz, CDCl$_3$) δ11.34 (br s, 1H), 8.25 (s, 1H), 8.21 (s, 1H), 8.11 (br s, 1H), 7.83 (s, 1H), 7.25 (mi, 1H), 7.18 (d, 1H, 7.12 (t, 1H), 6.97 (d, 1H), 6.80 (m, 2H), 6.70 (d, 1H, 6.61 (t, 1H), 4.05 (m, 2H), 3.52 (m, 2H), 3.32 (t, 1H), 3.17 (m, 1H), 2.91 (ddd, 2H), 2.69 (m, 1H), 2.36 (s, 3H), 2.27 (s, 3H), 1.04 (t, 3H). LRMS (APCI, Positive) m/e 431.9 (M+1).

Compound 293

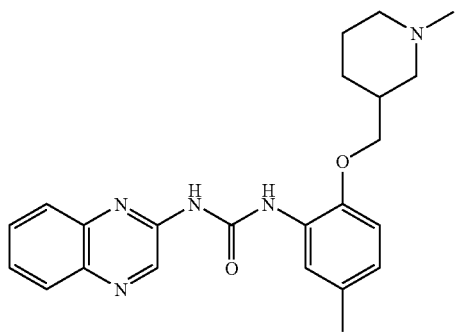

1-[5-Methyl-2-(1-methyl-piperidin-3-ylmethoxy)-phenyl]-3-quinoxalin-2-yl-urea

Step 1: Quinoxaline-2-carbonyl azide. A stirred solution quinoxaline-2-carboxylic acid (348 mg, 2 mmol) in THF (6 mL) at rt under nitrogen was treated with diisopropylethylamine (365 μL, 2.1 mmol) followed by diphenylphosphoryl azide (410 μL, 1.9 mmol). After stirring overnight the reaction was diluted to 60 mL with Et$_2$O and washed 2×60 mL with sat. NaCl. There was an insoluble brown oil, which was drained off with the aqueous layer and assumed to be a diphenyl phosphate impurity. The organics were dried (MgSO$_4$), filtered and concentrated to a tan solid, which corresponds to the acyl azide (350 mg, 92%). $^1$H-NMR (400 MHz, CDCl$_3$) δ9.58 (s, 1H), 8.32 (d, 1H), 8.21 (d, 1H), 7.94 (m, 2H)

Step 2: 1-[5-Methyl-2-(1-methyl-piperidin-3-ylmethoxy)-phenyl]-3-quinoxalin-2-yl-urea. A solution of quinoxaline-2-carbonyl azide (66 mg, 0.33 mmol) in toluene (1.7 mL) was stirred under nitrogen and immersed in a 90° C. heating bath. After 20 min. the reaction was cooled to 65° C. and solid 5-methyl-2-(1-methyl-piperidin-3-ylmethoxy)-phenylamine (70 mg, 0.3 mmol) was added. The reaction was stirred at 65° C. for 4 hours and then allowed to cool to rt overnight. The resulting precipitate was collected by filtration and washed with toluene (62 mg, 51 %). $^1$H-NMR (400 MHz, CDCl$_3$) δ11.58 (br s, 1H), 9.27 (br s, 1H), 8.63 (s, 1H), 8.22 (s, 1H), 8.03 (d, 1H), 7.91 (d, 1H), 7.76 (t, 1H), 6.86 (m, 2H), 4.03 (m, 2H), 2.91 (d, 1H), 2.61 (d, 1H), 2.37 (s, 3H), 2.25 (m, 1H), 2.09 (s, 1H), 1.81 (m, 3H), 1.57 (m, 2H), 1.05 (m, 1H). LRMS (APCI, Positive) m/e 405.9 (M+1).

Compound 294

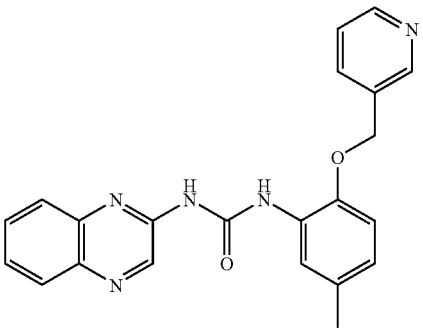

1-[5-Methyl-2-(pyridin-3-ylmethoxy)-phenyl]-3-quinoxalin-2-yl-urea

Step 1: 1-[5-Methyl-2-(pyridin-3-ylmethoxy)-phenyl]-3-quinoxalin-2-yl-urea. A stirred solution of quinoxaline-2-carbonyl azide (92 mg, 0.46 mmol, prepared as above) in 1.5 mL toluene under nitrogen was immersed in a 90° C. heating bath. After 20 min. the reaction was cooled to 65° C. and treated with solid 5-methyl-2-(pyridin-3-ylmethoxy)-phenylamine (90 mg, 0.42 mmol). The reaction was stirred at 65° C. for 4 hours and then allowed to cool to rt overnight. The resulting precipitate was collected by filtration. The crude product was chromatographed on a Biotage 12M column with ⅔ EtOAc/hexane to give pure urea as a tan solid (20 mg, 12%), $^1$H-NMR (400 MHz, CDCl$_3$) δ11.99 (br s, 1H), 9.64 (br s, 1H), 8.76 (s, 1H), 8.61 (s, 1H), 8.48 (d, 1H), 8.24 (s, 1H), 7.98 (d, 1H), 7.79 (d, 1H), 7.55 (t, 1H), 7.42 (t, 1H), 7.17 (d, 1H), 7.12 (m, 1H), 6.93 (m, 2H), 5.26 (s, 2H), 2.41 (s, 3H). LRMS (APCI, Positive) m/e 385.9 (M+1).

Compound 295

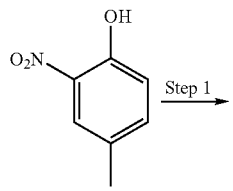

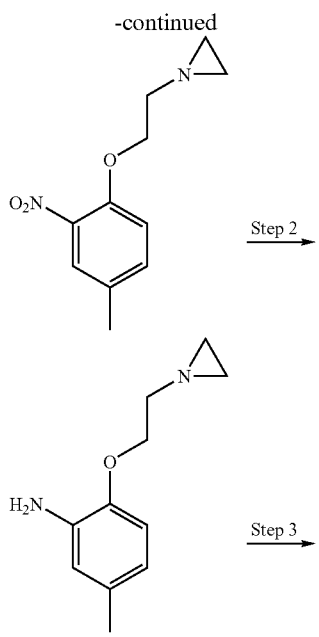

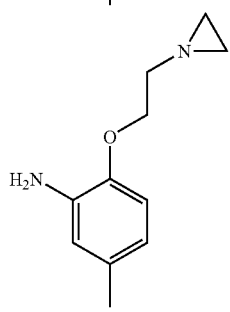

Compound 130

Step 1 Mitsunobo Procedure

1-[2-(4-Methyl-2-nitro-phenoxy)-ethyl]-aziridine. A solution of 2-nitro-4-methylphenol (505 mg, 3.3 mmol, 1.1 eq.) and 2-aziridin-1-yl-ethanol (3.0 mmol, 1 eq.) in 10 mL THF was stirred at 0° C. Triphenylphosphine (0.87 g, 3.30 mmol, 1.1 eq.) and diisopropylazodicarboxylate, (0.67 g 3.30 mmol, 1.1 eq.) were added, and the solution was allowed to warm to temperature. After 18 h, the reaction mixture was diluted with 100 mL EtOAc, and was washed with water (3×20 mL). The organic phase was washed again with 1 N HCl (3×20 ml). The aqueous layer was basified with 3 N NaOH to pH>12 and extracted with EtOAc, (3×50 mL) to give crude product. The final product was purified by flash chromatography eluting with 5-10 % MeOH in dichloromethane. $^1$H NMR (400 MHz, CDCl$_3$): δ7.66 (s, 1H), 7.32 (d, J=8.61 Hz, 1H), 7.01 (d, J=8.61 Hz, 1H), 4.26 (t, J=5.09 Hz, 2H), 2.67 (t J=5.48 Hz, 2H), 2.34 (s, 3H), 1.79 (m, 2H), 1.34 (m, 2H).

Step 2 Nitro Reduction 2-(2-Aziridin-1-yl-ethoxy)-5-methyl-phenylamine. A solution of 3-nitro-4-alkoxy toluene (1.0 mmol) in 20 mL EtOH was hydrogenated at 2 atm over 300 mg of 10% Pd on carbon for 30 minutes. The catalyst was removed by filtration through a glass fiber filter and the filtrate was concentrated to give the desired product, which was used directly without further purification.

Step 3 Urea Formation

1-[2-(2-Aziridin-1-yl-ethoxy)-5-methyl-phenyl]-3-(5-methyl-pyrazin-2-yl)-urea. A solution of 5-methylpyrazine-2-carboxylic azide (196 mg, 1.2 mmol, 1.2 eq.) in 20 mL anhydrous toluene was heated to 90° C. After 20 minutes N$_2$ evolution had subsided, and the reaction mixture was cooled to 60° C. before adding aniline (1.0 mmol, 1 eq.) as a solution in 2 mL toluene. After stirring for 4 h at 60° C. The reaction mixture was then partitioned between 50 mL EtOAc and sat. NaHCO$_3$. the organic phase was washed with brine, dried over MgSO$_4$, filtered and concentrated. The residue was purified by flash chromatography, eluting with 5 % MeOH in dichloromethane. $^1$H NMR (400 MHz, d6-DMSO): δ10.80 (s, 1H), 8.64 (s, 1H), 8.53 (s, 1H), 8.15 (s, 1H), 8.07 (s, 1H), 6.82 (m, 2H), 4.2 (m, 2H), 2.7 (m, 2H), 2.5 (s, 3H), 2.32 (s, 3H), 1.89 (s, 2H), 1.30 (m, 2H). MS APCI-Pos, M/e 328.0 (M+1)

Compound 296

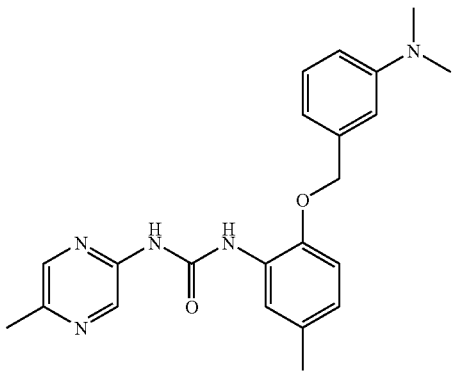

1-[2-(3-Dimethylamino-benzyloxy)-5-methyl-phenyl]-3-(5-methyl-pyrazin-2-yl)-urea Prepared from (3-dimethylamino-phenyl)-methanol, as described above for compound 295. $^1$H NMR (400 MHz, CDCl$_3$): δ11.69 (s, 1H), 8.26 (s, 1H), 8.11 (s, 1H), 7.93 (s, 1H), 7.26 (m, 1H), 6.87 (m, 6H), 5.01 (s, 2H), 2.93 (s, 6H), 2.35 (s, 6H). MS APCI-Pos, M/e 391.9 (M+1)

Compound 297

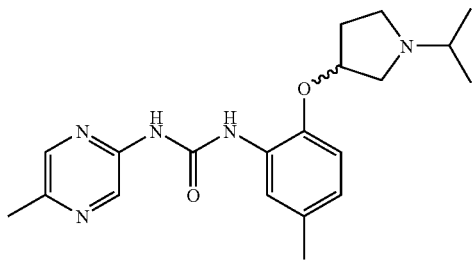

1-[2-(1-Isopropyl-pyrrolidin-3-yloxy)-5-methyl-phenyl]-3-(5-methyl-pyrazin-2-yl)-urea Prepared from 3-hydroxy-1-isopropyl-pyrrolidine, as described above for compound 295. $^1$H NMR (400 MHz, d6-DMSO): δ10.08 (s, 2H), 8.65 (s, 1H), 8.14 (s, 1H), 8.03 (s, 1H), 6.81 (d, J=7.83 Hz, 1H), 6.74 (d, J=8.61 Hz, 1H), 4.85 (s, 1H), 2.91 (m, 1H), 2.75 (m, 2H), 2.48 (m, 1H), 2.4 (s, 3H), 2.36 (m, 1H), 2.27 (m, 1H), 2.21 (s, 3H), 1.85 (m, 1H), 1.01 (m, 6H). MS APCI-Pos, M/e 369.9 (M+1)

Compound 298

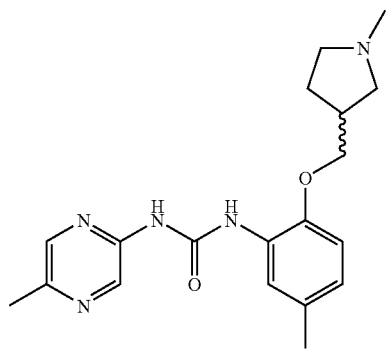

1-[5-Methyl-2-(1-methyl-pyrrolidin-3-ylmethoxy)-phenyl]-3-(5-methyl-pyrazin-2-yl)-urea.

Prepared from (1-methyl-pyrrolidin-3-yl)-methanol as described above for compound 295. $^1$H NMR (400 MHz, d6-DMSO): δ10.13 (s, 2H), 8.67 (s, 1H), 8.15 (s, 1H), 8.06 (s, 1H), 6.81 (d, J=8.61 Hz, 1H), 6.75 (d, J=7.83 Hz, 1H), 4.88 (s, 1H), 2.75 (m, 4H), 2.5 (m, 2H), 2.43 (s, 3H), 2.3 (s, 3H), 2.24 (s, 3H). MS APCI-Pos, M/e 341.9 (M+1)

Compound 299

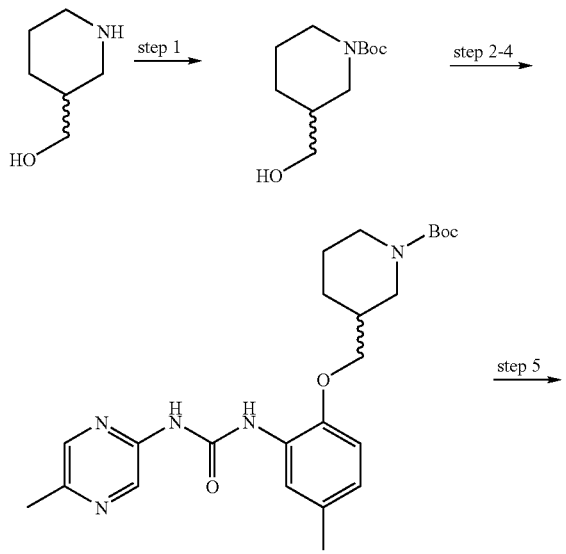

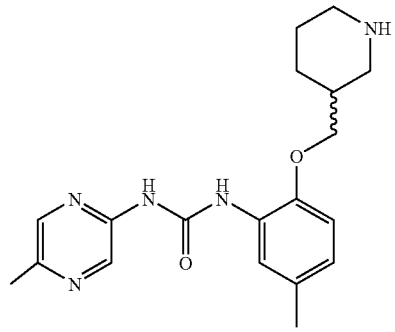

Compound 134

Step 1: 3-Hydroxymethyl-piperidine-1-carboxylic acid tert-butyl ester. To a stirred solution of 3-hydroxymethyl piperdine (403 mg, 3.5 mmol, 1 eq.) in 20 mL of CH$_2$Cl$_2$ and 5 mL of sat'd NaHCO$_3$, 0° C. was added di-tert-butyl dicarbonate (803 mg, 3.68 mmol, 1.05 eq.) in several portions. After stirring at 0° C. for 2 h, the solution was diluted with 10 mL of water and was extracted with 2×20 mL CH$_2$Cl$_2$ the combined extracts were washed with water, then brine and were dried over MgSO$_4$, filtered and concentrated to give the Boc protected amine which was used in the next step.

Steps 2-4: 3-{4-Methyl-2-[3-(5-methyl-pyrazin-2-yl)-ureido]-phenoxymethyl}-piperidine-1-carboxylic acid tert-butyl ester was prepared from 3-hydroxymethyl-piperidine-1-carboxylic acid tert-butyl ester, as described above for compound 295. It was purified by flash chromatography eluting with 5% MeOH in CH$_2$Cl$_2$ Step 5: 1-[5-Methyl-2-(piperidin-3-ylmethoxy)-phenyl]-3-(5-methyl-pyrazin-2-yl)-urea Removal of the Boc group was accomplished by treatment of a 0° C. solution of the protected derivative (180 mg, 0.395 mmol) in 15 mL CH$_2$Cl$_2$ with 2 mL of TFA. After stirring for 18h at room temperature, the reaction was concentrated in vacuo, and the residue was taken up in 20 mL of EtOAc and was washed with 10 mL, of NaHCO$_3$. The aqueous phase was extracted with EtOAc (2×30 mL), and the combined extracts were washed with 20 mL of brine, dried over MgSO$_4$, filtered and concentrated to give 128 mg (91%) of the desired amine. $^1$H NMR (400 MHz, d6-DMSO): δ10.16 (s, 1H), 10.09 (s, 1H), 8.53 (s, 1H), 8.11 (s, 1H), 7.97,(s, 1H), 6.8 (d, J=7.8 Hz, 1H), 6.69 (d, J=8.6 Hz, 1H), 3.77 (s, 2H), 3.09 (m, 1H), 2.82 (m, 1H), 2.34 (m, 2H), 2.3 (s, 3H), 2.27 (m, 1H), 2.15 (s, 3H), 1.92 (m, 1H), 1.75 (m, 1H), 1.53 (m, 1H), 1.37 (m, 1H), 1.11 (m, 1H). MS APCI-Pos, M/e 356.0 (M+1)

Compound 300

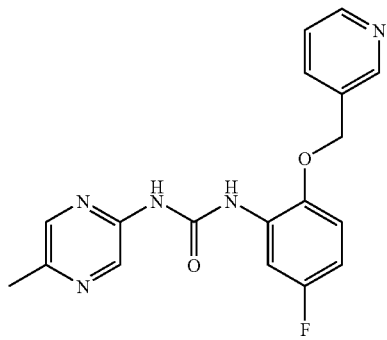

1-[5-Fluoro-2-(pyridin-3-ylmethoxy)-phenyl]-3-(5-methyl-pyrazin-2-yl)-urea

Step 1: 3-(4-Fluoro-2-nitro-phenoxymethyl)-pyridine. To a stirred, cooled (about 0° C.) solution of 1,4-Difluoro-2-nitro-benzene (3.0 mmol) and 3-pyridylcarbinol (3.1 mmol) in tetrahydrofuran ( 8 mL) was added lithium bis(trimethylsilyl)amide (3.2 mmol; 3.2 mL of a 1.0 M solution in tetrahydrofuran). After stirring for 12 hours, the reaction was diluted with 30 mL of ethyl acetate and washed with 30 mL of 10% aqueous sodium carbonate (2×30 mL), brine (1×30 mL), then dried (MgSO$_4$), and filtered. The filtered solution was concentrated under reduced pressure to provide the desired crude product.

Step 2: 5-Fluoro-2-(pyridin-3-ylmethoxy)-phenylamine. To a stirred, cooled (about 0° C.) solution of a 4-Fluoro-2-nitro-phenoxymethyl)-pyridine (1.0 mmol) in methanol (2 mL) and saturated aqueous ammonium chloride (1 mL) was added zinc dust (2.0 mmol). After stirring for 12 hours, the reaction was diluted with 30 mL of ethyl acetate and washed with 30 mL of 10% aqueous sodium carbonate (2×30 mL), brine (1×30 mL), then dried (MgSO$_4$), and filtered. The filtered solution was concentrated under reduced pressure to provide the desired crude product.

Step 3: Urea formation according to method for compound 295 (23% yield). $^1$H NMR (400 MHz, CDCl$_3$) δ11.62 (br s, 1H), 8.80 (s, 1H), 8.75 (d, 1H), 8.43 (br s, 1H), 8.25 (d, 1H), 8.15 (s, 1H), 7.85 (d, 1H), 7.43 (m, 1H), 6.95 (m, 2H), 6.68 (m, 1H), 5.15 (s, 2H), 2.43 (s, 3H). LRMS (ESI, Positive) m/e 354.10 (M+1).

Compound 301

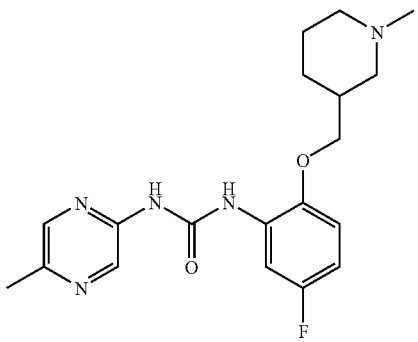

1-[5-Fluoro-2-(1-methyl-piperidin-3-ylmethoxy)-phenyl]-3-(5-methyl-pyrazin-2-yl)-urea

Steps 1-2: According to procedure for compound 300, using 1,4-difluoro-2-nitrobenzene and 1-methyl-3-hydroxymethyl piperidine.

Step 3: Urea formation according to method for compound 285 (62% yield). $^1$H NMR (400 MHz, CDCl$_3$) δ8.22 (m, 3H), 7.21 (m, 2H), 6.78 (m, 2H), 3.85 (m, 2H), 3.21 (m, 1H), 2.52 (s, 3H), 2.39 (s, 3H), 1.50-2.30 (m, 8H). LRMS (ESI, Positive) m/e 374.21 (M+1).

Compound 302

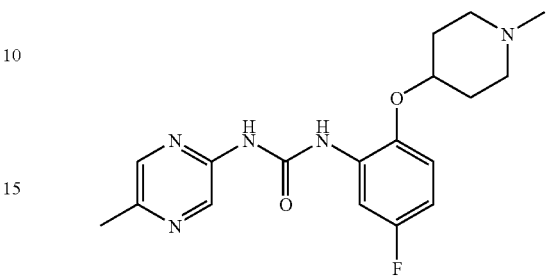

1-[5-Fluoro-2-(1-methyl-piperidin-4-yloxy)-phenyl]-3-(5-methyl-pyrazin-2-yl)-urea

Steps 1-2: According to procedure for compound 300, using 1,4-difluoro-2-nitrobenzene and 1-methyl-4-hydroxypiperidine.

Step 3: Urea formation according to method for compound 295 (78% yield). $^1$H NMR (400 MHz, CDCl$_3$) δ11.49 (br s, 1H), 8.89 (br s, 1H), 8.35 (s, 1H), 8.22 (d, 1H), 8.10 (s, 1H), 6.80 (m, 1H), 6.70 (m, 1H), 4.25 (, 1H), 2.90 (m, 2H), 2.55 (s, 3H), 2.38 (s, 3H), 2.35 (s, 3H), 1.80-2.30 (m, 6H). LRMS (ESI, Positive) m/e 359.91 (M+1).

Compound 303

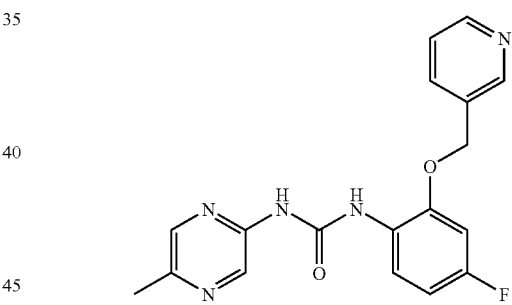

1-[4-Fluoro-2-(pyridin-3-ylmethoxy)-phenyl]-3-(5-methyl-pyrazin-2-yl)-urea

Step 1: 3-(5-Fluoro-2-nitro-phenoxymethyl)-pyridine To a stirred, cooled (about 0° C.) solution of 2-nitro-5-fluorophenol (2.0 mmol), triphenyl phosphine (2.0 mmol), and 3-hydroxymethylpyridine (2.0 mmol) in dry tetrahydrofuran (5 mL) was added diisopropyl azodicarboxylate (2.0 mmol in 1 mL of tetrahydrofuran). After stirring for 12 hours, the reaction was diluted with 30 mL of ethyl acetate and washed with 30 mL of 10% aqueous sodium carbonate (2×30 mL), brine (1×30 mL), then dried (MgSO$_4$), and filtered. The filtered solution was concentrated under reduced pressure to provide the desired crude product.

Step 2: 4-Fluoro-2-(pyridin-3-ylmethoxy)-phenylamine Nitro reduction according to the method for compound 300.

Step 3: Urea formation according to method for compound 295 (60% yield).

$^1$H NMR (400 MHz, CDCl$_3$) δ11.41 (br s, 1H), 8.85 (s, 1H), 8.75 (d, 1H), 8.40 (t, 1H), 8.18 (s, 1H), 7.88 (s, 1H), 7.80 (d, 1H), 7.43 (t, 1H), 7.00 (s, 1H), 6.80 (m, 2H), 5.12 (s, 2H), 2.43 (s, 3H). LRMS (ESI, Positive) m/e 354.21(M+1).

Compound 304

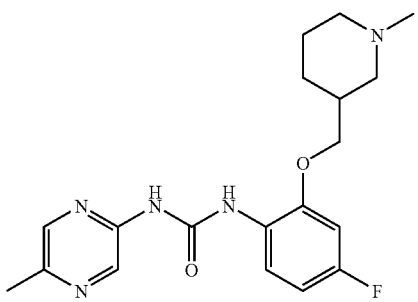

1-[4-Fluoro-2-(1-methyl-piperidin-3-ylmethoxy)-phenyl]-3-(5-methyl-pyrazin-2-yl)-urea Prepared according to the methods for compound 303, using 2-nitro-5-fluorophenol and 1-methyl-3-hydroxymethyl piperidine.

$^1$H NMR (400 MHz, CDCl$_3$) δ8.50 (br s, 1H), 8.19 (m, 2H), 6.65 (m, 2H), 3.85 (m, 2H), 3.60 (s, 3H), 2.80-3.20 (m, 2H), 2.54 (s, 3H), 2.39 (s, 3H), 1.60-2.10 (m 5H). LRMS (ESI, Positive) m/e 373.95 (M+1).

Compound 305

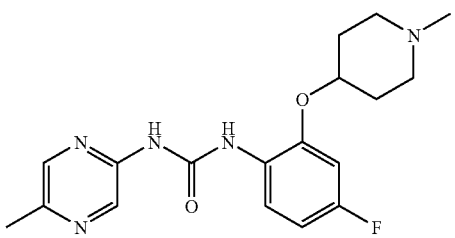

1-[4-Fluoro-2-(1-methyl-piperidin-4-yloxy)-phenyl]-3-(5-methyl-pyrazin-2-yl)-urea Prepared according to the methods for compound 303, using 2-nitro-5-fluorophenol and 1-methyl-4-hydroxypiperidine. $^1$H NMR (400 MHz, CDCl$_3$) δ11.35 (br s, 1H), 9.49 (s, 1H), 8.35 (m, 2H), 8.05 (s, 1H), 6.65 (m, 2H), 4.35 (m, 1H), 2.90 (m, 2H), 2.54 (s, 3H), 2.35 (s, 3H), 1.80-2.30 (m, 6H). LRMS (ESI, Positive) m/e 359.93 (M+1).

Compound 306

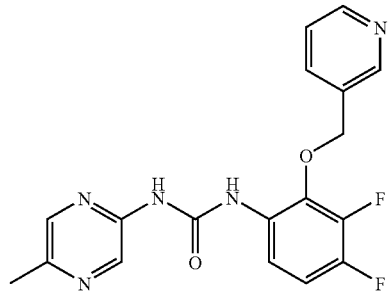

1-[3,4-Difluoro-2-(pyridin-3-ylmethoxy)-phenyl]-3-(5-methyl-pyrazin-2-yl )-urea

Step 1: 3-(2,3-Difluoro-6-nitro-phenoxymethyl)-pyridine To a stirred, cooled (about 0° C.) solution of 2,3-difluoro-6-nitrophenol (2.0 mmol), triphenyl phosphine (2.0 mmol), and 3-hydroxymethylpyridine (2.0 mmol) in dry tetrahydrofuran (5 mL) was added diisopropyl azodicarboxylate (2.0 mmol in 1 mL of tetrahydrofuran). After stirring for 12 hours, the reaction was diluted with 30 mL of ethyl acetate and washed with 30 mL of 10% aqueous sodium carbonate (2×30 mL), brine (1×30 mL), then dried (MgSO$_4$), and filtered. The filtered solution was concentrated under reduced pressure to provide the desired crude product.

Step 2: 3,4-Difluoro-2-(pyridin-3-ylmethoxy)-phenylamine Nitro reduction according to the method for compound 300.

Step 3: Urea formation according to method for compound 295 (20% yield). $^1$H NMR (400 MHz, CDCl$_3$) δ11.49 (br s, 1H), 8.89 (s, 1H), 8.85 (s, 1H), 8.65 (d, 1H), 8.25 (s, 1H), 8.10 (m, 1H), 7.88 (d, 1H), 7.35 (t, 1H), 7.18 (s, 1H), 6.98 (m, 1H), 5.25 (s, 2H), 2.52 (s, 3H). LRMS (ESI, Positive) m/e 372.10 (M+1).

Compound 307

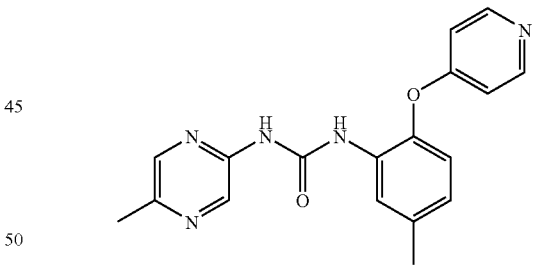

1-(5-Methyl-pyrazin-2-yl)-3-[5-methyl-2-(pyridin-4-yloxy)-phenyl]-urea

Step 1: 5-Methyl-2-(pyridin-4-yloxy)-phenylamine To a stirred solution of 2-amino-4-methyl phenol (616 mg; 5.0 mmol) and 4-chloro pyridine (625 mg; 5.5 mmol) in dimethyl sulfoxide (5 mL) was added sodium hydroxide (600 mg; 15.0 mmol, in 1 mL of water). The reaction was heated to 100° C. and stirred for 12 hours. The reaction was cooled to room temperature, diluted with 50 mL of ethyl acetate and washed with aqueous 10% sodium carbonate (1×50 mL), and brine (50 mL), then dried (MgSO$_4$), and filtered. The crude product was purified using the biotage 40M cartridge eluting with methylene chloride:methanol:ammonia (90:8:2) to yield a light yellow oil (10% yield).

Step 2: Urea formation according to method for compound 295 (36% yield). $^1$H NMR (400 MHz, CDCl$_3$) δ11.41 (br s, 1H), 8.52 (m. 3H), 8.33 (s, 1H), 8.22 (s, 1H), 7.61 (s, 1H), 6.80-7.00 (m, 4H), 2.49 (s, 3H), 2.45 (s, 3H). LRMS (ESI, Positive) m/e 335.91 (M+1).

Compound 308

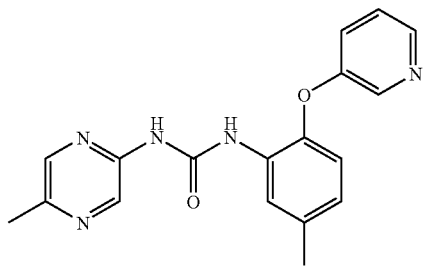

1-(5-Methyl-pyrazin-2-yl)-3-[5-methyl-2-(pyridin-3-yloxy)-phenyl]-urea

Step 1: 3-(4-Methyl-2-nitro-phenoxy)-pyridine To a stirred solution of 1-chloro-4-methyl-2-nitrobenzene (686 mg; 4.0 mmol) and pyridin-3-ol (418 mg; 4.40 mmol) in dimethylforamide (5 mL) was added potassium carbonate (1.22 g, 8.80 mmol). The reaction was heated to 50° C. and stirred for 12 hours. The reaction was cooled to room temperature, diluted with 50 mL of ethyl acetate and washed with aqueous 10% sodium carbonate (1×50 mL), and brine (50 mL), then dried (MgSO$_4$), and filtered. The crude product was purified using the biotage 40M cartridge eluting with hexanes and ethyl acetate (1: 1) to yield a light yellow oil (27% yield).

Step 2: 5-Methyl-2-(pyridin-3-yloxy)-phenylamine To a stirred, cooled (about 0° C.) solution of 3-(4-Methyl-2-nitro-phenoxy)-pyridine (1.0 mmol) in methanol (2 mL) and saturated aqueous ammonium chloride (1 mL) was added zinc dust (2.0 mmol). After stirring for 12 hours, the reaction was diluted with 30 mL of ethyl acetate and washed with 30 mL of 10% aqueous sodium carbonate (2×30 mL), brine (1×30 mL), then dried (MgSO$_4$), and filtered. The filtered solution was concentrated under reduced pressure to yield a brown oil (95% yield).

Step 3: Urea formation according to method for compound 295 (45% yield). $^1$H NMR (400 MHz, CDCl$_3$) δ11.49 (br s, 1H), 8.55 (s, 1H), 8.39 (d, 1H), 8.35 (s, 1H), 8.15 (s, 1H), 8.05 (br s 1H), 7.21 (m, 2H), 6.92 (m, 2H), 2.49 (s, 3H), 2.45 (s, 3H). LRMS (ESI, Positive) m/e 335.91 (M+1).

Compound 309

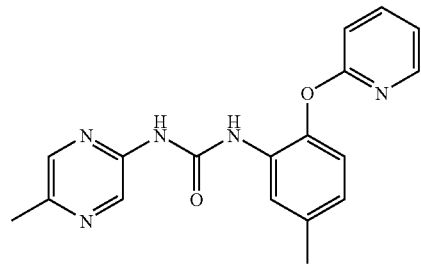

1-(5-Methyl-pyrazin-2-yl)-3-[5-methyl-2-(pyridin-2-yloxy)-phenyl]-urea

Step 1: 2-(4-Methyl-2-nitro-phenoxy)-pyridine To a stirred solution of 1-chloro-4-methyl-2-nitrobenzene (686 mg; 4.0 mmol) and pyridin-2-ol (418 mg; 4.40 mmol) in dimethylforamide (5 mL) was added potassium carbonate (1.22 g, 8.80 mmol). The reaction was heated to 50° C. and stirred for 12 hours. The reaction was cooled to room temperature, diluted with 50 mL of ethyl acetate and washed with aqueous 10% sodium carbonate (1×50 mL), and brine (50 mL), then dried (MgSO$_4$) and filtered. The crude product was purified using the biotage 40M cartridge eluting with hexanes and ethyl acetate (1:1) to yield a light yellow oil (11% yield).

Step 2: 5-Methyl-2-(pyridin-2-yloxy)-phenylamine To a stirred, cooled (about 0° C.) solution of 2-(4-Methyl-2-nitro-phenoxy)-pyridine (1.0 mmol) in methanol (2 mL) and saturated aqueous ammonium chloride (1 mL) was added zinc dust (2.0 mmol). After stirring for 12 hours, the reaction was diluted with 30 mL of ethyl acetate and washed with 30 mL of 10% aqueous sodium carbonate (2×30 mL), brine (1×30 mL), then dried (MgSO$_4$), and filtered. The filtered solution was concentrated under reduced pressure to yield a white foam (77% yield).

Step 3: Urea formation according to method for compound 295 (43% yield). $^1$H NMR (400 MHz, CDCl$_3$) δ8.51 (br s, 1H), 8.42 (br s, 1H), 8.00 (s, 1H), 7.80 (s, 1H), 7.51 (t, 1H), 7.29 (d, 1H), 7.05 (d, 1H), 6.95 (d, 1H), 6.75 (d, 1H), 6.35 (t, 1H), 2.49 (s, 3H), 2.45 (s, 3H). LRMS (ESI, Positive) m/e 335.91 (M+1).

Substituted Aminopyrazine Ureas General Procedure

To a 0.3 M stirred solution of the aminopyrazine derivative (1 equiv.) in dichloroethane at room temperature under nitrogen was added 2-methoxy-5-methylphenylisocyanate (1 equiv.). The reaction was warmed to 80° C. overnight and then cooled to room temperature. In most cases, the product precipitated and was isolated by filtration. Alternatively the product could be isolated by silica gel chromatography using EtOAc/hexane or CH$_2$Cl$_2$/MeOH as eluant.

Compound 310

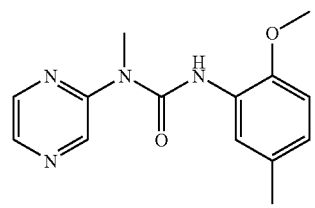

3-(2-Methoxy-5-methyl-phenyl)-1-methyl-1-pyrazin-2-yl-urea

Step 1: 2-methylaminopyrazine. To a stirred solution of 2M methylamine in 1 mL of methanol, at room temperature, was added 2-chloropyrazine. The reaction was sealed and heated to 60° C. for 24 hours. The reaction was concentrated to a mixture of starting material and the desired 2-methylaminopyrazine in a 1:2 ratio. The material was used crude in a urea forming reaction. $^1$H-NMR (400 MHz, CDCl$_3$) δ7.97 (d, 1H), 7.85 (s, 1H), 7.73 (d, 1H), 2.96 (s, 3H)

Step 2: To a 0.3 M stirred solution of 2-methylaminopyrazine (1 equiv.) in dichloroethane at room temperature under nitrogen was added 2-methoxy-5-methylphenylisocyanate (1 equiv.). The reaction was warmed to 80° C. overnight and then cooled to room temperature. In most cases, the product precipitated and was isolated by filtration. Alternatively the product could be isolated by silica gel chromatography using EtOAc/hexane or CH$_2$Cl$_2$/MeOH as eluant. $^1$H-NMR (400 MHz, CDCl$_3$) δ8.57 (s, 1H), 8.32 (s, 1H), 8.31 (s, 1H), 8.17 (s, 1H), 6.80 (i, 2H), 3.90 (s, 3H), 3.56 (s, 3H), 2.32 (s, 3H). LRMS (ESI, Positive) m/e 273.2 (M+1).

Compound 311

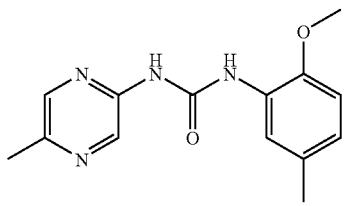

1-(2-Methoxy-5-methyl-phenyl)-3-(5-methyl-pyrazin-2-yl)-urea

Prepared according to general procedure described for compound 310, using 2-amino-4-methylpyrazine. $^1$H-NMR (400 MHz, CDCl$_3$) δ11.12 (br s, 1H), 8.28 (s, 1H), 8.17 (s, 1H), 8.09 (s, 1H), 6.81 (m, 2H), 3.91 (s, 3H), 2.54 (s, 3H), 2.35 (s, 3H). LRMS (ESI, Positive) m/e 273.2 (M+1).

Compound 312

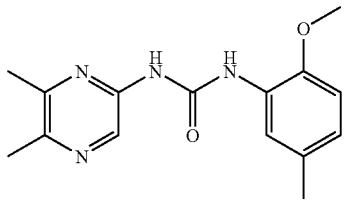

1-(5,6-Dimethyl-pyrazin-2-yl)-3-(2-methoxy-5-methyl-phenyl)-urea

Step 1: 2-Amino-5,6-dimethylpyrazine. Glycine amidine dihydrobromide (620 mg, 2.64 mmol) was stirred in 6 mL of MeOH at -30° C (acetonitrile/CO$_2$ bath) in a capped flask. Butanedione (232 μL, 2.64 mmol) was stirred separately in 6 mL H$_2$O with sodium acetate (700 mg) until homogeneous. The diketone was added to the amidine solution by pipet followed by 2.5 mL of 3.6 M NaOH. The yellow solution was allowed to warm slowly to RT and was then stirred overnight. MeOH was removed by rotovap and the aqueous solution extracted 3×30 mL with EtOAc. The combined organic extracts were dried (MgSO$_4$), filtered and concentrated to a yellow solid which contained some impurities. The solid was triturated with EtOAc/Et$_2$O and filtered to give pure compound (55 mg, 17%). $^1$H-NMR (400 MHz, CDCl$_3$) δ7.76 (s, 1H), 4.25 (br s, 2H), 2.40 (s, 3H), 2.37 (s, 3H)

Step 2: Prepared according to general procedure described for compound 310, using 2-amino-5,6-dimethylpyrazine. $^1$H-NMR (400 MHz, CDCl$_3$) δ11.43 (br s, 1H), 8.23 (s, 1H), 8.00 (s, 1H), 7.64 (br s, 1H), 6.81 (m, 2H), 3.95 (s, 3H), 2.59 (s, 3H), 2.52 (s, 3H), 2.35 (s, 3H). LRMS (APCI, Positive) m/e 287.1 (M+1).

Compound, 313

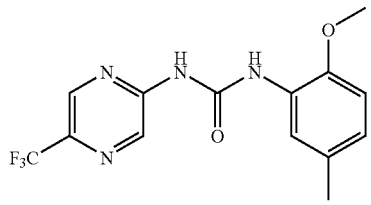

1-(2-Methoxy-5-methyl-phenyl)-3-(5-trifluoromethyl-pyrazin-2-yl)-urea

Step 1: 2-amino-5-trifluoromethylpyrazine. Prepared according to the method of Miesel, J. U.S. Pat. No. 4,293,552 (1981), Step 2: Prepared according to general procedure described for compound 310, using 2-amino-5-trifluoromethylpyrazine. $^1$H-NMR (400 MHz, d6-DMSO) δ10.59 (s, 1H), 9.78 (br s, 1H), 9.06 (s, 1H), 8.80 (s, 1H), 8.00 (s, 1H), 6.96 (d, 1H), 6.81 (d, 1H), 3.87 (s, 3H), 2.22 (s, 3H). LRMS (ESI, Positive) m/e 327.1 (M+1).

Compound 314

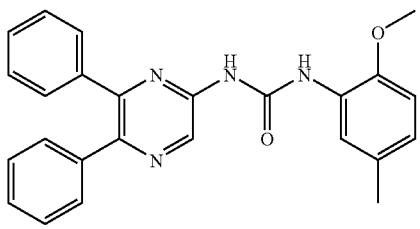

1-(5,6-Diphenyl-pyrazin-2-yl)-3-(2-methoxy-5-methyl-phenyl)-urea

Step 1: 2-Hydroxy-5,6-diphenylpyrazine. To a stirred suspension of glycinamide hydrochloride (1.1 gm, 10 mmol) in 20 mL MeOH at 0° C. was added 20% NaOH (10 mL, 50 mmol). A clear solution formed and was treated slowly portionwise with benzil (2.1 gm, 10 mmol) as a solid. The yellow solution was stirred at 0° C. for 2 hours and then neutralized to approximately pH=7 with concentrated HCl. The bright yellow color disappeared and a tan precipitate formed. The material was isolated by filtration with MeOH and triturated with EtOAc to give 2-hydroxy-5,6-diphenylpyrazine (2 gm, 80%). $^1$H-NMR (400 MHz, CDCl$_3$) δ8.24 (s, 1H), 7.42-7.31 (m, 4H), 7.39-7.21 (m, 6H).

Step 2: 2-Chloro-5,6-diphenylpyrazine. A stirred solution of 2-Hydroxy-5,6-diphenylpyrazine (430 mg, 1.7 mmol) in 5.2 mL POCl$_3$ in a capped reaction vial was heated to 100° C. for 4 hours. The orange solution was cooled to room temperature and stirred rapidly in a mixture of CH$_2$Cl$_2$ (100 mL) and ice cold 10% Na$_2$CO$_3$ (100 mL) for 15 minutes. The organic layer was isolated and washed 2×100 mL with 10% Na$_2$CO$_3$. The organics were isolated, dried (MgSO$_4$), filtered and concentrated to the chloropyrazine, which existed as white solid (450 mg, quantitative). $^1$H-NMR (400 MHz, CDCl$_3$) δ8.59 (s, 1H), 7.45-7.39 (m, 4H), 7.36-7.24 (m, 6H).

Step 3: 2-Azido-5,6-diphenylpyrazine. To a stirred solution of 2-Chloro-5,6-diphenylpyrazine (45 mg, 0.17 mmol) in 500 μL DMF at room temperature under nitrogen was added sodium azide (11 mg, 0.17 mmol) and the reaction was warmed to 100° C. After stirring overnight, the reaction was cooled to room temperature, diluted with EtOAc (30 mL) and washed 4×30 mL with H2O and 1×30 mL with saturated NaCl. The organics were islolated, dried (MgSO$_4$), filtered and concentrated to the 2-azidopyrazine, which exists as a yellow solid (45 mg, quantitative). $^1$H-NMR (400 MHz, CDCl$_3$) δ9.73 (s, 1H), 7.58-7.42 (m, 6H), 7.36-7.23 (m, 4H).

Step 4: 2-Amino-5,6-diphenylpyrazine. To a stirred solution of 2-Azido-5,6-diphenylpyrazine (45 mg, 0.17 mmol) in 50 mL EtOAc at room temperature was added triethylamine (100 μL) followed by Pearlman's Catalyst (50 mg). The suspension was put through a vacuum/purge cycle three times with hydrogen gas and then held under 1 atmosphere of hydrogen for 2 hours. The suspension was then filtered through GF/F filter paper with EtOAc and concentrated. The crude product was eluted through a Biotage 12S column with 1/1 EtOAc/hexane to give pure product, as a clear oil (25 mg, 59%). $^1$H-NMR (400 MHz, CDCl$_3$) δ8.04 (s, 1H), 7.42-7.20 (m, 10H), 4.62 (br s, 2H)

Step 5: Prepared according to general procedure described for compound 310, using 2-amino-5,6-diphenylpyrazine. $^1$H-NMR (400 MHz, CDCl$_3$) δ8.34 (s, 1H), 8.13 (s, 1H), 7.80 (s, 1H), 7.46 (d, 2H), 7.37-7.23 (m, 10H), 6.81 (d, 11), 6.66 (d, 1H), 3.17 (s, 3H), 2.33 (s, 3H)

Compound 315

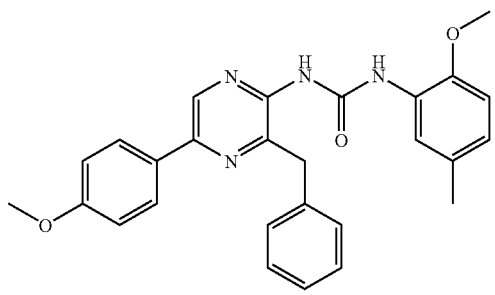

1-[3-Benzyl-5-(4-methoxy-phenyl)-pyrazin-2-yl]-3-(2-methoxy-5-methyl-phenyl)-urea Prepared according to general procedure described for compound 310, using 2-amino-3-benzyl-4-(4-methoxyphenyl)pyrazine $^1$H-NMR (400 MHz, CDCl$_3$) δ8.51 (s, 1H), 8.11 (s, 1H), 7.96 (d, 2H), 7.34 (m, 5H), 7.03 (d, 2H), 6.80 (m, 2H), 4.28 (s, 2H), 3.95 (s, 3H), 3.90 (s, 3H). LRMS (ESI, Positive) m/e 477.2 (M+1).

Compound 316

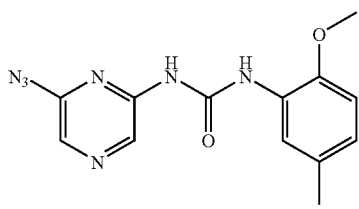

1-(6-Azido-pyrazin-2-yl)-3-(2-methoxy-5-methyl-phenyl)-urea

Step 1: Tetrazolo[1,5-a]pyrazin-5-ylamine. Prepared according to the method of Shaw, J. T.; et al. J. Heterocyclic Chem. 1980, 17, 11.

Step 2: Prepared using p-nitrophenyl carbamate general procedure described for compound 166 (step 2) using Tetrazolo[1,5-a]pyrazin-5-ylamine. $^1$H-NMR (400 MHz, CDCl$_3$) δ9.72 (br s, 1H), 8.23 (s, 1H), 7.97 (s, 1H), 7.87 (s, 1H), 7.8,0 (br s, 1H), 6.88 (d, 1H), 6.80 (d, 1H), 3.84 (s, 3H), 2.36 (s, 3H). LRMS (ESI, Positive) m/e 300.0 (M+1).

Compound 317

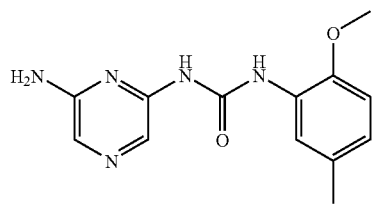

1-(6-Amino-pyrazin-2-yl)-3-(2-methoxy-5-methyl-phenyl)-urea

To a stirred solution of 1-(6-azido-pyrazin-2-yl)-O-(2-methoxy-5-methyl-phenyl)-urea (8 mg, 27 μmol) 95% EtOH (2mL) at room temperature was added concentrated NH$_4$OH (10 μL) and 10% Pd on C (25 mg). The suspension was put through a vacuum/purge cycle three times with, hydrogen gas and then held under 50 psi of hydrogen pressure and shaken on a Parr Shaker. After 2 hours the vacuum/purge cycle was repeated and the reaction held under hydrogen for another 2 hours. The suspension was then filtered through GF/F filterpaper with EtOH and concentrated to a yellow film (3 mg, 41%). $^1$H-NMR (400 MHz, CDCl$_3$) δ8.19 (s, 1H), 7.61 (s, 1H), 7.56 (s, 1H), 6.83 (s, 2H), 3.95 (s, 3H), 2.33 (s, 3H). LRMS (ESI, Positive) m/e 274.2 (M+1).

Compound 318

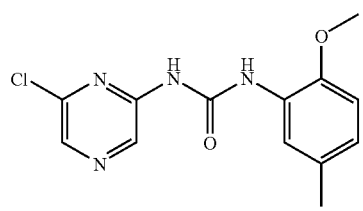

1-(6-Chloro-pyrazin-2-yl)-3-(2-methoxy-5-methyl-phenyl)-urea

To a stirred solution of 2-amino-6-chloropyrazine (130 mg, 1 mmol) in 3 mL THF at 0° C. under nitrogen was added methyl magnesium iodide (3M in Et$_2$O, 330 μL, 1 mmol) to give a yellow suspension that was stirred at 0° C. for 15 minutes. The suspension was treated with the isocyanate neat (147 μL, 1 mmol) and allowed to warm to room temperature overnight. The reaction was partitioned between EtOAc (30 mL) and 10% Na$_2$CO$_3$ (30 mL). The organics were isolated and washed 1×30 mL with 10% Na$_2$CO$_3$ and 1×30 mL with saturated NaCl. The organics were dried (MgSO$_4$), and concentrated to a crude residue that was triturated with EtOAc to give, after filtration, the urea product as a white solid (27 mg, 9%). $^1$H-NMR (400 MHz, CDCl$_3$) δ8.26 (s, H), 8.23 (s, 1H), 8.17 (s, 1H), 8.09 (br s, 1H), 6.84 (d, 1H), 6.81 (d, 1H), 3.96 (s, 3H), 2.35 (s, 3H). LRMS (ESI, Positive) m/e 293.0 (M+1).

Compound 319

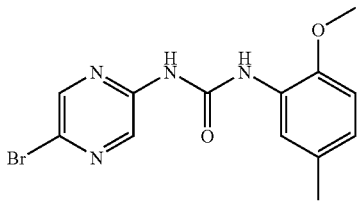

1-(5-Bromo-pyrazin-2-yl)-3-(2-methoxy-5-methyl-phenyl)-urea

Step 1: 2-amino-5-bromopyrazine. To a stirred, cooled (0° C) solution of amino pyrazine (5.0 g, 52.6 mmol) in methylene chloride (200 mL) was added N-bromosuccinimide (9.39 g, 52.8 mmol). After stirring for 24 hours, the reaction was washed with aqueous 10% sodium carbonate (3×50 mL), water (50 mL), then dried (MgSO$_4$), and filtered. The filtered material was concentrated under reduced pressure, taken up in minimal ethyl acetate (5 mL) followed by hexanes (200 mL). Yellow crystals formed which were filtered and dried. (56 % yield).

Step 2: Prepared according to general procedure described for compound 310, using 2-amino-4-bromopyrazine. $^1$H-NMR (400 MHz, CDCl$_3$/CD$_3$OD) δ8.55 (s, 1H), 8.32 (s, 1H), 8.03 (s, 1H), 6.81 (m, 2H), 3.92 (s, 3H), 2.34 (s, 3H).

Compound 320

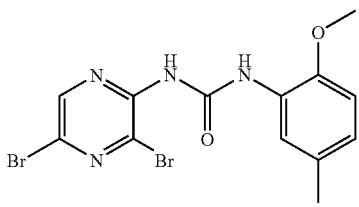

1-(3,5-Dibromo-pyrazin-2-yl)-3-(2-methoxy-5-methyl-phenyl)-urea

Prepared according to general procedure described for compound 310, using 2-amino-4,6-dibromopyrazine. $^1$H-NMR (400 MHz, CDCl$_3$) δ7.98 (s, 1H), 7.13 (s, 1H), 6.79 (m, 2H), 3.83 (s, 3H), 2.32 (s, 3H)

Compound 321

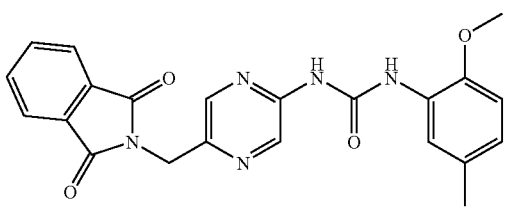

1-[5-(1,3-Dioxo-1,3-dihydro-isoindol-2-ylmethyl)-pyrazin-2-yl]-3-(2-methoxy-5-methyl-phenyl)-urea Step 1: (5-Bromomethyl-pyrazin-2-yl)-carbatic acid tert-butyl ester. To a stirred solution of 2-Boc-amino-5-methyl pyrazine (1.34 gm, 6.4 mmol), in 20 mL CCl$_4$ at room temperature under nitrogen was added N-bromosuccinimide (1.14 gm, 6.4 mmol) followed by benzoyl peroxide (125 mg). The solution was irradiated with a 100 watt flood lamp, which caused the reaction to reflux vigorously. After 2 hours, the reaction was cooled to room temperature, diluted to 125 mL with CH$_2$Cl$_2$ and washed 1×125 mL with 10% sodium bisulfite solution and 1×125 mL with saturated NaCl. The organics were dried (MgSO$_4$), filtered and concentrated to a brown oil, which was directly loaded onto a Biotage 40S column with CH$_2$Cl$_2$ and eluted with 15/85 EtOAc/hexane to give the desired benzylic bromide as a yellow solid (954 mg, 51%). $^1$H-NMR (400 MHz, CDCl$_3$) δ9.22 (s, 1H), 8.29 (s, 1H), 7.37 (br s, 1H), 4.54 (s, 2H), 1.55 (s, 9H).

Step 2: [5-(1,3-Dioxo-1,3-dihydro-isoindol-2-ylmethyl)-pyrazin-2-yl]-carbamic acid tert-butyl ester. To a stirred solution of phthalimide (971 mg, 6.6 mmol) and powdered K$_2$CO$_3$ (1.37 gm, 9.9 mmol) in acetonitrile (9.9 mL) at room temperature under nitrogen was added the bromide (954 mg, 3.3 mmol) as a solid. The suspension was heated to 65° C. for 4 hours. After cooling to room temperature the reaction was partitioned between EtOAc (60 mL) and H$_2$O (60 mL). The organics were isolated and washed 2×50 mL with H$_2$O and 1×50 mL with saturated NaCl. The organics were dried (MgSO$_4$), filtered and concentrated. The crude product was triturated with CH$_2$Cl$_2$ and filtered to remove solid excess phthalimide and the filtrated partially concentrated and loaded directly onto a Biotage 40S column and eluted with 3/7 EtOAc/hexane to give the desired phthalimide as a white solid (495 mg, 42%). $^1$H-NMR (400 MHz, CDCl$_3$) δ9.17 (s, 1H), 8.23 (s, 1H), 7.85 (m, 2H), 7.71 (m, 2H), 7.39 (br s, 1H), 4.97 (s, 2H), 1.52 (s, 9H)

Step 3: 2-(5-Amino-pyrazin-2-ylmethyl)-isoindole-1,3-dione. To a stirred solution of the phthalimide (495 mg, 1.4 mmol) in 7 mL CH$_2$Cl$_2$ at room temperature in a capped flask was added trifluoroacetic acid (7 mL). After stirring overnight, the reaction was concentrated to remove excess trifluoroacetic acid and was then dissolved in 200 mL 10/1 CH$_2$Cl$_2$/MeOH, stirred rapidly, and treated with a solution of 10% Na$_2$CO$_3$ (200 mL). The organics were isolated, dried (MgSO$_4$), filtered and concentrated to give the free aminopyrazine as a yellow solid (260 mg, 73%). $^1$H-NMR (400 MHz, CDCl$_3$) δ8.25 (s, 1H), 7.85 (m, 2H), 7.77 (s, 1H), 7.74 (m, 2H), 4.83 (s, 2H)

Step 4: Prepared according to general procedure described for compound 310 using 2-(5-Amino-pyrazin-2-ylmethyl)-isoindole-1,3-dione. $^1$H-NMR (400 MHz, CDCl$_3$) δ8.38 (s, 1H), 8.29 (s, 1H), 8.03 (s, 1H), 7.86 (m, 2H), 7.76 (m, 2H), 6.81 (m, 2H), 4.98 (s, 2H), 3.91 (s, 3H), 2.31 (s, 3H). LRMS (ESI, Positive) m/e 418.1 (M+1).

Compound 322

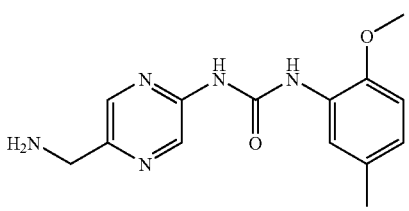

1-(5-Aminomethyl-pyrazin-2-yl)-3-(2-methoxy-5-methyl-phenyl)-urea

To a stirred solution of 1-[5-(1,3-dioxo-1,3-dihydro-isoindol-2-ylmethyl)-pyrazin-2-yl]-3-(2-methoxy-5-methyl-phenyl)-urea (16 mg, 38 µmol) in 380 µL 95% EtOH and 100 μL DMF at room temperature in a capped reaction vial was added hydrazine monohydrate (3.8 μL, 76 μmol). After stirring overnight at room temperature, a white precipitate formed. The precipitate was filtered off, dried and triturated with EtOAc to remove phthalimide based impurities to provide the product as a white solid (7.9 mg, 72%). $^1$H-NMR (400 MHz, d$_6$-DMSO) δ9.54 (s, 1H), 8.80 (s, 1H), 8.46 (s, 1H), 8.02 (s, 1H), 6.93 (d, 1H), 6.79 (d, 1H), 4.51 (d, 2H), 4.39 (br s, 2H), 3.89 (s, 3H), 2.23 (s, 3H). LRLCMS (ESI, Positive) m/e 288.2 (M+1).

Compound 323

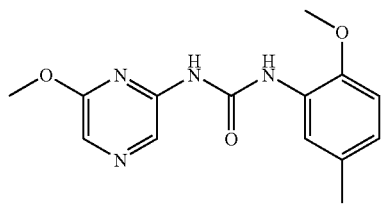

1-(2-Methoxy-5-methyl-phenyl)-3-(6-methoxy-pyrazin-2-yl)-urea

Step 1: 2-amino-6-methoxypyrazine. To a stirred solution of methanol (89 μL; 2.2 mmol) in dioxane (1 mL) was added sodium hydride (53 mg; 2.2 mmol). After stirring for 30 minutes, 2-amino-6-chloropyrazine (258 mg; 2.0 mmol) was added and the reaction was heated to 90° C. After stirring for 12 hours, the reaction was cooled to room temperature, diluted with 30 mL of ethyl acetate and washed with aqueous 10% sodium carbonate (1×30 mL), and brine (30 mL), then dried (MgSO$_4$), and filtered. The crude product was purified using the Biotage 12i cartridge eluting with hexane and ethyl acetate (3:1) to yield a white solid (11% yield).

Step 2: Prepared according to general procedure described for compound 310 using 2-amino-6-methoxypyrazine. (8% yield). $^1$H NMR (400 MHz, CDCl$_3$) δ8.15 (s, 1H), 8.05 (br s, 1H), 7.92 (s, 1H), 7.82 (s, 1H), 6.89 (d, 1H), 6.80 (d, 1H), 4.05 (s, 3H), 3.81 (s, 3H), 2.38 (s, 3H). LRMS (ESI, Positive) m/e 289.10 (M+1).

Compound 324

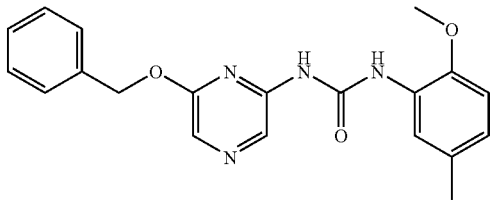

1-(6-Benzyloxy-pyrazin-2-yl)-3-(2-methoxy-5-methyl-phenyl)-urea

Step 1: 2-amino-6-benzyloxypyrazine. To a stirred solution of benzyl alcohol (432 μL; 4.0 mmol) in dioxane (2 mL) was added sodium hydride (96 mg; 4.0 mmol). After stirring for 30 minutes, 2-amino-6-chloropyrazine (258 mg; 2.0 mmol) was added and the reaction was heated to 90° C. After stirring for 12 hours, the reaction was cooled to room temperature, diluted with 30 mL of ethyl acetate and washed with aqueous 10% sodium carbonate (1×30 mL), and brine (30 mL), then dried (MgSO$_4$) and filtered. The crude product was purified using the biotage 12i cartridge eluting with hexane and ethyl acetate (3:1) to yield a white solid (33% yield).

Step 2: Prepared according to general procedure described for compound 310 using 2-amino-6-benzyloxypyrazine. (34% yield). $^1$H NMR (400 MHz, d6-DMSO) δ9.99 (s, 1H), 9.18 (s, 1H), 8.62 (s, 1H), 7.99 (s, 1H), 7.95 (s, 1H), 7.52 (d, 2H), 7.41 (m, 3H), 6.92 (d, 1H), 6.80 (d, 1H), 5.39 (s, 2H), 3.80 (s, 3H), 2.21 (s, 3H). LRMS (ESI, Positive) m/e 365.10 (M+1).

Compound 325

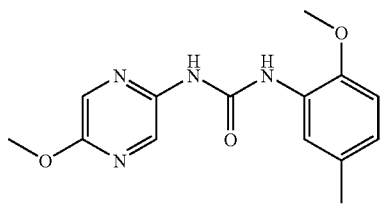

1-(2-Methoxy-5-methyl-phenyl)-3-(5-methoxy-pyrazin-2-yl)-urea

To a stirred solution of 1-(5-bromo-pyrazin-2-yl)-3-(2-methoxy-5-methyl-phenyl)-urea (47 mg; 0.14 mmol) in N-methyl pyrrolidinone (300 μL) was added sodium methoxide (0.5 mmol). The reaction was heated to 100° C. After stirring for 12 hours, the reaction was cooled to room temperature, diluted with 30 mL of ethyl acetate and washed with aqueous 10% sodium carbonate (1×30 mL), brine (30 mL), then dried (MgSO$_4$), and filtered. The crude product was purified using a 0.5 mm prep plate eluting with hexane and ethyl acetate (1:1) to yield a yellow solid (13% yield). $^1$H NMR (400 MHz, CDCl$_3$) δ8.12 (s, 1H), 7.99 (s, 1H), 7.91 (s, 1H), 6.80 (dd, 2H), 3.95 (s, 3H), 3.89 (s, 3H), 2.38 (s, 3H). LRMS (ESI, Positive) m/e 289.10 (M+1).

Compound 326

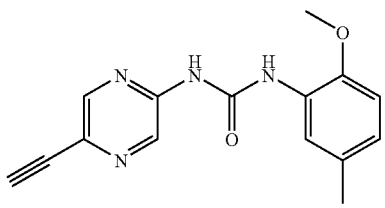

1-(5-Ethynyl-pyrazin-2-yl)-3-(2-methoxy-5-methyl-phenyl)-urea

Step1: 2-Amino-5-alkynylpyrazine. To a stirred solution of 5-bromo-2-aminopyrazine (432 mg; 2.5 mmol), Pd(Ph$_3$P)$_2$Cl$_2$ (91 mg; 0.13 mmol), CuI (1.2 g, 6.5 mmol) in triethylamine (8 mL) was added TMS-acetylene. The reaction was stirred at 60° C. for 12 hours. The reaction was cooled to room temperature, diluted with 30 mL of ethyl acetate and washed with aqueous 10% sodium carbonate (1×30 mL), brine (30 mL), then dried (MgSO$_4$), and filtered. The crude product was diluted in 1 mL of methanol and sodium hydroxide (10 mL of a 1N aqueous solution). After stirring for 12 hours the reaction was diluted with 30 mL of ethyl acetate and washed with aqueous 10% sodium carbonate (1×30 mL), brine (30 mL), then dried (MgSO₄), and filtered. The crude product was purified using a biotage 12L column eluting with methylene chloride and methanol (98:2) to yield an off white solid (40% yield).

Step 2: Prepared according to general procedure described for compound 310 using 2-Amino-5-alkynylpyrazine. (20% yield). ¹H NMR (400 MHz, d6-DMSO) δ10.25 (s, 1H), 9.80 (br s, 1H), 8.90 (s, 1H), 8.50 (s, 1H), 8.00 (s, 1H), 6.95 (d, 1H), 6.82 (d, 1H), 4.42 (s, 1H), 3.82 (s, 3H), 2.22 (s, 3H). LRMS (ESI, Positive) m/e 283.10 (M+1).

Compound 327

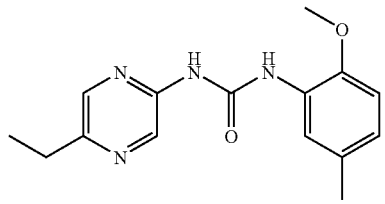

1-(5-Ethyl-pyrazin-2-yl)-3-(2-methoxy-5-methyl-phenyl)-urea

Step 1: 2-Amino-5-ethylpyrazine. To a stirred solution of 5-ethynyl-2-aminopyrazine (18 mg; 0.151 mmol), in ethyl acetate (500 μL) was added triethylamine (63 μL; 0.45 mmol) and Pd(OH)₂ (0.01 mmol; 20% wt on carbon). The reaction was placed under a hydrogen atmosphere at 45 psi and shook for 6 hours. The reaction was filtered and concentrated under reduced pressure to yield an off white solid (84% yield).

Step 2: Prepared according to general procedure described for compound 310 using 2-Amino-5-ethylpyrazine. (27% yield). ¹H NMR (400 MHz, CDCl₃) δ8.65 (s, 1H), 8.38 (s, 1H), 8.18 (s, 1H), 8.08 (s, 1H), 6.80 (dd, 2H), 3.92 (s, 3H), 2.81 (q, 2H), 2.39 (s, 3H), 1.39 (t, 3H). LRMS (ESI, Positive) m/e 287.21 (M+1).

Compound 328

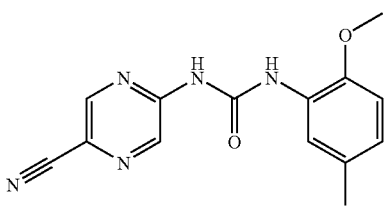

1-(5-Cyano-pyrazin-2-yl)-3-(2-methoxy-5-methyl-phenyl)-urea

Step 1: 2-amino-5-cyanopyrazine. To a stirred solution of 5-bromo-2-aminopyrazine (1.0 g) 5.8 mmol), CuI (2.76 g, 14.5 mmol), 18-crown-6 (121 mg; 0.46 mmol), potassium cyanide (943 mg; 14.5 mmol) in dimethylformamide (20 mL) was added Pd(PPh₃)₄ (196 mg; 0.17 mmol). After stirring at room temperature for 20 minutes the reaction was placed in an oil bath at 155° C. for 2 hours. The reaction was allowed to cool to room temperature and then poured into chloroform (300 mL). A precipitate formed that was filtered and triturated with hexanes to yield an off white solid (60% yield).

Step 2: Prepared according to general procedure described for compound 310 using 2-amino-5-cyanopyrazine. (30% yield). ¹H NMR (400 MHz, d6-DMSO) δ8.89 (s, 1H), 8.79 (s, 1H), 8.05(s, 1H), 6.91 (d, 1H), 6.80 (d, 1H), 3.85 (s, 3H), 2.22 (s, 3H). LRMS (ESI, Positive) m/e 283.91 (M+1).

Compound 329

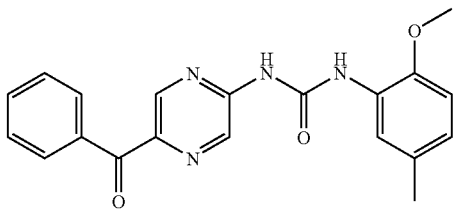

1-(5-Benzoyl-pyrazin-2-yl)-3-(2-methoxy-5-methyl-phenyl)-urea

Step 1: 5-Benzoyl-pyrazine-2-carboxylic acid. To a stirred, cooled (0° C.) solution of 2-pyrazine carboxylic acid (3.0 g, 24.2 mmol) and benzaldehyde (7.4 mL; 73 mmol) in a 50% aqueous solution of sulfuric acid (40 mL) and 25 mL of acetic acid was added FeSO₄ 7 H₂O (20.3 g, 73 mmol dissolved in 50 mL of water) and t-butyl peroxide (9.2 mL; 73 mmol) simultaneously. After stirring for 1 hour, the reaction was treated with 200 mL of water. A precipitate formed which was filtered and washed with methylene chloride (3×100 mL) to yield a tan solid (36% yield).

Step 2: 1-(5-Benzoyl-pyrazin-2-yl)-3-(2-methoxy-5-methyl-phenyl)-urea. To a stirred solution of 5-Benzoyl-pyrazine-2-carboxylic acid (912 mg; 4.0 mmol) and triethylamine (584 μL; 4.2 mmol) in toluene (12 mL) was added diphenyl phosphoryl azide (860 μL; 4.0 mmol). The reaction was stirred for 30 minutes followed by the addition of t-butanol (764 μL; 8.0 mmol). The reaction was heated to 90° C. and stirred for 3 hours. The reaction was cooled to room temperature, diluted with 30 mL of ethyl acetate and washed with aqueous 10% sodium carbonate (1×30 mL), brine (30 mL), then dried (MgSO₄), and filtered. The material was purified using a biotage 40M cartridge eluting with hexane and ethyl acetate (1:1) to yield an off white solid (14% yield). ¹H NMR (400 MHz, CDCl₃) δ9.41 (s, 1H), 9.01 (s, 1H), 8.45 (s, 1H), 8.18 (s, 1H), 8.08 (d, 2H), 7.61 (t, 1H), 7.52 (t, 2H), 6.90 (d, 1H), 6.82 (d, 1H), 3.92 (s, 3H), 2.39 (s, 3H). LRMS (ESI, Positive) m/e 363.21 (M+1).

Compound 330

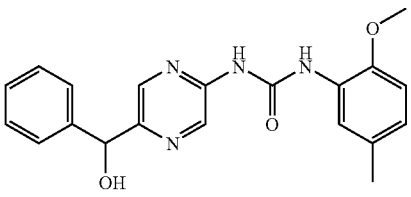

1-[5-(Hydroxy-phenyl-methyl)-pyrazin-2-yl]-3-(2-methoxy-5-methyl-phenyl)-urea

To a stirred solution of 1-(5-benzoyl-pyrazin-2-yl)-3-(2-methoxy-5-methyl-phenyl)-urea (22 mg; 0.061 mmol) in methanol (1 mL) was added sodium borohydride (10 mg; 0.3 mmol). After stirring for 12 hours, the reaction diluted with 30 mL of ethyl acetate and washed with aqueous 10% sodium carbonate (1×30 mL), brine (30 mL), then dried (MgSO₄), and filtered. The filtered material was concentrated under reduced pressure to yield a white solid (91% yield). $^1$H NMR (400 MHz, CDCl$_3$) δ8.48 (br s, 1H), 8.39 (s, 1H), 8.22 (s, 1H), 8.12 (s, 1H), 7.25-7.45 (m, 5H), 6.89 (d, 1H), 6.80 (d, 1H), 5.85 (d, 1H), 3.88 (s, 3H), 2.37 (s, 3H). LRMS (ESI, Positive) m/e 365.24 (M+1).

Compound 331

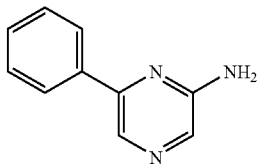

Suzuki Procedure

Step 1: To a stirred solution of 2-amino-6-chloro pyrazine (400 mg; 3.1 mmol) and phenyl boronic acid (415 mg; 3.4 mmol) in dioxane (6 mL) and ethanol (3 mL) was added cesium carbonate (2.28 g, 7.0 mmol in 3 mL of water) followed by Pd(PPh$_3$)$_4$ (185 mg; 0.16 mmol). The reaction was heated to 75° C. and stirred for 12 hours. The reaction was cooled to room temperature, diluted with 50 mL of ethyl acetate and washed with aqueous 10% sodium carbonate (1×50 mL), brine (50 mL), then dried (MgSO$_4$), and filtered. The material was purified using a biotage 40M cartridge eluting with ethyl acetate to yield an off white solid (84% yield).

Step 2: Prepared according to general procedure described for compound 310 using 2-amino-6-phenylpyrazine. (33% yield). $^1$H NMR (400 MHz, CDCl$_3$) δ11.11 (br s, 1H), 8.612 (s, 1H), 8.29 (s, 1H), 8.24 (s, 1H), 8.14 (s, 1H), 8.03 (m, 2H), 7.51 (m, 3H), 6.87 (d, 1H), 6.77 (d, 1H). LRMS (ESI, Positive) m/e 355.6 (M+1).

Compound 332

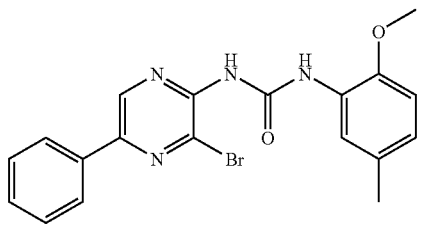

1-(3-Bromo-5-phenyl-pyrazin-2-yl)-3-(2-methoxy-5-methyl-phenyl)-urea

Step 1: 2-amino-3-bromo-5-phenylpyrazine. To a stirred solution of 3,5-dibromo-2-aminopyrazine (200 mg; 0.79 mmol) and phenyl boronic acid (106 mg; 0.87 mmol) in dioxane (4 mL) and ethanol (2 mL) was added cesium carbonate (571 mg; 1.75 mmol in 2 mL of water) followed by Pd(PPh$_3$)$_4$ (46 mg; 0.04 mmol). The reaction was heated to 75° C. and stirred for 12 hours. The reaction was cooled to room temperature, diluted with 50 mL of ethyl acetate and washed with aqueous 10% sodium carbonate (1×50 mL), brine (50 mL), then dried (MgSO$_4$), and filtered. The material was purified using a biotage 12L cartridge eluting with hexanes and ethyl acetate (3:1) to yield an off white solid (88% yield).

Step 2: Prepared according to general procedure described for compound 310 using 2-amino-3-bromo-5-phenylpyrazine. (18% yield). $^1$H NMR (400 MHz, CDCl$_3$) δ8.36 (s, 1H), 8.09 (s, 1H), 7.63 (d, 2H), 7.59 (m, 3H), 6.85 (dd, 2H), 3.92 (s, 3H), 2.39 (s, 3H). LRMS (ESI, Positive) m/e 413.2 415.2 (M+1).

Compound 333

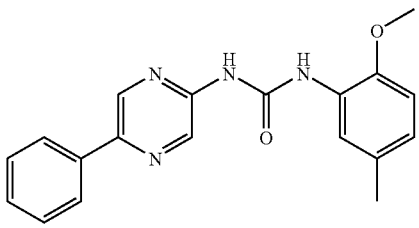

1-(2-Methoxy-5-methyl-phenyl)-3-(5-phenyl-pyrazin-2-yl)-urea

Step 1: 2-amino-5-phenylpyrazine. To a stirred solution of 3-bromo-5-phenyl-2-amino pyrazine (80 mg; 0.32 mmol), in ethyl acetate (1 mL) was added triethylamine (139 µL; 1.0 mmol) and Pd(OH)$_2$ (10 mg; 20% wt on carbon). The reaction was placed under a hydrogen atmosphere at 45 psi and shook for 6 hours. The reaction was filtered and concentrated under reduced pressure. The product was purified using a biotage 12L eluting with ethyl acetate to yield an off white solid (75% yield).

Step 2: Prepared according to general procedure described for compound 310 using 2-amino-5-phenylpyrazine. (25% yield). $^1$H NMR (400 MHz, CDCl$_3$) δ8.36 (s, 1H), 8.22 (s, 1H), 8.18 (s, 1H), 7.63 (m, 2H), 7.59 (m, 3H), 7.28 (br s, 1H), 6.82 (m, 2H), 3.92 (s, 3H), 2.33 (s, 3H). LRMS (ESI, Positive) m/e 335.21 (M+1).

Compound 334

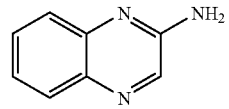

Quinoxalin-2-ylamine

Step 1: To 2-chloroquinoxaline (1.0 g, 6 mmol) was added ammonia in methanol (8 mL of a 2M solution). The reaction was sealed in a vial, heated to 80° C., and stirred for 12 hours. The reaction was cooled to room temperature and concentrated under reduced pressure. The residue was taken up in methylene chloride and filtered. Hexane was added until a precipitate formed which was filtered and found to be the desired product (5% yield).

Step 2: Prepared according to general procedure described for compound 310 using Quinoxalin-2-ylamine. (26% yield). $^1$H NMR (400 MHz, D$_6$-DMSO) δ11.63 (br s, 1H), 10.59 (br s, 1H), 8.80 (s, 1 H), 8.15 (s, 1H), 7.97 (d, 1H), 7.81 (m, 2H), 7.64 (m, 1H), 6.98 (d, 1H), 6.82 d, 1H), 3.97 (s, 3H), 2.23 (s, 3H). LRMS (ESI, Positive) m/e 309.4 (M+1).

Compound 335

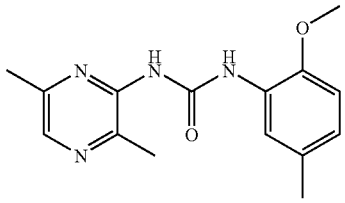

1-(3,6-Dimethyl-pyrazin-2-yl)-3-(2-methoxy-5-methyl-phenyl)-urea

Step 1: 2-Azido-3,6-dimethylpyrazine. To a stirred solution of 2-chloro-3,5-dimethyl pyrazine (1.0 mL; 8.3 mmol) in dimethylformamide (10 ml,) was added sodium azide (539 mg; 8.3 mmol). The reaction was heated to 100° C. and stirred for 12 hours. The reaction was cooled to room temperature, diluted with 50 mL of ethyl acetate and washed with aqueous 10% sodium carbonate (1×50 mL), brine (50 mL), then dried (MgSO$_4$), and filtered. The material was purified using a biotage 12L cartridge eluting with hexanes and ethyl acetate (3: 1) to yield an off white solid (42% yield).

Step 2: 2-Amino-3,6-dimethylpyrazine. To a stirred solution of 3-azido-2,5-dimethyl pyrazine (100 mg; 0.66 mmol) in methanol (800 µL) was added 12N HCl (100 µL) and tin chloride dihydrate (149 mg; 0.66 mmol). The reaction was heated to 60° C. and stirred for 12 hours. The reaction was cooled to room temperature, diluted with 50 mL of ethyl acetate and washed with aqueous 10% sodium carbonate (1×50 mL), brine (50 mL), then dried (MgSO$_4$), and filtered. The material was purified using a biotage 12i cartridge eluting with ethyl acetate to yield an off white solid (38% yield).

Step 3: Prepared according to general procedure described for compound 310 using 2-Amino-3,6-dimethylpyrazine. (15% yield). $^1$H NMR (400 MHz, CDCl$_3$) δ8.22 (br s, 1H), 8.01 (s, 1H), 6.82 (m, 2H), 3.92 (s, 3H), 2.59 (s, 3H), 2.55 (s, 3H), 2.38 (s, 3H). LRMS (ESI, Positive) m/e 287.20 (M+1).

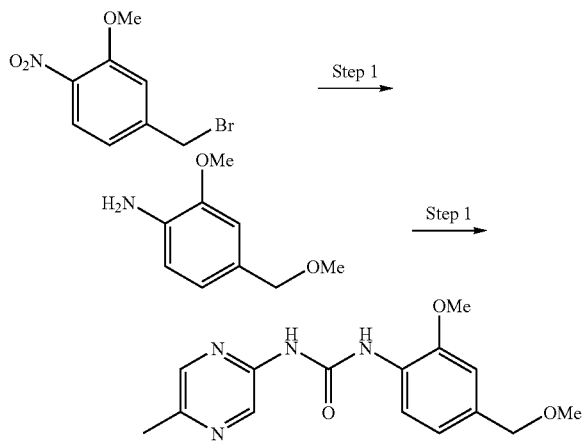

Step 1: 2-Methoxy4-methoxymethyl-1-nitro-benzene To a 250 mL round bottomed flask containing 5.4 g (39 mmol) of 3-methoxy-4-nitrobenzyl alcohol in 30 mL THF and 30 mL DMF was added, 38 g (117 mmol, 3 eq.) of finely powdered cesium carbonate followed by 24 mL (390 mmol, 10 eq.) iodomethane. The mixture was stirred at room temperature for 18 h, and was then partitioned between 100 mL water and 100 mL diethyl ether. The aqueous phase was extracted with ether (2×100 mL), and the combined organic extracts were washed with brine (2×50 mL), dried over MgSO$_4$, filtered through a short plug of silica, and concentrated. The residue was purified by flash chromatography, eluting with 1:1 EtOAc-Hexane, to give 6.76 g (88%) of the methyl ether as a yellow oil. $^1$H NMR (400 MHz CDCl$_3$): δ7.84, (d, J=8.2 Hz, 1H) 7.10 (s, 1H), 6.94 (d, J=9.1 Hz, 1H), 4.51 (s, 2H), 3.98 (s, 3H), 3.44 (s, 3H).

Step 2: 2-Methoxy-4-methoxymethyl-phenylamine. In a 250 mL Parr apparatus, 2.1 g (10.6 mmol) of 2-methoxy-4-methoxymethyl-1-nitro-benzene, in 40 mL of ethanol was hydrogenated at 2 atm over 300 mg of 10% Pd on carbon for 2.5 h. The catalyst was removed by filtration through a glass fiber filter and the filtrate was concentrated to give 1.61 g (91%) of product as a light yellow oil. $^1$H NMR (400 MHz, CDCl$_3$): δ6.80 (s, 1H), 6.74 (d, J=7.8 Hz, 1H), 6.67 (d, J=7.8 Hz), 4.35 (s, 2H), 3.86 (s, 3H), 3.78 (br d, 2H), 3.35 (s, 3H). MS ESI-pos, M+1=168.1

Step 3: 1-(2-Methoxy-4-methoxymethyl-phenyl)-3-(5-methyl-pyrazin-2-yl)-urea. General diphenylphosphoryl azide coupling method: To a solution of 5-methylpyrazine-2-carboxylic acid (365 mg, 2.64 mmol) in 20 mL of anhydrous toluene, was added, diisopropylethylamine (483 µL, 2.77 mmol) and the mixture was stirred at room temperature until the solid dissolved. Then diphenylphosphoryl azide was added and the solution was heated to 90° C. After 20 minutes N$_2$ evolution had subsided, and the caramel colored reaction mixture was cooled to 60° C. at 60° C., the mixture was cooled to room temperature and diluted with 20 mL of 5% NH$_4$OH, and extracted with EtOAc (3×50 mL). The combined extracts were washed with 20 mL water and 20 mL brine then dried over MgSO$_4$, filtered and concentrated. The brown residue was purified by flash chromatography (eluting with 5% MeOH in CH$_2$Cl$_2$) to give 219 mg (27%) of the desired product. $^1$H NMR (400 MHz, CDCl$_3$): δ11.36 (s, 1H), 9.47, (s, 1H) 8.40, (s, 1H), 8.31 (s, 1H), 8.08 (s, 1H), 6.95 (s, 1H), 6.94 (d, J=7.8 Hz, 1H), 4.45 (s, 2H), 3.97 (s, 3H), 3.39 (s, 3H), 2.52 (s, 3H). MS ESI-pos M+1=303.2

Compound 337

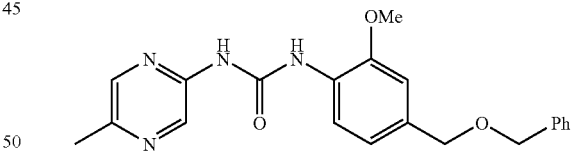

1-(4-Benzyloxymethyl-2-methoxy-phenyl)-3-(5-methyl-pyrazin-2-yl)-urea

Step 1: 4-Benzyloxymethyl-2-methoxy-1-nitro-benzene. To a stirred suspension of finely powdered cesium carbonate (8.0 g, 24.5 mmol) was added 3-methoxy-4-nitrobenzyl alcohol (1.5 g, 8.18 mmol), followed by benzyl bromide, (2 mL, 16.4 mmol). After stirring at room temperature for 18 h, the suspension diluted with 100 mL diethyl ether, and washed with 3×50 mL water, then 50 mL brine. The organic phase was dried over MgSO$_4$, filtered through a plug of silica, and concentrated. The resulting orange oil was purified by flash chromatography, eluting with 2:1 hexane-EtOAc, to give 1.87 g, (84%) of the benzyl ether. $^1$H NMR (400 MHz, CDCl$_3$): δ7.85 (d, J=8.2 Hz, 1H) 7.3-7.4 (m, 5H), 7.26 (s, 1H), 6.97 (d, J=8.2 Hz, 1H), 4.61 (s, 2H), 4.59(s, 2H), 3.96 (s, 3H).

Step 2: 4-Benzyloxymethyl-2-methoxy-phenylamine. A solution of 4-nitro-3-methoxybenzylbenzyl ether (2.2 g, 8.1 mmol) and ammonium acetate (2.46 g, 32 mmol, 4 eq.) in 30 mL MeOH was stirred at 0° C. and 1.3 g (20 mmol, 2.5 eq.) of zinc dust was added in several portions. After 1 h, the reaction mixture was partitioned between 40 mL water and 40 mL ethyl acetate. The organic phase was dried over MgSO$_4$ and concentrated. The residue was used directly in next step without further purification. $^1$H NMR (400 MHz, CDCl$_3$): δ7.35 (m, 5H), 6.82 (s, 1H), 6.77 (d, J=6.3 Hz, 1H). 6.67 (d, J=7.8 Hz, 1H), 4.51 (s, 2H), 4.45 (s, 2H), 3.85 (s, 3H), 3.79 (s, 2H). MS ESI-pos, M+1=244.2.

Step 3: 1-(4-Benzyloxymethyl-2-methoxy-phenyl)-3-(5-methyl-pyrazin-2-yl)-urea. Prepared according to the general diphenylphosphoryl azide coupling method described above for compound 336. $^1$H NMR (400 MHz, CDCl$_3$): δ11.36, (s, 1H), 9.23 (s, 1H), 8.39 (s, 1H), 8.32 (d, J=7.8 Hz, 1H), 8.09 (s, 1H), 7.38 (m, 5H), 6.97, (s, 2H), 4.56 (s, 4H), 3.96 (s, 3H), 2.53 (s, 3H).). MS APCI-pos, M+1=379.3

Compound 338 as a yellow oil. $^1$H NMR (400 MHz, CDCl$_3$): δ7.84 (d, J=8.61 Hz, 1H), 7.34 (m, 5H), 7.16,(s, 1H), 6.99 (d,J=8.61 Hz, 1H), 3.97 (s, 3H), 3.86 (s, 2H), 3.81 (s, 2H).

Step 3: Benzyl-(3-methoxy-4-nitro-benzyl)-carbamic acid tert-butyl ester. To a 150 mL round bottomed flask containing 0.92 g (3.4 mmol, 1 eq.) of N-benzyl-N-(3-methoxy-4-nitro-benzyl)-amine in 2 mL dichloromethane was added Boc anhydride (0.74 g, 3.4 mmol, 1 eq.) then stirred at room temperature for 18 h. The reaction mixture was then partitioned between 40 mL water and 40 mL ethyl acetate. The organic phase was dried over MgSO$_4$ and concentrated. No further purification was necessary. $^1$H NMR (400 MHz, CDCl$_3$): δ $^1$H NMR (400 MHz, CDCl$_3$): δ7.81 (d, J=8.61 Hz, 1H), 7.2-7.3 (m, 6H), 6.93 (m, 1H), 6.82 (s, 1H), 4.39 (m, 4H), 3.88 (s, 3H), 1.53 (s, 9H).

Steps 4-6: 1-{4-[(Benzyl-methyl-amino)-methyl]-2-methoxy-phenyl}-3-(5-methyl-pyrazin-2-yl)-urea. Benzyl-(3-methoxy-4-nitro-benzyl)-carbamic acid tert-butyl ester was reduced to the corresponding aniline according to the general hydrogenation procedure detailed above for compound 336. The crude aniline was used in the coupling step as follows: A solution of 5-methylpyrazine-2-carboxylic acid (34.5 mg, 0.25 mmol) and added triethylamine (28 mg,

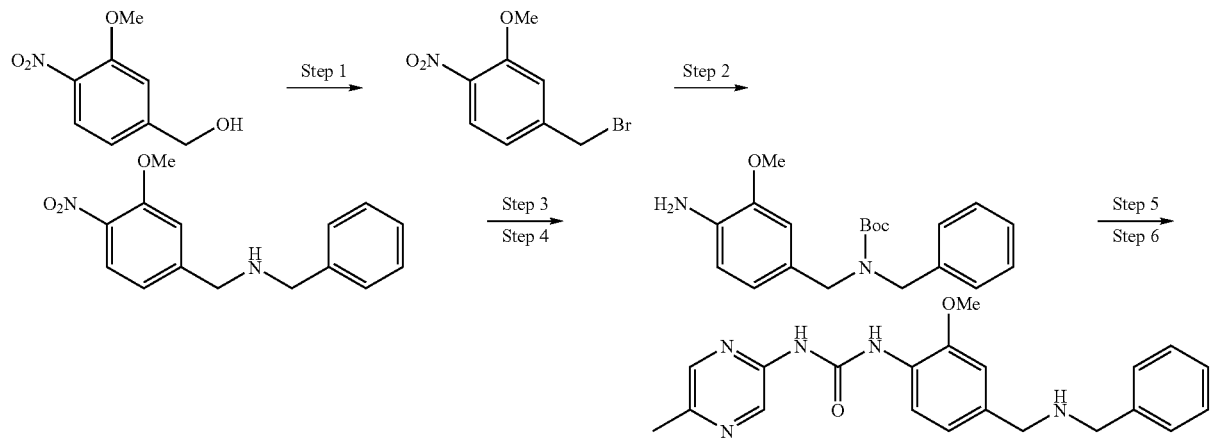

1-{4-[(Benzyl-methyl-amino)-methyl]-2-methoxy-phenyl}-3-(5-methyl-pyrazin-2-yl)-urea Step 1: 3-Methoxy-4-nitro-benzyl bromide. To a 250 mL round bottomed flask containing 10 g (54.6 mmol) of 4-nitro-3-methoxybenzyl alcohol in 30 mL THF was added, 36 g (109 mmol, 2 eq ) of carbon tetrabromide followed by 15.9 g (60 mmol, 1.1 eq.) triphenylphosphine at 0° C. The mixture was stirred at 0° C. for 3 hours. Upon removal of the solvent, the residue was purified by flash chromatography, eluting with 10:90 EtOAc-Hexane, to give 11 g (82%) of the product as a yellow solid. $^1$H NMR (400 MHz, CDCl$_3$): δ7.86 (s, 1H), 7.84 (m, 1H), 7.12 (s, 1H), 7.07 (m, 1H), 4.47 (s, 2H), 4.00 (s, 3H).

Step 2: N-Benzyl-N-(3-methoxy-4-nitro-benzyl)-amine. To a 150 mL round bottomed flask containing 1.97 g (8.0 mmol) of 3-methoxy-4-nitro-benzyl bromide in 20 mL THF was added, 2.4 g (24 mmol, 3eq.) of triethylamine followed by 2.5 g (24 mmol, 3 eq.) of benzylamine. The mixture was stirred at room temperature for 2 h, and was then partitioned between 50 mL ethyl acetate and brine. The organic phase was dried over MgSO$_4$ and concentrated. The residue was purified by flash chromatography, eluting with 1-4% MeOH in dichloromethane to give 1.6 g (73%) of the benzyl amine 0.275 mmol) in 5 mL of anhydrous toluene was stirred at room temperature until the solid dissolved. Diphenylphosphoryl azide (62 mg, 0.225 mmol) was added and the solution heated to 90° C. for 20 min. The reaction pot was then transferred to a 60° C. oil bath, and the aniline (0.25 mmol) was added as a solution in 2 mL toluene. After stirring for 4.5 hr at 60° C., the mixture was cooled to room temperature, diluted with EtOAc, washed with sat'd NaHCO$_3$, then brine. The organic phase was dried over MgSO$_4$, filtered and concentrated. The resulting residue was purified by preparative TLC, eluting with 5% MeOH in CH$_2$Cl$_2$, to give the desired urea. The Boc group was removed by treatment of the Boc protected amine in 15 mL of CH$_2$Cl$_2$ with 3 mL TFA and stirring at room temperature for 3h. The mixture was diluted with EtOAc (50 mL), washed with 20 mL of sat'd NaHCO$_3$ followed by 20 mL of brine. The organic phase was then dried over MgSO$_4$, filtered and concentrated to give the free amine $^1$H NMR (400 MHz, d6-DMSO): δ11.35 (s, 1H), 9.68 (s, 1H), 8.41 (s, 1H), 8.28 (d, J=8.21 Hz, 1H), 8.06 (s, 1H, 7.36 (s, 6H), 6.96 (s, 1H), 6.94 (d, J=8.21 Hz, 1H), 3.95 (s, 3H), 3.84 (s, 2H), 3.81 (s, 2H), 2.52 (s, 3H), 2.13 (s, 1H). MS APCI-pos, M+1=377.9

Compound 339

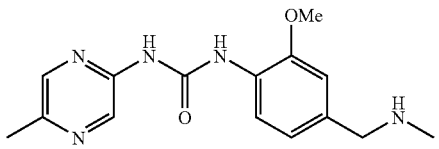

1-(2-Methoxy-4-methylaminomethyl-phenyl)-3-(5-methyl-pyrazin-2-yl)-urea

Step 1+2: (3-Methoxy-4-nitro-benzyl)-methyl-carbamic acid tert-butyl ester. In a fashion similar to that described above for the analogous benzyl derivative compound 338, 3-methoxy-4-nitro-benzyl bromide was alkylated with methylamine, and the resulting secondary amine was protected as the Boc derivative. $^1$H NMR (400 MHz, CDCl$_3$): δ7.84 (d, J=8.61 Hz, 1H), 6.98 (s, 1H), 6.87 (d, J=8.61 Hz, 1H), 4.46 (s, 2H), 3.95 (s, 7H), 2.85 (s, 3H), 1.53 (s, 9H).

Step 3: (4-Amino-3-methoxy-benzyl)-methyl-carbamic acid tert-butyl ester. In a 250 mL Parr apparatus, 0.98 g (3.5 mmol) of (3-methoxy-4-nitro-benzyl)-methyl-carbamic acid tert-butyl ester in 40 mL of ethanol was hydrogenated at 2 atm over 300 mg of 10% Pd on carbon for 15 minutes. The catalyst was removed by filtration through a glass fiber filter and the filtrate was concentrated to give a crude product as light yellow oil. $^1$H NMR (400 MHz, CDCl$_3$): δ6.69 (m, 3H), 3.95 (s, 2H), 3.84 (s, 3H), 2.8 (m, 2H), 2.75 (s, 3H), 1.51 (s, 9H).

Step 4+5: 1-(2-Methoxy-4-methylaminomethyl-phenyl)-3-(5-methyl-pyrazin-2-yl)-urea. A solution of (4-amino-3-methoxy-benzyl)-methyl-carbamic acid tert-butyl ester was converted to the urea according to the general diphenylphosphoryl azide coupling method detailed for compound 336. The Boc group was removed as described for above for compound 338. $^1$H NMR (400 MHz, d6-DMSO): δ9.91 (s, 2H), 8.78 (s, 1H), 8.21 (s, 1H), 8.07 (d, J=8.61 Hz, 1H), 7.01 (s, 1H), 6.85 (d, J=8.61 Hz, 1H), 3.89 (s, 3H), 3.59 (s, 1H), 2.42 (s, 3H), 2.26 (s, 3H). MS APCI-Pos, M+1=301.8.

Compound 340

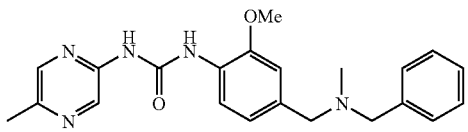

1-{4-[(Benzyl-methyl-amino)-methyl]-2-methoxy-phenyl}-3-(5-methyl-pyrazin-2-yl)-urea Step 1: N-Benzyl-N-(3-methoxy-4-nitro-benzyl)-methyl-amine. A solution of N-methyl-benzyl amine was alkylated with 3-methoxy-4-nitro-benzyl bromide as described above for compound 338. $^1$H NMR (400 MHz, CDCl$_3$): δ7.83 (d, J=8.6 Hz, 1H), 7.35 (s, 4H), 7.26 (s, 1H), 7.17 (s, 1H), 7.01 (d, J=7.04 Hz, 1H), 3.97 (s, 3H), 3.55 (s, 4H), 2.22 (s, 3H).

Step 2: 4-[(Benzyl-methyl-amino)-methyl]-2-methoxy-phenylamine. Nickel boride Reduction General Method: To a stirred solution of nickel chloride hexahydrate (820 mg, 3.45 mmol) in 12 mL EtOH and 3 mL THF, at 0° C., NaBH$_4$ (130 mg, 3.45 mmol) was added. The resulting black suspension was stirred at 0° C. while N-benzyl-(3-methoxy-4-nitro-benzyl)-methyl-amine was added as a solution in 5 mL THF. After several minutes, 260 mg of NaBH$_4$ was added in several portions over 10 minutes, and the reaction mixture was subsequently allowed to warm to room temperature. After 2 h, TLC indicated complete conversion to a new, more polar product. At this point, 1.5 mL of 5% NH$_4$OH was added and the reaction was stirred for about 10 min, until the black solids achieved a granular consistency. The reaction was filtered through a glass fiber filter, rinsing with THF. The clear colorless filtrate was concentrated to about ¼ volume, diluted with 30 mL water and extracted with EtOAc (3×30 mL). The combined extracts were washed with brine, dried over MgSO$_4$ and filtered through a short plug of silica and concentrated in vacuo to afford 575 mg (65%) of the desired product as an off-white solid. $^1$H NMR (400 MHz, CDCl$_3$): δ7.2-7.4 (m, 5H), 7.85 (s, 1H), 6.85 (s, 1H), 6.74 (d, J=8.2 Hz, 1H), 6.66 (d, J=8.2 Hz, 1H), 3.87 (s, 3H), 3.73 (br. s, 2H) 3.49 (s, 2H), 3.45 (s, 2H), 2.18 (s, 3H). MS (APCI-pos)M+1=256.9

Step 3: 1-{4-[(Benzyl-methyl-amino)-methyl]-2-methoxy-phenyl}-3-(5-methyl-pyrazin-2-yl)-urea. In a 50 mL round bottom flask, 5-methylpyrazine-2-carboxylic acid (250 mg, 1.8 mmol) and diisopropylethylamine (330 µL, 1.9 mmol) in 20 mL toluene, was stirred under a nitrogen atmosphere until the acid dissolved. Diphenylphosphoryl azide (523 mg, 1.9 mmol) was added and the solution was heated to 90° C. After 20 minutes, nitrogen evolution had subsided, and the solution had darkened to a caramel color. The reaction was cooled to 65° C., and 4-[(benzyl-methyl-amino)-methyl]-2-methoxy-phenylamine (486 mg, 1.9 mmol) was added as a solution in 5 mL toluene. The reaction was allowed to stir at 65° C. for 6 h, and was then cooled to room temperature, diluted with 30 mL EtOAc, and washed with 15 mL 5% NH$_4$OH. The aqueous phase was extracted with EtOAc (2×20 mL) and the combined organics were washed with 30 mL brine, dried over MgSO$_4$, filtered, and concentrated. The resulting residue was purified by flash chromatography to give 285 mg (40%) of the desired product, which was further purified by trituration with diethyl ether. Mp=142-143° C. $^1$H NMR (400 MHz, CDCl$_3$): δ11.33 (s, 1H), 9.51 (s, 1H), 8.41 (s, 1H), 8.27 (d, J=8.61 Hz, 1H), 8.08 (s, 1H), 7.2-7.4 (m, 5H), 6.96 (d, J=7.83 Hz, 1H) 3.97 (s, 3H), 3.53 (s, 4H), 2.53 (s, 3H), 2.22 (s, 1H). $^{13}$C NMR (400 MHz, CDCl$_3$): δ153.70, 149.03, 147.48, 147.4, 145.99, 138.73, 137.38, 134.81, 129.19, 128.42, 127.16, 121.89, 119.81, 111.05, 104.49, 94.98, 87.22, 61.81, 56.37, 42.5. MS (APCI-pos)M+1=392.0.

Compound 341

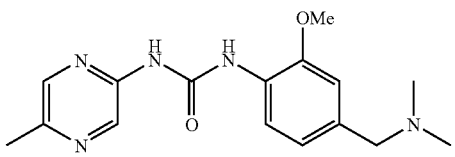

1-(4-Dimethylaminomethyl-2-methoxy-phenyl)-3-(5-methyl-pyrazin-2-yl)-urea

Step 1: (3-Methoxy-4-nitro-benzyl)-dimethyl-amine According to the method described above for compound 338, 3-methoxy-4-nitro-benzyl bromide was treated with dimethyl amine to give the desired product. $^1$H NMR (400 MHz, CDCl$_3$): δ7.86 (d, J=7.8 Hz, 1H), 7.3 (s, 1H), 6.98 (d, J=8.6 Hz, 1H), 4.01 (s, 3H), 3.5 (s, 2H), 2.3 (s, 6H).

Step 2: 4-Dimethylaminomethyl-2-methoxy-phenylamine According to the nickel-boride method described for compound 340 above,(3-methoxy-4-nitrobenzyl)-dimethyl-amine, was reduced to the corresponding aniline and was used in the next step without characterization.

Step 3: 1-(4-Dimethylaminomethyl-2-methoxy-phenyl)-3-(5-methyl-pyrazin-2-yl)-urea. According to the diphenylphosphoryl azide method described above for compound 336, 4-dimethylaminomethyl-2-methoxy-phenylamine was converted to the (5-methyl-pyrazin-2-yl)-urea. The crude product was purified by preparative TLC, eluting with 5% MeOH in CH$_2$Cl$_2$. $^1$H NMR (400 MHz, d6-DMSO): δ11.21 (s, 1H), 8.95 (s, 1H), 8.39 (s, 1H), 8.21 (d, J=7.83 Hz, 1H), 8.04 (s, 1H), 7.01 (s, 1H), 6.89 (d, J=7.83 Hz, 1H), 3.98 (s, 3H), 3.92 (s, 2H), 2.26 (s, 3H), 2.24 (s, 6H). MS APCI-Pos, M+1=316.0.

Compound 342

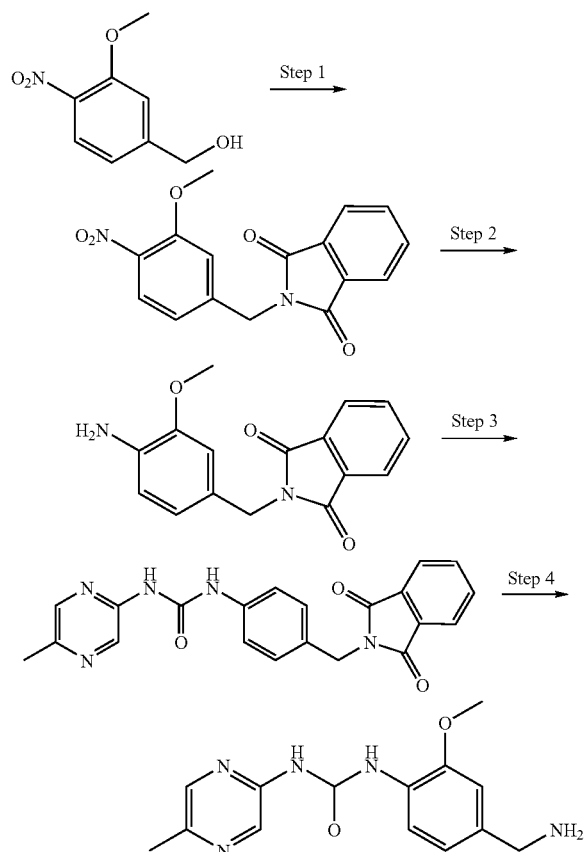

1-(4-Aminomethyl-2-methoxy-phenyl)-3-(5-methyl-pyrazin-2-yl)-urea

Step 1: 2-(3-Methoxy-4-nitro-benzyl)-isoindole-1,3-dione. To a 250 mL round bottomed flask containing 10 g (55 mmol) of 4-nitro-3-methoxybenzyl alcohol in 150 mL THF was added, diethylazodiacarboxylate (8.03 g, 54.6 mmol, 1 eq.) and triphenylphosphine (15.0 g, 57.3 mmol) followed by 11.6 g of phthalimide (57.3 mmol) at 0° C. Reaction was then allowed to gradually warm to room temperature over night. A white precipitate formed and was collected by suction filtration. Recrystallization from acetonitrile gave 13.8 g (81%) of the desired product. $^1$H NMR (400 MHz, d6-DMSO): δ7.79 (m, 5H), 7.19 (s, 1H), 7.08 (d, J=8.80 Hz, 1H), 4.91 (s, 2H), 3.87 (s, 3H).

Step 2: 2-(4-Amino-3-methoxy-benzyl)-isoindole-1,3-dione. In a 500 mL Parr vessel, a partially dissolved suspension of 2-(3-methoxy-4-nitro-benzyl)-isoidole-1,3-dione (1.50 g, 4.80 mmol) in 100 mL EtOH and 30 mL THF was hydrogenated over 250 mg 10% Pd-C at 2.5 atm for 1 h. The catalyst was removed by filtration through a glass fiber filter, and the clear light yellow filtrate was concentrated in vacuo. The product was washed with 30 mL of diethyl ether and collected by suction filtration to give 1.28 g (95%) of the aniline as fine, light green needles. $^1$H NMR (400 MHz, CDCl$_3$): δ7.82 (m, 2H), 7.81 (m, 2H), 6.93 (s, 1H), 6.9 (d, J=7.8 Hz, 1H), 6.63 (d, J=7.8 Hz, 1H), 4.74 (s, 2H), 3.84 (s, 3H).

Step 3: Acyl Azide coupling General Method 1-[4-(1,3-Dioxo-1,3-dihydro-isoindol-2-ylmethyl)-2-methoxy-phenyl]-3-(5-methyl-pyrazin-2-yl)-urea. In a 50 mL round bottom flask, a solution of 5-methyl-pyrazine-2-carbonyl azide (510 mg, 3.15 mmol) in 15 mL of anhydrous toluene was stirred under a nitrogen atmosphere. The reaction flask was immersed in a 90° C. oil bath, and as the internal temperature approached 90° C., N$_2$ release was evident and the solution started to darken. After 20 min, effervescence had subsided, and the solution had darkened to a caramel color. The reaction flask was moved to a 65° C. bath, and 2-(4-amino-3-methoxy-benzyl)-isoindole-1,3-dione (884 mg, 3.15 mmol) suspended in toluene (5 mL) was added. The reaction was stirred at 65° C. for 6 h, then cooled to room temperature. The product precipitated from solution after cooling to room temperature, and was collected by suction filtration.

In cases where the product does not precipitate from the reaction mixture, the following work-up is applied: After cooling to room temperature, the brown solution is diluted with 5% aq. NH$_4$OH and the extracted with EtOAc (3×). The combined extracts are washed with brine, dried over MgSO$_4$, filtered and concentrated. The residue is then purified by flash chromatography in an appropriate solvent system.

Step 4: 1-(4-Aminomethyl-2-methoxy-phenyl)-3-(5-methyl-pyrazin-2-yl)-urea In a 100 mL round bottom flask, a suspension of 1-[4-(1,3-dioxo-1,3-dihydro-isoindol-2-ylmethyl)-2-methoxy-phenyl]-3(5-methyl-pyrazin-2-yl)-urea (620 mg, 1.48 mmol) in 22 mL of EtOH, under a nitrogen atmosphere, was warmed, with stirring, to 70° C. Hydrazine monohydrate (1.4 mL) was added, and the reaction was stirred at 70° C. . After 10 minutes, the reaction had become a completely homogenous caramel colored solution. After several minutes more, product started to precipitate from the solution. After 20 min, the reaction was cooled to room temperature, and the white solid product was collected by suction filtration. The crude product, which contained some phthalhydrazide by-product, was taken up in 80 mL of EtOAc, and washed with water (3×20 mL). The washings were back extracted with 30 mL EtOAc, and the combined organics were washed with brine, then dried over MgSO$_4$, filtered, and concentrated in vacuo to afford 400 mg, (94%) of the desired amine. Mp=168-169° C. $^1$H NMR (400 MHz, d6-DMSO): δ9.88 (br.s, 2H), 8.78 (s, 1H), 8.21 (s, 1H), 8.05 (d, J=8.2 Hz, 1H), 7.05 (s, 1H), 6.85 (d, J=8.1 Hz, 1H), 3.89 (s, 3H), 3.68 (s, 2H), 2.42 (s, 3H) 1.80 (br.s, 2H, NH$_2$). MS (APCI-pos)M−17 (—NH3)=270.1 apci-neg M−1=285.8.

Alkyl Derivatives of Compound 342

Compound 343

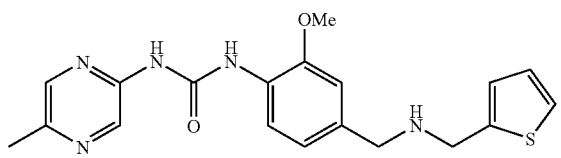

A solution of 1-(4-aminomethyl-2-methoxy-phenyl)-3-(5-methyl-pyrazin-2-yl)-urea (0.25 mmol, 1.0 eq.) and 1 mL trimethylorthoformate in 4 mL MeOH was stirred at room temperature, then thiophene-2-carboxaldehyde (2.5 mmol, 10 eq.) was added and the mixture was heated at 80° C. After 18 h the reaction was cooled to room temperature and was concentrated in vacuo. The resulting imine was taken up in 5 mL of anhydrous MeOH and stirred at 0° C. Sodium borohydride (0.75 mmol, 3 eq.) was added, and the reaction was stirred at 0° C. for 30 minutes and was then diluted with 2 mL of water and partitioned between 50 mL EtOAc and 30 mL sat. NaHCO$_3$. The organic phase was washed with brine, dried over MgSO$_4$, filtered and concentrated. If needed, the product was purified by flash chromatography, eluting with an appropriate MeOH—CH$_2$Cl$_2$ mixture.

1-(2-Methoxy-4-{[(thiophen-2-ylmethyl)-amino]-methyl}-phenyl)-3-(5-methyl-pyrazin-2-yl)-urea $^1$H NMR (400 MHz, d6-DMSO): δ10.01 (s, 2H), 8.79 (s, 1H), 8.23 (s, 1H), 8.17 (d, J=8.61 Hz, 1H), 7.59 (d, J=6.26 Hz, 1H), 7.33 (s, 1H), 7.15 (m, 2H), 7.05 (s, 1H), 6.97 (d, J=8.61 Hz, 1H), 4.02 (s, 2H), 3.91 (s, 3H), 3.88 (s, 1H), 3.78 (s, 1H), 2.43 (s, 3H). MS APCI-Pos no detectable molecular ion.

Compound 344

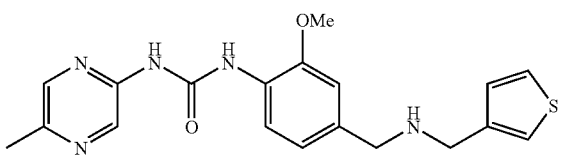

Prepared according to the general procedure described for compound 343 using thiophene-3-carboxaldehyde.

1-(2-Methoxy-4-{[(thiophen-3-ylmethyl)-amino]-methyl}-phenyl)-3-(5-methyl-pyrazin-2-yl)-urea $^1$H NMR (400 MHz, d6-DMSO): δ9.92 (s, 2H), 8.78 (s, 1H), 8.21 (s, 1H), 8.07 (d, J=7.81 Hz, 1H), 7.47 (s, 1H), 7.3 (s, 1H), 7.11 (d, J=4.88 Hz, 1H), 7.04 (s, 1H), 6.87 (d, J=7.81 Hz 1H), 3.9 (s, 3H), 3.67 (s, 2H), 3.65 (s, 2H), 2.42 (s, 3H). MS APCI-Neg, M−1=382.0.

Compound 345

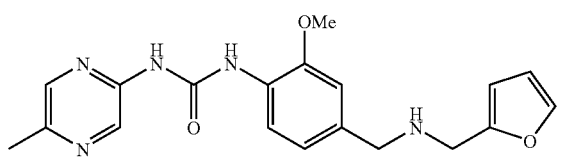

Prepared according to the general procedure described for compound 343 using furfural.

1-(4-{[(Furan-2-ylmethyl)-amino]-methyl}-2-methoxy-phenyl)-3-(5-methyl-pyrazin-2-yl)-urea $^1$H NMR (400 MHz, MeOD): δ8.57 (s, 1H), 8.2 (s, 1H), 8.1 (d, J=8.61 Hz, 1H), 7.46 (s, 1H), 7.03 (s, 1H), 6.88 (d, J=8.61 Hz, 1H), 6.36 (s, 1H), 6.27 (s, 1H), 3.96 (s, 3H), 3.74 (s, 2H), 3.71 (s, 2H), 2.48 (s, 3H). MS APCI-Neg, M−1=366.0.

Compound 346

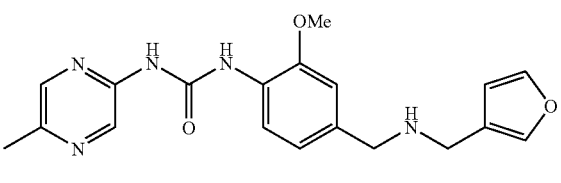

Prepared according to the general procedure described for compound 343 using furan-3-carboxaldehyde.

1-(4-{[(Furan-3-ylmethyl)-amino]-methyl}-2-methoxy-phenyl)-3-(5-methyl-pyrazin-2-yl)-urea $^1$H NMR (400 MHz, MeOD): δ8.58 (s, 1H), 8.21 (s, 1H), 8.13 (d, J=7.83 Hz, 1H), 7.49 (s, 1H), 7.05 (s, 1H), 6.91 (d, J=7.04 Hz, 1H), 6.5 (s, 1H), 3.97 (s, 3H), 3.78 (s, 2H), 3.69 (s, 2H), 2.49 (s, 3H). MS APCI-Neg, M−1=366.0

Compound 347

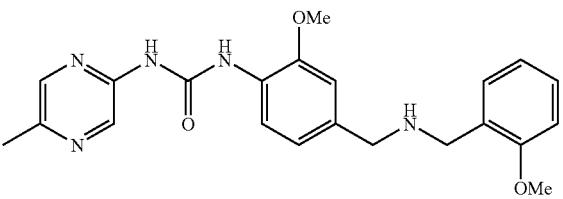

Prepared according to the general procedure described for compound 343 using 2-methoxybenzaldehyde.

1-{2-Methoxy-4-[(2-methoxy-benzylamino)-methyl]-phenyl}-3-(5-methyl-pyrazin-2-yl)-urea $^1$H NMR (400 MHz, CDCl$_3$): δ11.3 (s, 1H), 9.97 (s, 1H), 8.44 (s, 1H), 8.22 (d, J=7.83 Hz, 1H), 7.98 (s, 1H), 7.28 (m, 2H), 7.06 (s, 1H), 6.88 (m, 3H), 4.G8 (s, 1H), 3.93 (s, 5H), 3.81 (s, 5H), 2.5 (s, 3H). MS APCI-Pos, M+1=407.8.

Compound 348

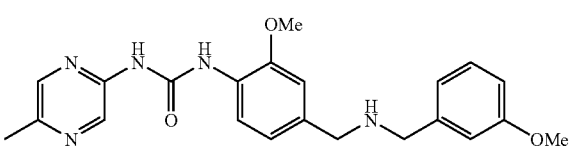

Prepared according to the general procedure described for compound 343 using 3-methoxybenzaldehyde.

1-{2-Methoxy-4-[(3-methoxy-benzylamino)-methyl]-phenyl}-3-(5-methyl-pyrazin-2-yl)-urea $^1$H NMR (400 MHz, d6-DMSO): δ8.57 (s, 1H), 8.20 (s, 1H), 8.11 (d, J=8.61 Hz, 1H), 7.22 (t, J7.83 Hz, 1H), 7.04 (s, 1H), 6.91 (m, 3H), 6.83 (d, J=8.61 Hz, 1H), 3.96 (s, 3H), 3.79 (s, 3H), 3.75 (s, 4H), 2.48 (s, 3H). MS APCI-Neg, M−1=406.0

Compound 349

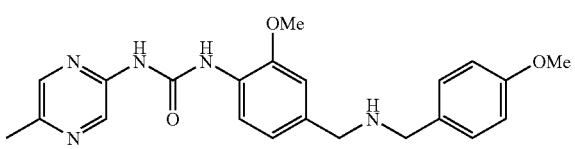

Prepared according to the general procedure described for compound 343 using 4-methoxybenzaldehyde.

1-{2-Methoxy-4-[(4-methoxy-benzylamino)-methyl]-phenyl}-3-(5-methyl-pyrazin-2-yl)-urea $^1$H NMR (400 MHz, d6-DMSO): δ9.91 (s, 2H), 8.78 (s, 1H), 8.21 (s, 1H), 8.07 (d, J=7.81 Hz, 1H), 7.25 (d, J=8.78 Hz, 2H), 7.03 (s, 1H), 6.88 (m, 2H), 3.89 (s, 3H), 3.73 (s, 3H), 3.62 (s, 2H), 3.6 (s, 2H), 2.42 (s, 3H). MS APCI-Pos, M+1=407.9.

Acyl Derivatives

Compound 350

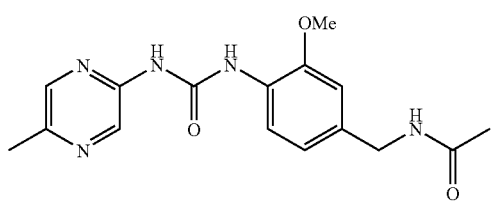

A solution of 1-(4-aminomethyl-2-methoxy-phenyl)-3-(5-methyl-pyrazin-2-yl)-urea (100 mg, 0.35 mmol) in 30 mL THF and 15 mL aqueous NaHCO$_3$, was treated with 3.7 mmol, (1.05 eq.) of acetyl chloride. The biphasic reaction mixture was vigorously stirred at room temperature and after 2h was diluted with 10 mL water and extracted with EtOAc (3×20 mL). The combined extracts were washed with brine, dried over MgSO$_4$, and filtered through a short plug of silica. The filtrate was concentrated and the resulting residue was triturated with diethyl ether. If required, further purification was accomplished by flash chromatography, eluting with an appropriate methanol-CH$_2$Cl$_2$ solvent system.

N-{3-Methoxy-4-[3-(5-methyl-pyrazin-2-yl)-ureido]-benzyl}-acetamide $^1$H NMR (400 MHz, d6-DMSO): δ9.92 (s, 2H), 8.75 (s, 1H), 8.28 (t, J=5.87 Hz, 1H), 8.19 (s, 1H), 8.07 (d, J=8.61 Hz, 1H), 6.92 (s, 1H), 6.78 (d, J=8.61 Hz, 1H), 4.19 (s, 1H), 4.18 (s, 1H), 3.87 (s, 3H), 2.4 (s, 3H), 1.85 (s, 3H). MS ESI-pos, M+1=330.2.

Compound 351

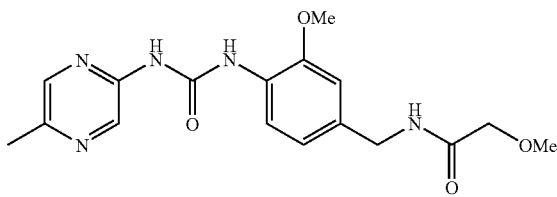

Prepared according to the general procedure described for compound 350 using methoxyacetyl chloride.

2-Methoxy-N-{3-methoxy-4-[3-(5-methyl-pyrazin-2-yl)-ureido]-benzyl}-acetamide $^1$H NMR (400 MHz, d6-DMSO): δ9.51 (s, 2H), 8.34 (s, 1H), 7.89 (t, J=6.26Hz, 1H), 7.78 (s, 1H), 7.65 (d, J=7.83 Hz, 1H), 6.54 (s, 1H), 6.38 (d, J=7.83 Hz, 1H), 4.2 (s, 1H), 4.19 (s, 1H), 3.82 (s, 3H), 3.79 (s, 2H), 3.29 (s, 3H), 2.35 (s, 3H). MS APCI-Pos, M+1=359.9.

Compound 352

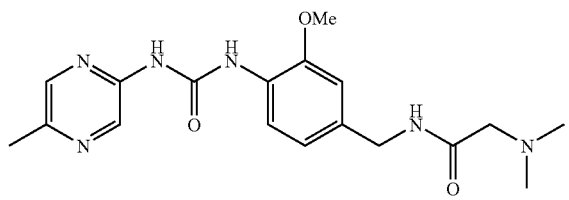

Prepared according to the general procedure described for compound 350 using dimethylamino-acetyl chloride.

2-Dimethylamino-N-{3-methoxy-4-[3-(5-methyl-pyrazin-2-yl)-ureido]-benzyl}-acetamide $^1$H NMR (400 MHz, MeOD): δ8.56 (s, 1H), 8.18 (s, 1H), 8.09 (d, J=7.83 Hz, 1H), 6.97 (s, 1H), 6.86 (d, J=7.83 Hz, 1H), 4.37 (s, 2H), 3.94 (s, 3H), 3.03 (s, 2H), 2.47 (s, 3H), 2.3 (s, 6H). MS APCI-Neg, M−1=370.9.

Compound 353

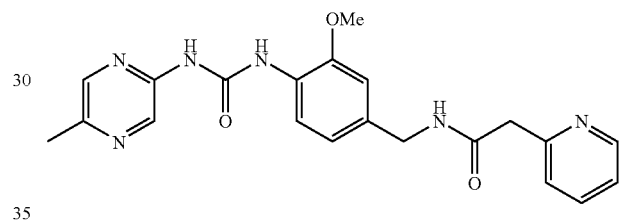

Prepared according to the general procedure described for compound 350 using 2-(2-pyridyl)-acetyl chloride.

N-{3-Methoxy4-[3-(5-methyl-pyrazin-2-yl)-ureido]-benzyl}-2-pyridin-2-yl-acetamide $^1$H NMR (400 MHz, d6-DMSO): δ9.94 (s, 2H), 8.77 (s, 1H), 8.63 (t, J=5.87 Hz, 1H), 8.49 (s, 1H), 8.44 (d, J=6.26 Hz, 1H), 8.22 (s, 1H), 8.08 (d, J=7.83 Hz, 1H), 7.7 (d, J=10.17 Hz, 1H), 7.35 (q, J=5.74 Hz, 1H), 6.87 (s, 1H), 6.79 (d, J=9.39 Hz, 1H), 4.25 (s, 1H), 4.24 (s, 1H), 3.82 (s, 3H), 3.53 (s, 2H), 2.42 (s, 3H). MS APCI-Pos M+1=407.1.

Compound 354

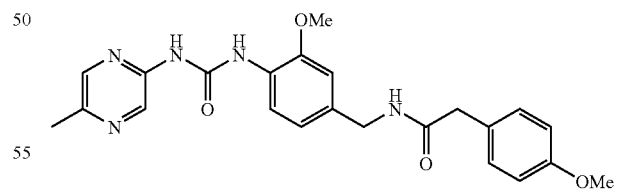

Prepared according to the general procedure described for compound 350 using 2-(4-methoxyphenyl)-acetyl chloride.

N-{3-Methoxy4-[3-(5-methyl-pyrazin-2-yl)-ureido]-benzyl}-2-(4-methoxy-phenyl)-acetamide $^1$H NMR (400 MHz, d6-DMSO): δ9.94 (s, 2H), 8.77 (s, 1H), 8.54 (t, J=4.7 Hz, 1H), 8.21 (s, 1H), 8.08 (d J=7.83 Hz, 2H), 7.89 (m, 1H), 7.22 (t, J=7.83 Hz, 1H), 6.89 (s, 3H), 4.25 (s, 1H), 4.23 (, 1H), 3.8 (s, 3H), 3.73 (s, 2H), 3.45 (s, 2H), 2.42 (s, 3H). MS (APCI-Pos) M+1=436.2.

Compound 355

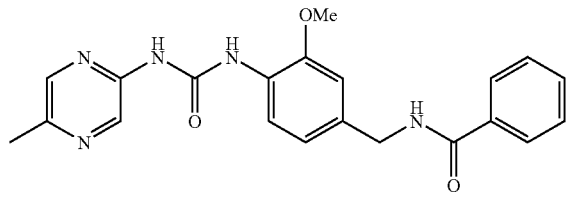

Prepared according to the general procedure described for compound 350 using benzoyl chloride.

N-{3-Methoxy-4-[3-(5-methyl-pyrazin-2-yl)-ureido]-benzyl}-benzamide $^1$H NMR (400 MHz, d6-DMSO): δ9.95 (s, 2H), 9.02 (t, J=5.48 Hz, 1H), 8.77 (s, 1H), 8.22 (s, 1H), 8.1 (d, J=8.61 Hz, 1H), 7.9 (d, J=7.83 Hz, 2H), 7.48 (m, 3H), 7.04 (s, 1H), 6.88 (d, J=10.17 Hz, 1H), 4.46 (s, 1H), 4.44 (s, 1H), 3.89 (s, 3H), 2.42 (s, 3H). MS APCI-Pos, M+1=391.9.

Compound 356

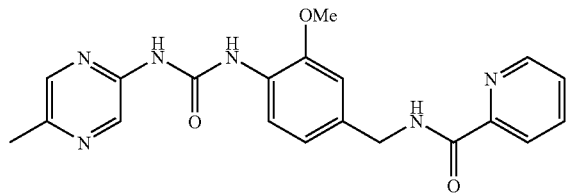

Prepared according to the general procedure described for compound 350 using pyridine-2-carbonyl chloride.

Pyridine-2-carboxylic acid 3-methoxy-4-[3-(5-methyl-pyrazin-2-yl)-ureido]-benzylamide $^1$H NMR (400 MHz, d6-DMSO): δ9.94 (s, 2H), 9.29 (t, J=6.26 Hz, 1H), 8.77 (m, 1H), 8.65 (m, 1H), 8.21 (s, 1H), 8.05 (m, 3H), 7.61 (m, 1H), 7.07 (s, 1H), 6.89 (d, J=8.61 Hz, 1H), 4.47 (s, 1H), 4.45 (s, 1H), 3.88 (s, 1H), 2.42 (s, 3H). MS APCI-Pos no detectable molecular ion.

Compound 357

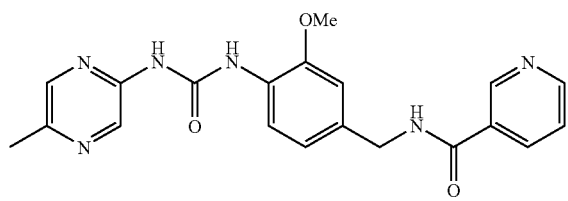

Prepared according to the general procedure described for compound 350 using nicotinoyl chloride.

N-{3-Methoxy-4-[3-(5-methyl-pyrazin-2-yl)-ureido]-benzyl}-nicotinamide $^1$H NMR (400 MHz, d6-DMSO): δ10 (s, 2H), 9.26 (t, J=5.87 Hz, 1H), 9.11 (s, 1H), 8.82 (s, 1H), 8.77 (d, J=4.7 Hz, 1H), 8.27 (s, 2H), 8.16 (d, J=7.83 Hz, 1H), 7.58 (m, 1H), 7.09 (s, 1H), 6.95 (d, J=8.61 Hz, 1H), 4.53 (s, 1H), 4.51 (s, 1H), 3.95 (s, 3H), 2.47 (s, 3H). MS APCI-Pos, M−1=397.9.

Compound 358

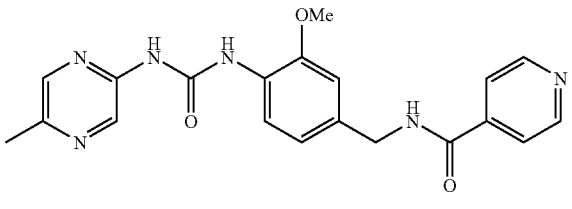

Prepared according to the general procedure described for compound 350 using isonicotinoyl chloride.

N-{3-Methoxy-4-[3-(5-methyl-pyrazin-2-yl)-ureido]-benzyl}-isonicotinamide $^1$H NMR (400 MHz, d6-DMSO): δ9.92 (s, 2H), 9.27 (t, J=5.87 Hz, 1H), 8.74 (s, 1H), 8.71 (d, J=6.3 Hz, 2H), 8.18 (s, 1H), 8.08 (d, J=8.6 Hz, 1H), 7.77 (d, J=6.3 Hz. 2H), 7 (s, 1H), 6.86 (d, J=8.6 Hz, 1H), 4.44 (s, 1H), 4.43 (s, 1H), 3.86 (s, 3H), 2.39 (s, 3H). MS APCI-pos no detectable molecular ion.

Compound 359

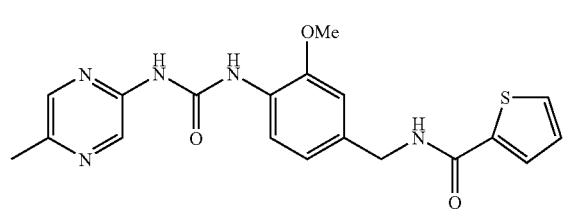

Prepared according to the general procedure described for compound 350 using thiophene-2-carbonyl chloride.

Thiophene-2-carboxylic acid 3-methoxy-4-[3-(5-methyl-pyrazin-2-yl)-ureido]-benzylamide $^1$H NMR (400 MHz, d6-DMSO): δ9.96 (s, 2H), 9.03 (t, J=6.26 Hz, 1H), 8.78 (s, 1H), 8.22 (s, 1H), 8.11 (d, J=7.83 Hz, 1H), 7.82 (d, J=4.7 Hz, 1H), 7.77 (d, J=3.91 Hz, 1H), 7.16 (d, J=3.91 Hz, 1H), 7.03 (s, 1H), 6.88 (d, J=10.17 Hz, 1H), 4.43 (s, 1H), 4.42 (s, 1H), 3.89 (s, 3H), 2.42 (s, 3H). MS APCI-pos, M−1=397.9.

Compound 360

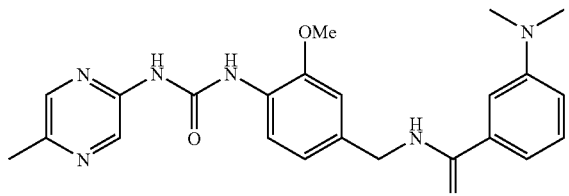

Prepared according to the general procedure described for compound 350 using 4-dimethylamino-2-carbonyl chloride.

3-Dimethylamino-N-{3-methoxy-4-[3-(5-methyl-pyrazin-2-yl)-ureido]-benzyl}-benzamide $^1$H NMR (400 MHz, d6-DMSO): δ9.94 (s, 2H), 8.9 (t, J=5.87 Hz, 1H), 8.77 (s, 1H), 8.21 (s, 1H), 8.09 (d, J=8.61 Hz, 1H), 7.26 (t, J=7.83 Hz, 1H), 7.2 (s, 2H), 7.02 (s, 1H), 6.87 (d, J=8.61 Hz, 2H), 4.44 (s, 1H), 4.42 (s, 1H), 3.88 (s, 3H), 2.93 (s, 6H), 2.42 (s, 3H). MS APCI-pos, M+1=434.9.

Compound 361

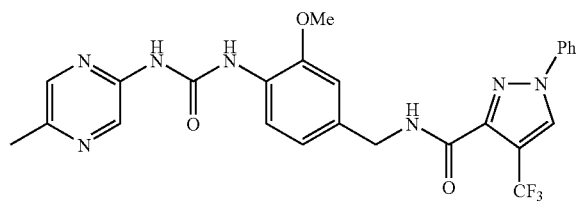

Prepared according to the general procedure described for compound 350 using 1-phenyl-4-trifluoromethyl-1H-pyrazole-3-carbonyl chloride.

1-Phenyl-4-trifluoromethyl-1H-pyrazole-3-carboxylic acid 3-methoxy-4-[3-(5-methyl-pyrazin-2-yl)-ureido]-benzylamide $^1$H NMR (400 MHz, d6-DMSO): δ9.96 (s, 2H), 9.09 (t, J=6.26 Hz, 1H), 8.78 (s, 1H), 8.22 (s, 1H), 8.19 (s, 1H), 8.12 (d, J=7.83 Hz, 1H), 7.59 (m, 6H), 7.02 (s, 1H), 6.89 (d, J=8.61 Hz, 1H), 4.43 (s, 1H), 4.42 (s, 1H), 3.9 (s, 3H), 2.42 (s, 3H). MS TIC-pos M+1=526.2.

Sulfonylated Derivatives

Compound 362

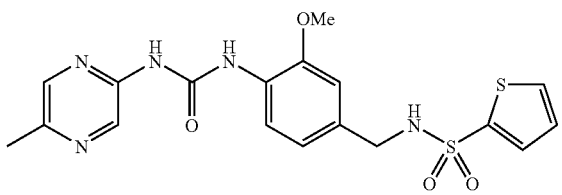

A solution of 1-(4-aminomethyl-2-methoxy-phenyl)-3-(5-methyl-pyrazin-2-yl)-urea (0.25 mmol, 1.0 eq.), 4-dimethylaminopyridine (5 mg), diisopropylethylamine (36 mg, 0.275 mmol, 1.1 eq.) in THF (5 mL) was prepared and thiophene-2-sulfonyl chloride (0.275 mmol, 1.1 eq.) was added. The mixture was stirred at room temperature for 24 h. The reaction mixture was partitioned between EtOAc (75 mL) and sat. NaHCO$_3$. After separation of the layers, the organic layer was washed with water, saturated brine, dried over MgSO$_4$, filtered and concentrated. The residue was purified by flash chromatography eluting with 5 % MeOH in dichloromethane and trituration with ether to give pure products.

Thiophene-2-sulfonic acid 3-methoxy-4-[3-(5-methyl-pyrazin-2-yl)-ureido]-benzylamide $^1$H NMR (400 MHz, d6-DMSO): δ9.96 (s, 2H), 8.77 (s, 1H), 8.33 (t, J=7.04 Hz, 1H), 8.31 (s, 1H), 8.07 (d, J=7.83 Hz, 1H), 7.93 (d, J=4.7 Hz, 1H), 7.59 (s, 1H), 7.18 (t, J=3.91 Hz, 1H), 6.9 (s, 1H), 6.8 (t, J=7.04 Hz, 1H), 4.05 (s, 1H), 4.03 (s, 1H), 3.85 (s, 3H), 2.51 (s, 3H). MS APCI-Pos, M+1=433.9.

Compound 363

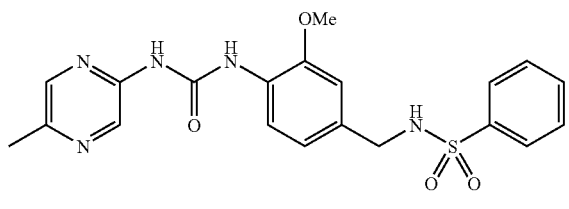

Prepared according to the general procedure described for compound 362 using benzenesulfonyl chloride.

N-{3-Methoxy-4-[3-(5-methyl-pyrazin-2-yl)-ureido]-benzyl}-benzenesulfonamide $^1$H NMR (400 MHz, d6-DMSO): δ9.95 (s, 2H), 8.77 (s, 1H), 8.21 (s, 1H), 8.13 (t, J=6.26 Hz, 1H), 8.05 (d, J=8.61 Hz, 1H), 7.81 (d, J=7.04 Hz, 2H), 7.58 (m, 3H), 6.85 (s, 1H), 6.77 (d, J=8.61 Hz, 1H), 3.96 (s, 1H), 3.95 (s, 1H), 3.81 (s, 3H), 2.42 (s, 3H). MS APCI-Pos, M+1=428.2.

Compound 364

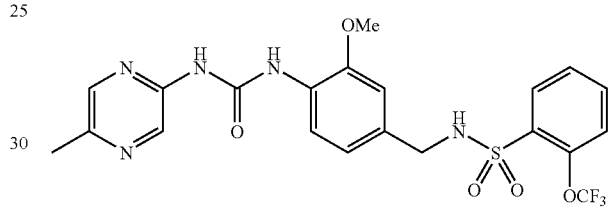

Prepared according to the general procedure described for compound 362 using 2-trifluoromethoxybenzenesulfonyl chloride.

N-{3-Methoxy4-[3-(5-methyl-pyrazin-2-yl)-ureido]-benzyl}-2-trifuoromethoxy-benzenesulfonamide $^1$H NMR (400 MHz, d6-DMSO): δ9.94 (s, 2H), 8.77 (s, 1H), 8.38 (s, 1H), 8.21 (s, 1H), 8.02 (d, J=8.61 Hz, 1H),;7.89 (m, 1H), 7.72 (t, J=7.83 Hz, 1H), 7.51 (d, J=7.83 Hz, 2H), 6.88 (s, 1H), 6.75 (d, J=10.17 Hz, 1H), 4.11 (s, 2H), 3.82 (s, 3H), 2.42 (s, 3H). MS APCI-Pos, M+1=512.0.

Compound 365

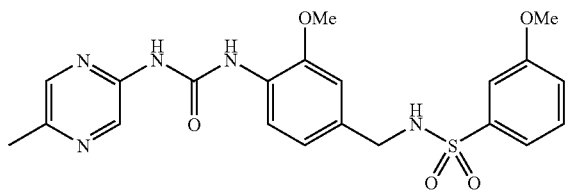

Prepared according to the general procedure described for compound 362 using 3-methoxybenzenesulfonyl chloride.

3-Methoxy-N-{3-methoxy-4-[3-(5-methyl-pyrazin-2-yl)-ureido]-benzyl}-benzenesulfonamide $^1$H NMR (400 MHz, d6-DMSO): δ9.92 (s, 2H), 8.73 (s, 1H), 8.17 (s, 1H), 8.08 (s, 1H), 8.01 (d, J=7.83 Hz, 1H), 7.45 (t, J=7.83 Hz, 1H), 7.34 (d, J=7.83 Hz, 1H), 7.24 (s, 1H), 7.14 (m, 1H), 6.81 (s, 1H), 6.74 (d, J=7.83 Hz, 1H), 3.93 (s, 2H), 3.77 (s, 3H), 3.76 (s, 3H), 2.38 (s, 3H). MS APCI-Pos, M+1=458.0.

Compound 366

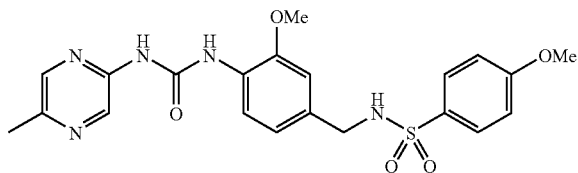

Prepared according to the general procedure described for compound 362 using 4-methoxybenzenesulfonyl chloride.

4-Methoxy-N-{3-methoxy-4-[3-(5-methyl-pyrazin-2-yl)-ureido]-benzyl}-benzenesulfonamide $^1$H NMR (400 MHz, d6-DMSO): δ9.93 (s, 2H), 8.74 (s, 1H), 8.18 (s, 1H), 8.02 (d, J=8.61 Hz, 1H), 7.92 (s, 1H), 7.69 (d, J=8.61 Hz, 2H), 7.05 (d, J=9.39 Hz, 2H), 6.81 (s, 1H), 6.74 (d, J=7.83 Hz, 1H), 3.88 (s, 2H), 3.79 (s, 6H), 2.39 (s, 3H). MS APCI-Pos, M+1=458.2.

Compound 367

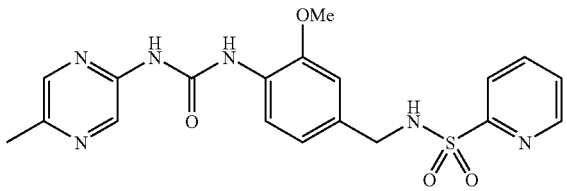

Prepared according to the general procedure described for compound 362 using pyridine-2-sulfonyl chloride.

Pyridine-2-sulfonic acid 3-methoxy-4-[3-(5-methyl-pyrazin-2-yl)-ureido]-benzylamide $^1$H NMR (400 MHz, d6-DMSO): δ9.91 (s, 2H), 8.74 (s, 1H), 8.68 (d, J=4.7 Hz, 1H), 8.17 (s, 1H), 7.99 (m, 2H), 7.86,(d, J=7.83 Hz, 1H), 7.6 (s, 1H), 6.86 (s, 1H), 6.74 (d, J=8.61 Hz, 1H), 4.1 (s, 2H), 3.80 (s, 3H), 3.32 (s, 1H), 2.38 (s, 3H). MS APCI-Pos, M+1=428.9

Additional preferred compounds of the present invention include

N-(2-dimethylamino-1-phenyl-ethyl)-3-methoxy-4-[3-(5-methyl-pyrazin-2-yl)-ureido]-benzamine;

N-(1-aza-bicyclo[2.2.2]oct-3-yl)-3-methoxy-4-[3-(5-methyl-pyrazin-2-yl)-ureido]-benzamide;

N-(3-R-1-cyclohexylmethyl-pyrrolidin-3-yl)-3-methoxy-4-[3- (5-methyl-pyrazin-2-yl)-ureido]-benzamide;

1-[2-(2-dimethylamino-ethoxy)-5-methyl-phenyl]-3-pyrazin-2-yl-urea;

1-[2-(3-dimethylamino-propoxy)-5-methyl-phenyl]-3-(5-methyl-pyrazin-2-yl)-urea;

1-(5-methyl-pyrazin-2-yl)-3-[5-methyl-2-(pyridin-3-ylmethoxy)-phenyl]-urea;

1-[2-(2-dimethylamino-1-dimethylaminomethyl-ethoxy)-5-methyl-phenyl]-3-(5-methyl-pyrazin-2-yl)-urea;

1-[5-methyl-2-(2-S-1-methyl-pyrrolidin-2-ylmethoxy)-phenyl]-3-(5-methyl-pyrazin-2-yl)-urea;

1-{5-methyl-2-[2-(1-methyl-pyrrolidin-2-yl)-ethoxy]-phenyl}-3-(5-methyl-pyrazin-2-yl)-urea;

1-{5-methyl-2-(1-methyl-piperidin-4-yloxy)-phenyl]-3-(5-methyl-pyrazin-2-yl)-urea;

1-[5-methyl-2-(3-(S)-1-methyl-piperidin-3-ylmethoxy)-phenyl]-3-(5-methyl--pyrazin-2-yl)-urea;

1-[5-methyl-2-(3-(R)-1-methyl-piperidin-3-ylmethoxy)-phenyl]-3-(5-methyl-pyrazin-2-yl)-urea;

1-[5-methyl-2-(1-methyl-piperidin-2-ylmethoxy)-phenyl]-3-(5-methyl-pyrazin-2-yl)-urea;

1-[5-methyl-2-(1-methyl-piperidin-3-yloxy)-phenyl]-3-(5-methyl-pyrazin-2-yl)-urea;

1-[5-methyl-2-(1-methyl-piperidin-3-ylmethoxy)-phenyl]-3-quinoxalin-2-yl-urea;

1-[5-methyl-2-(piperidin-3-ylmethoxy)-phenyl]-3-(5-methyl-pyrazin-2-yl)-urea;

1-[5-fluoro-2-(1-methyl-piperidin-3-ylmethoxy)-phenyl]-3-(5-methyl-pyrazin-2-yl)-urea;

1-[5-fluoro-2-(1-methyl-piperidin-4-yloxy)-phenyl]-3-(5-methyl-pyrazin-2-yl)-urea;

1-[4-fluoro-2-(1-methyl-piperidin-4-yloxy)-phenyl]-3-(5-methyl-pyrazin-2-yl)-urea;

1-(2-methoxy-4-methylaminomethyl-phenyl)-3-(5-methyl-pyrazin-2-yl)-urea;

1-(4-{[(furan-3-ylmethyl)-amino]-methyl}-2-methoxy-phenyl)-3-(5-methyl-pyrazin-2-yl)-urea; and 1-{2-methoxy-4-[(4-methoxy-benzylamino)-methyl]-phenyl}-3-(5-methyl-pyrazin-2-yl)-urea.

Example 15

Identification of Chk1 Inhibitors

The human Chk1 cDNA was identified and cloned as described previously in International Application No. PCT/US98/18558, filed Sep. 4, 1998. A FLAG® tag was inserted in frame with the amino terminus of the full-length Chk1. The 5' primer contains an EcoRI site, a Kozak sequence, and also encodes a FLAG® tag for affinity purification using the M2 Antibody (Sigma, Saint Louis, Ill.). The 3' primer contains a SalI site. The PCR-amplified fragment was cloned into pCI-Neo as an EcoRI-SalI fragment (Invitrogen, Carlsbad, Calif.), then subcloned as an EcoRI-NotI fragment into pFastBacI (Gibco-BRL, Bethesda, Md.). Recombinant baculovirus was prepared as described in the GibcoBRL Bac-to-Bac manual and used to infect Sf-9 cells grown in CCM3 medium (HyClone Laboratories, Logan, Utah) for expression of FLAG®-tagged Chk1 protein.

FLAG®-tagged Chk1 was purified from frozen pellets of baculovirus-infected SF9 cells. Frozen cell pellets were mixed with an equal volume of 2× lysis buffer containing 100 mM Tris-HCl pH 7.5, 200 mM NaCl, 50 mM B-glycerophosphate, 25 mM NaF, 4 mM MgCl$_2$, 0.5 mM EGTA, 0.2% TWEEN®-20, 2 mM sodium vanadate, 2 mM DTT, and a cocktail of protease inhibitors (Complete mini, Boehringer Mannheim 2000 catalog #1836170). Cells were then dounced 20 times with the loose pestle of a dounce homogenizer and centrifuged at 48,400×g for 1 hour. The M2 affinity was prewashed with 10 column volumes of 50 mM glycine pH 3.5 followed by 20 mM Tris pH 7.5, 150 mM NaCl alternating three times and ending with a Tris NaCl wash. The column was then washed with 25 column volumes of 20 mM Tris pH 7.5, 150 mM NaCl, 0.1% TWEEN®-20, 1 mM EGTA, 1 mM EDTA and 1× complete mini protease tablets. The cleared lysate was then bound to M2 affinity resin in batch at 4° C. for 4 hours. The mixture of resin and lysate was then poured into a column and the flow through collected. The resin was washed with 10 column volumes of 20 mM Tris pH 7.5, 150 mM NaCl, and 3 mM N-octyl glucoside. FLAG®-tagged Chk1 was then eluted from the column with 6 column volumes of cold 20 mM Tris pH 7.5, 150 mM NaCl, 3 mM N-octyl glucoside containing 0.5 mg/mL FLAG® peptide (Sigma, 2000 Catalog # F-3290). Three fractions were collected an analyzed for the presence of FLAG-tagged Chk1.

The protein kinase was used to developed an assay for Chk1 kinase activity that includes 100 ng purified FLAG®-Chk1 (150 pmol of ATP/min), 20 μm Cdc25C peptide (H-leu-tyr-arg-ser-pro-ser-met-pro-glu-asn-leu-asn-arg-arg-arg-OH) (SEQ ID NO: 1), 400 μm ATP, 2 μCi [$^{32}$P]-gATP, 20 mM Hepes pH 7.2, 5 mM MgCl$_2$, 0.1% NP40 and 1 mM DTT. This assay was used to screen approximately 100,000 small molecule inhibitors. Reactions were initiated by the addition of ATP-containing reaction mix and carried out at room temperature for 10 min. Reactions were stopped by the addition of phosphoric acid (150 mM final concentration) and transferred to phosphocellulose discs. The phosphocellulose discs were washed five times with 150 mM phosphoric acid and air-dried. Scintillation fluid was added and discs were counted in a Wallac scintillation counter. The screen identified a number of Chk1 inhibitors having IC$_{50}$ values in the range of 1 to 100 μM.

Example 16

Chk1 Kinase Inhibitors are Selective

Chk1 inhibitors of the invention were tested for selectivity as against one or more other protein kinases, i.e., DNA-PK, Cdc2, Casein Kinase I (CKI), Chk2, p38,MAP kinase, Protein Kinase A (PKA), and calcium-calmodulin protein kinase II (CaM KII). Assay procedures for all of these kinases except Chk2 have been previously described in the literature, including U.S. provisional patent application No. 60/229,899, filed Sep. 1, 2000, and U.S. patent application Ser. No. 08/184,605, filed Jan. 21, 1994, both of which are herein incorporated by reference. Activity of the compounds against Chk2 was assayed as follows: 128 ng of purified His-tagged Chk2 was incubated with up to 100 mM Chk1 inhibitor in the presence of 4 mM ATP, 1 mCi [32P]g-ATP, 20 mM Hepes pH 7.5, 5 mM MgCl$_2$, and 0.25% NP40 for 20 minutes at room temperature. Reactions were stopped with a final concentration of 150 mM phosphoric acid, and ⅝ of the reaction mixture was transferred to phosphocellulose discs. The discs were washed five times with 150 mM phosphoric acid, and air-dried. Scintillant was added and radioactivity was counted using a Wallac beta counter. p38 MAP kinase, PKA, CaM KII, and Cdc2 were purchased from New England Biolabs, and assays were performed according to the manufacturer's instructions using 4-50 μM ATP and testing Chk1 inhibitor concentrations as high as 100 μM. All inhibitors tested were showed at least 5-fold selectivity for Chk1 over the other enzymes.

Example 17

Chk1 Inhibitors Block Chk1 Function in Cells

Chk 1 is activated in response to ionizing radiation and certain chemical DNA damaging agents. In the presence of DNA damage, Chk1 is activated and causes a cell cycle arrest. In mammalian cells, the best-characterized cell cycle arrest invoked by Chk1 is a G2 arrest. Activation of Chk 1 by DNA damage results in the phosphorylation and inactivation of Cdc25C, the dual specificity phosphatase that normally dephosphorylates cyclin B/cdc2 as cells progress into mitosis (Funari et al., Science, Sep. 5, 1997; 277(5331) 1495-7; Sanchez et al.; Matsuoka et al.; and Blasina et al.). This negative regulation of Cdc2 activity causes cell cycle arrest in order to prevent cells from entering mitosis in the presence of DNA damage or unreplicated DNA. Inhibition of Chk1 , therefore, allows cells to progress through the cell cycle in the presence of DNA damage of unreplicated DNA.

To establish that the Chk1 inhibitors prevented Chk1 function in cells, inhibitors were tested in molecular cell-based assays. Since mammalian Chk1 has been shown to phosphorylate Cdc25C in vitro, suggesting that it negatively regulates cyclin B/cdc2 in response to DNA damage, the ability of the Chk1 inhibitors to enhance the activity of CyclinB/cdc2 was analyzed. The experiment was designed as follows: HeLa cells were irradiated with 800 rads and incubated for 7 hours at 37° C. Because these cells are functionally p53 negative, they arrest exclusively in G2. Then, nocodazole was added to a concentration of 0.5 μg/mL and incubated for 15 hours at 37° C. The addition of nocodazole was designed to trap any cells that progressed through the G2 arrest into M. Finally, a Chk1 inhibitor was added for 8 hours, the cells harvested, lysed and immuno-precipitated equal amounts of protein with an antibody to Cyclin B1 (New England Biolabs) as suggested by the manufacturer. IPs then were analyzed for CyclinB-associated cdc2 kinase activity by assaying histone H1 kinase activity (Yu et al., J Biol Chem. Dec. 11, 1998;273 (50):33455-64). The results demonstrated that Compound 29 overrides the IR-induced inactivation of Cyclin B/Cdc2.

In addition, whether the Chk1 inhibitors abrogate the IR-induced G2 DNA damage checkpoint as assayed by mitotic index experiments was tested. HeLa cells (approximately 1×10$^6$) were treated as described above. Cells were harvested by centrifugation, washed once with PBS, then resuspended in 2.5 mL 75 mM KCl and centrifuged again. The cells then were fixed in 3 mL of freshly prepared cold, acetic acid: methanol (1:3) and incubated on ice for 20 minutes. Cells were pelleted, fix solution aspirated and resuspended in 0.5 mL of PBS. Mitotic spreads were prepared by pipeting 100 μL of the fixed cells onto a glass microscope slide and flooding the sample with 1 ml of fix solution. Slides were then air dried, stained with Wrights stain (Sigma) for 1 minutes, followed by one wash in water and one wash in 50% methanol. The presence of condensed chromosomes and lack of nuclear envelope identified mitotic cells. Both Compounds 12 and 29 showed an increase in the number of mitotic cells in the presence of irradiation demonstrating abrogation of the IR-induced G2 arrest.

Abrogation of the IR-induced G2 checkpoint allows the cells to continue through the cell cycle, presumably in the presence of DNA damage, as demonstrated by analysis of DNA content by FACS profile. 293T cells were treated with 800 rads of ionizing radiation and increasing concentrations (up to 80 mM) of some of the Chk1 inhibitors. The cells then were harvested and fixed with 5 mL of cold 70% ethanol at −20° C. overnight. The cells then were pelleted by centifugation at 1000×g for 10 minutes, and stained with 1 mL of solution containing 50 mg/mL propidium iodide and 250 mg/mL RNase for 30 minutes at room temperature. Stained cells were then analyzed by FACS on FL2 using a Becton-Dickinson apparatus. These experiments demonstrated that, while the cells treated with radiation and vehicle alone remained arrested in G2, the Chk1 inhibitor treated cells were distributed in G1 and S phase. These data, taken together with the data above, suggest that the Chk1 inhibitors allow cells to continue cycling in the presence of ionizing radiation.

Example 18

Chk1 Inhibitors Enhance Killing of Cells by Cancer Treatments

To test the hypothesis that inhibition of Chk1 potentiates the killing effect of DNA-damaging agents, cells were incubated in the presence of selective Chk1 inhibitors and either irradiation or chemical DNA-damaging agents. Cells plated at a density of 1000-2000 per well in 96-well microtitre plates were grown in RMPI 1640 containing 10% FBS, 100 U/mL penicillin and 100 µg/mL streptomycin for 18 hours at 37° C. in a humidified incubator with 5% $CO_2$. Cells tested included HeLa, ACHN, 786-0, HCT116, SW620, HT29, Colo205, SK-MEL-5, SK-MEL-28, A549, H322, OVCAR-3, SK-OV-3, MDA-MB-231, MCF-7, PC-3, HL-60, K562, and MOLT4. All cell line designations refer to human cell lines and refer to the following:

| | |
|---|---|
| HeLa | cervical adenocarcinoma |
| ACHN | renal adenocarcinoma |
| 786-0 | renal adenocarcinoma |
| HCT116 | colon carcinoma |
| SW620 | colon carcinoma, lymph node metastasis |
| HT-29 | colonrectal adenocarcinoma |
| Colo205 | colon adenocarcinoma |
| SK-MEL-5 | melanoma |
| SK-MEL-28 | malignant melanoma |
| A549 | lung carcinoma |
| H322 | broncholoalveolar carcinoma |
| OVCAR-3 | ovarian adenocarcinoma |
| SK-OV-3 | ovarian adenocarcinoma |
| MDA-MB-231 | breast adenocarcinoma |
| MCF-7 | breast adenocarcinoma |
| PC-3 | prostate adenocarcinoma, from metastasis to bone |
| HL-60 | acute promyelocytic leukemia |
| K562 | chronic myelogenous leukemia |
| MOLT4 | acute lymphoblastic leukemia; T lymphoblast |

Cells were treated with media containing chemotherapeutic drugs alone or chemotherapeutic drugs and Compounds 12 and 29. Cells were incubated for approximately 5 days before growth was measured by determination of levels of $^3$H-thymidine uptake. Chemotherapeutic drugs included etoposide, doxorubicin, cisplatin, chlorambucil, 5-fluorouracil (5-FU). The drug concentration necessary to inhibit cell growth to 90% of untreated control cells was defined as the $GI_{90}$. At concentrations less than 100 µM, Compounds 12 and 29 enhanced the killing of 5-FU from 2- to 10-fold.

Compounds 2 and 12 were tested with additional antimetabolites, including methotrexate, hydroxyurea, 2-chloroadenosine, fludarabine, azacytidine, and gemcitibine for an ability to enhance killing of the agents. These Chk1 inhibitors were found to enhance the killing of cells to hydroxyurea, fludarabine, 5-azacytidine, and methotrexate suggesting that the combination of inhibition of Chk1 and blocking of DNA synthesis leads to increased cell death by these agents.

In addition, the ability of the Chk1 inhibitor to enhance killing by irradiation was tested. In HeLa cells, Compounds 12 and 29 were found to enhance killing by irradiation 2-3 fold.

Example 19

Animal Tumor Models

To test the ability of the Chk1 inhibitors to enhance the killing of tumors by 5-FU in mice, xenograft tumor models using colon tumor cell lines were established. Colo205 and HT29 cells (human colon carcinoma) were used to propagate xenograft tumors in 6-8 week old female thymic Balb/c (nu/nu) mice. Mice were maintained in a laminar airflow cabinet under pathogen-free conditions and fed sterile food and water ad libitum. Cell lines were grown to subconfluence in RPMI 1640 media supplemented with 10% FBS, 100 U/mL penicillin, 100 µg/mL streptomycin, and 1.5 mM L-glutamine in a 5% $CO_2$ humidified environment. Single cell suspensions were prepared in CMF-PBS, and cell concentration adjusted to $1\times10^8$ cells/mL. Mice were inoculated subcutaneously (s.c). on the right flank or right leg with a total of $1\times10^7$ cells (100 µL).

Mice were randomized (5 mice/group) into four treatment groups and used when tumors reached a weight of 75-100 mg (usually 7-11 days post-inoculation). Tumors were measured with vernier calipers and tumor weights were estimated using the empirically derived formula: tumor weight (mg)=tumor length (mm)×tumor width $(mm)^2/3.3$. Treatment consisted of i) 100 µL intraperitoneal (i.p). injection of 5-FU at 50 mg/kg, 100 mg/kg, or 150 mg/kg. A dose-dependent delay in tumor growth was observed in-the mice treated with 5-FU. Tumor size was monitored every other day for the duration of the experiment.

Obviously, many modifications and variations of the invention as hereinbefore set forth can be made without departing from the spirit and scope thereof, and, therefore, only such limitations should be imposed as are indicated by the appended claims.

What is claimed is:

1. A method of inhibiting checkpoint kinase 1 in a cell comprising a step of contacting the cell with a therapeutically effective amount of a compound of formula

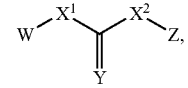

wherein $X^1$ is —O—, —S—, —$CH_2$—, or —N($R^1$)—;
$X^2$ is —O—, —S—, or —N($R^1$)—;
Y is O or S;
W is

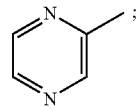

Z is

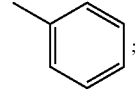

wherein Z is optionally substituted with one to four substituents represented by $R^2$, and W is optionally substituted with one to three substituents represented by $R^5$;

$R^1$ is selected from the group consisting of hydro, $C_{1-6}$alkyl, $C_{2-6}$alkenyl, $C_{2-6}$alkynyl, and aryl;

$R^2$ is selected from the group consisting of halo, optionally substituted $C_{1-6}$alkyl, $C_{2-6}$alkenyl, $OCF_3$, $NO_2$, CN, NC, N($R^3$)$_2$, $OR^3$, $CO_2R^3{}_1$, C(O)N($R^3$)$_2$, C(O)$R^3$, N($R^1$)C(O)$R^3$, N($R^1$)C(O)O$R^3$, N($R^3$)C(O)O$R^3$, N($R^3$)C(O)$C_{1-3}$alkyleneC(O)$R^3$, N($R^3$)C(O)$C_{1-3}$alkyleneC(O)O$R^3$, N($R^3$)C(O)$C_{1-3}$alkyleneO$R^3$, N($R^3$)C(O)$C_{1-3}$alkyleneNHC(O)O$R^3$, N($R^3$)C(O)$C_{1-3}$alkyleneSO$_2$N$R^3$, $C_{1-3}$alkyleneO$R^3$, and S$R^3$;

$R^3$ is selected from the group consisting of hydro, $C_{1-6}$alkyl, $C_{2-6}$alkenyl, cycloalkyl, aryl, heteroaryl, $SO_2R^4$, $C_{1-6}$alkyl substituted with one or more of halo, hydroxy, aryl, heteroaryl, heterocycloalkyl, $N(R^4)_2$, and $SO_2R^4$, $C_{1-3}$alkylenearyl, $C_{1-3}$alkyleneheteroaryl, $C_{1-3}$alkyleneC$_{3-8}$heterocycloalkyl, $C_{1-3}$alkyleneSO$_2$aryl, optionally substituted $C_{1-3}$alkyleneN(R$^4$)$_2$, OCF$_3$, $C_{1-3}$alkyleneN(R$^4$)$_3^+$, $C_{3-8}$heterocycloalkyl, and CH($C_{1-3}$alkyleneN(R$^4$)$_2$)$_2$, or two R$^3$ groups are taken together to form an optionally substituted 3- to 6-membered aliphatic ring;

$R^4$ is selected from the group consisting of hydro, $C_{1-6}$alkyl, cycloalkyl, aryl, heteroaryl, $C_{1-3}$alkylenearyl, and SO$_2$C$_{1-6}$alkyl, or two R$^4$ groups are taken together to form an optionally substituted 3- to 6-membered ring;

$R^5$ is selected from the group consisting of $C_{1-6}$alkyl, aryl, $N(R^3)_2$, OR$^3$, halo, N$_3$, CN, $C_{1-3}$alkylenearyl, $C_{1-3}$alkyleneN(R$^3$)$_2$, C(O)R$^3$, and

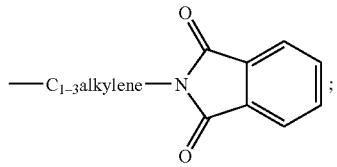

or pharmaceutically acceptable salts, or prodrugs, or solvates thereof.

2. The method of claim 1 wherein
X$^1$ and X$^2$ are —N(H)—;
Y is O or S;
W is optionally substituted with from one to three substituents selected from the group consisting of $C_{1-6}$alkyl, aryl, N(R$^3$)$_2$, OR$^3$, and halo;
Z is

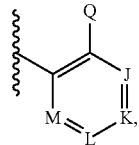

wherein Q is selected from the group consisting of hydro, OR$^3$, SR$^3$, and N(R$^3$)$_2$;
J is CR$^{20}$;
K is CR$^{21}$;
L is CR$^{22}$;
M is CR$^{23}$;
wherein:
R$^{20}$, R$^{21}$, and R$^{22}$ are each independently selected from the group consisting of hydro, halo, optionally substituted $C_{1-6}$alkyl, C$_{2-6}$alkenyl, OCF$_3$, NO$_2$, CN, NC, N(R$^{25}$)$_2$, OR$^{25}$, CO$_2$R$^{25}$, C(O)N(R$^{25}$)$_2$, C(O)R$^{25}$, N(R$^4$)C(O)R$^{25}$, N(R$^{24}$)C(O)OR$^{25}$, N(R$^{25}$)C(O)OR$^{25}$, N(R$^{25}$)C(O)C$_{1-3}$alkyleneC(O)R$^{25}$, N(R$^{25}$)C(O)C$_{1-3}$alkyleneC(O)OR$^{25}$, N(R$^{25}$)C(O)C$_{1-3}$alkyleneOR$^{25}$, N(R$^{25}$)C(O)C$_{1-3}$alkyleneNHC(O)OR$^{25}$, N(R$^{25}$)C(O)C$_{1-3}$alkyleneSO$_2$NR$^{25}$, CF$_3$, $C_{1-3}$alkyleneN(R$^{25}$)SO$_2$aryl, $C_{1-3}$alkyleneN(R$^{25}$)SO$_2$heteroaryl, $C_{1-3}$alkyleneOC$_{1-3}$alkylenearyl, $C_{1-3}$alkyleneN(R$^{25}$)C$_{1-3}$alkylenearyl, $C_{1-3}$alkyleneN(R$^{25}$)C$_{1-3}$alkyleneheteroaryl, $C_{1-3}$alkyleneN(R$^{25}$)C(O)R$^7$, $C_{1-3}$alkyleneN(R$^{25}$)C(O)C$_{1-3}$alkyleneOR$^{25}$, $C_{1-3}$alkyleneN(R$^{25}$)C(O)aryl, $C_{1-3}$alkyleneN(R$^{25}$)C(O) $C_{1-3}$alkyleneN(R$^{25}$)$_2$, $C_{1-3}$alkyleneN(R$^{25}$)C(O) heteroaryl, $C_{1-3}$alkyleneOR$^{25}$, and SR$^{25}$;

R$^{23}$ is selected from the group consisting of null, hydro, optionally substituted $C_{1-6}$alkyl, and halo;

R$^{24}$ is selected from the group consisting of hydro, $C_{1-6}$alkyl, C$_{2-6}$alkenyl, C$_{2-6}$alkynyl, and aryl;

R$^{25}$ is selected from the group consisting of hydro, $C_{1-6}$alkyl, C$_{2-6}$alkenyl, cycloalkyl, heterocycle, aryl, heteroaryl, SO$_2$R$^{26}$, and $C_{1-6}$alkyl substituted with halo, hydroxy, aryl, heteroaryl, heterocycloalkyl, N(R$^{26}$)$_2$, or SO$_2$R$^{26}$; and R$^{26}$ is selected from the group consisting of hydro, $C_{1-6}$alkyl, cycloalkyl, aryl, and SO$_2$C$_{1-6}$alkyl, or two R$^4$ groups are taken together to form an optionally substituted 3- to 6-membered ring.

3. The method of claim 2 wherein W is optionally substituted with from one to three substituents selected from the group consisting of optionally substituted $C_{1-6}$alkyl, aryl, N(R$^3$)$_2$, OR$^3$, and halo.

4. The method of claim 2 wherein
J is CR$^{20}$, wherein R$^{20}$ is selected from the group consisting of hydro, optionally substituted $C_{1-6}$alkyl, and halo;
K is CR$^{21}$;
L is CR$^{22}$; and
one of R$^{21}$ and R$^{22}$ is hydro and the other is a substituent selected from the group consisting of C$_2$R$^{25}$, C(O)N(R$^{25}$)$_2$, C(O)R$^{25}$, N(R$^4$)C(O)R$^{25}$, N(R$^{24}$)C(O)OR$^{25}$, N(R$^{25}$)C(O)OR$^{25}$, N(R$^{25}$)C(O)C$_{1-3}$alkyleneC(O)R$^{25}$, N(R$^{25}$)C(O)C$_{1-3}$alkyleneC(O)OR$^{25}$, N(R$^{25}$)C(O)C$_{1-3}$alkyleneOR$^{25}$, N(R$^{25}$)C(O)C$_{1-3}$alkyleneNHC(O)OR$^{25}$, N(R$^{25}$)C(O)C$_{1-3}$alkyleneSO$_2$NR$^{25}$, CF$_3$, $C_{1-3}$alkyleneN(R$^{25}$)SO$_2$aryl, $C_{1-3}$alkyleneN(R$^{25}$)SO$_2$heteroaryl, $C_{1-3}$alkyleneOC$_{1-3}$alkylenearyl, $C_{1-3}$alkyleneN(R$^{25}$)C$_{1-3}$alkylenearyl, $C_{1-3}$alkyleneN(R$^{25}$)C$_{1-3}$alkyleneheteroaryl, $C_{1-3}$alkyleneN(R$^{25}$)C(O)R$^7$, $C_{1-3}$alkyleneN(R$^{25}$)C(O)C$_{1-3}$alkyleneOR$^2$, $C_{1-3}$alkyleneN(R$^{25}$)C(O)aryl, $C_{1-3}$alkyleneN(R$^{25}$)C(O) $C_{1-3}$alkyleneN(R$^{25}$)$_2$, $C_{1-3}$alkyleneN(R$^{25}$)C(O) heteroaryl, $C_{1-3}$alkyleneOR$^{25}$, and SR$^{25}$.

5. A method of sensitizing cells in an individual undergoing a chemotherapeutic or radiotherapeutic treatment for a medical condition, comprising administering a therapeutically effective amount of a compound of formula (I) in combination with a therapeutically effective amount of a chemotherapeutic agent, a radiotherapeutic agent, or a mixture thereof to the individual, said compound of formula (I) having a structure

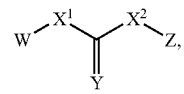

wherein X$^1$ is —O—, —S—, —CH$_2$—, or —N(R$^1$)—;
X$^2$ is —O—, —S—, or —N(R$^1$)—;
Y is O or S;

W is

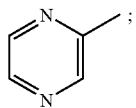

Z is

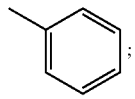

wherein Z is optionally substituted with one to four substituents represented by $R^2$, and W is are optionally substituted with one to three substituents represented by $R^5$;

$R^1$ is selected from the group consisting of hydro, $C_{1-6}$alkyl, $C_{2-6}$alkenyl, $C_{2-6}$alkynyl, and aryl;

$R^2$ is selected from the group consisting of halo, optionally substituted $C_{1-6}$alkyl, $C_{2-6}$alkenyl, $OCF_3$, $NO_2$, CN, NC, $N(R^3)_2$, $OR^3$, $C_2R^3$, $C(O)N(R^3)_2$, $C(O)R^3$, $N(R^1)C(O)R^3$, $N(R^1)C(O)OR^3$, $N(R^3)C(O)OR^3$, $N(R^3)C(O)C_{1-3}$alkyleneC(O)$R^3$, $N(R^3)C(O)C_{1-3}$alkyleneC(O)OR$^3$, $N(R^3)C(O)C_{1-3}$alkyleneOR$^3$, $N(R^3)C(O)C_{1-3}$alkyleneNHC(O)OR$^3$, $N(R^3)C(O)C_{1-3}$alkyleneSO$_2$NR$^3$, $C_{1-3}$alkyleneOR$^3$, and SR$^3$;

$R^3$ is selected from the group consisting of hydro, $C_{1-6}$alkyl, $C_{2-6}$alkenyl, cycloalkyl, aryl, heteroaryl, $SO_2R^4$, $C_{1-6}$alkyl substituted with one or more of halo, hydroxy, aryl, heteroaryl, heterocycloalkyl, $N(R^4)_2$, and $SO_2R^4$, $C_{1-3}$alkylenearyl, $C_{1-3}$alkyleneheteroaryl, $C_{1-3}$alkyleneC$_{3-8}$heterocycloalkyl, $C_{1-3}$alkyleneSO$_2$aryl, optionally substituted $C_{1-3}$alkyleneN(R$^4$)$_2$, $OCF_3$, $C_{1-3}$alkyleneN(R$^4$)$_3^+$, $C_{3-8}$heterocycloalkyl, and CH(C$_{1-3}$alkyleneN(R$^4$)$_2$)$_2$, or two $R^3$ groups are taken together to form an optionally substituted 3- to 6-membered aliphatic ring;

$R^4$ is selected from the group consisting of hydro, $C_{1-6}$alkyl, cycloalkyl, aryl, heteroaryl, $C_{1-3}$-alkylenearyl, and $SO_2C_{1-6}$alkyl, or two $R^4$ groups are taken together to form an optionally substituted 3- to 6-membered ring;

$R^5$ is selected from the group consisting of $C_{1-6}$alkyl, aryl, $N(R^3)_2$, $OR^3$, halo, $N^3$, CN, $C_{1-3}$alkylenearyl, $C_{1-3}$alkyleneN(R$^3$)$_2$, $C(O)R^3$, and

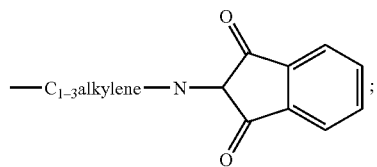

or pharmaceutically acceptable salts, or prodrugs, or solvates thereof.

6. The method of claim 5 further comprising administering a therapeutically effective amount of at lease one or more cytokine, lymphokine, growth factor, or other hematopoietic factor.

7. The method of claim 5 wherein:

$X^1$ and $X^2$ are —N(H)—;

Y is O or S;

W is optionally substituted with from one to three substituents selected from the group consisting of $C_{1-6}$alkyl, aryl, $N(R^3)_2$, $OR^3$, and halo;

Z is

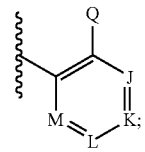

wherein Q is selected from the group consisting of hydro, $OR^3$, $SR^3$, and $N(R^3)_2$;

J is $CR^{20}$;

K is $CR^{21}$;

L is $CR^{22}$;

M is $CR^{23}$;

wherein:

$R^{20}$, $R^{21}$, and $R^{22}$ are each independently selected from the group consisting of hydro, halo, optionally substituted $C_{1-6}$alkyl, $C_{2-6}$alkenyl, $OCF_3$, $NO_2$, CN, NC, $N(R^{25})_2$, $OR^{25}$, $CO_2R^{25}$, $C(O)N(R^{25})_2$, $C(O)R^{25}$, $N(R^{24})C(O)R^{25}$, $N(R^{24})C(O)OR^{25}$, $N(R^{25})C(O)OR^{25}$, $N(R^{25})C(O)C_{1-3}$alkyleneC(O)R$^{25}$, $N(R^{25})C(O)C_{1-3}$alkyleneC(O)OR$^{25}$, $N(R^{25})C(O)C_{1-3}$alkyleneOR$^{25}$, $N(R^{25})C(O)C_{1-3}$alkyleneNHC(O)OR$^{25}$, $N(R^{25})C(O)C_{1-3}$alkyleneSO$_2$NR$^{25}$, $CF_3$, $C_{1-3}$alkyleneN(R$^{25}$)SO$_2$aryl, $C_{1-3}$alkyleneN(R$^{25}$)SO$_2$heteroaryl, $C_{1-3}$alkyleneOC$_{1-3}$alkylenearyl, $C_{1-3}$alkyleneN(R$^{25}$)C$_{1-3}$alkylenearyl, $C_{1-3}$alkyleneN(R$^{25}$)C$_{1-3}$alkyleneheteroaryl, $C_{1-3}$alkyleneN(R$^{25}$)C(O)R$^7$, $C_{1-3}$alkyleneN(R$^{25}$)C(O)C$_{1-3}$alkyleneOR$^{25}$, $C_{1-3}$alkyleneN(R$^{25}$)C(O)aryl, $C_{1-3}$alkyleneN(R$^{25}$)C(O)heteroaryl, $C_{1-3}$alkyleneN(R$^{25}$)$_2$, $C_{1-3}$alkyleneN(R$^{25}$)C(O)heteroaryl, $C_{1-3}$alkyleneOR$^{25}$, and SR$^{25}$;

$R^{23}$ is selected from the group consisting of null, hydro, optionally substituted $C_{1-6}$alkyl, and halo;

$R^{24}$ is selected from the group consisting of hydro, $C_{1-6}$alkyl, $C_{2-6}$alkenyl, $C_{2-6}$alkynyl, and aryl;

$R^{25}$ is selected from the group consisting of hydro, $C_{1-6}$alkyl, $C_{2-6}$alkenyl, cycloalkyl, heterocycle, aryl, heteroaryl, $SO_2R^{26}$, and $C_{1-6}$alkyl substituted with halo, hydroxy, aryl, heteroaryl, heterocycloalkyl, $N(R^{26})_2$, or $SO_2R^{26}$; and $R^{26}$ is selected from the group consisting of hydro, $C_{1-6}$alkyl, cycloalkyl, aryl, and $SO_2C_{1-6}$alkyl, or two $R^4$ groups are taken together to form an optionally substituted 3- to 6-membered ring.

8. The method of claim 7 wherein W is optionally substituted with from one to three substituents selected from the group consisting of optionally substituted $C_{1-6}$alkyl, aryl, $N(R^3)_2$, $OR^3$, $C_{1-3}$alkylenearyl, $C_{1-3}$alkyleneheteroaryl, $C_{1-3}$alkyleneC$_{3-8}$heterocycloalkyl, $C_{1-3}$alkyleneSO$_2$aryl, optionally substituted $C_{1-3}$alkyleneN(R$^4$)$_2$, $OCF_3$, $C_{1-3}$alkyleneN(R$^4$)$_3^+$, $C_{3-8}$heterocycloalkyl, CH(C$_{1-3}$alkyleneN(R$^4$)$_2$)$_2$, and halo.

9. The method of claim 7 wherein

J is $CR^{20}$, wherein $R^{20}$ is selected from the group consisting of hydro, optionally substituted $C_{1-6}$alkyl, and halo;

K is $CR^{21}$;

L is $CR^{22}$;

one of $R^{21}$ and $R^{22}$ is hydro and the other is a substituent selected from the group consisting of $CO_2R^{25}$, $C(O)N(R^{25})_2$, $C(O)R^{25}$, $N(R^{24})C(O)R^{25}$, $N(R^{24})C(O)OR^{25}$, $N(R^{24})C(O)OR^{25}$, $N(R^{25})C(O)OR^{25}$, $N(R^{25})C(O)C_{1-3}$alkyleneC(O)R$^{25}$, $N(R^{25})C(O)C_{1-3}$alkyleneC(O)OR$^{25}$, $N(R^{25})C(O)C_{1-3}$alkyleneOR$^{25}$, $N(R^{25})C(O)C_{1-3}$ alkyleneNHC(O)OR$^{25}$, N(R$^{25}$)C(O)C$_{1-3}$alkyleneSO$_2$NR$^{25}$, C$_{1-3}$alkyleneOR$^{25}$, CF$_3$, C$_{1-3}$alkyleneN(R$^{25}$)SO$_2$aryl, C$_{1-3}$alkyleneN(R$^{25}$)SO$_2$heteroaryl, C$_{1-3}$alkyleneOC$_{1-3}$alkylenearyl, C$_{1-3}$alkyleneN(R$^{25}$)C$_{1-3}$alkylenearyl, C$_{1-3}$alkyleneN(R$^{25}$)C$_{1-3}$alkyleneheteroaryl, C$_{1-3}$alkyleneN(R$^{25}$)C(O)R$^3$, C$_{1-3}$alkyleneN(R$^{25}$)C(O)C$_{1-3}$alkyleneOR$^3$, C$_{1-3}$alkyleneN(R$^{25}$)C(O)aryl, C$_{1-3}$alkyleneN(R$^{25}$)C(O)C$_{1-3}$alkyleneN(R$^{25}$)$_2$, C$_{1-3}$alkyleneN(R$^{25}$)C(O)heteroaryl, and SR$^{25}$.

10. The method of claim 5 wherein the chemotherapeutic agent is selected from the group consisting of an alkylating agent, an antimetabolite, a hormone or antagonist thereof, a radioisotope, an antibody, and mixtures thereof.

11. The method of claim 5 wherein the radiotherapeutic agent is selected from the group consisting of gamma-radiation, X-ray radiation, ultraviolet light, visible light, infrared radiation, and microwave radiation.

12. The method of claim 5 wherein the condition is a cancer selected from the group consisting of a colorectal cancer, a head and neck cancer, a pancreatic cancer, a breast cancer, a gastric cancer, a bladder cancer, a vulvar cancer, a leukemia, a lymphoma, a melanoma, a renal cell carcinoma, an ovarian cancer, a brain tumor, an osteosarcoma, and a lung carcinoma.

13. The method of claim 5 wherein the condition is a cancer selected from the group consisting of myxoid and round cell carcinoma, a locally advanced tumor, metastatic cancer, Ewing's sarcoma, a cancer metastase, a lymphatic metastase, squamous cell carcinoma, esophageal squamous cell carcinoma, oral carcinoma, multiple myeloma, acute lymphocytic leukemia, acute nonlymphocytic leukemia, chronic lymphocytic leukemia, chronic myelocytic leukemia, hairy cell leukemia, effusion lymphomas (body cavity based lymphomas), thymic lymphoma lung cancer, small cell carcinoma, cutaneous T cell lymphoma, Hodgkin's, lymphoma, non-Hodgkin's lymphoma, cancer of the adrenal cortex, ACTH-producing tumors, nonsmall cell cancers, breast cancer, small cell carcinoma, ductal carcinoma, stomach cancer, colon cancer, colorectal cancer, polyps associated with colorectal neoplasia, pancreatic cancer, liver cancer, bladder cancer, primary superficial bladder tumors, invasive transitional cell carcinoma of the bladder, muscle-invasive bladder cancer, prostate cancer, ovarian carcinoma, primary peritoneal epithelial neoplasms, cervical carcinoma, uterine endometrial cancers, vaginal cancer, cancer of the vulva, uterine cancer and solid tumors in the ovarian follicle, testicular cancer, penile cancer, renal cell carcinoma, intrinsic brain tumors, neuroblastoma, astrocytic brain tumors, gliomas, metastatic tumor cell invasion in the central nervous system, osteomas and osteosarcomas, malignant melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

14. The method of claim 5 wherein the treatment is administered for an inflammatory condition selected from the group consisting of rheumatoid arthritis, psoriasis, vitiligo, Wegener's granulomatosis, and systemic lupus erythematosus.

15. A compound having a formula

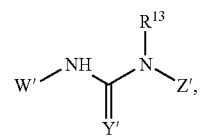

wherein Y' is O or S;

W' is

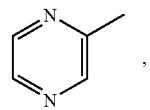

optionally substituted with from one to three substituents selected from the group consisting of C$_{1-6}$alkyl, aryl, N(R$^7$)$_2$, OR$^7$, N$_3$, CN, C(O)R$^7$, C$_{1-3}$alkylenearyl, C$_{1-3}$alkyleneN(R$^2$)$_2$,

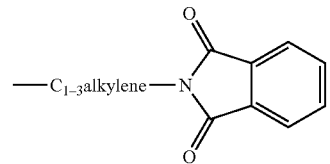

and halo;

Z' is:

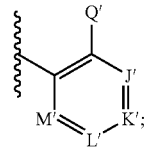

wherein:
Q' is selected from the group consisting of OR$^7$, SR$^7_1$, and N(R$^7$)$_2$;
J' is CR$^8$;
K' is CR$^9$;
L' is CR$^{10}$;
M' is CR$^{11}$;
wherein:
R$^7$, independently, is selected from the group consisting of hydro, C$_{1-6}$alkyl, C$_{2-6}$alkenyl, cycloalkyl, aryl, heteroaryl, SO$_2$R$^{12}$, C$_{1-6}$alkyl substituted with one or more of halo, hydroxy, aryl, heteroaryl, heterocycloalkyl, N(R$^{12}$)$_2$, and SO$_2$R$^{12}$, C$_{1-3}$alkylenearyl, C$_{1-3}$alkyleneheteroaryl, C$_{1-3}$alkyleneC$_{3-8}$heterocycloalkyl, C$_{1-3}$alkyleneSO$_2$aryl, optionally substituted C$_{1-3}$alkyleneN(R$^{12}$)$_2$, OCF$_3$, C$_{1-3}$alkyleneN(R$^{12}$)$_3^+$, C$_{3-8}$heterocycloalkyl, and CH(C$_{1-3}$alkyleneN(R$^{12}$)$_2$)$_2$, or two R$^7$ groups are taken together to form an optionally substituted 3- to 6-membered aliphatic ring;
R$^8$, R$^9$, and R$^{10}$ are each independently selected from the group consisting of hydro, halo, optionally substituted C$_{1-6}$alkyl, C$_{2-6}$alkenyl, OCF$_3$, NO$_2$, CN, NC, N(R$^7$)$_2$, OR$^7$, CO$_2$R$^7$, C(O)N(R$^7$)$_2$, C(O)R$^7$, N(R$^{13}$)C(O)R$^7$, N(R$^{13}$)C(O)OR$^7$, N(R$^7$)C(O)OR$^7$, N(R$^7$)C(O)C$_{1-3}$alkyleneC(O)R$^7$, N(R$^7$)C(O)C$_{1-3}$alkyleneC(O)OR$^7$, N(R$^7$)C(O)C$_{1-3}$alkyleneOR$^7$, N(R$^7$)C(O)C$_{1-3}$alkyleneNHC(O)OR$^7$, N(R$^7$)C(O)C$_{1-3}$alkyleneSO$_2$NR$^7$, CF$_3$, C$_{1-3}$alkyleneN(R$^{12}$)SO$_2$aryl, C$_{1-3}$alkyleneN(R$^{12}$)SO$_2$heteroaryl, C$_{1-3}$alkyleneOC$_{1-3}$alkylenearyl, C$_{1-3}$alkyleneN(R$^{12}$)C$_{1-3}$alkylenearyl, C$_{1-3}$alkyleneN(R$^{12}$)C$_{1-3}$alkyleneheteroaryl, C$_{1-3}$alkyleneN(R$^{12}$)C(O)R$^7$, C$_{1-3}$alkyleneN(R$^{12}$)C(O)C$_{1-3}$alkyleneOR$_2$, C$_{1-3}$alkyleneN(R$^{12}$)C(O)aryl, C$_{1-3}$alkyleneN(R$^{12}$)C(O)C$_{1-3}$alkyleneN(R$^{12}$)$_2$, C$_{1-3}$alkyleneN(R$^{12}$)C(O)heteroaryl, C$_{1-3}$alkyleneOR$^7$, and SR$^7$, wherein R$^7$ is as defined above;
R$^{11}$ is selected from the group consisting of hydro, optionally substituted C$_{1-6}$alkyl, and halo;

$R^{12}$ is selected from the group consisting of hydro, $C_{1-6}$alkyl, cycloalkyl, aryl, heteroaryl, $C_{1-3}$alkylenearyl, and $SO_2C_{1-6}$alkyl, or two $R^{12}$ groups are taken together to form an optionally substituted 3- to 6-membered ring; and $R^{13}$ is selected from the group consisting of hydro, $C_{1-6}$alkyl, $C_{2-6}$alkenyl, $C_{2-6}$alkynyl, and aryl;

provided that when Q' $OCH_3$, at least one of $R^8$, $R^9$, and $R^{10}$ is different from hydro, $CH_3$, $OCH_3$, and halo, or pharmaceutically acceptable salts, or prodrugs, or solvates thereof.

16. The compound of claim 15 wherein W' is substituted with one to three substituents selected from the group consisting of methyl, $CF_3$, optionally substituted aryl, $N_3$, benzyl, $C(O)R^7$, $C_{1-3}$alkyleneN$(R^{12})_2$, $OR^7$, $N(R^7)_2$, halo, and

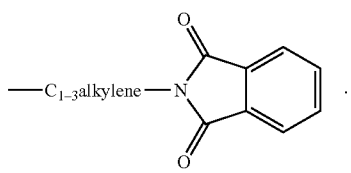

17. The compound of claim 15 wherein Q' is $OR^7$.
18. The compound of claim 17 wherein Q' is $OCH_3$.
19. The compound of claim 15 wherein $R^{13}$ is hydro.
20. The compound of claim 15 wherein
J' is $CR^8$, wherein $R^8$ is hydro, $C_{1-6}$alkyl, and halo;
K' is $CR^9$;
L' is $CR^{10}$; and
one of $R^9$ and $R^{10}$ is hydro and the other is a substituent selected from the group consisting of $CO_2R^7$, C(O)N$(R^7)_2$, $C(O)R^7$, $N(R^{13})C(O)R^7$, $N(R^{13})C(O)OR^7$, $N(R^7)C(O)OR^7$, $N(R^7)C(O)C_{1-3}$alkyleneC(O)$R^7$, $N(R^7)C(O)C_{1-3}$alkyleneC(O)$OR^7$, $N(R^7)C(O)C_{1-3}$alkyleneOR$^7$, $N(R^7)C(O)C_{1-3}$alkyleneOR$^7$, $N(R^7)C(O)C_{1-3}$alkyleneNHC(O)OR$^7$, $N(R^7)C(O)C_{1-3}$alkyleneSO$_2$NR$^7$, $C_{1-3}$alkylene-OR$^7$, $CF_3$, $C_{1-3}$alkyleneN$(R^{12})SO_2$aryl, $C_{1-3}$alkyleneN$(R^{12})SO_2$heteroaryl, $C_{1-3}$alkyleneOC$_{1-3}$alkylenearyl, $C_{1-3}$alkyleneN$(R^{12})C_{1-3}$alkylenearyl, $C_{1-3}$alkyleneN$(R^{12})C_{1-3}$alkyleneheteroaryl, $C_{1-3}$alkyleneN$(R^{12})C(O)R^7$, $C_{1-3}$alkyleneN$(R^{12})C(O)C_{1-3}$alkyleneOR$^2$, $C_{1-3}$alkyleneN$(R^{12})C(O)$aryl, $C_{1-3}$alkyleneN$(R^{12})C(O)C_{1-3}$alkyleneN$(R^{12})_2$, $C_{1-3}$alkyleneN$(R^{12})C(O)$heteroaryl, and $SR^7$.

21. A method of sensitizing cells in an individual undergoing a chemotherapeutic or radiotherapeutic treatment for a medical condition, comprising administering a therapeutically effective amount of a compound of claim 15 in combination with a chemotherapeutic agent, a radiotherapeutic agent, or a mixture thereof to the individual.

22. A compound having a structure

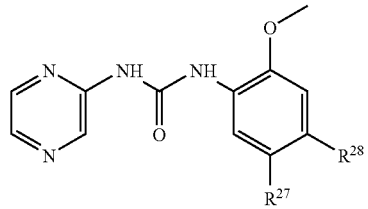

wherein $R^{27}$ and $R^{28}$ are

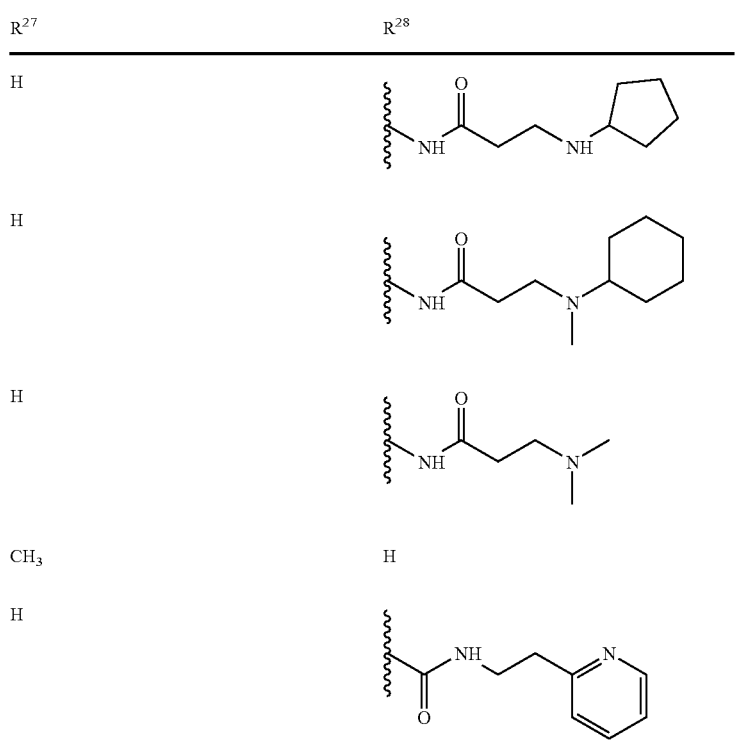

| $R^{27}$ | $R^{28}$ |
| --- | --- |
| H | (NH-C(O)-CH2CH2-NH-cyclopentyl) |
| H | (NH-C(O)-CH2CH2-N(CH3)-cyclohexyl) |
| H | (NH-C(O)-CH2CH2-N(CH3)2) |
| CH$_3$ | H |
| H | (C(O)-NH-CH2CH2-2-pyridyl) |

-continued

| R²⁷ | R²⁸ |
|---|---|
| H | 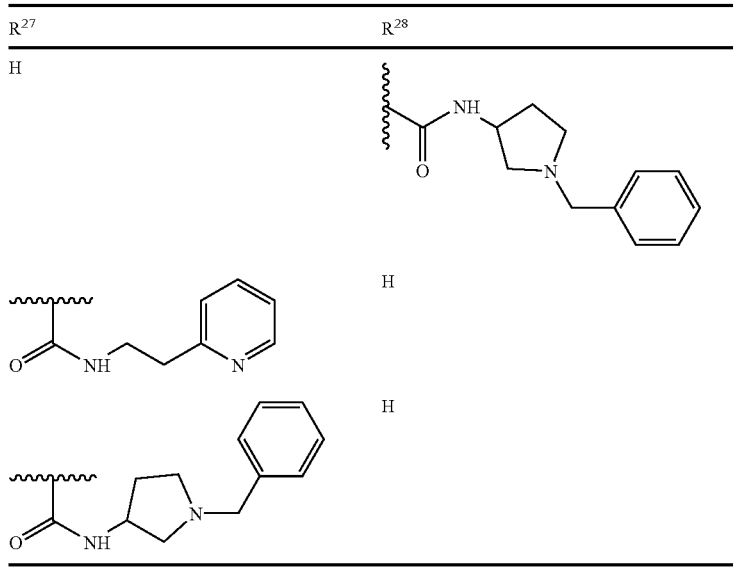 |
| 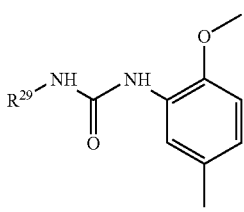 | H |
| 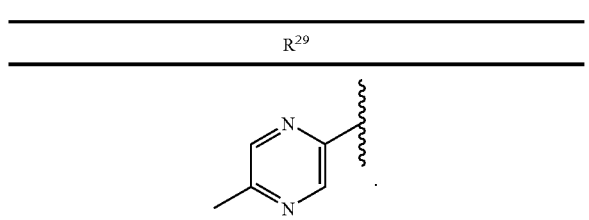 | H | or

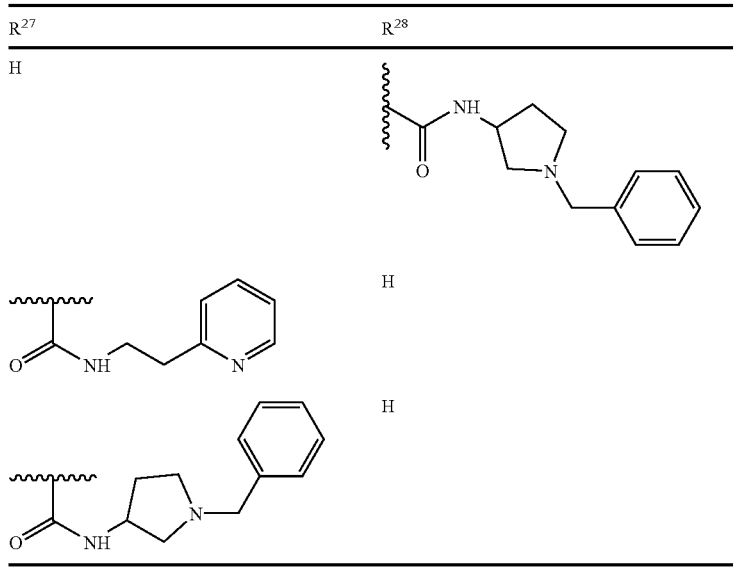

wherein R²⁹ is

| R²⁹ |
|---|
| 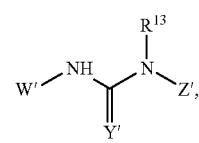 |

23. A compound selected from the group consisting of:
N-(2-dimethylamino-1-phenyl-ethyl)-3-methoxy-4-[3-(5-methyl-pyrazin-2-yl)-ureido]-benzamine;
N-(1-aza-bicyclo[2.2.2]oct-3-yl)-3-methoxy-4-[3-(5-methyl-pyrazin-2-yl)-ureido]-benzamide;
N-(3-R-1-cyclohexylmethyl-pyrrolidin-3-yl)-3-methoxy-4-[3-(5-methyl-pyrazin-2-yl)-ureido]-benzamide;
1-[2-(2-dimethylamino-ethoxy)-5-methyl-phenyl]-3-pyrazin-2-yl-urea;
1-[2-(3-dimethylamino-propoxy)-5-methyl-phenyl]-3-(5-methyl-pyrazin-2-yl)-urea;
1-(5-methyl-pyrazin-2-yl)-3-[5-methyl-2-(pyridin-3-ylmethoxy)-phenyl]-urea;
1-[2-(2-dimethylamino-1-dimethylaminomethyl-ethoxy)-5-methyl-phenyl]-3-(5-methyl-pyrazin-2-yl)-urea;
1-[5-methyl-2-(2-S-1-methyl-pyrrolidin-2-ylmethoxy)-phenyl]-3-(5-methyl-pyrazin-2-yl)-urea;
1-{5-methyl-2-[2-(1-methyl-pyrrolidin-2-yl)-ethoxy]-phenyl}-3-(5-methyl-pyrazin-2-yl)-urea;
1-{5-methyl-2-(1-methyl-piperidin-4-yloxy)-phenyl]-3-(5-methyl-pyrazin-2-yl)-urea;
1-[5-methyl-2-(3-(S)-1-methyl-piperidin-3-ylmethoxy)-phenyl]-3-(5-methyl-pyrazin-2-yl)-urea;
1-[5-methyl-2-(3-(R)-1-methyl-piperidin-3-ylmethoxy)-phenyl]-3-(5-methyl-pyrazin-2-yl)-urea;
1-[5-methyl-2-(1-methyl-piperidin-2-ylmethoxy)-phenyl]-3-(5-methyl-pyrazin-2-yl)-urea;
1-[5-methyl-2-(1-methyl-piperidin-3-yloxy)-phenyl]-3-(5-methyl-pyrazin-2-yl)-urea;
1-[5-methyl-2-piperidin-3-ylmethoxy)-phenyl]-3-(5-methyl-pyrazin-2-yl)-urea;
1-[5-fluoro-2-(1-methyl-piperidin-3-ylmethoxy)-phenyl]-3-(5-methyl-pyrazin-2-yl)-urea;
1-[5-fluoro-2-(1-methyl-piperidin-4-yloxy)-phenyl]-3-(5-methyl-pyrazin-2-yl)-urea;
1-[4-fluoro-2-(1-methyl-piperidin-4-yloxy)-phenyl]-3-(5-methyl-pyrazin-2-yl)-urea;
1-(2-methoxy-4-methylaminomethyl-phenyl)-3-(5-methyl-pyrazin-2-yl)-urea;
1-(4-{[(furan-3-ylmethyl)-amino]-methyl}-2-methoxyphenyl)-3-(5-methyl-pyrazin-2-yl)-urea; and
1-{2-methoxy-4-[(4-methoxy-benzylamino)-methyl]-phenyl}-3-(5-methyl-pyrazin-2-yl)-urea.

24. A composition comprising a compound of formula (II) and a pharmaceutically acceptable carrier, said compound of formula (II) having a formula

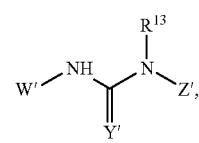

(II)

wherein Y' is O or S;

W' is

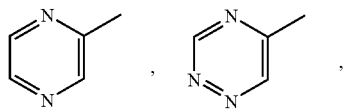

optionally substituted with from one to three substituents selected from the group consisting of $C_{1-6}$alkyl, aryl, $N(R^7)_2$, $OR^7$, $N_3$, CN, $C(O)R^7$, $C_{1-3}$alkylenearyl, $C_{1-3}$alkyleneN$(R^{12})_2$,

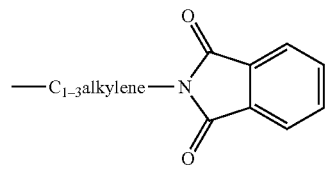

and halo;

Z' is

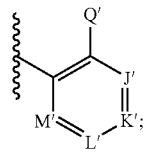

wherein:
Q' is selected from the group consisting of $OR^7$, $SR^7$, and $N(R^7)_2$;
J' is $CR^8$;
K' is $CR^9$;
L' is $CR_{10}$;
M' is $CR^{11}$;
wherein:
$R^7$, independently, is selected from the group consisting of hydro, $C_{1-6}$alkyl, $C_{2-6}$alkenyl, cycloalkyl, aryl, heteroaryl, $SO_2R^{12}$, $C_{1-6}$alkyl substituted with one or more of halo, hydroxy, aryl, heteroaryl, heterocycloalkyl, $N(R^{12})_2$, and $SO_2R^{12}$, $C_{1-3}$alkylenearyl, $C_{1-3}$alkyleneheteroaryl, $C_{1-3}$alkyleneC$_{3-8}$heterocycloalkyl, $C_{1-3}$alkyleneSO$_2$aryl, optionally substituted $C_{1-3}$alkyleneN$(R^{12})_2$, $OCF_3$, $C_{1-3}$alkyleneN$(R^{12})_3^+$, $C_{3-8}$heterocycloalkyl, and $CH(C_{1-3}$alkyleneN$(R^{12})_2)_2$, or two $R^7$ groups are taken together to form an optionally substituted 3- to 6-membered aliphatic ring;
$R^8$, $R^9$, and $R^{10}$ are each independently selected from the group consisting of hydro, halo, optionally substituted $C_{1-6}$alkyl, $C_{2-6}$alkenyl, $OCF_3$, $NO_2$, CN, NC, $N(R^7)_2$, $OR^7$, $CO_2R^7$, $C(O)N(R^7)_2$, $C(O)R^7$, $N(R^{13})C(O)R^7$, $N(R^{13})C(O)OR^7$, $N(R^7)C(O)OR^7$, $N(R^7)C(O)C_{1-3}$alkyleneC(O)$R^7$, $N(R^7)C(O)C_{1-3}$alkyleneC(O)OR$^7$, $N(R^7)C(O)C_{1-3}$alkyleneOR$^7$, $N(R^7)C(O)C_{1-3}$alkyleneNHC(O)OR$^7$, $N(R^7)C(O)C_{1-3}$alkyleneSO$_2$NR$^7$, $C_{1-3}$alkyleneOR$^7$, and SR$^7$, wherein $R^7$ is as defined above;
$R^{11}$ is selected from the group consisting of hydro, optionally substituted $C_{1-6}$alkyl, and halo;
$R^{12}$ is selected from the group consisting of hydro, $C_{1-6}$alkyl, cycloalkyl, aryl, heteroaryl, $C_{1-3}$alkylenearyl, and $SO_2C_{1-6}$alkyl, or two $R^{12}$ groups are taken together to form an optionally substituted 3- to 6-membered ring; and $R^{13}$ is selected from the group consisting of hydro, $C_{1-6}$alkyl, $C_{2-6}$alkenyl, $C_{2-6}$alkynyl, and aryl;
provided that when Q' is hydro or $OCH_3$, at least one of $R^8$, $R^9$, and $R^{10}$ is different from hydro, $CH_3$, $OCH_3$, and halo,
or pharmaceutically acceptable salts, or prodrugs, or solvates thereof.

25. A compound selected from the group consisting of

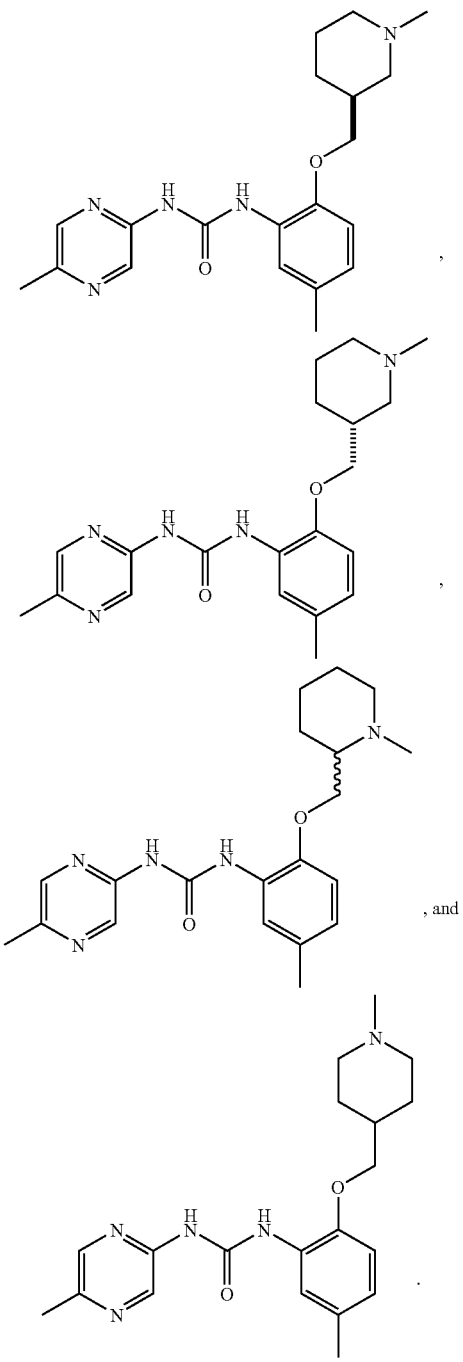

, and

* * * * *

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 3, line 36, "199, 7;" should be -- 1997; --

Column 4, line 40, "$C_{1-3}$alkylene-heteroaryl" should be -- $C_{1-3}$alkyleneheteroaryl --

Column 4, line 42, "$C_{1-3}$alkylene-N(R$^4$)$_2$" should be -- $C_{1-3}$alkyleneN(R$^4$)$_4$ --

Column 4, line 47, "$C_{1-3}$-alkylenearyl" should be -- $C_{1-3}$alkylenearyl --

Column 6, line 64, "R$^{16}$" should be -- OR$^{16}$ --

Column 6, lines 65-66, "N(R$^{15}$)COR$^{16}$N(R$^{15}$)C(O)OR$^{16}$" should be -- N(R$^{15}$)COR$^{16}$ N(R$^{15}$)C(O)OR$^{16}$ --

Column 6, last line, "N(R$^{1-6}$) . . ." should be -- N(R$^{16}$) . . . --

Column 7, lines 10-11, "$C_{1-3}$alkyleneC$_{3-6}$heterocycloalkyl" should be -- $C_{1-3}$alkyleneC$_{3-8}$heterocycloalkyl --

Column 7, line 12, " . . . N(R$^{17}$)$_{3+}$" should be -- . . . N(R$^{17}$)$_3^+$ --

Column 8, line 49, "R$^1$" should be -- R$^2$ --

Column 9, line 50, "N(R$^{24}$)-C(O)" should be -- N(R$^{24}$)C(O) --

Column 10, line 53, "N(R$^{25}$)-C(O)C$_{1-3}$ . . ." should be -- N(R$^{25}$)C(O)C$_{1-3}$ . . . --

Column 10, lines 54-55, "N(R$^{25}$)C(O)CC$_{1-3}$ . . ." should be -- N(R$^{25}$)C(O)C$_{1-3}$ . . . --

Column 11, line 47, "C(O)R$^7_1$" should be -- C(O)R$^7$, --

Column 12, line 8, "C-R$_{10}$" should be -- C-R$^{10}$ --

Column 12, line 38, ". . . (R$^2$)-C(O) . . ." should be -- . . . (R$^{12}$)C(O) . . . --

Column 13, line 19, "N(R$^{13}$)C(o)OR$^7$" should be -- N(R$^{13}$)C(O)OR$^7$ --

Column 13, line 26, "$C_{1-3}$alkyleneN(R$_{1-2}$) . . ." should be -- $C_{1-3}$alkyleneN(R$^{12}$) . . . --

Column 13, line 27, ". . . alkyleneOR$^{12}$," should be -- . . . alkyleneOR$^2$, --

Page 1 of 13

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 13, lines 55-56, "$N(R^{16})C(O)C,alkyleneC(O) R^{16}$" should be -- $N(R^{16})C(O)C_{1-3}alkyleneC(O)R^{16}$ --

Column 13, line 64, "$C_{16}alkyl$" should be -- $C_{1-6}alkyl$ --

Column 13, line 65, "$SO_2R^7$" should be -- $SO_2R^{17}$ --

Column 13, lines 66-67, "$C_{1-3}alkyleneC_{1-3},heterocycloalkyl$" should be -- $C_{1-3}alkyleneC_{3-8}heterocycloalkyl$ --

Column 13, line 67, "$C_{1-3}alkyleneSOaryl$" should be -- $C_{1-3}alkyleneSO_2aryl$ --

Column 14, line 21, "bicyclo-[3.2.1]octyl" should be -- bicyclo[3.2.1]octyl --

Column 14, line 24, "$(N(Ra)_2)$" should be -- $(N(R^a)_2)$ --

Column 14, line 25, "$(SO_2Ra)$" should be -- $(SO_2R^a)$ --

Column 14, line 31, delete the comma after "Heterocycloalkyl"

Column 14, line 41, delete the hyphen between "alkylene" and "heteroaryl"

Column 18, line 28, delete the "I" before "Suitable"

Column 18, line 62, the paragraph starring with "Theoretical" should be a continuation of the previous paragraph, not a new paragraph.

Column 19, lines 2-31, delete lines starting with "structural" on line 2 through "This concentration is defined as" on lines 30-31

Column 20, lines 41-43, the phrase "growth related protein," is repeated four times, delete all but one of these occurrences Column 20, line 44, delete the "*" from between "growth" and "factor"

Column 20, line 49, delete second occurrence of "nerve growth factor"

Column 21, line 24, "orchemotherapy" should be -- or chemotherapy --

Column 21, line 28, delete the hyphen between "administered" and "before"

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 21, line 57, delete the period after "that"

Column 22, line 36, delete the dash between "5-fluorouracil" and "(5-FU)"

Column 69, line 10, "(5.8 9;" should be -- (5.8 g; --

Column 69, line 33, "Step (4): Lithium Hydroxide Hydrolysis Procedure" should be a new heading Column 69, line 54, "aminioethyl" should be -- aminoethyl --

Column 72, under the heading "Characterization" line starting with "12" "Mhz" both occurrences, should be -- MHz --

Column 73, line 29, delete the hyphen in "dimethoxy-ethane"

Column 73, line 33, "Mhz" should be -- MHz --

Column 73, line 57, "2--" should be -- 2- --

Column 73, line 65, "Mhz" should be -- MHz --

Column 74, line 18, "iso-cyanate" should be -- isocyanate --

Column 74, line 62, "Mhz" should be -- MHz --

Column 74, line 65, "Mhz" should be -- MHz --

Column 75, line 29, "J 8.8" should be -- J=8.8 --

Column 75, line 65, "(10.16-10.06, m, 3H)" should be -- 10.16-10.06 (m, 3H) --

Column 77, line 24, "iso-cyanate" should be -- isocyanate --

Column 77, line 56, "$H_2$in" should be -- $H_2$ in --

Column 78, line 28, "vacac" should be -- vacuo --

Column 79, line 33, "7.43(d" should be -- 7.43 (d --

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 79, line 34, "7.09(dd," should be -- 7.09 (dd --

Column 79, line 37, "1.10(m," should be -- 1.10 (m, --

Column 79, line 62, "8.03(d," should be -- 8.03 (d, --

Column 79, line 62, "7.47,(d," should be -- 7.47 (d, --

Column 79, line 63, "7.04(dd," should be -- 7.04 (dd, --

Column 80, line 17, "3methoxybenzoic" should be -- 3-methoxybenzoic --

Column 81, line 19, "300 mL" should be -- 300 µL --

Column 81, line 23, "H2O" should be -- $H_2O$ --

Column 81, line 27, "3.97 (s." should be -- 3.97 (s, --

Column 81, line 49, 7.23 (i," should be -- 7.23 (m, --

Column 82, line 2, "8.22 (d" should be -- 8.22 (d, --

Column 83, line 17, delete the comma between "using" and "2"

Column 83, line 59, "N-(H" should be -- N-(1H --

Column 84, line 20, "7.05 (d 3H), 3.56" should be
-- 7.05 (dd, 1H), 6.98 (dd, 1H), 3.97 (s, 3H), 3.56 --

Column 84, line 21, "(in," should be -- (m, --

Column 84, line 66, "7.51 s" should be -- 7.51 (s --

Column 85, line 1, "(in," should be -- (m, --

Column 85, line 49, "2.41 (m" should be -- 2.41 (m, --

Column 86, lines 46-47 "3.05 (m (m." should be -- 3.05 (m, --

Column 87, line 19, "$^3$-morpholin" should be -- 3-morpholin --

UNITED STATES PATENT AND TRADEMARK OFFICE
CERTIFICATE OF CORRECTION

PATENT NO.      : 7,067,506 B2
APPLICATION NO. : 10/087715
DATED           : June 27, 2006
INVENTOR(S)     : Kathleen S. Keegan et al.

It is certified that error appears in the above-identified patent and that said Letters Patent is hereby corrected as shown below:

Column 87, line 38, "$^3$-Methoxy" should be -- 3-Methoxy --

Column 87, line 39, "$^4$-($^3$-pyrazin" should be -- 4-(3-pyrazin --

Column 87, line 41, "$^3$-($^4$-methyl" should be -- 3-(4-methyl --

Column 88, line 23, "IN" should be -- 1N --

Column 88, line 46, "(IN)" should be -- (1N) --

Column 91, line 23, "pyridin4" should be -- pyridin-4 --

Column 91, line 65, "$^1$H)" should be -- 1H) --

Column 96, line 19, "trifluorace" should be -- trifluoroacetic acid --

Column 96, line 42, "6 8.79" should be -- δ 8.79 --

Column 101, line 4, "2.39 (m, 2.24" should be -- 2.39 (m, 2H), 2.24 --

Column 101, line 5, "mile" should be -- m/e --

Column 103, line 62, "8.32 (d, 1H," should be -- 8.32 (d, 1H), --

Column 105, line 30, "(, 11H)" should be -- (m, 1H) --

Column 106, line 32, "$CH_2C_{12}$" should be -- $CH_2Cl_2$ --

Column 107, line 29, "3methoxy" should be -- 3-methoxy --

Column 107, line 58, "(s, 2H), 2H)," should be -- (s, 2H), --

Column 107, last line, "2H), 7.52 (m, 7H), 489.1." should be
-- 2H). MS APCI-pos, M+1=489.1. --

Column 108, line 49, "$NH_4OH$," should be -- $NH_4OH$, --

Column 109, line 30, "about 1 of" should be -- about 1/2 of --

Column 109, line 38, "mmol) 50" should be -- mmol) in 50 --

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 109, line 55, "4.33 (, 11H)," should be -- 4.22 (m, 1H), --

Column 109, lines 57-58, "1.70-1.77 (n, 11H)," should be -- 1.70-1.77 (m, 1H), --

Column 110, line 66, "H2O" should be -- $H_2O$ --

Column 111, line 9, "H2O" should be -- $H_2O$ --

Column 111, line 9, "dryed" should be -- dried --

Column 111, line 30, "8.12 (s, 2H)," should be -- 8.12 (s, 1H), --

Column 112, line 8, "22 ml," should be -- 22 mL, --

Column 112, line 43, "S 8.57" should be -- δ 8.57 --

Column 113, line 48 "arid" should be -- and --

Column 113, line 62, "7.65 (d, 1H," should be -- 7.65 (d, 1H), --

Column 114, line 46, "8.39 (d, 1H," should be -- 8.39 (d, 1H), --

Column 115, lines 20-21, "7.39 (M, 1H)," should be -- 7.39 (m, 1H), --

Column 115, line 35, "8.61 (d, 1H," should be -- 8.61 (d, 1H), --

Column 116, line 1, "8.68 (d, 1H," should be -- 8.68 (d, 1H), --

Column 116, line 2, "8.48 (d, 1H," should be -- 8.48 (d, 1H), --

Column 117, line 28, "8.43 (d, 1H," should be -- 8.43 (d, 1H), --

Column 118, line 29, "8.21 (s, 111)," should be -- 8.21 (s, 1H), --

Column 118, line 29, "7.24 (d, 111)," should be -- 7.24 (d, 1H), --

Column 118, lines 29-30, "6.76 (m, 1H1)," should be -- 6.76 (m, 1H), --

Column 118, line 30, "3.56 (m, 21H)," should be -- 3.56 (m, 2H), --

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 118, line 31, "2.24 (s, 1H), 2.13 (m, 1H" should be -- 2.24 (s, 6H), 2.13 (m, 2H) --

Column 118, lines 65-66, "2.37 (s, 13H)," should be -- 2.37 (s, 3H), --

Column 120, line 30, "8.66 (d, 1H," should be -- 8.66 (d, 1H), --

Column 120, line 65, "8.26 (d, 1H," should be -- 8.26 (d, 1H), --

Column 121, line 29, "8.66 (d, 1H," should be -- 8.66 (d, 1H), --

Column 121, lines 64-65, "8.33 (d, 1H, 8.00 (d, 1H," should be -- 8.33 (d, 1H), 8.00 (d, 1H), --

Column 121, line 66, ".25 (m, 1H)," should be -- 7.25 (m, 1H), -- .

Column 122, line 63, "tl$_6$-DMSO" should be -- d$_6$-DMSO --

Column 122, lines 64-65, "8.29 (d, 1H, 8.03 (d, 1H," should be -- 8.29 (d, 1H), 8.03 (d, 1H), --

Column 123, lines 29-30, "8.33 (d, 1H, 8.00 (d, 1H," should be -- 8.33 (d, 1H), 8.00 (d, 1H), --

Column 124, line 25, "8.66 (d, 1H," should be -- 8.66 (d, 1H), --

Column 124, line 26, "8.28 (d, 1H," should be -- 8.28 (d, 1H), --

Column 124, line 27, "7.55 (d, 1H," should be -- 7.55 (d, 1H), --

Column 125, line 16, "20 ml" should be -- 20 mL --

Column 126, line 55, "1-[5-" should be -- 1-{5- --

Column 127, line 28, "6.79 (d, 1H," should be -- 6.79 (d, 1H), --

Column 129, line 31, "6.75 (d, 1H," should be -- 6.75 (d, 1H), --

Column 130, line 31, insert -- 2.35 (s, 3H). -- between "2.38 (s, 3H)" and "LRMS"

UNITED STATES PATENT AND TRADEMARK OFFICE
CERTIFICATE OF CORRECTION

PATENT NO.      : 7,067,506 B2
APPLICATION NO. : 10/087715
DATED           : June 27, 2006
INVENTOR(S)     : Kathleen S. Keegan et al.

It is certified that error appears in the above-identified patent and that said Letters Patent is hereby corrected as shown below:

Column 132, lines 9-10, "7.70 (d, 1H, 7.19 (d, 1H," should be -- 7.70 (d, 1H), 7.19 (d, 1H), --

Column 132, line 11, "2.5 (s, 3H)." should be --2.35 (s, 3H). --

Column 133, line 40, "6.75 (d, 1H," should be -- 6.75 (d, 1H), --

Column 134, line 34, "3.15 (br d, 1H," should be -- 3.15 (br d, 1H), --

Column 135, line 33, "6.79 (d, 1H, 6.75 (d, 1H," should be -- 6.79 (d, 1H), 6.75 (d, 1H), --

Column 136, line 21, delete the comma after "and"

Column 136, line 52, "ylmethoxy)5-" should be -- ylmethoxy)-5- --

Column 137, Compound 277, the dashed bond at the top of the structure should be a solid bond Column 138, line 26, "1H NMR" should be -- $^{1}$H NMR --

Column 138, line 64, "8.49 (d, 1H," should be -- 8.49 (d, 1H), --

Column 138, line 65, "7.65 (d, 1H," should be -- 7.65 (d, 1H),. --

Column 138, line 67, "(M4 1)." should be -- (M+1). --

Column 139, line 65, "8.20 (s, 1(dd, 2H)," should be -- 8.20 (s, 1H), 8.10 (s, 1H), 6.81 (dd, 2H), --

Column 139, line 67, "2.36 (s, 3H), 2H)." should be -- 2.36 (s, 3H), 2.19 (m, 4H), 1.90 (m, 2H). --

Column 141, line 35, "Compound 286" should be a heading

Column 143, line 40, "(M4 1)" should be -- (M+1) --

Column 144, line 28, "to the give the" should be -- to give the --

Column 144, line 30, "7.96 (d, 11H)" should be -- 7.96 (d, 1H) --

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 144, line 31, "11H)" should be -- 1H) --

Column 144, line 55, "3.52 (n,11H)" should be -- 3.52 (m, 1H) --

Column 145, lines 15-16, "6.65 (dd, 1H, 6.51 (d, 1H, 3.96 (mi, 2H)" should be -- 6.65 (dd, 1H), 6.51 (d, 1H), 3.96 (m, 2H) --

Column 146, line 9, "6.58 (d, 1H," should be -- 6.58 (d, 1H), --

Column 146, line 9, "3.57 (d, 1H," should be -- 3.57 (d, 1H), --

Column 146, line 61, "5 7.92" should be -- δ 7.92 --

Column 146, line 61, "7.08 (dd, 1H," should be -- 7.08 (dd, 1H), --

Column 146, line 63, "(dd, 1H," should be -- (dd, 1H), --

Column 147, line 24, "7.25 (mi, 1H)," should be -- 7.25 (m, 1H), --

Column 147, lines 24-25, "7.18 (d, 1H," should be -- 7.18 (d, 1H), --

Column 147, line 25, "6.70 (d, 1H," should be -- 6.70 (d, 1H), --

Column 148, line 6, after "7.76 (t, 1H)," please insert -- 7.61 (5, 1H), --

Column 149, line 61, "2-(2-Aziridin-" should be -- 1-[2-(2-Aziridin- --

Column 161, line 25, "(d, 11)," should be -- (d, 1H), --

Column 161, line 49, after "3.90 (s, 3H)" please insert -- 2.30 (s, 3H) --

Column 162, line 23, "-O-" should be -- -3- --

Column 162, line 27, please delete the comma after "with"

Column 162, line 65, "8.26 (s, H)," should be -- 8.26 (s, 1H), --

Column 163, line 64, "-carbatic" should be -- -carbamic --

Column 167, line 56, "(1.0 g)" should be -- (1.0 g, --

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 169, please replace the structure for Compound 331 and insert therefor

-- 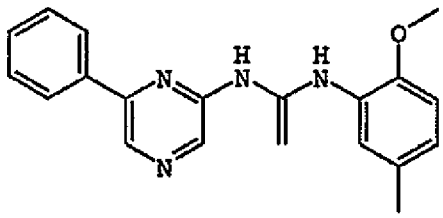 --

1-(2-Methoxy-5-methyl-phenyl) -
3-(6-phenyl-pyrazin-2-yl)-urea

Column 171, line 45, after "Step 1" please insert

-- 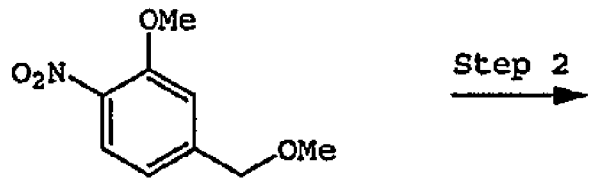 --

Column 171, line 52, "Step 1" should be -- Step 3 --

Column 172, line 30, after "60°C" first occurrence, please insert -- before adding 2-methoxy-4-methoxymethylaniline as a solution in 4 mL toluene. After stirring for 6 hr --

Column 173, line 21, delete ") ." second occurrence

Column 174, lines 13-14, delete "$^1$H NMR (400 MHz, CDCl$_3$): δ" second occurrence Column 174, line 64, "8.06 (s, 1H," should be -- 8.06 (s, 1H), --

Column 177, line 37, "and the" should be -- and then --

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 178, line 67, "(-NH3)" should be -- (-NH$_3$) --

Column 180, line 46, "4.G8" should be -- 4,08 --

Column 180, line 65, "J7.83" should be -- J=7.83 --

Column 182, line 61, "Methoxy4" should be -- Methoxy-4 --

Column 182, line 64, "4.23 (," should be -- 4.23 (s, --

Column 185, Compound 361, right-hand side of structure,

"... 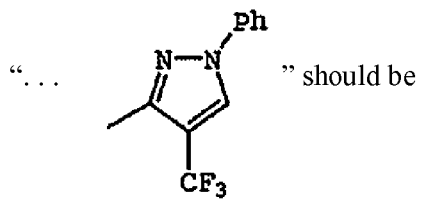 " should be

-- ... 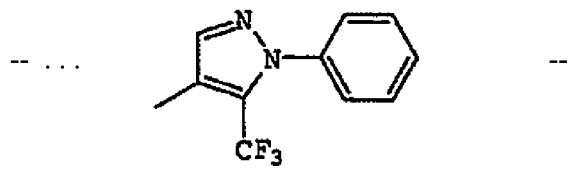 --

Compound 186, line 39, "Methoxy4" should be -- Methoxy-4 --

Column 186, line 42, ";7.89" should be -- 7.89 --

Column 188, line 33, "The,5'" should be -- The 5' --

Column 188, line 35, "Saint Louis, IL" should be -- Saint Louis, MO --

Column 189, line 4, "developed" should be -- develop --

Column 189, line 27, delete the comma between "p38" and "MAP"

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 189, line 56, "Chk 1" should be -- Chk1 --

Column 189, line 60, "Chk 1" should be -- Chk1 --

Column 190, line 37, "minutes" should be -- minute --

Column 192, line 16, delete the hyphen between "in" and "the"

Column 192, line 60, "$CO_2R^3_1$," should be -- $CO_2R^3$, --

Column 194, line 3, delete "null,"

Column 194, line 33, "$C_2R^{25}$" should be -- $CO_2R^{25}$ --

Column 195, line 17, delete "are"

Column 195, line 23, "$C_2R^3$" should be -- $CO_2R^3$ --

Column 195, line 59, "lease one or more" should be -- least one of a --

Column 196, line 53, "$OCF_3$" should be -- $OCF^3$ --

Column 197, line 34, "Hodgkins, lymphoma" should be -- Hodgkin's lymphoma --

Column 198, line 32, "$SR^7_1$," should be -- $SR^7$, --

UNITED STATES PATENT AND TRADEMARK OFFICE
CERTIFICATE OF CORRECTION

PATENT NO. : 7,067,506 B2
APPLICATION NO. : 10/087715
DATED : June 27, 2006
INVENTOR(S) : Kathleen S. Keegan et al.

It is certified that error appears in the above-identified patent and that said Letters Patent is hereby corrected as shown below:

Column 199, line 8, insert --is-- between "Q'" and "OCH$_3$"

Column 202, line 40, insert -- ( -- before "piperidin"

Column 203, line 35, "CF$_{10}$" should be -- CR$^{10}$ --

Signed and Sealed this

Twentieth Day of February, 2007

JON W. DUDAS
*Director of the United States Patent and Trademark Office*